US006696281B1

(12) United States Patent
Chambers et al.

(10) Patent No.: US 6,696,281 B1
(45) Date of Patent: Feb. 24, 2004

(54) CHIMERIC FLAVIVIRUS VACCINES

(75) Inventors: Thomas J. Chambers, St. Louis, MO (US); Thomas P. Monath, Harvard, MA (US); Farshad Guirakhoo, Melrose, MA (US)

(73) Assignees: Acambis, Inc., Cambridge, MA (US); St. Louis University, St. Louis, MO (US)

( * ) Notice: Subject to any disclaimer, the term of this patent is extended or adjusted under 35 U.S.C. 154(b) by 0 days.

(21) Appl. No.: 09/452,638

(22) Filed: Dec. 1, 1999

Related U.S. Application Data

(63) Continuation-in-part of application No. 09/121,587, filed on Jul. 23, 1998, which is a continuation-in-part of application No. PCT/US98/03894, filed on Mar. 2, 1998, which is a continuation-in-part of application No. 09/007,664, filed on Jan. 15, 1998, now abandoned, which is a continuation-in-part of application No. 08/807,445, filed on Feb. 28, 1997, now abandoned.

(51) Int. Cl.[7] ........................... C12N 7/01; C12N 7/04; C12N 15/79; C12P 39/00; A61K 39/12

(52) U.S. Cl. ............................... 435/235.1; 435/230.1; 435/69.1; 435/69.3; 435/236.1; 424/93.2; 424/218.1; 424/199.1; 424/204.1; 424/202.1; 424/192.1

(58) Field of Search ........................... 424/204.1, 218.1, 424/205.1, 192.1, 93.2, 199.1, 202.1; 435/235.1, 320.1, 69.1, 69.3, 236

(56) References Cited

U.S. PATENT DOCUMENTS 6,184,024 B1 2/2001 Lai et al.

FOREIGN PATENT DOCUMENTS

| | | |
|---|---|---|
| WO | WO 93/06214 | 4/1993 |
| WO | 98/37911 | 9/1998 |

OTHER PUBLICATIONS

Lai et al. Clin Diagn. Virol. Jul. 1998, vol. 10, pp. 173–179.*
Arroyo et al., "Yellow Fever Vector Live–Virus Vaccines: West Nile Virus Vaccine Development," Trends in Molecular Medicine 7:350–354 (2001).
Caufour et al., "Construction, Characterization and Immunogenicity of Recombinant Yellow Fever 17D–Dengue Type 2 Viruses," Virus Research 79:1–14 (2001).
Chambers et al., "Mutagenesis of the Yellow Fever Virus NS2B/3 Cleavage Site: Determinants of Cleavage Site Specificity and Effects on Polyprotein Processing and Viral Replication," Journal of Virology 69:1600–1605 (1995).
Chambers et al., "Vaccine Development Against Dengue and Japanese Encephalitis: Report of a World Health Organization Meeting," Vaccine 15:1494–1502 (1997).
Coia et al., "Nucleotide and Complete Amino Acid Sequences of Kunjin Virus: Definitive Gene Order and Characteristics of the Virus–Specified Proteins," J. Gen. Virol. 69:1–21 (1988).
Galler et al., "The Yellow Fever 17D Vaccine Virus: Molecular Basis of Viral Attenuation and its Use as an Expression Vector," Brazilian Journal and Biological Research 30:157–168 (1997).
Galler et al., "Genetic Variability Among Yellow Fever Virus 17D Substrains," Vaccine 16:1–5 (1998).
Guirakhoo et al., "Construction, Safety, and Immunogenicity in Nonhuman Primates of a Chimeric Yellow Fever–Dengue Virus Tetravalent Vaccine," Journal of Virology 75:7290–7304 (2001).
Mandl et al., "Sequence of the Genes Encoding the Structural Proteins of the Low–Virulence Tick–Borne Flaviviruses Langat TP21 and Yelantsev," Virology 185:891–895 (1991).
Mandl et al., "Complete Genomic Sequence of Powassan Virus: Evaluation of Genetic–Elements in Tick–Borne Versus Mosquito–Borne Flaviviruses," Virology 194:173–184 (1993).
Pletnev et al., "Construction and Characterization of Chimeric Tick–Borne Encephalitis/Dengue Type 4 Viruses," Proc. Natl. Acad. Sci. U.S.A. 89:10532–10536 (1992).
Shiu et al., "Genomic Sequence of the Structural Proteins of Louping Ill Virus: Comparative Analysis with Tick–Borne Encephalitis Virus," Virology 180:411–415 (1991).
Stocks et al., "Signal Peptidase Cleavage at the Flavivirus C–prM Junction: Dependence on the Viral NS2B–3 Protease for Efficient Processing Requires Determinants in C, the Signal Peptide, and prM," Journal of Virology 72:2141–2149 (1998).
Bray et al., "Construction of Intertypic Chimeric Dengue Viruses by Substitution of Structural Protein Genes," Proc. Natl. Acad. USA 88:10342–10346 (1991).
Galler et al., "Genetic Variability Among Yellow Fever Virus 17D Substrains," Vaccine 16:1–5 (1998).
Marchevsky et al., "Phenotypic Analysis of Yellow Fever Virus Derived from Complementary DNA," American J. Tropical Medicine & Hygiene 52:75–80 (1995).
Rice et al., "Transcription of Infectious Yellow Fever RNA from Full–Length cDNA Templates Produced by In Vitro Ligation," The New Biologist 1:285–296 (1989).
Venugopal et al., "Towards a New Generation of Flavivirus Vaccines," Vaccines 12:966–975 (1994).
Chambers et al., "Yellow Fever/Japanese Encephalitis Chimeric Viruses: Construction and Biological Properties," *Journal of Virology* 73:3095–3101 (1999).
Duarte dos Santos et al., "Complete nucleotide sequence of yellow fever virus vaccine strains 17DD and 17D–213," *Virus Research* 35:35–41 (1995).

* cited by examiner

*Primary Examiner*—James Housel
*Assistant Examiner*—Bao Qun Li
(74) *Attorney, Agent, or Firm*—Clark & Elbing LLP

(57) ABSTRACT

A chimeric live, infectious, attenuated virus containing a yellow fever virus, in which the nucleotide sequence for a prM-E protein is either deleted, truncated, or mutated, so that functional prM-E protein is not expressed, and integrated into the genome of the yellow fever virus, a nucleotide sequence encoding a prM-E protein of a second, different flavivirus, so that the prM-E protein of the second flavivirus is expressed.

9 Claims, 34 Drawing Sheets

Virus names abbreviations

YF = yellow fever
JE = Japanese encephalitis
TBE = Tick-borne encephalitis
MVE = Murray Valley encephalitis
SLE = Saint Louis encephalitis
DEN1-4 = dengue serotypes 1-4

DEN4
prM signal
Capsid
prM
Envelope
NS1
NS5
NS2B/NS3 site
prM begins
DEN4 ILNGRKR STITLLCLLIPTVMA FSL
TBE signal sequence
prM begins
TBE QKRGKRR SAVDWTGWLLVVVLLGVTLA ATV
DEN4/TBE
Capsid
prM
Envelope
NS1
NS5
Replaced w/ TBE sequence

Figure 3:
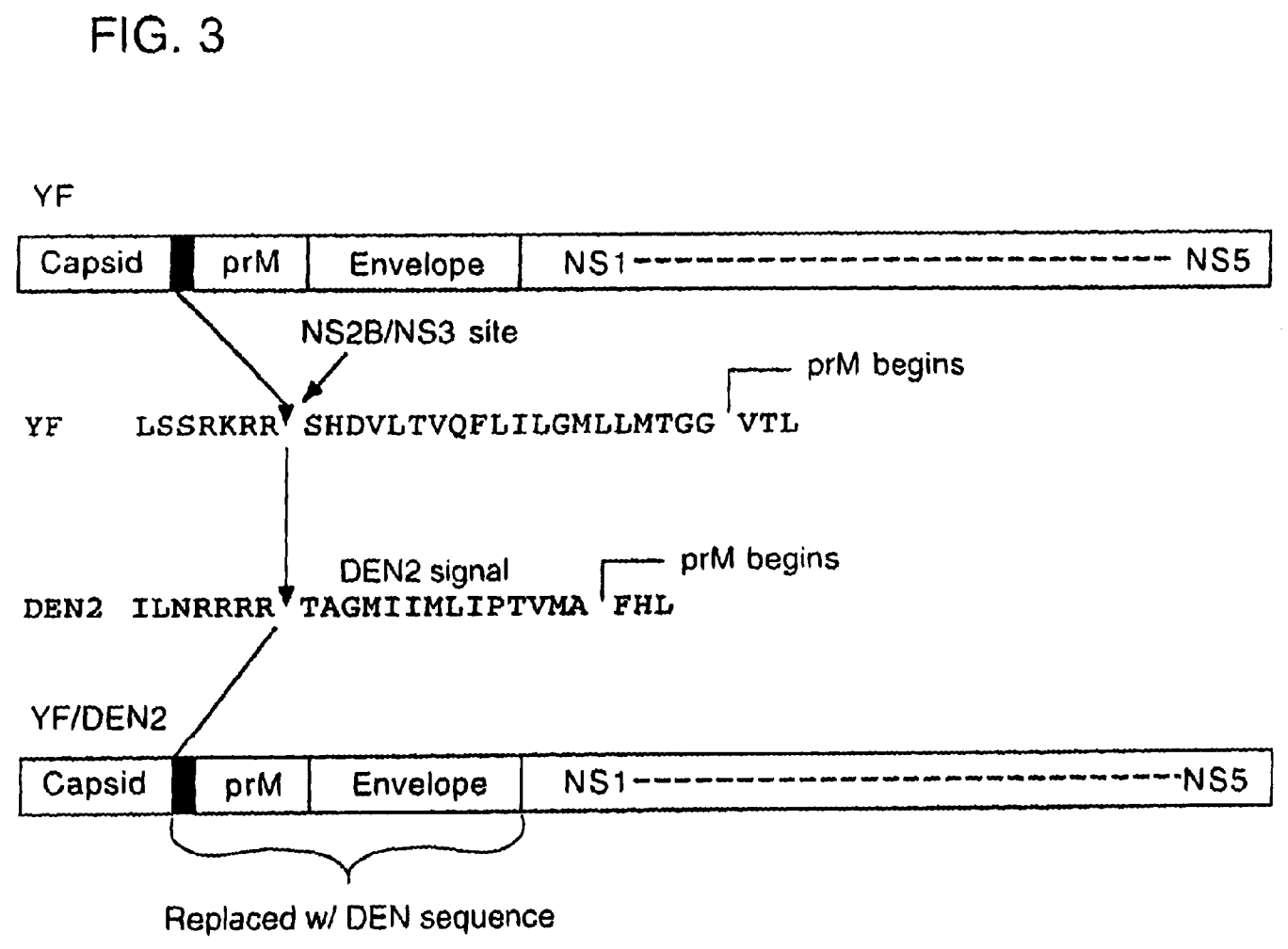

Capsid | prM | Envelope | NS1 ------------------------ NS5

NS2B/NS3 site prM begins

YF LSSRKRR SHDVLTVQFLILGMLLMTGG VTL

DEN2 signal prM begins

DEN2 ILNRRRR TAGMIIMLIPTVMA FHL

YF/DEN2

Capsid | prM | Envelope | NS1 ------------------------ NS5

Replaced w/ DEN sequence

YF-Vax
YF/JE

Titer(pfu/ml)
1.00E+05
1.00E+04
1.00E+03
1.00E+02

1 2 3 4 5 6 7 8 9 10
Days post infection

FIG. 12

MICE: 4 week old ICR males/females

VIRUS DOSE: $10^4$ pfu intracerebrally

No. of mice surviving 15
10
5
0

0 5 10 15 20

Days post infection

YF5.2iv $JESA_{14}$-14-2

YF/JE $SA_{14}$-14-2

| Virus | Survival | P |
|---|---|---|
| YF5.2iv | 0/12 (0%) | |
| $JESA_{14}$-14-2 | 12/12 (100%) | <0.001 |
| YF/JE $SA_{14}$-14-2 | 13/13 (100%) | <0.001 |

FIG. 13

Geom. mean titer (Stdev)

120
100
80
60
40
20
0

Dose 4 log 5 log

Min. protective N titer 1:8

ChimeriVax™
YF/Nakayama
JE Nakayama
SA14-14-2 (BHK1)
YF-Vax®
JE-Vax®
YF5.2 (17D inf. clone)
50% PRNT
$\log_{10}$ PFU
mouse 1
mouse 2
mouse 3
mouse 4
mouse 5
mouse 6
mouse 7
mouse 8

ChimeriVax™ (10^7.0 pfu)
PFU/ml
Rh191
Rh290
Rh431
PFU/ml
15000
10000
5000
0
0
1
2
3
4
5
6
YF-Vax (10^5.0 pfu)
Rh030
Rh192
Rh179
PFU/ml
1500
1000
500
0
0
1
2
3
4
5

FIG. 19

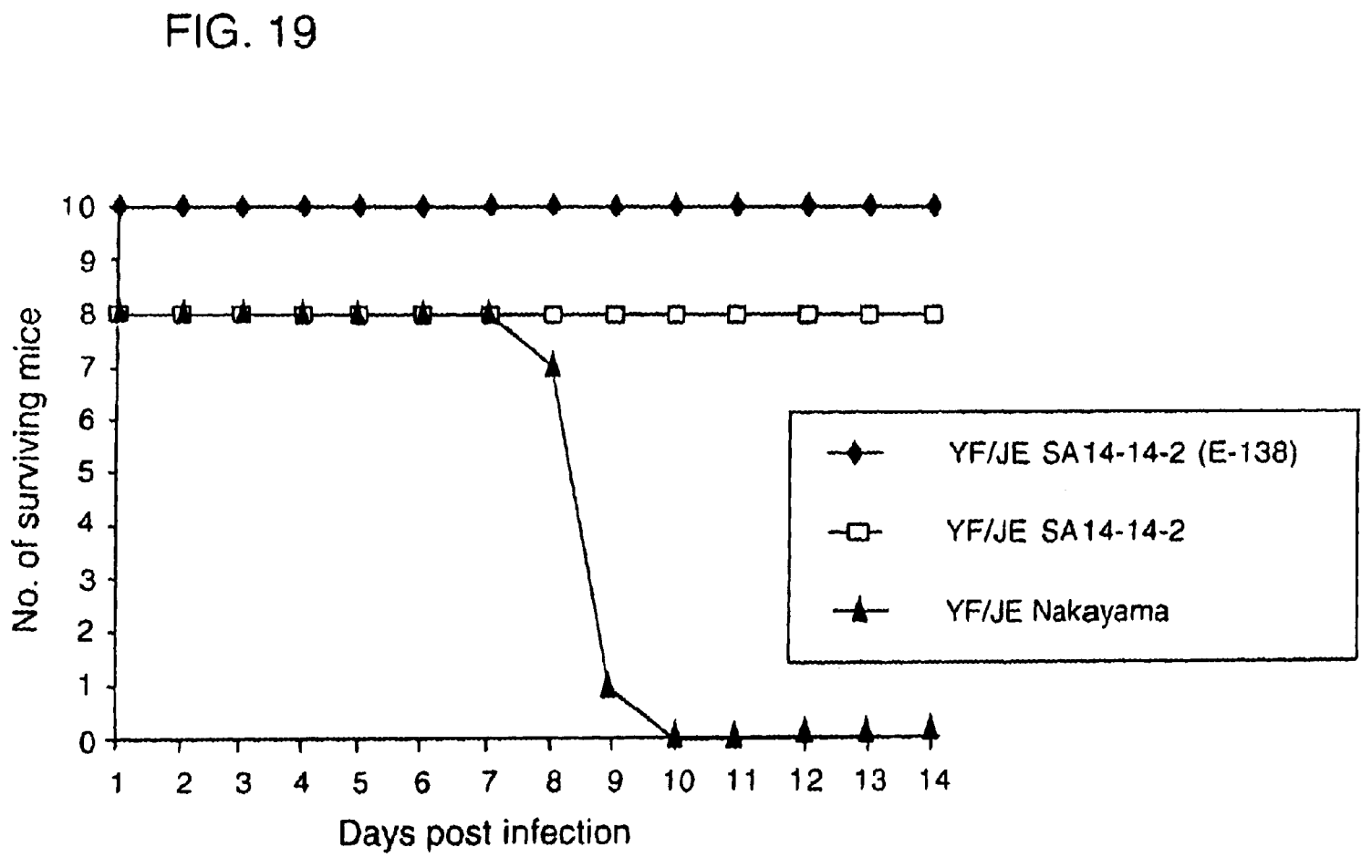

YF/JE SA14-14-2 (E-138)
YF/JE SA14-14-2
YF/JE Nakayama

No. of surviving mice
0 1 2 3 4 5 6 7 8 9 10

Days post infection
1 2 3 4 5 6 7 8 9 10 11 12 13 14

CHIMERIC FLAVIVIRUS VACCINES

This is a continuation-in-part of U.S. Ser. No. 09/121,587, filed on Jul. 23, 1998, which is a continuation-in-part of PCT/US98/03894, filed on Mar. 2, 1998, which is a continuation-in-part of U.S. Ser. No. 09/007,664, filed on Jan. 15, 1998 now abandoned, which is a continuation-in-part of U.S. Ser. No. 08/807,445, filed on Feb. 28, 1997 now abandoned.

BACKGROUND OF THE INVENTION

This invention relates to infectious, attenuated viruses useful as vaccines against diseases caused by flaviviruses.

Several members of the flavivirus family pose current or potential threats to global public health. For example, Japanese encephalitis is a significant public health problem involving millions of at risk individuals in the Far East. Dengue virus, with an estimated annual incidence of 100 million cases of primary dengue fever and over 450,000 cases of dengue hemorrhagic fever worldwide, has emerged as the single most important arthropod-transmitted human disease.

Other flaviviruses continue to cause endemic diseases of variable nature and have the potential to emerge into new areas as a result of changes in climate, vector populations, and environmental disturbances caused by human activity. These flaviviruses include, for example, St. Louis encephalitis virus, which causes sporadic, but serious, acute disease in the midwest, southeast, and western United States; West Nile virus, which causes febrile illness, occasionally complicated by acute encephalitis, and is widely distributed throughout Africa, the Middle East, the former Soviet Union, and parts of Europe; Murray Valley encephalitis virus, which causes endemic nervous system disease in Australia; and Tick-borne encephalitis virus, which is distributed throughout the former Soviet Union and eastern Europe, where its Ixodes tick vector is prevalent and responsible for a serious form of encephalitis in those regions.

Hepatitis C virus (HCV) is another member of the flavivirus family, with a genome organization and replication strategy that are similar, but not identical, to those of the flaviviruses mentioned above. HCV is transmitted mostly by parenteral exposure and congenital infection, is associated with chronic hepatitis that can progress to cirrhosis and hepatocellular carcinoma, and is a leading cause of liver disease requiring orthotopic transplantation in the United States.

The Flaviviridae family is distinct from the alphaviruses (e.g., WEE, VEE, EEE, SFV, etc.) and currently contains three genera, the flaviviruses, the pestiviruses, and the hepatitis C viruses. Fully processed mature virions of flaviviruses contain three structural proteins, envelope (E), capsid (C), and membrane (M), and seven non-structural proteins (NS1, NS2A, NS2B, NS3, NS4A, NS4B, and NS5). Immature flavivirions found in infected cells contain pre-membrane (prM) protein, which is the precursor to the M protein.

After binding of virions to host cell receptors, the E protein undergoes an irreversible conformational change upon exposure to the acidic pH of endosomes, causing fusion between the envelope bilayers of the virions and endocytic vesicles, thus releasing the viral genome into the host cytosol. PrM-containing tick-borne encephalitis (TBE) viruses are fusion-incompetent, indicating that proteolytic processing of prM is necessary for the generation of fusion-competent and fully infectious virions (Guirakhoo et al., J. Gen. Virol. 72(Pt. 2):333–338, 1991). Using ammonium chloride late in the virus replication cycle, prM-containing Murray Valley encephalitis (MVE) viruses were produced and shown to be fusion incompetent. By using sequence-specific peptides and monoclonal antibodies, it was demonstrated that prM interacts with amino acids 200–327 of the E protein. This interaction is necessary to protect the E protein from the irreversible conformational changes caused by maturation in the acidic vesicles of the exocytic pathway (Guirakhoo et al., Virology 191:921–931, 1992).

The cleavage of prM to M protein occurs shortly before release of virions by a furin-like cellular protease (Stadler et al., J. Virol. 71:8475–8481, 1997), which is necessary to activate hemagglutinating activity, fusogenic activity, and infectivity of virions. The M protein is cleaved from its precursor protein (prM) after the consensus sequence R-X-R/K-R (X is variable), and incorporated into the virus lipid envelope together with the E protein.

Cleavage sequences have been conserved not only within flaviviruses, but also within proteins of other, unrelated viruses, such as PE2 of murine coronaviruses, PE2 of alphaviruses, HA of influenza viruses, and p 160 of retroviruses. Cleavage of the precursor protein is essential for virus infectivity, but not particle formation. It was shown that, in case of a TBE-dengue 4 chimera, a change in the prM cleavage site resulted in decreased neurovirulence of this chimera (Pletnev et al., J. Virol. 67:4956–4963, 1993), consistent with the previous observation that efficient processing of the prM is necessary for full infectivity (Guirakhoo et al., 1991, supra; Guirakhoo et al., 1992, supra; Heinz et al., Virology 198:109–117, 1994). Antibodies to prM protein can mediate protective immunity, apparently due to neutralization of released virions that contain some uncleaved prM. The proteolytic cleavage site of the PE2 of VEE (4 amino acids) was deleted by site-directed mutagenesis of the infectious clone (Smith et al., ASTMH meeting, Dec. 7–11, 1997). Deletion mutants replicated with high efficiency and PE2 proteins were incorporated into particles. This mutant was evaluated in lethal mouse and hamster models and shown to be attenuated; in non-human primates it caused 100% seroconversion and protected all immunized monkeys from a lethal challenge.

SUMMARY OF THE INVENTION

The invention features chimeric, live, infectious, attenuated viruses that are each composed of:

(a) a first yellow fever virus (e.g., strain 17D), representing a live, attenuated vaccine virus, in which the nucleotide sequence encoding the prM-E protein is either deleted, truncated, or mutated so that the functional prM-E protein of the first flavivirus is not expressed, and (b) integrated into the genome of the first flavivirus, a nucleotide sequence encoding the viral envelope (prM-E) protein of a second, different flavivirus, so that the prM-E protein of the second flavivirus is expressed from the altered genome of the first flavivirus.

The chimeric virus is thus composed of the genes and gene products responsible for intracellular replication belonging to the first flavivirus and the genes and gene products of the envelope of the second flavivirus. Since the viral envelope contains antigenic determinants responsible for inducing neutralizing antibodies, the result of infection with the chimeric virus is that such antibodies are generated against the second flavivirus.

A preferred live virus for use as the first yellow fever virus in the chimeric viruses of the invention is YF 17D, which has been used for human immunization for over 50 years. YF 17D vaccine is described in a number of publications, including publications by Smithburn et al. ("Yellow Fever Vaccination," World Health Org., p. 238, 1956), and Freestone (in Plotkin et al., (Eds.), Vaccines, $2^{nd}$ edition, W. B. Saunders, Philadelphia, 1995). In addition, the yellow fever virus has been studied at the genetic level (Rice et al., Science 229:726–733, 1985) and information correlating genotype and phenotype has been established (Marchevsky et al., Am. J. Trop. Med. Hyg. 52:75–80, 1995). Specific examples of yellow fever substrains that can be used in the invention include, for example, YF 17DD (GenBank Accession No. U 17066), YF 17D-213 (GenBank Accession No. U17067), YF 17D-204 France (X15067, X15062), and YF-17D-204, 234 US (Rice et al., Science 229:726–733, 1985; Rice et al., New Biologist 1:285–296, 1989; C 03700, K 02749). Yellow Fever virus strains are also described by Galler et al., Vaccine 16 (9/10):1024–1028, 1998.

Preferred flaviviruses for use as the second flavivirus in the chimeric viruses of the invention, and thus sources of immunizing antigen, include Japanese Encephalitis (JE, e.g., JE SA14-14-2), Dengue (DEN, e.g., any of Dengue types 1–4; for example, Dengue-2 strain PUO-218) (Gruenberg et al., J. Gen. Virol. 67:1391–1398, 1988) (sequence appendix 1; SEQ ID NO:50; nucleotide sequence of Dengue-2 insert; Pr-M: nucleotides 1–273; M: nucleotides 274–498; E: nucleotides 499–1983) (sequence appendix 1; SEQ ID NO:51; amino acid sequence of Dengue-2 insert; Pr-M: amino acids 1–91; M: amino acids 92–166; E: amino acids 167–661), Murray Valley Encephalitis (MVE), St. Louis Encephalitis (SLE), West Nile (WN), Tick-borne Encephalitis (TBE) (i.e., Central European Encephalitis (CEE) and Russian Spring-Summer Encephalitis (RSSE) viruses), and Hepatitis C (HCV) viruses. Additional flaviviruses for use as the second flavivirus include Kunjin virus, Powassan virus, Kyasanur Forest Disease virus, and Omsk Hemorrhagic Fever virus. As is discussed further below, the second flavivirus sequences can be provided from two different second flaviviruses, such as two Dengue strains.

It is preferable to use attenuated inserts, for example, in the case of inserts from neurotropic viruses, such as JE, MVE, SLE, CEE, and RSSE. In the case of non-neurotropic viruses, such as dengue viruses, it may be preferable to use unmodified inserts, from unattenuated strains. Maintenance of native sequences in such inserts can lead to enhanced immunogenicity of the proteins encoded by the inserts, leading to a more effective vaccine.

In a preferred chimeric virus of the invention, the prM-E protein coding sequence of the second flavivirus is substituted for the prM-E protein coding sequence of the live yellow fever virus. Also, as is described further below, the prM portion of the protein can contain a mutation or mutations that prevent cleavage to generate mature membrane protein. Finally, as is discussed in detail below, the chimeric viruses of the invention include the prM signal of yellow fever virus.

Also included in the invention are methods of preventing or treating flavivirus infection in a mammal, such as a human, by administering a chimeric flavivirus of the invention to the mammal; use of the chimeric flaviviruses of the invention in the preparation of medicaments for preventing or treating flavivirus infection; nucleic acid molecules encoding the chimeric flaviviruses of the invention; and methods of manufacturing the chimeric flaviviruses of the invention.

The invention provides several advantages. For example, because they are live and replicating, the chimeric viruses of the invention can be used to produce long-lasting protective immunity. Also, because the viruses have the replication genes of an attenuated virus (e.g., Yellow Fever 17D), the resulting chimeric virus is attenuated to a degree that renders it safe for use in humans.

Other features and advantages of the invention will be apparent from the following detailed description, the drawings, and the claims.

BRIEF DESCRIPTION OF THE DRAWINGS

FIG. 3 is a schematic representation of an attempt to use the method of C. J. Lai (WO 93/06214) with a yellow fever backbone (SEQ ID NOs:73 and 74).

FIG. 8 is a set of growth curves for chimeric YF/JE viruses of the invention in cell cultures of vertebrate and mosquito origin.

FIG. 10 is a graph showing a growth comparison between RMS (YF/JE SA14-14-2) and YF-Vax® (Yellow Fever 17D Vaccine) in MRC-5 cells.

FIG. 12 is a graph and a table showing the results of a mouse neurovirulence analysis carried out with a YF/JE chimeric virus of the invention.

FIG. 13 is a graph showing the neutralizing antibody response of mice immunized with a YF/JE SA14-14-2 chimeric vaccine of the invention. Three week old mice were immunized, and samples for testing were taken at 6 weeks.

FIG. 14A is a graph showing the results of neurovirulence testing of YF-Vax® (Yellow Fever 17D Vaccine) in 4 week old ICR mice by the i.c. route.

FIG. 14B is a graph showing the results of neurovirulence testing of YF/JE SA14-14-2 in 4 week old ICR mice by the i.c. route.

FIG. 19 is a graph showing the results of neurovirulence testing of YF/JE SA14-14-2 (E-138 K→mutant).

FIGS. 25A–C are graphs showing the growth of JE SA14, JE SA14-14-2, CHIMERIVAX-JE™ (chimeric flavivirus vaccine comprising Japanese Encephalitis virus prM and E proteins) and YF 17D IT orally exposed mosquitoes: (A) *Cx. tritaeniorhynchus* mosquitoes, (B) *Ae. albopictus* mosquitoes, and (C) *Ae. aegypti* mosquitoes. Mean titer= geometric mean of the titers of three individual mosquitoes; $\log_{10}$ pfu/mosquito.

DETAILED DESCRIPTION

The invention provides chimeric flaviviruses that can be used in vaccination methods against flavivirus infection. Construction and analysis of chimeric flaviviruses of the invention, such as chimeras of yellow fever virus and Japanese Encephalitis (JE), Dengue types 1–4 (DEN1–4), Murray Valley Encephalitis (MVE), St. Louis Encephalitis (SLE), West Nile (WN), Tick-borne Encephalitis (TBE), and Hepatitis C (HCV) viruses are described as follows.

Yellow fever (YF) virus is a member of the Flaviviridae family of small, enveloped positive-strand RNA viruses. Flavivirus proteins are produced by translation of a single long open reading frame to generate a polyprotein, and a complex series of post-translational proteolytic cleavages of the polyprotein by a combination of host and viral proteases, to generate mature viral proteins (Amberg et al., J. Virol. 73:8083–8094, 1999; Fields, "Flaviviridae," In Virology, Fields (ed.), Raven-Lippincott, New York, 1995, Volume I, p. 937). The virus structural proteins are arranged in the order C-prM-E, where "C" is capsid, "prM" is a precursor of the viral envelope-bound M protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polyprotein. The amino termini of prM, E, NS1, and NS4B are generated by host signalase cleavage within the lumen of the endoplasmic reticulum (ER), while most cleavages within the non-structural region are mediated by a viral protease complex known as NS2B-NS3 (Fields, "Flaviviridae," In Virology, Fields (ed.), Raven-Lippincott, New York, 1995, Volume I, p. 937). In addition, the NS2B-NS3 protease complex is responsible for mediating cleavages at the C terminus of both the C protein and the NS4A protein (Amberg et al., J. Virol. 73:8083–8094, 1999).

Several research efforts suggest a regulatory role for NS2B-NS3-mediated cleavage at the C terminus of the capsid protein. This site is the only site in the structural region of polyprotein that is cleaved by the NS2B-NS3 protease and, in addition, it includes a highly conserved dibasic-site motif of flaviviruses, which indicates a functional role (Amberg et al., J. Virol. 68.3794–3802, 1994; Yamshchikov et al., J. Virol. 68:5765–5771, 1994). In vitro data from various flavivirus models suggest that efficient generation of the prM protein, an early step in proper release of structural proteins, is dependent on the function of the viral protease at the capsid protein site (see summary in Amberg et al., J. Virol. 73:8083–8094, 1999).

Figure 1A:
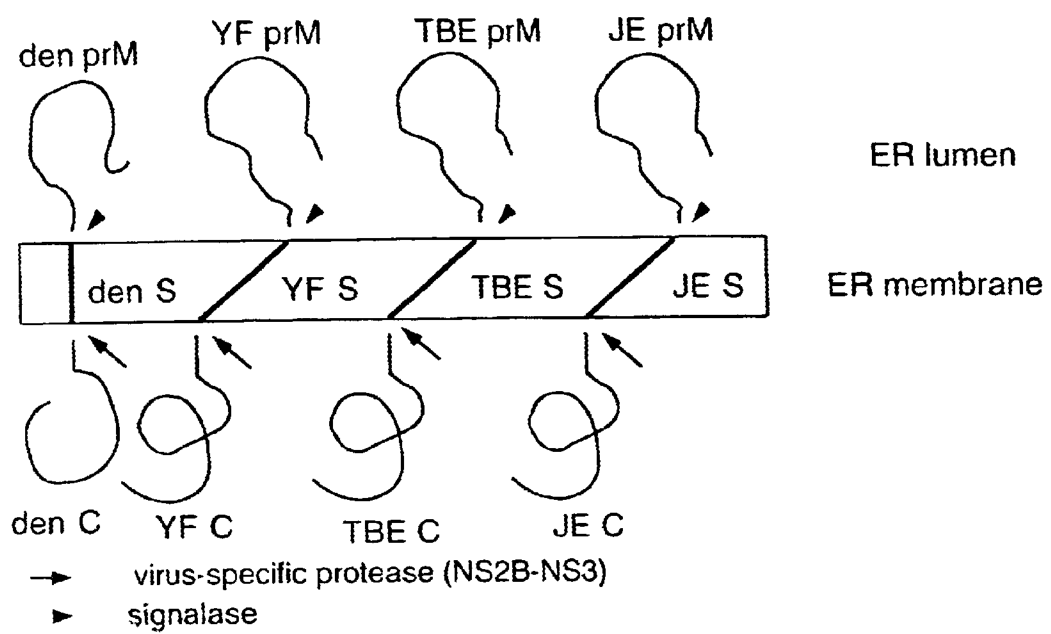
FIG. 1A is a schematic representation of processing events at the C/prM junction of parental viruses that can be used in the invention.
Figure 1B:
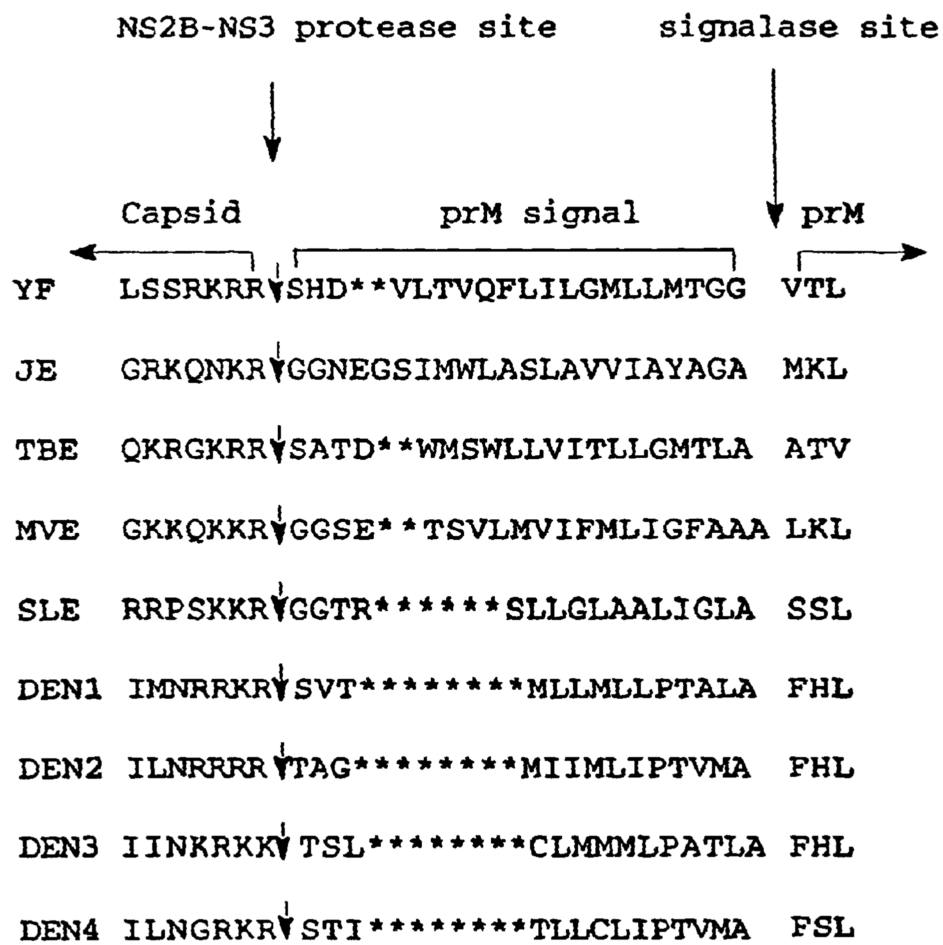
FIG. 1B is a schematic representation of the sequences in the capsid, prM signal, and prM regions of flaviviruses that can be used in the invention (SEQ ID NOs:54–70).

Maintenance of this mechanism of coordinate cleavages by NS2B-NS3 at the C terminus of the capsid protein and signalase at the N terminus of prM in the chimeras described below is central to the present invention. In particular, in the chimeras of the present invention, the length of the so-called "prM signal," which separates the two cleavage sites by 20 amino acids in YF (FIGS. 1A and 1B), is substantially maintained, to ensure polyprotein proteolytic processing and subsequent growth of chimeric viruses that are created in a YF backbone. A hydrophobic domain within this signal serves to direct the translocation of prM into the ER lumen, where efficient signalase cleavage occurs only after cleavage at the NS2B-NS3 site in the capsid protein (Amberg et al., J. Virol. 73:8083–8094, 1999; FIGS. 1A and 1B).

Figure 2:
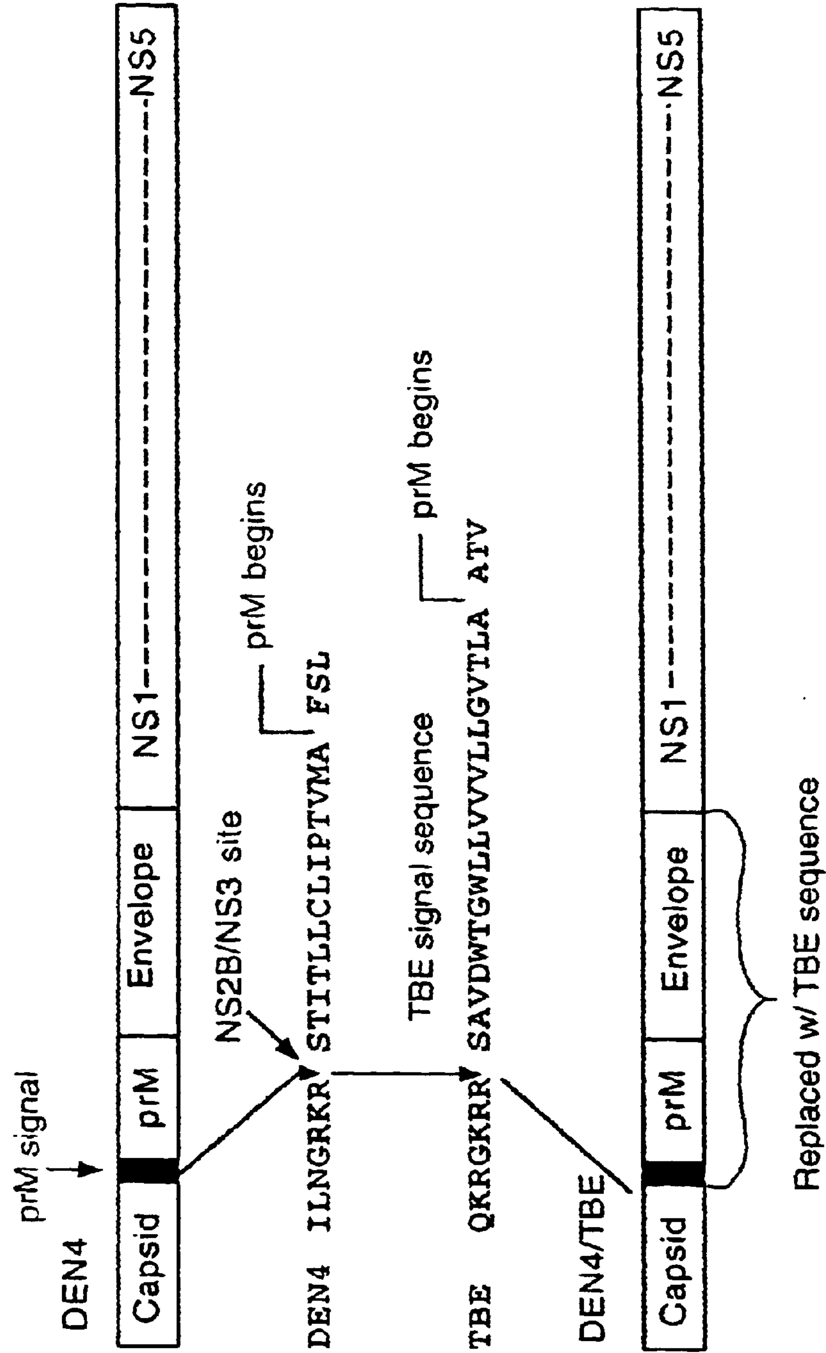
FIG. 2 is a schematic representation of the approach to making chimeric flaviviruses at the prM signal region (SEQ ID NOs:71 and 72) used by C. J. Lai (WO 93/06214).

In the chimeras of the present invention, only the regions encoding the membrane and envelope proteins (i.e., the prME region) of a non-yellow fever flavivirus are used to replace the corresponding genes in a yellow fever virus clone. The prM signal of the yellow fever virus backbone is maintained. Another method, described in a patent application by C. J. Lai, WO 93/06214, suggests a universal approach to constructing chimeric flaviviruses, involving cloning the prME region of a donor virus into the backbone of an acceptor virus, such that the prM signal sequence is contributed by the incoming prM protein gene. This approach was illustrated using dengue 4 virus as the backbone (acceptor) and tick-borne encephalitis as the donor prME gene. As is illustrated in FIG. 2, the approach described in WO 93/06214 suggests that variability in this cloning strategy, with other chimeric models using flaviviruses as backbone, will have no effect on proper processing of the resulting polyprotein. That is, that flavivirus prM signals are exchangeable when producing viable chimeric viruses. However, attempts to use this approach with YF as a backbone for the insertion of prME genes of dengue 2 virus to create a chimera in which dengue 2 sequences were inserted at the 5' NS2B/NS3 cleavage site (e.g., by R. Galler, see FIG. 3) failed to produce a viable virus, and the use of the 14 amino acid signal of the dengue 2 virus prM in this construct explains why. When the cloning strategy was altered to maintain the YF prM signal of 20 amino acids (i.e., only the Den 2 prME region was replaced), it was successful. The failure to make a viable chimera in YF using the shorter signal of dengue prM demonstrates that the approach described in WO 93/06214 does not work for all chimeras, such as those including a YF backbone.

Figure 4:
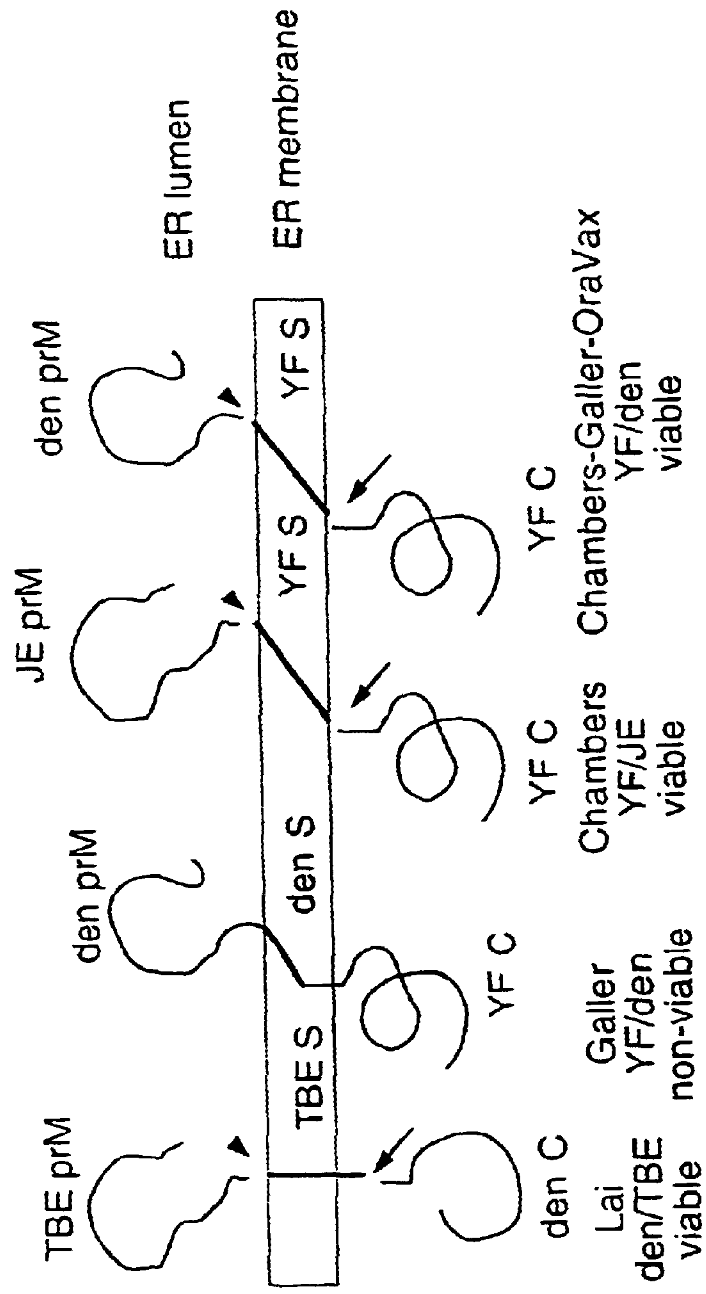
FIG. 4 is a schematic representation illustrating that the viability of flavivirus chimeras depends on the choice of signal.

The explanation of the success of the approach described in WO 93/06214, using a dengue virus backbone, is that both the viral protease and the prM signal of dengue viruses were maintained. The dengue prM signal is 6–8 amino acids shorter than that of other flaviviruses, such as YF, TBE, MVE, and JE. Dengue, and chimeric flaviviruses with a dengue backbone, rely on dengue NS2B-NS3 protease complex for eventual signalase cleavage at the prM signal. Possibly dengue strain evolution favors a short signal sequence for optimum cascade-event processing of structural viral proteins, proper assembly, and virus production. If a longer signal is cloned in a dengue chimera, the amino acid additions favors translocation of prME, and perhaps cleavage, but not necessarily optimal viral growth. On the other hand, YF, TBE, MVE, and JE have evolved using a long prM signal, and cloning of a shorter signal in any of these backbones obliterates C-prM-E processing and viral growth (FIG. 4).

Figure 5:
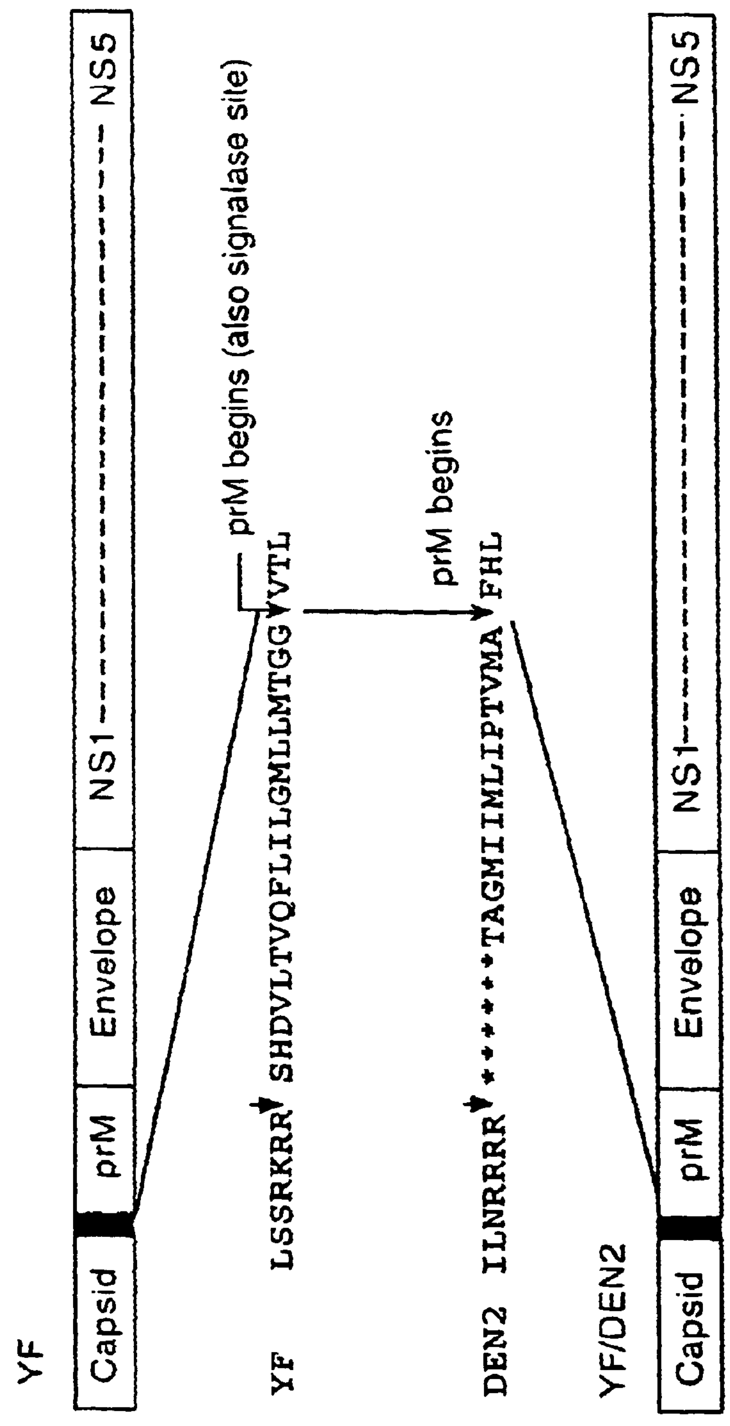
FIG. 5 is a schematic representation of the cloning method used in the present invention, at the prM signal region (SEQ ID NOs:75–77).

Thus, central to the present invention is the length of the prM signal (FIG. 5). The cloning of the prME region of any flavivirus into a YF backbone according to the invention always takes place after the prM signal sequence (i.e., LMTGG/VTL for yellow fever); in this way, all prME chimeras encode the yellow fever prM signal, thus ensuring proper processing of the polyprotein. In addition, it is preferable to maintain the length and sequence of the YF prM signal in the chimeras of the invention. That is, preferably, the length of the prM signal is 20 amino acids. Less preferably, the length of the prM signal is 15, 16, 17, 18, 19, or more than 20 amino acids in length. Also, it is preferable that the amino acid sequence of the YF prM signal is maintained in the chimeras of the invention, although this sequence can be modified using, for example, conservative amino acid substitutions. Preferably, the sequence of the prM signal is 100%, less preferably, 90%, 80%, 70%, 60%, 50%, or 40% identical to the YF prM signal.

Figure 6:
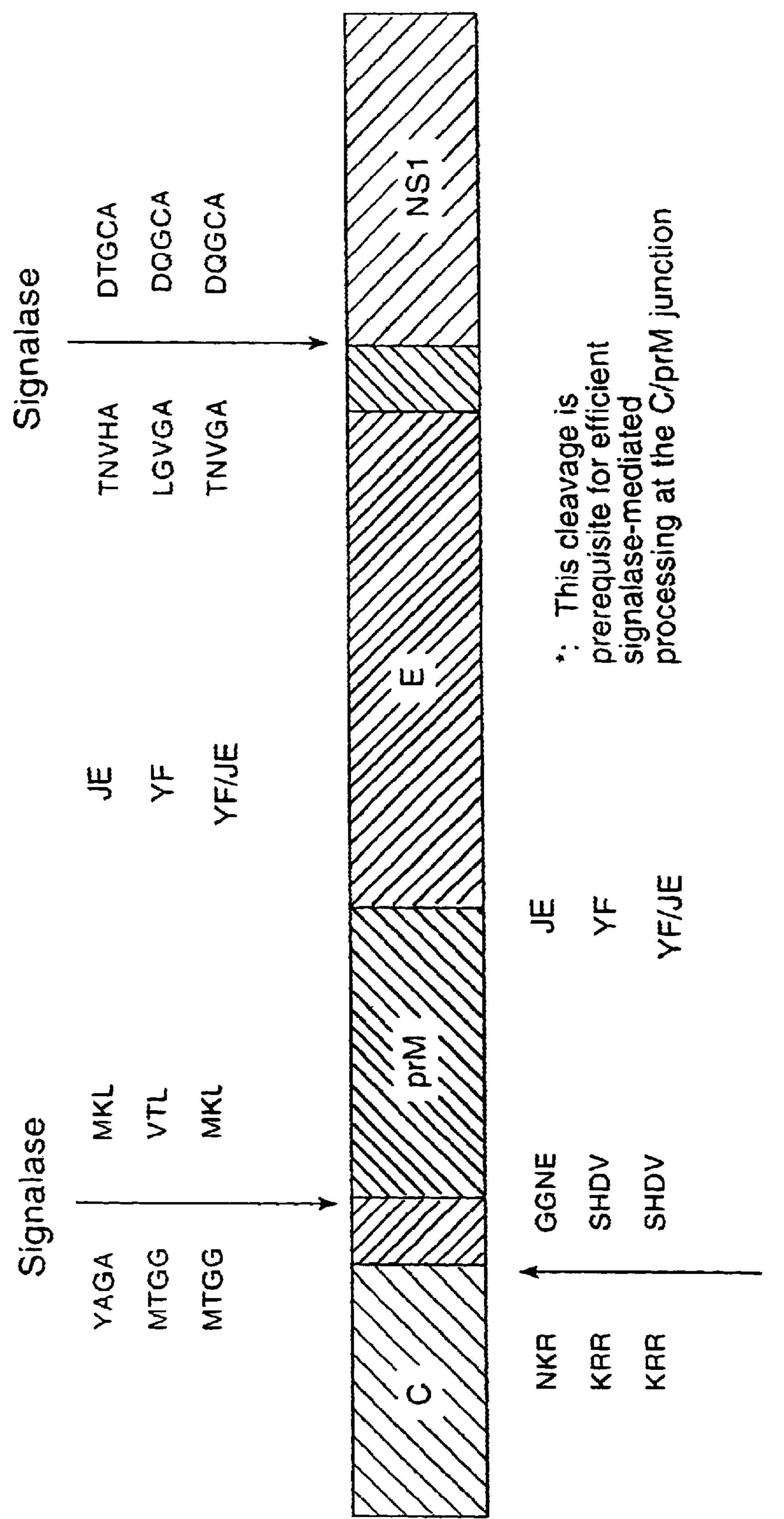
FIG. 6 is a schematic representation of the C, prM, E, and NS1 regions and junction sequences of a YF/JE chimera of the invention. The amino acid sequences flanking cleavage sites at the junctions are indicated for JE, YF, and the YF/JE chimera (SEQ ID NOs:78–85).

As an example of construction of a chimera of the invention, FIG. 6 illustrates a YF/JE chimera in which the YF NS2B-NS3 protease recognition site is maintained. Thus, the recognition site for cleavage of the cytosolic from membrane-associated portions of capsid is homologous for the YF NS2B-NS3 enzyme. At the C/pr-M junction, the portion of the signalase recognition site upstream of the cleavage site is that of the backbone, YF, and the portion downstream of the cleavage site is that of the insert, JE. At the E/NS1 junction, the portion of the signalase recognition site upstream of the cleavage site is similar to that of the insert, JE (four of five of the amino acids are identical to those of the JE sequence), and the portion downstream of the cleavage site is that of the backbone, YF. It is preferable to maintain this or a higher level of amino acid sequence identity to the viruses that form the chimera. Alternatively, at least 25, 50, or 75% sequence identity can be maintained in the three to five amino acid positions flanking the signalase and NS2B-NS3 protease recognition sites.

Also possible, though less preferable, is the use of any of numerous known signal sequences to link the C and pre-M or E and NS1 proteins of the chimeras (see, e.g., von Heijne, Eur. J. Biochem. 133:17–21, 1983; von Heijne, J. Mol. Biol. 184:99–105, 1985) or, for example, using the known sequences for guidance, one skilled in the art can design additional signal sequences that can be used in the chimeras of the invention. Typically, for example, the signal sequence will include as its last residue an amino acid with a small, uncharged side chain, such as alanine, glycine, serine, cysteine, threonine, or glutamine. Other requirements of signal sequences are known in the art (see, e.g., von Heijne, 1983, supra; von Heijne, 1985, supra).

Following the approach described above, we have succeeded in making viable YF chimeric constructs for JE (section 1) and dengue serotypes 1 through 4 (sections 2–5, respectively). Construction and characterization of these, as well as other, constructs are described further below.

1.0 Construction of cDNA Templates for Generation of YF/JE Chimeric Virus

The derivation of full-length cDNA templates for YF/JE chimeras of the invention described below employed a strategy similar to that earlier workers used to regenerate YF 17D from cDNA for molecular genetic analysis of YF replication. The strategy is described, e.g., by Nestorowicz et al. (Virology 199:114–123, 1994).

Briefly, derivation of a YF/JE chimera of the invention involves the following. YF genomic sequences are propagated in two plasmids (YF5'3'1V and YFM5.2), which encode the YF sequences from nucleotides 1–2,276 and 8,279–10,861 (YF5'3'IV) and from 1,373–8,704 (YFM5.2) (Rice et al., The New Biologist 1:285–296, 1989). Full-length cDNA templates are generated by ligation of appropriate restriction fragments derived from these plasmids. This method has been the most reliable for ensuring stable expression of YF sequences and generation of RNA transcripts of high specific infectivity.

Figure 7:
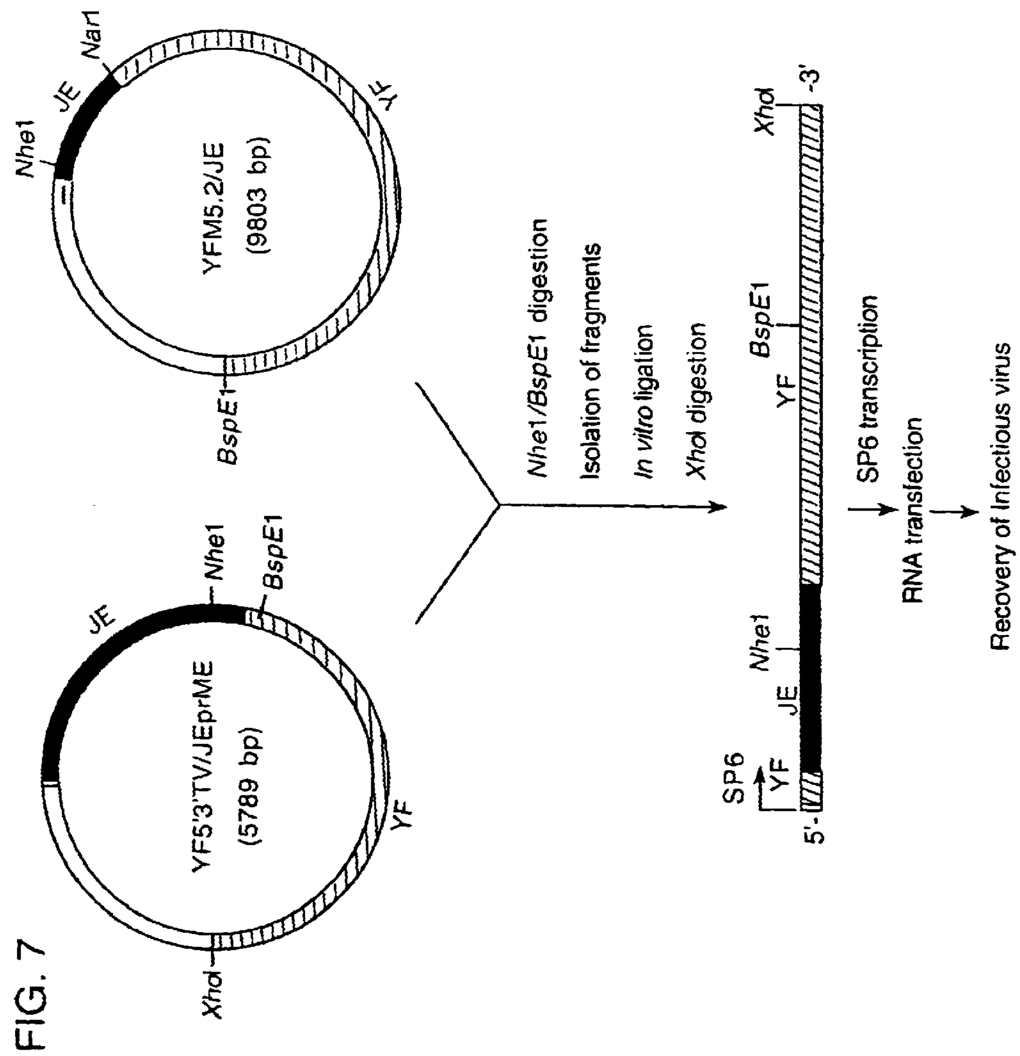
FIG. 7 is a schematic representation of genetic manipulation steps that were carried out to construct a Yellow-Fever/Japanese Encephalitis (YF/JE) chimeric virus of the invention.

Our strategy for construction of chimeras involves replacement of YF sequences within the YF5'3'IV and YFM5.2 plasmids by the corresponding JE sequences from the start of the prM protein (nucleotide 478, amino acid 128) through the E/NS1 cleavage site (nucleotide 2,452, amino acid 817). In addition to cloning of JE cDNA, several steps were required to introduce or eliminate restriction sites in both the YF and JE sequences to permit in vitro ligation. The structure of the template for regenerating chimeric YF (C)/JE (prM-E) virus is shown in FIG. 7. A second chimera, encoding the entire JE structural region (C-prM-E) was engineered using a similar strategy. The second chimera was not able to generate RNA of high infectivity.

1.1 Molecular Cloning of the JE Virus Structural Region

Clones of authentic JE structural protein genes were generated from the JE SA14-14-2 strain (JE live, attenuated vaccine strain), because the biological properties and molecular characterization of this strain are well-documented (see, e.g., Eckels et al., Vaccine 6:513–518, 1988; JE SA14-14-2 virus is available from the Centers for Disease Control, Fort Collins, Colo. and the Yale Arbovirus Research Unit, Yale University, New Haven, Conn., which are World Health Organization-designated Reference Centers for Arboviruses in the United States). JE SA14-14-2 virus at passage level PDK-5 was obtained and passaged in LLC-$MK_2$ cells to obtain sufficient amounts of virus for cDNA cloning. The strategy used involved cloning the structural region in two pieces that overlap at an NheI site (JE nucleotide 1,125), which can then be used for in vitro ligation.

RNA was extracted from monolayers of infected LLC-$MK_2$ cells and first strand synthesis of negative sense cDNA was carried out using reverse trariscriptase with a negative sense primer (JE nucleotide sequence 2,456–71) containing nested XbaI and NarI restriction sites for cloning initially into pBluescript II KS(+), and subsequently into YFM5.2 (NarI), respectively. First strand cDNA synthesis was followed by PCR amplification of the JE sequence from nucleotides 1,108–2,471 using the same negative sense primer and a positive sense primer (JE nucleotides sequence 1,108–1,130) containing nested XbaI and NsiI restriction sites for cloning into pBluescript and YFM5.2(NarI), respectively. JE sequences were verified by restriction enzyme digestion and nucleotide sequencing. The JE nucleotide sequence from nucleotides 1 to 1,130 was derived by PCR amplification of negative strand JE cDNA using a negative sense primer corresponding to JE nucleotides 1,116 to 1,130 and a positive sense primer corresponding to JE nucleotides 1 to 18, both containing an EcoRI restriction site. PCR fragments were cloned into pBluescript and JE sequences were verified by nucleotide sequencing. Together, this represents cloning of the JE sequence from nucleotides 1–2,471 (amino acids 1–792).

1.2 Construction of YF5'3'IV/JE and YFM5.2/JE Derivatives

To insert the C terminus of the JE envelope protein at the YF E/NS1 cleavage site, a unique NarI restriction site was introduced into the YFM5.2 plasmid by oligonucleotide-directed mutagenesis of the signalase sequence at the E/NS1 cleavage site (YF nucleotides 2,447–2,452, amino acids 816–817) to create YFM5.2(NarI). Transcripts derived from templates incorporating this change were checked for infectivity and yielded a specific infectivity similar to the parental templates (approximately 100 plaque-forming units/250 nanograms of transcript). The JE sequence from nucleotides 1,108 to 2,471 was subcloned from several independent PCR-derived clones of pBluescript/JE into YFM5.2(NarI) using the unique NsiI and NarI restriction sites. YF5'3'IV/JE clones containing the YF 5' untranslated region (nucleotides 1–118) adjacent to the JE prM-E region were derived by PCR amplification.

To derive sequences containing the junction of the YF capsid and JE prM, a negative sense chimeric primer spanning this region was used with a positive sense primer corresponding to YF5'3'IV nucleotides 6,625–6,639 to generate PCR fragments that were then used as negative sense PCR primers in conjunction with a positive sense primer complementary to the pBluescript vector sequence upstream of the EcoRI site, to amplify the JE sequence (encoded in reverse orientation in the pBluescript vector) from nucleotide 477 (N-terminus of the prM protein) through the NheI site at nucleotide 1,125. The resulting PCR fragments were inserted into the YF5'3'IV plasmid using the NotI and EcoRI restriction sites. This construct contains the SP6 promoter preceding the YF 5'-untranslated region, followed by the sequence: YF (C) JE (prM-E), and contains the NheI site (JE nucleotide 1,125) required for in vitro ligation.

1.3 Engineering YFM5.2 and YF5'3'IV to Contain Restriction Sites for in vitro Ligation To use the NheI site within the JE envelope sequence as a 5' in vitro ligation site, a redundant NheI site in the YFM5.2 plasmid (nucleotide 5,459) was eliminated. This was accomplished by silent mutation of the YF sequence at nucleotide 5,461 (T C; alanine, amino acid 1820). This site was incorporated into YFM5.2 by ligation of appropriate restriction fragments and introduced into YFM5.2(NarI)/JE by exchange of an NsiI/NarI fragment encoding the chimeric YF/JE sequence.

To create a unique 3' restriction site for in vitro ligation, a BspEI site was engineered downstream of the AatII site normally used to generate full-length templates from YF5'3'IV and YFM5.2. (Multiple AatII sites are present in the JE structural sequence, precluding use of this site for in vitro ligation.) The BspEI site was created by silent mutation of YF nucleotide 8,581 (A C; serine, amino acid 2,860), and was introduced into YFM5.2 by exchange of appropriate restriction fragments. The unique site was incorporated into YFM5.2/JE by exchange of the XbaI/SphI fragment, and into the YF5'3'IV/JE(prM-E) plasmids by three-piece ligation of appropriate restriction fragments from these parent plasmids and from a derivative of YFM5.2 (BspEI) deleting the YF sequence between the EcoRI sites at nucleotides 1 and 6,912.

1.4 Exchange of JE Nakayama cDNA Into YF/JE Chimeric Plasmids

Because of uncertainty about the capacity of the PCR-derived JE SA14-14-2 structural region to function properly in the context of the chimeric virus, we used cDNA from a clone of the JE Nakayama strain that has been extensively characterized in expression experiments and for its capacity to induce protective immunity (see, e.g., Mclda et al., Virology 158:348–360, 1987; the JE Nakayama strain is available from the Centers for Disease Control, Fort Collins, Colo., and the Yale Arbovirus Research Unit, Yale University, New Haven, Conn.). The Nakayama cDNA was inserted into the YF/JE chimeric plasmids using available restriction sites (HindIII to PvuII and BpmI to MunI) to replace the entire prM-E region in the two plasmid system except for a single amino acid, serine, at position 49, which was left intact in order to utilize the NheI site for in vitro ligation. The entire JE region in the Nakayama clone was sequenced to verify that the replaced cDNA was authentic (Table 1).

1.5 Generation of Full-Length cDNA Templates, RNA Transfection, and Recovery of Infectious Virus Procedures for generating full-length cDNA templates are essentially as described in Rice et al. (The New Biologist 1:285–96, 1989; also see FIG. 7). In the case of chimeric templates, the plasmids YF5'3'IV/JE (prM-E) and YFM5.2/JE are digested with NheI/BspEI and in vitro ligation is performed using 300 nanograms of purified fragments in the presence of T4 DNA ligase. The ligation products are linearized with XhoI to allow run-off transcription. SP6 transcripts are synthesized using 50 nanograms of purified template, quantitated by incorporation of $^3$H-UTP, and integrity of the RNA is verified by non-denaturing agarose gel electrophoresis. Yields range from 5 to 10 micrograms of RNA per reaction using this procedure, most of which is present as full-length transcripts. Transfection of RNA transcripts in the presence of cationic liposomes is carried out as described by Rice et al. (supra) for YF 17D. In initial experiments, LLC-$MK_2$ cells were used for transfection and quantitation of virus, since we have determined the permissiveness for replication and plaque formation of the parental strains of YF and JE. Table 2 illustrates typical results of transfection experiments using Lipofectin (GIBCO/BRL) as a transfection vehicle. Vero cell lines have also been used routinely for preparation of infectious virus stocks, characterization of labeled proteins, and neutralization tests.

Amplification products from Vero cells were sent to the FDA (CBER) for preparation of the RMS in diploid, Fetal Rhesus lung cells. Fetal rhesus lung cells were received from the ATCC as cultured cells and were infected with YF/JE SA14-14-2 (clone A-1) at an MOI of 1.0. After 1 hour of incubation at 37° C., the inoculum was aspirated and replaced with 50 ml of EMEM, containing 2% FBS. Virus was harvested 78 hours later, aliquoted into 1 ml vials (a total of 200 vials) and frozen at −70° C. Virus titers were determined in Vero, LLC MK2, and CV-1 cells using a standard plaque assay. Titers (pfu/ml) were $1.6\times10^6$ in Vero cells, $1.25\times10^6$ in LLC MK2 cells, and $1.35\times10^5$ in CV-1 cells.

1.6 Nucleotide Sequencing of Chimeric cDNA Templates

Plasmids containing the chimeric YF/JE cDNA were subjected to sequence analysis of the JE portion of the clones to identify the correct sequences of the SA14-14-2 and Nakayama envelope protein. The nucleotide sequence differences between these constructs in comparison to the reported sequences (McAda et al., supra) are shown in Table 1.

Five amino acid differences at positions 107, 138, 176, 264, and 279 separate the virulent from the attenuated strains of JE virus. Amino acid differences map to three subregions of Domains I and II of the flavivirus E protein model (Rey et al., Nature 375:291–298, 1995). These include the putative fusion peptide (position 107), the hinge cluster (positions 138, 279), the exposed surface of Domain I (positions 176 and 177), and the alpha-helix located in the dimerization Domain II (position 264). Changes at position 107, 138, 176, and 279 were selected early in the passage history, resulting in attenuation of JE SA14-14-2, and remained stable genetic differences from the $SA_{14}$-14-2 parent (Ni et al., J. Gen. Virol. 75:1505–1510, 1994), showing that one or more of these mutations are critical for the attenuation phenotype. The changes at positions 177 and 264 occurred during subsequent passage, and appear to be genetically unstable between two SA14-14-2 virus passages in PHK and PDK cells, showing that this mutation is less critical for attenuation.

The nucleotide sequence of the E protein coding region of the RMS was determined to assess potential sequence variability resulting from viral passage. Total RNA was isolated from RMS-infected Vero cells, reversed transcribed, and PCR amplified to obtain sequencing templates. Several primers specific for SA14-14-2 virus were used in individual sequencing reactions and standard protocols for cycle sequencing were performed.

Sequence data revealed two single nucleotide mutations in the RMS E protein, when compared to the published SA14-14-2 JE strain sequence data. The first mutation is silent, and maps to amino acid position 4 (CTT to CTG); the second is at amino acid position 243 (AAA to GAA) and introduces a change from lysine to glutamic acid. Both mutations identified are present in the sequence of the JE wild type strains Nakayama, SA14 (parent of SA14-14-2), and JaOArS982 (Sumiyoshi et al., J. Infect. Dis. 171:1144–1151, 1995); thus, they are unlikely to contribute to virulence phenotype. We conclude that in vitro passage in FRhL cells to obtain the RMS did not introduce unwanted mutations in the E protein.

1.7 Structural and Biological Characterization of Chimeric YF/JE Viruses

The genomic structure of chimeric YF/JE viruses recovered from transfection experiments was verified by RT/PCR-based analysis of viral RNA harvested from infected cell monolayers. These experiments were performed to eliminate the possibility that virus stocks were contaminated during transfection procedures. For these experiments, first-pass virus was used to initiate a cycle of infection, to eliminate any possible artifacts generated by the presence of residual transfected viral RNA. Total RNA extracts of cells infected with either the YF/JE (prM-E)-SA14-14-2 or YF/JE (prM-E)-Nakayama chimera were subjected to RT/PCR using YF and JE-specific primers that allowed recovery of the entire structural region as two PCR products of approximately 1 kilobase in size. These products were then analyzed by restriction enzyme digestion using the predicted sites within the JE SA14-14-2 and Nakayama sequences that allow differentiation of these viruses. Using this approach, the viral RNA was demonstrated to be chimeric and the recovered viruses were verified to have the appropriate restriction sites. The actual C-prM boundary was then verified to be intact at the sequence level by cycle sequence analysis across the chimeric YF/JE C-prM junction.

The presence of the JE envelope protein in the two chimeras was verified by both immunoprecipitation with JE-specific antisera and by plaque reduction neutralization testing using YF and JE-specific antisera. Immunoprecipitation of $^{35}$S-labeled extracts of LLC-$MK_2$ cells infected with the chimeras using a monoclonal antibody to the JE envelope protein showed that the JE envelope protein could be recovered as a 55 kDa protein, while the same antisera failed to immunoprecipitate a protein from YF-infected cells. Both JE and YF hyperimmune sera demonstrated cross-reactivity for the two envelope proteins, but the size difference between the proteins (YF=53 kDa, unglycosylated; JE=55 kDa, glycosylated) could reproducibly be observed. Use of YF monoclonal antibodies was not satisfactory under the immunoprecipitation conditions, thus, the specificity was dependent on the JE monoclonal antibodies in this analysis.

Plaque reduction neutralization testing (PRNT) was performed on the chimeric viruses and the YF and JE SA14-14-2 viruses using YF and JE-specific hyperimmune ascitic fluid (ATCC) and YF-specific purified IgG (monoclonal antibody 2E10). Significant differences in the 50% plaque reduction titer of these antisera were observed for the chimeras when compared to the control viruses in these experiments (Table 3). The YF/JE SA14-14-2 chimeric vaccine candidate, as well as the Nakayama chimera and SA14-14-2 viruses, were neutralized only by JE ascitic fluid, whereas YF 17) was neutralized in a specific fashion by YF ascites and the monoclonal antibody (Table 3). Thus, epitopes required for neutralization are expressed in the infectious chimeric YF/JE viruses, and are specific for the JE virus.

1.8 Growth Properties in Cell Culture

Figure 8:
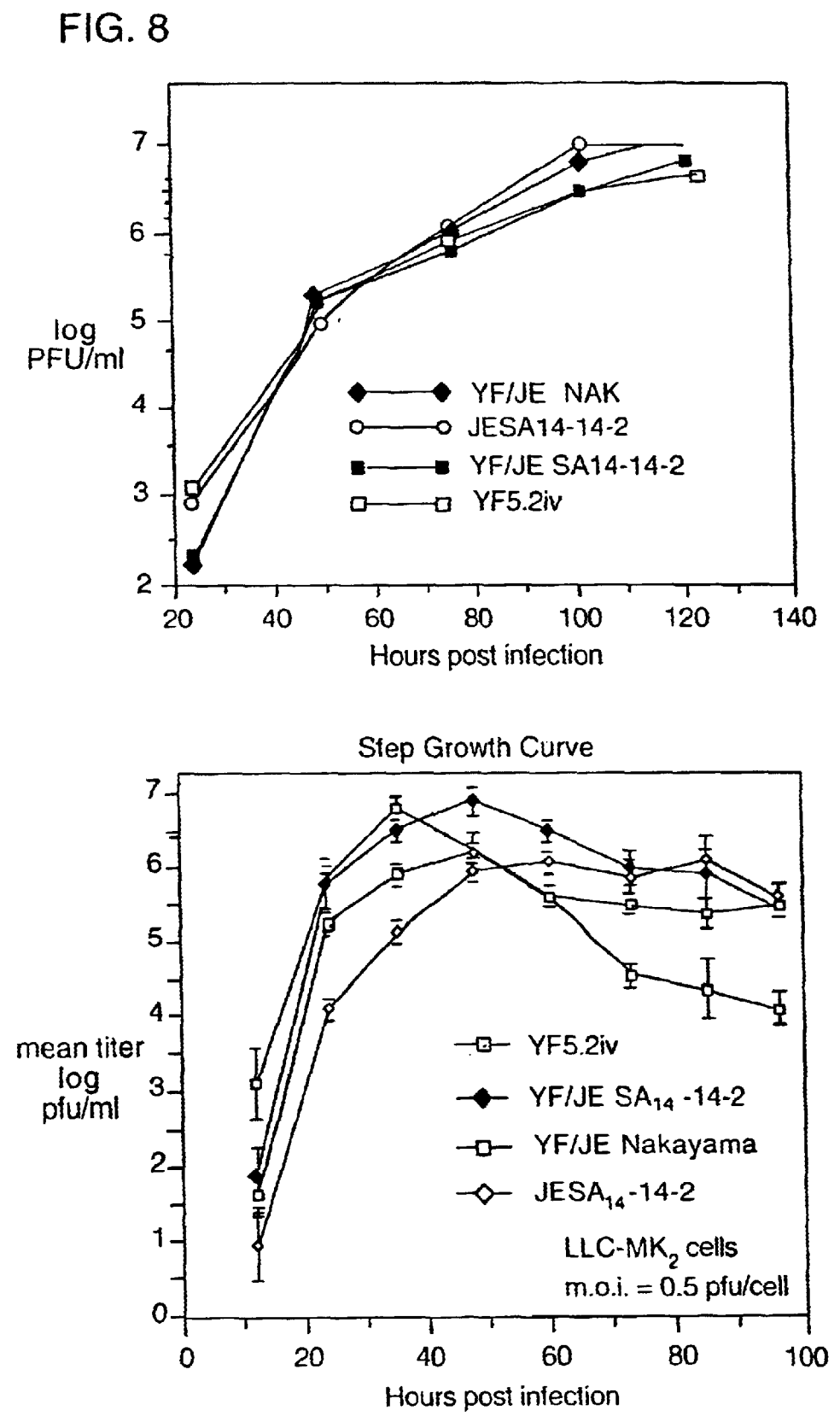

The growth capacity of the chimeras has been examined quantitatively in cell lines of both primate and mosquito origin. FIG. 8 illustrates the cumulative growth curves of the chimeras on LLC-$MK_2$ cells after low multiplicity infection (0.5 plaque-forming units/cell). In this experiment, YF5.2iv (cloned derivative) and JE SA14-14-2 (uncloned) viruses were used for comparison. Both chimeric viruses reached a maximal virus yield of approximately one log higher than either parental virus. In the case of the YF/JE $SA_{14}$-14-2 chimera, the peak of virus production occurred 12 hours later than the YF/JE Nakayama chimera (50 hours vs. 38 hours). The YF/JE Nakayama chimera exhibited considerably more cytopathic effects than the YF/JE SA14-14-2 chimera on this cell line.

A similar experiment was carried out in C6/36 cells after low multiplicity infection (0.5 plaque-forming units/cell). FIG. 8 also illustrates the growth kinetics of the viruses in this invertebrate cell line. Similar virus yields were obtained at all points used for virus harvest in this experiment, further substantiating the notion that chimeric viruses are not impaired in replication efficiency.

Figure 9:
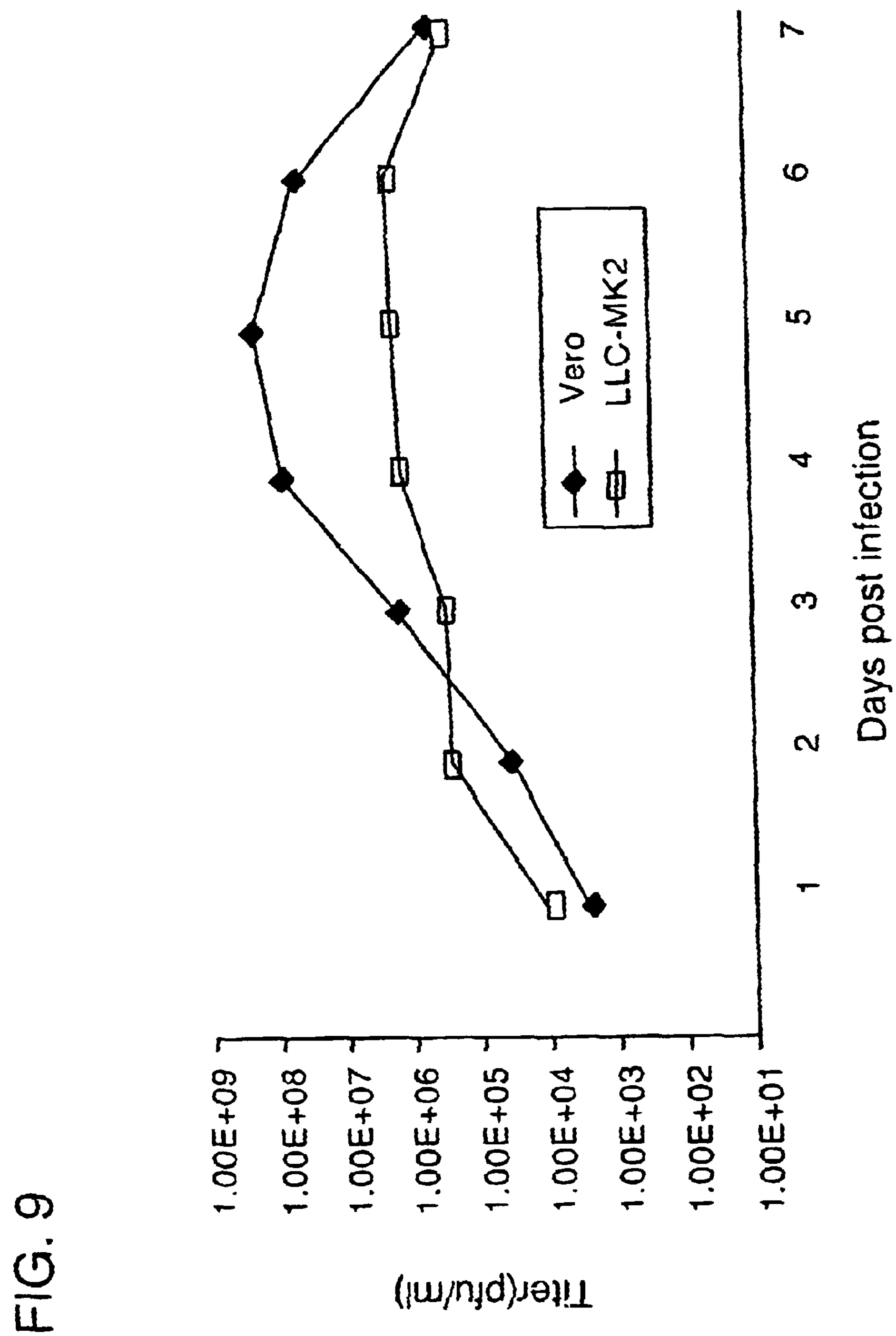
FIG. 9 is a growth curve of RMS (Research Master Seed, YF/JE SA14-14-2) in Vero and LLC-MK2 cells.

Additional experiments showing the growth properties of RMS are shown in FIG. 9. Briefly, Vero cells were grown in EMEM, 1% L-Glutamine, 1% non-essential amino acid, and 10% FBS buffered with sodium bicarbonate. LLC-MK2 cells were purchased from the ATCC (CLL-7.1, passage 12) and were grown in the same medium as Vero cells. Cells were inoculated with the RMS virus at an MOI of 0.1. Supernatant fluid was sampled at 24 hour intervals for 7 days and frozen at −70° C. for subsequent plaque assay. Plaque assays were performed in 6-well plates. The RMS reached more than 8 $\log_{10}$ pfu/ml in 5 days. In LLC-MK2 cells, the RMS grew slower and peaked (6 $\log_{10}$ pfu/ml) at about 6 days.

1.9 Comparison of Growth Kinetics of the RMS (YF/JE SA14-14-2) With YF 17D Vaccine in MRC-5 Cells An experiment was performed to assess the ability of the vaccine candidate to propagate in a cell line acceptable for human vaccines. Commercial Yellow Fever 17D vaccine (YF-VAX® (Yellow Fever 17D Vaccine) was obtained from Connaught Laboratories, Swiftwater, PA. MRC-5 (diploid human embryonal lung cells) were purchased from ATCC (171-CCL, Batch#: F-14308, passage 18) and grown in EMEM, 2 mM L-Gln, Earle's BSS adjusted to contain 1.5 g/L sodium bicarbonate, 0.1 mM non-essential amino acids, and 10% FBS.

Figure 10:
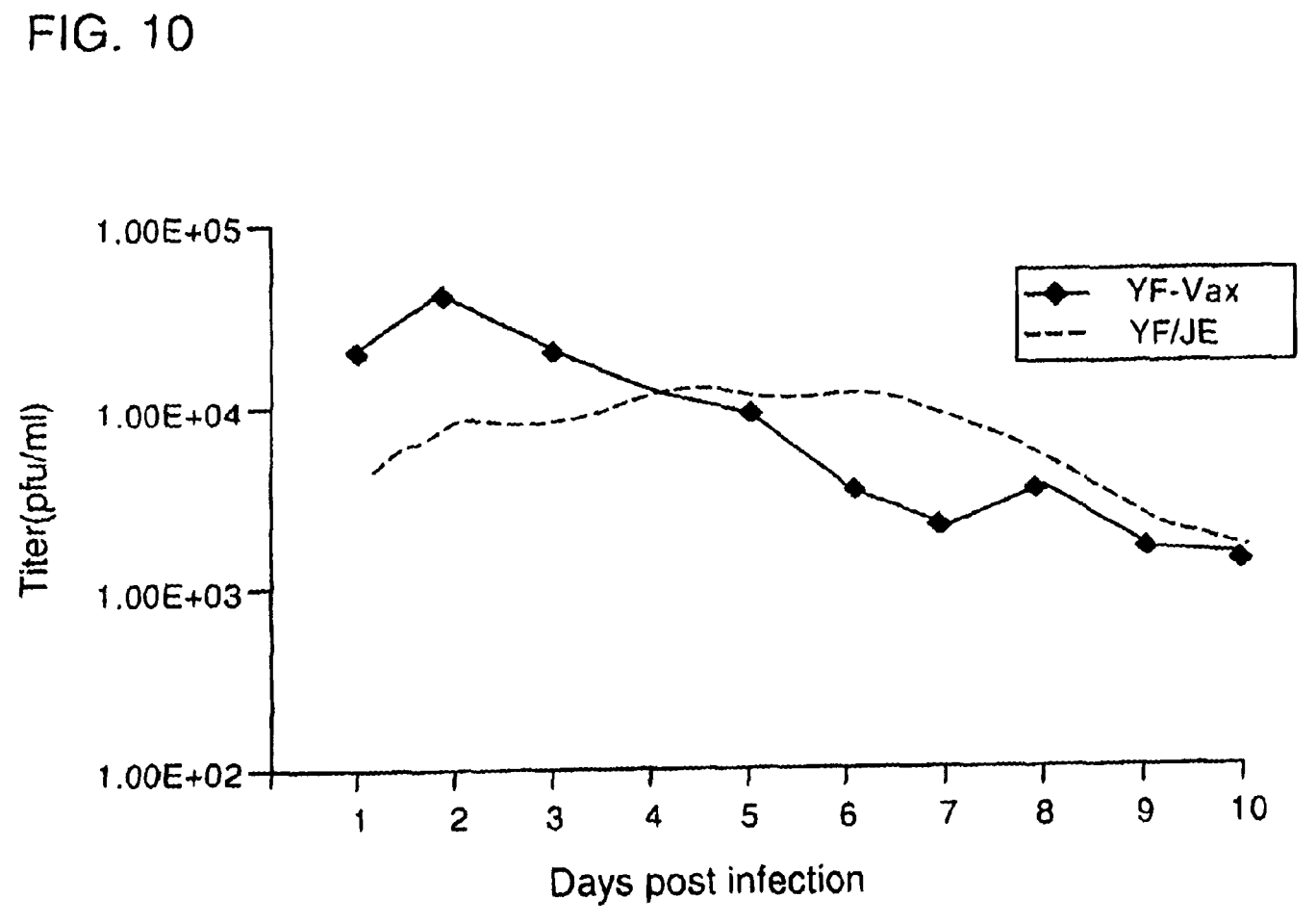

To compare growth kinetics of RMS (sequence appendices 2 and 3; Research Master Seed, YF/JE SA14-14-2; nucleotide sequence of ORF; C: nucleotides 119–421; Pr-M: nucleotides 422–982; E: nucleotides 983–2482; and Non-structural proteins: 2483–10381); (amino acid sequence of ORF; C: amino acids 1–101; Pr-M: amino acids 102–288; E: amino acids 289–788; and Non-structural proteins: amino acids 789–3421); (nucleotide sequence of RMS; the coding sequence is from nucleotide 119 to nucleotide 10381)) with YF-VAX® (Yellow Fever 17D Vaccine), cells were grown to 90% confluency and infected with RMS or YF-VAX® (Yellow Fever 17D Vaccine) at an MOI of 0.1 pfu. Since MRC-5 cells generally grow slowly, these cells were kept for 10 days post inoculation. Samples were frozen daily for 7–10 days and infectivity determined by plaque assay in Vero cells. YF-VAX® (Yellow Fever 17D Vaccine) and the YF/JE chimera grew to modest titers in MRC-5 cells (FIG. 10). The peak titer was ~4.7 $\log_{10}$ pfu for YF-VAX® (Yellow Fever 17D Vaccine) achieved on the second day and was slightly lower, 4.5 $\log_{10}$ pfu, for the RMS after 6 days.

1.10 Growth Curve of YF/JE SA14-14-2 in FRhL Cells With and Without IFN-inhibitors Fetal rhesus lung cells were obtained from the ATCC and propagated as described for MRC-5 cells. Growth kinetics of the RMS were determined with and without interferon inhibitors.

Double-stranded RNA appears to be the molecular species most likely to induce interferon (IFN) in many virus infected cells. Induction of interferon apparently plays a significant role in the cellular defense against viral infection. To escape cellular destruction, many viruses have developed strategies to down-regulate induction of interferon-dependent activities. Sindbis virus and vesicular stomatitis virus have been shown to be potent IFN inducers. Using chick embryo cells, mouse L cells, and different viral inducers of IFN, it was shown that 2-aminopurine (2AP) and indomethacin (IM) efficiently and reversibly inhibit IFN action (Sekellick et al., J. IFN Res. 5:651, 1985; Marcus et al., J. Gen. Virol. 69:1637, 1988).

Figure 11A:
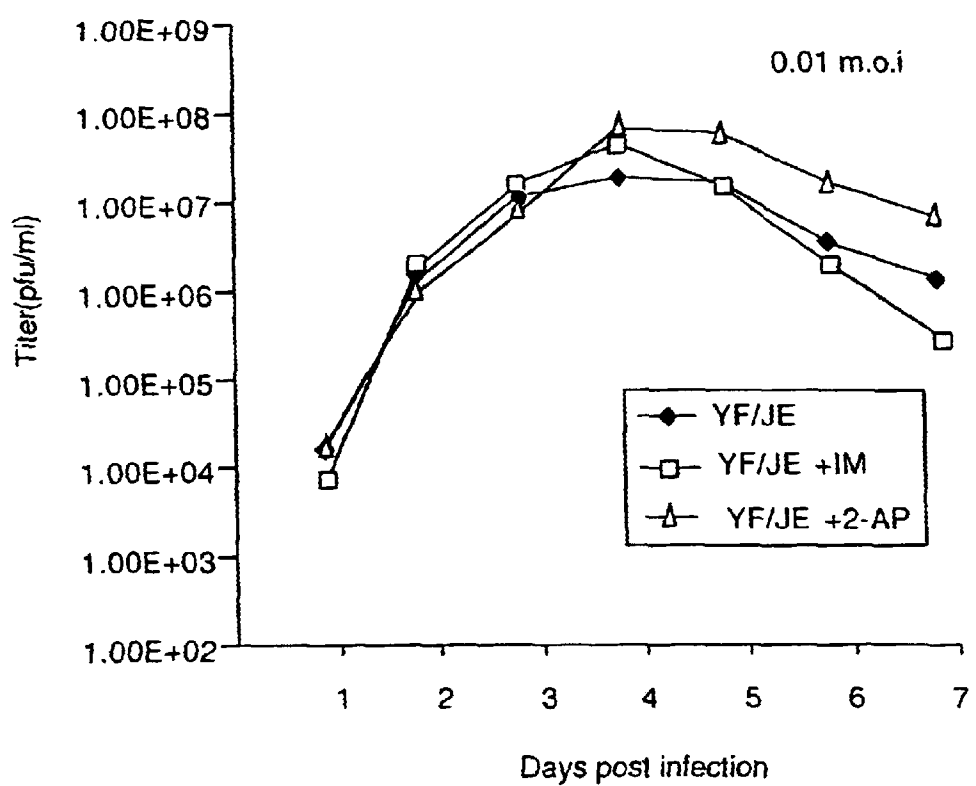
FIG. 11A is a graph showing the effects of indomethacin (IM) or 2-aminopurine (2-AP) on growth kinetics of YF/JE SA14-14-2 (0.01 MOI) in FRhL cells.
Figure 11B:
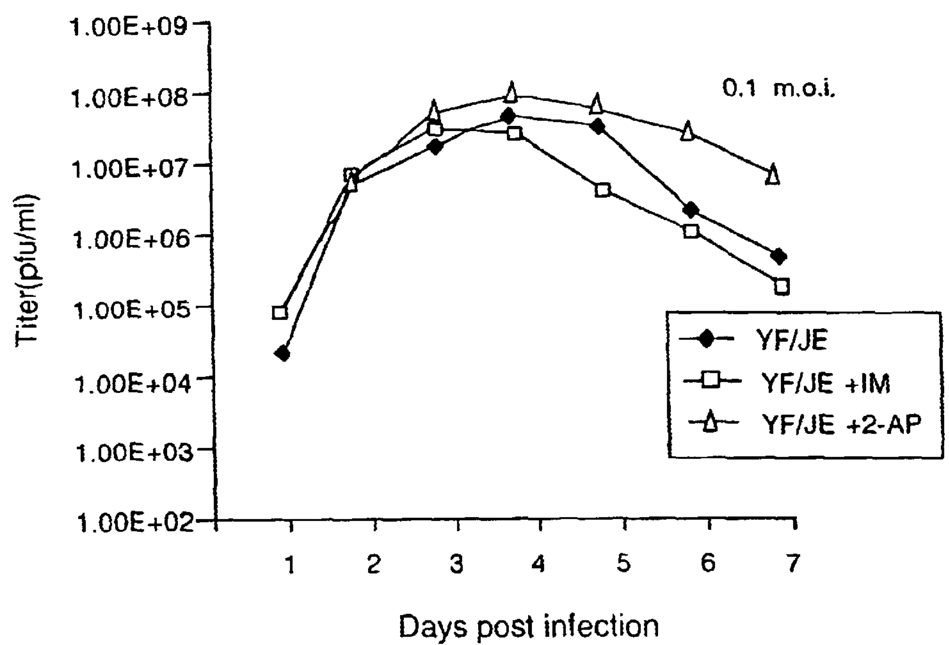
FIG. 11B is a graph showing the effects of indomethacin (IM) or 2-aminopurine (2-AP) on growth kinetics of YF/JE SA14-14-2 (0.1 MOI) in FRhL cells.

To test whether inhibition of IFN (if present) in FRhL cells will increase the virus yield, we added 2AP at a concentration of 10 mM or IM at a concentration of 10 mg/ml to the FRhL cells at the time of infection with 0.1 or 0.01 MOI of RMS. Samples were taken daily and frozen for determination of virus infectivity by plaque assay. As shown in FIG. 11A, virus titers peaked on day 4 in the presence or absence of inhibitors. When cells were infected at 0.01 MOI (FIG. 11A), virus titer reached $2.65\times10^7$ pfu/ml on day 4 in the absence of inhibitors. In cells infected in the presence of IM, virus titer was increased about 2-fold, to $5.95\times10^7$ pfu/ml on day 4. This increase was more dramatic (4-fold) when 2AP was used ($9.7\times10^7$ pfu/ml). Addition of IM did not increase virus yield when cells were infected at a higher MOI (0.1). A titer of $5.42\times10^7$ was reached without inhibitor and $3.45\times10^7$ was achieved in the presence of IM. Addition of 2AP increased virus yields to $1.1\times10^8$ pfu/ml by day 4 and only 1 $\log_{10}$ pfu was lost in the following 3 days ($9.5\times10^6$ pfu/ml on day 7) (FIG. 11B). We conclude from this experiment that the YF/JE SA14-14-2 vaccine candidate replicates to titers of 7.5 $\log_{10}$/ml in an acceptable cell substrate. The addition of interferon inhibitors can result in a modest increase in yields, but is not a requirement for vaccine production.

1.11 Neurovirulence Testing in Normal Adult Mice

The virulence properties of the YF/JE SA14-14-2 chimera was analyzed in young adult mice by intracerebral inoculation. Groups of 10 mice (4 week old male and female ICR mice, 5 each per group) were inoculated with 10,000 plaque-forming units of the YF/JE SA14-14-2 chimera, YF 17D 5.2iv, or the Chinese vaccine strain JE SA14-14-2 and observed daily for 3 weeks. The results of these experiments are illustrated in FIG. 12. Mice receiving the YF5.2iv parent succumbed by approximately one week post-inoculation. No mortality or illness was observed among mice receiving either the JE SA14-14-2 parent or the chimera. The inocula used for the experiments were titered at the time of injection and a subgroup of the surviving mice were tested for the presence of neutralizing antibodies to confirm that infection had taken place. Among those tested, titers against the JE SA14-14-2 virus were similar for animals receiving either this strain or the chimera.

The results of additional experiments investigating the neurovirulence of the YF/JE SA14-14-2 chimera in mice are illustrated in Table 4. In these experiments, all of the mice inoculated with YF5.2iv died within 7–8 days. In contrast, none of the mice inoculated with YF/JE SA14-14-2 died during two weeks of post-inoculation observation.

Figure 13:
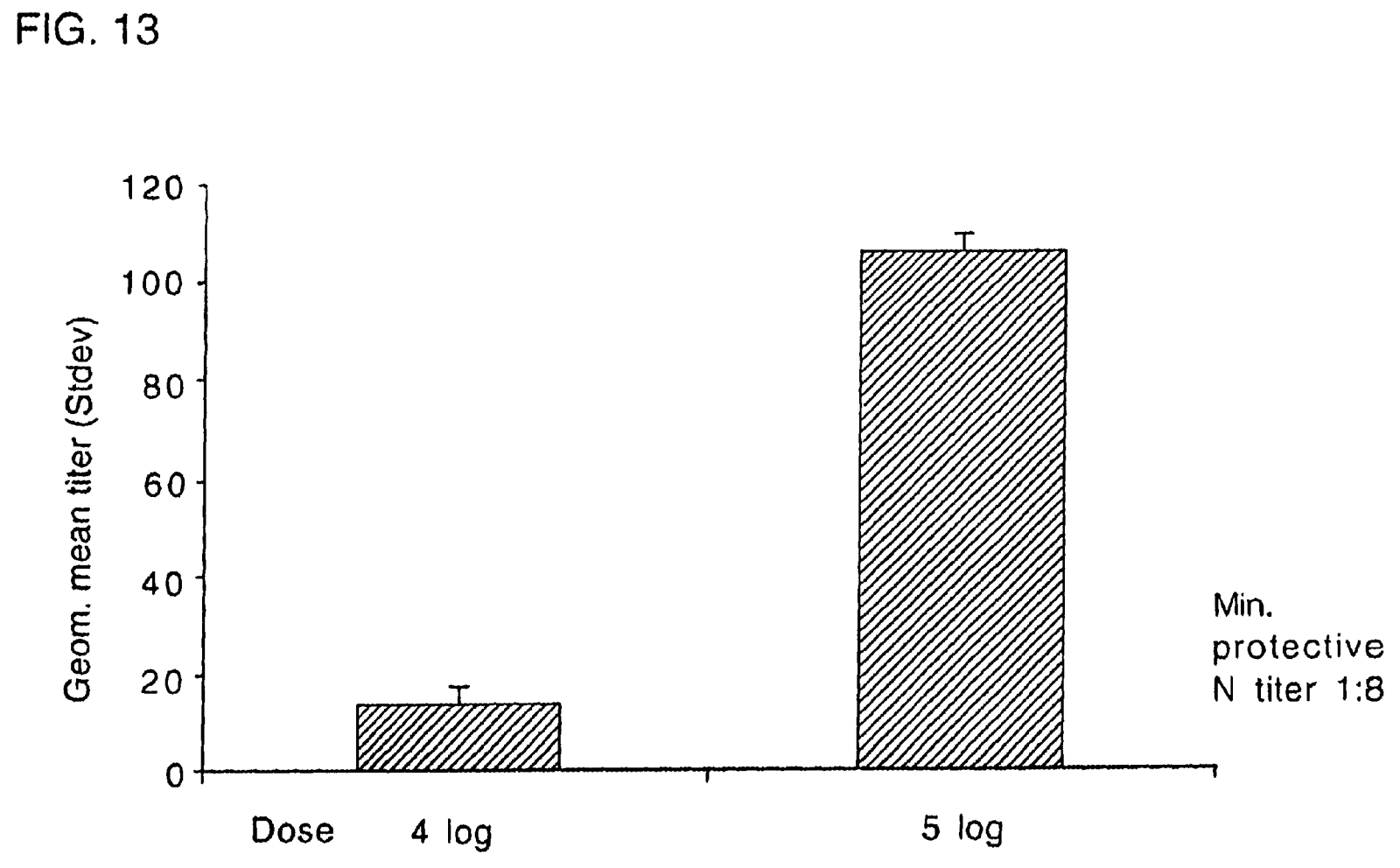

The results of experiments investigating the neuroinvasiveness and pathogenesis of YF/JE chimeras are illustrated in Table 5. In these experiments, the chimeric viruses were inoculated into 3 week old mice at doses varying between 10,000 and 1 million plaque-forming units via the intraperitoneal route. None of the mice inoculated with YF/JE Nakayama or YF/JE SA14-14-2 died during three weeks of post-inoculation observation, indicating that the virus was incapable of causing illness after peripheral inoculation. Mice inoculated with YF/JE SA14-14-2 developed neutralizing antibodies against JE virus (FIG. 13).

In additional experiments testing the neurovirulence phenotype and immunogenicity of the RMS, 4-week old ICR mice (n=5) were inoculated by the i.c. route with 0.03 ml of graded doses of the RMS or YF-VAX® (Yellow Fever 17D Vaccine) (Table 6). Control mice received only diluent medium by this route. Mice were observed daily and mortality rates were calculated.

Figures 14A, 14B:
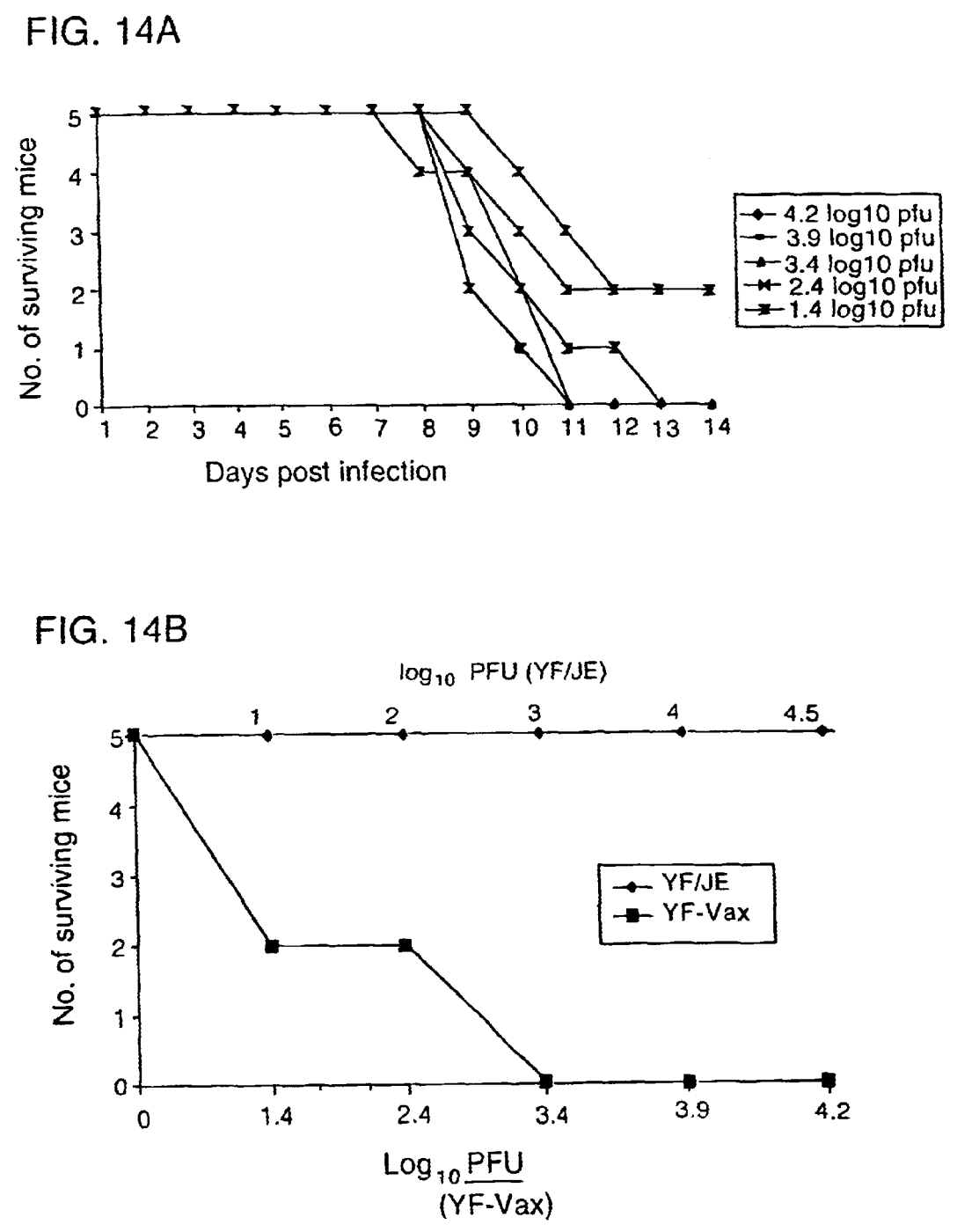

Mice inoculated with YF-VAX® (Yellow Fever 17D Vaccine) started to die on day 7 (FIG. 14A). The $icLD_{50}$ of unpassaged YF-VAX® (Yellow Fever 17D Vaccine), calculated by the method of Reed and Muench, was 1.62 $\log_{10}$ and the average survival time (AST) at the highest dose (4.2 $\log_{10}$ pfu) was 8.8 days. In contrast, all mice receiving the RMS survived challenge at all doses (FIG. 14B), indicating that the virus is not neurovirulent for mice. None of the mice inoculated with YF-VAX® (Yellow Fever 17D Vaccine) or the RMS by the peripheral (subcutaneous) route (as shown in Table 6) showed signs of illness or death. Thus, as expected, yellow fever 17D virus was not neuroinvasive.

1.12 Comparison of Immunogenicity of YF/JE RMS With YF 17D Vaccine

The immunogenicity of the of the RMS was compared with that of the YF 17D vaccine in outbred ICR mice. Groups of five 4 week-old mice received graded doses of the vaccines shown in Table 6. Mice were inoculated with 100 μl of each virus dilution by the s.c. route. For comparison, two groups of mice received two weekly doses of commercial inactivated JE vaccine prepared in mouse brain tissue JE-VAX® (inactivated Japanese encephalitis virus vaccine) at 1:30 and 1:300 dilution, representing 10× and 1× the human equivalent dose based on body weight, respectively. Animals were bled 3 and 8 weeks later and neutralizing antibody titers were measured in heat-inactivated sera against homologous viruses by PRNT. End-point titers were the highest dilution of sera that reduced the number of viral plaques by 50% compared to a normal mouse serum control.

Figure 15:
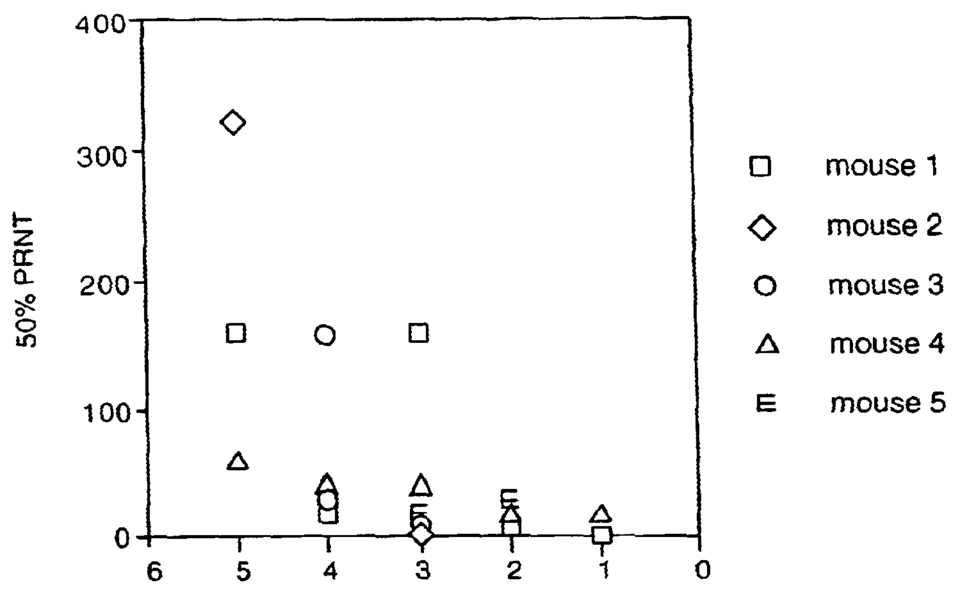
FIG. 15 is a set of graphs showing the results of PRNT analysis of neutralizing antibody titers in mice inoculated s.c. with graded doses of YF/JE vaccine. The results in the top graph are 3 weeks post immunization, and the results in the bottom graph are 8 weeks post immunization.
Figure 15:
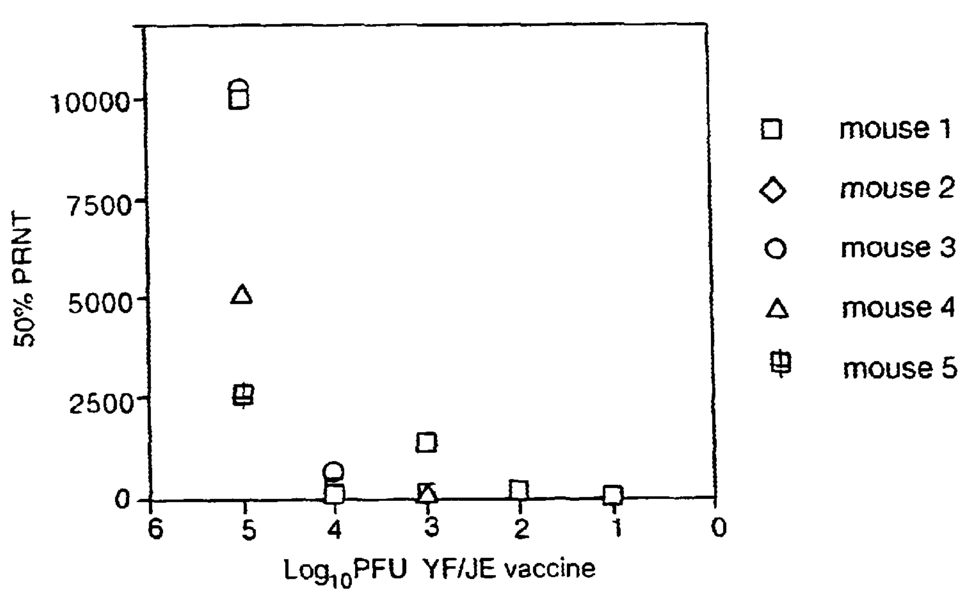

The highest N antibody titers were observed 8 weeks after immunization in mice receiving 5 $\log_{10}$ pfu of the RMS (FIG. 15 and Table 7). The geometric mean N antibody titer in these mice was 5,614. N antibody responses induced by YF/JE SA14-14-2 vaccine against JE were higher than N antibody responses against YF induced by YF 17D vaccine. Interestingly, the highest concentration of the YF 17D vaccine did not induce significant titers of neutralizing antibodies 3 or 8 weeks post immunization, but antibodies were elicited at lower doses.

Very low doses (1.4–2.4 $\log_{10}$ PFU) of YF 17D vaccine elicited an immune response in mice 8 weeks after inoculation (Table 7). This result may indicate delayed replication of the vaccine in mice receiving low virus inocula. In contrast, the YF/JE SA14-14-2 chimeric vaccine in this dose range was not immunogenic. It is likely that the chimeric vaccine is somewhat less infectious for mice than YF 17D. However, when inoculated at an infective dose, the chimera appears to elicits a higher immune response. This may be due to higher replication in, or altered tropism for, host tissues. Animals that received two doses of JE-VAX® (inactivated Japanese Encephalitis virus vaccine) did not mount a significant antibody response. Only one animal in the 1:30 dose group developed a neutralizing titer of 1:10 eight weeks after immunization. This might be due to the route (s.c.) and dilution (1:30) of the vaccine.

1.13 Protection of YF/JE SA14-14-2 RMS Immunized Mice Against Challenge With Virulent JE The YF/JE SA14-14-2 RMS and other viruses were evaluated for immunogenicity and protection in C57/BL6 mice in collaboration with Dr. Alan Barrett, Department of Pathology, University of Texas Medical Branch, Galveston. Experimental groups are shown in Table 8. Ten-fold dilutions ($10^2$–$10^5$) of each virus were inoculated by the s.c. route into groups of 8 mice. Mice were observed for 21 days, at which time surviving animals were bled from the retro-orbital sinus and serum frozen for neutralization tests. The 50% immunizing dose ($ID_{50}$) for each virus and GMT was determined (see below).

Surviving mice that received viruses by the s.c. route were challenged on day 28 by i.p. inoculation of 158 $LD_{50}$ (2,000 PFU) of JE virus (JaOArS982, IC37). Animals were observed for 21 days following challenge. Protection is expressed as the proportion of mice surviving challenge (Table 9).

As expected, YF 17D virus afforded minimal cross-protection against JE challenge. The YF/JE SA14-14-2 RMS chimera was protective at doses $\geqq 10^3$ PFU. The 50% protective dose of the chimeric vaccine was 2.32 $\log_{10}$ PFU. Animals that received 3 doses of JE-VAX® (inactivated Japanese Encephalitis virus vaccine) were solidly protected against challenge. Mice given a single dose of the SA14-14-2 vaccine were poorly protected. Wild-type Nakayama virus was lethal for a proportion of animals, in a dose-dependent fashion; survivors were poorly protected against challenge indicating that the lethal dose was close to the infecting dose for this virus.

The $YF/JE_{Nakayama}$ chimeric virus was somewhat more virulent than the Nakayama strain, in that all mice given $10^5$ of the chimera died after inoculation. This is in contrast to earlier studies in outbred mice, in which this virus was not neuroinvasive, confirming the increased susceptibility of C57/BL6 mice to peripheral challenge with JE viruses. Survivors were fully protected against challenge, showing that the infection established by the chimeric virus was more active (immunogenic) than infection by Nakayama virus without the YF replication background. These results show that the combination of viral envelope determinants of a neurovirulent strain (Nakayama) with a replication-efficient virus (YF 17D) can enhance virulence of the recombinant, emphasizing the need for genetic stability of the mutations conferring attenuation in the $YF/JE_{Nakayama}$ chimera.

1.14 Serological Response

Sera from mice in groups shown in Table 8 were tested 21 days after immunization for neutralizing antibodies. N tests were performed as follows. Six-well plates were seeded with Vero cells at a density of $10^6$ cells/well in MEM alpha containing 10% FBS, 1% nonessential amino acids, buffered with sodium bicarbonate. One hundred $\mu$l of each test serum (inactivated at 60° C. for 30 minutes) diluted two-fold was mixed with an equal volume of virus containing 200–300 PFU. The virus-serum mixtures were incubated at 4° C. overnight and 100 $\mu$l added to each well after removal of growth medium. The plates were overlaid after 1 hour incubation at 37° C. with 0.6% agarose containing 3% fetal calf serum, 1% L-glutamine, 1% HEPES, and 1% pen-strep-amphotericin mixed 1:1 with 2×M199. After 4 days of incubation at 37° C., 5% $CO_2$, a second overlay containing 3% Neutral red was added. After appearance of plaques, the monolayer was fixed with 1% formaldehyde and stained with crystal violet. The plaque reduction titer is determined as the highest dilution of serum inhibiting 50% of plaques compared with the diluent-virus control.

Figure 16:
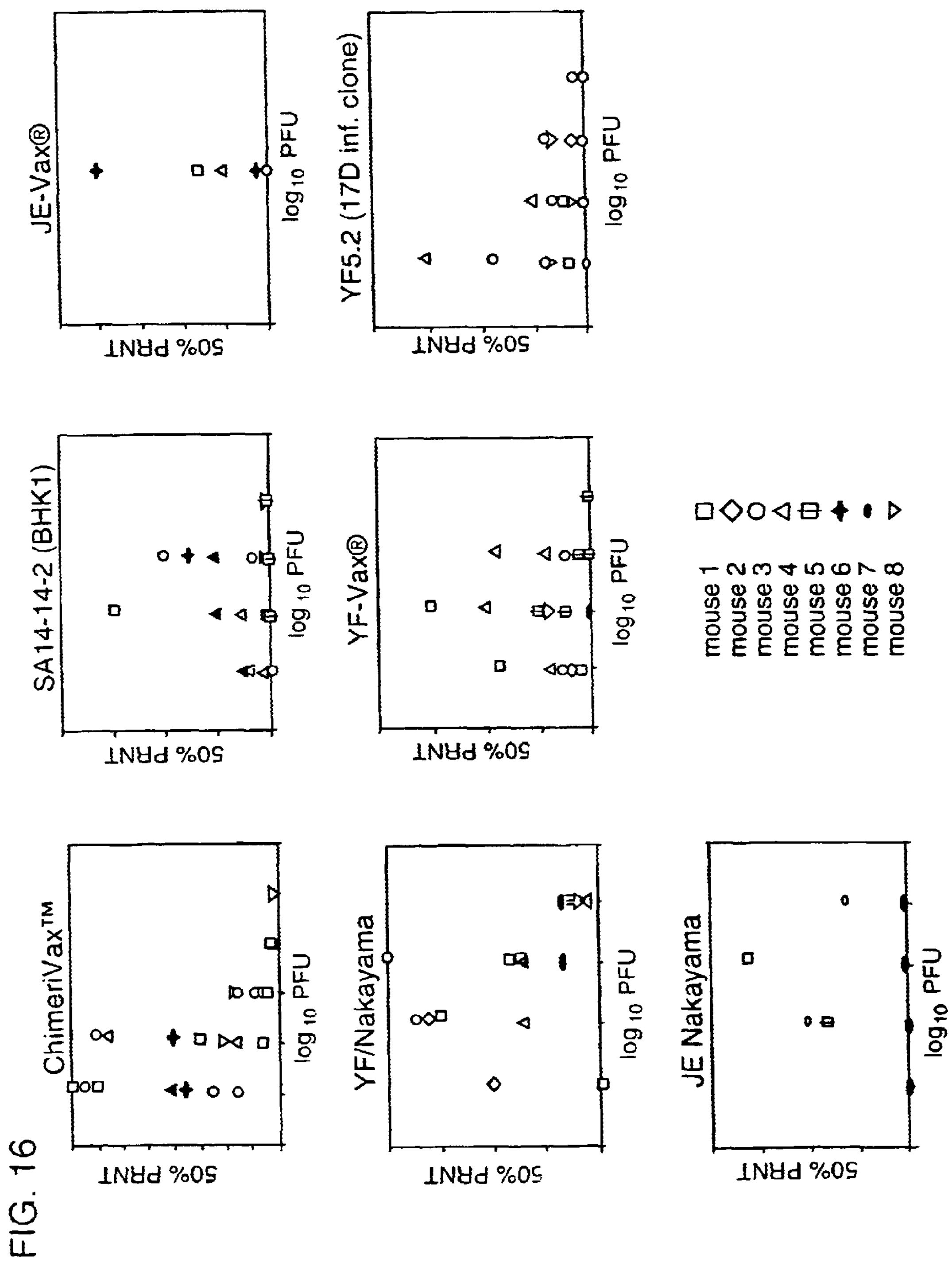
FIG. 16 is a series of graphs showing the serological responses of mice immunized with a single dose of the live viruses indicated in the figure.

Results are shown in Table 10 and FIG. 16. NT antibody responses in mice immunized with the YF/JE SA14-14-2 chimera showed a dose response and good correlation with protection. At doses of 4–5 logs, the chimeric vaccine elicited higher N antibody responses against JE than either SA14-14-2 virus or wild-type Nakayama virus. Responses were superior to those elicited by YF-VAX® (Yellow Fever 17D Vaccine) against YF 17D virus. No prozone effect was observed in animals receiving the chimera or infectious-clone derived YF 5.2iv; responses at the highest vaccine dose (5 logs) were higher than at the next lower dose (4 logs). In contrast, mice that received SA14-14-2, Nakayama, and YF-VAX® (Yellow Fever 17D Vaccine) at the highest dose responded less well than animals inoculated with diluted virus.

1.15 Safety and Immunogenicity of CHIMERIVAX™ (Chimeric Flavivirus Vaccine) in Monkeys The safety of RMS was tested in monkeys, essentially as described in WHO Biological Standards for YF 17D vaccine with minor modifications (see below). Two groups (N=3) of rhesus monkeys were bled and shown to be free from HI antibodies to YF, JE, and SLE. Group 1 received undiluted CHIMERIVAX™ (chimeric flavivirus vaccine) (Vero-passage 2) by the I.C. route (frontal lobe). Group 2 (N=3) received 0.25 ml of 1:10 diluted commercial YF 17D vaccine (YF-VAX® (Yellow Fever 17D Vaccine) by the same route. The virus inocula were frozen, back titrated, and shown to contain 7.0 and 5.0 $\log_{10}$ pfu/0.25 ml of YF/JE SA14-14-2 and YF-VAX® (Yellow Fever 17D Vaccine), respectively.

Monkeys were observed daily for clinical signs and scored as in WHO standards. Sera were collected daily for 7 days after inoculations and tested for viremia by plaque assay in Vero cells. Blood collected 2 and 4 weeks post inoculation and tested for NT antibodies to the homologous viruses. None of the monkeys showed sign of illness. Monkeys were euthanized on Day 30, and brains and spinal cords were examined for neuropathology as described in the WHO standards. A sample of the brain and spinal cord from each animal was collected and stored frozen for virus isolation attempts and immunocytochemistry experiments.

Figure 17:
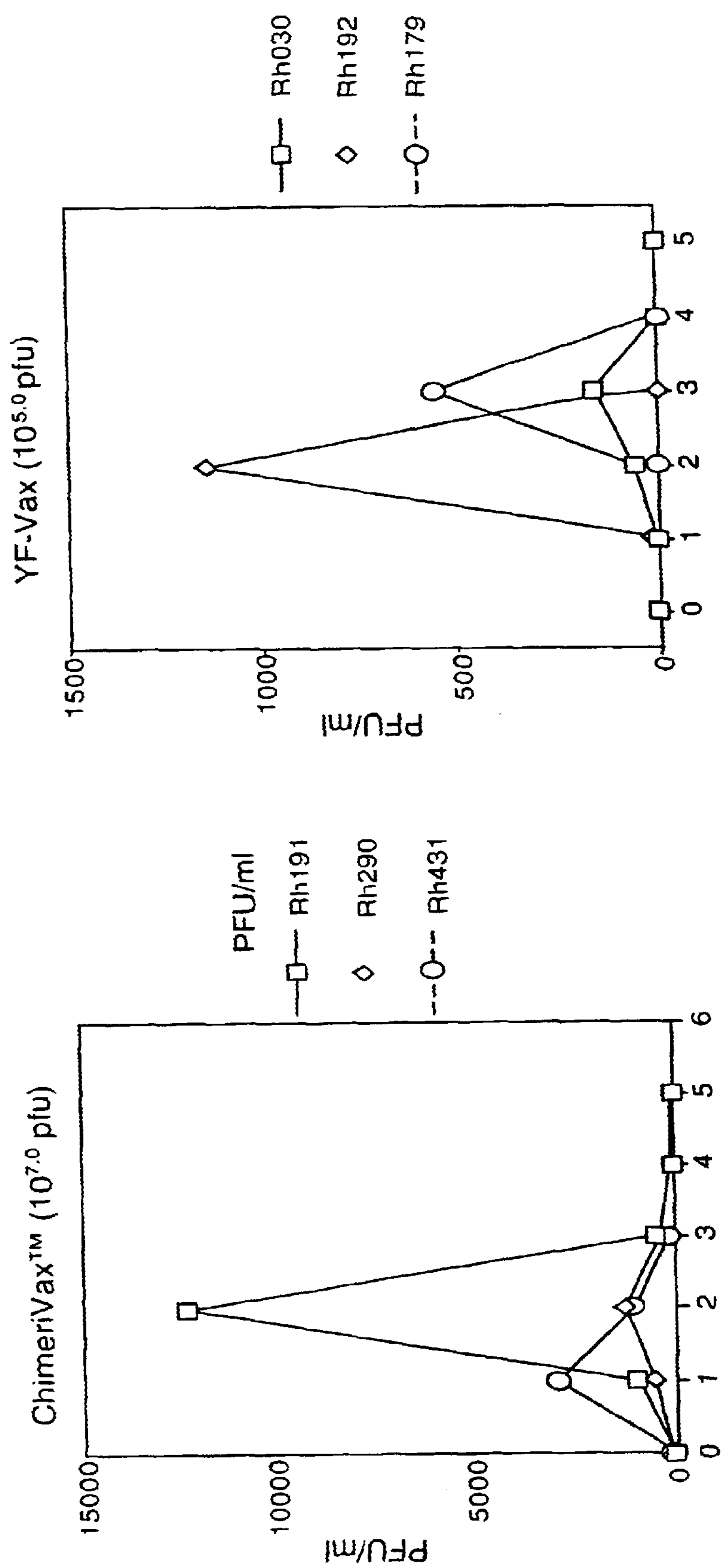
FIG. 17 is a set of graphs showing viremia and GMT of viremia in 3 rhesus monkeys inoculated with CHIMERIVAX™ (chimeric flavivirus vaccine) or YF-Vax® (Yellow Fever 17D Vaccine) by the i.c. route.

As shown in FIG. 17, a low level viremia was detected in all animals in both groups, and lasted for 2–3 days for the RMS and 1–2 days for YF-VAX® (Yellow Fever 17D Vaccine). All viruses were cleared from the blood by Day 4. According to the WHO standards, monkeys receiving 5,000–50,000 (3.7–4.7 $\log_{10}$) pfu should not have viremia greater than 165,000 pfu/ml (approximately 16,500 $mLD_{50}$). None of the monkeys in the experiments had viremia of more than 15,000 pfu/ml, despite receiving 6 $\log_{10}$ pfu of the RMS.

Figure 18:
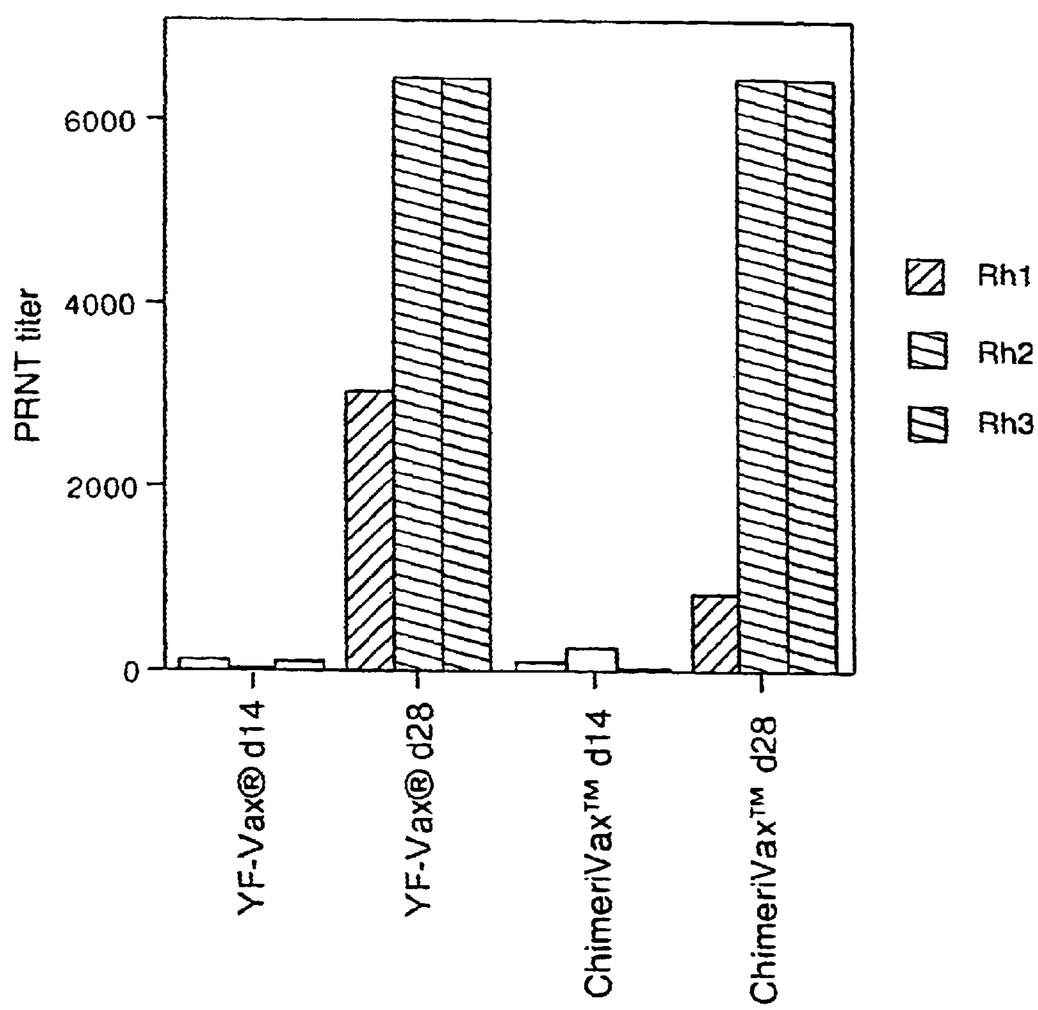
FIG. 18 is a graph showing the PRNT neutralizing antibody titers (50%) in rhesus monkeys 2 and 4 weeks post inoculation with a single dose of YF-Vax® (Yellow Fever 17D Vaccine) or CHIMERIVAX™ (chimeric flavivirus vaccine) vaccines by the i.c. route.

Neutralizing antibody titers were measured at 2 and 4 weeks post inoculation (FIG. 18). All monkeys seroconverted and had high titers of neutralizing antibodies against the inoculated viruses. The level of neutralizing antibodies in 2 of 3 monkeys in both groups exceeded a titer of 1:6,400 (the last dilution of sera tested) at 4 weeks post inoculation. The geometric mean antibody titers for CHIMERIVAX™ (chimeric flavivirus vaccine) were 75 and 3,200 after 2 and 4 weeks respectively and were 66 and 4971 for the YF-VAX® (Yellow Fever 17D Vaccine) for the same time points (Table 11).

Histopathological examination of coded specimens of brain and spinal cord were performed by an expert neuropathologist (Dr. I. Levenbook, previously CBER/FDA), according to the WHO biological standards for yellow fever vaccine. There were no unusual target areas for histopathological lesions in brains of monkeys inoculated with CHIMERIVAX™-JE (chimeric flavivirus vaccine comprising Japanese Encephalitis virus prM and E proteins. Mean lesion scores in discriminator areas were similar in monkeys inoculated with YF-VAX® (Yellow Fever 17D Vaccine) (0.08) and monkeys inoculated with a 100-fold higher dose of (CHIMERIVAX-JE™ (chimeric flavivirus vaccine comprising Japanese Encephalitis virus prM and E proteins)

(0.07). Mean lesion scores in discriminator +target areas were higher in monkeys inoculated with YF-VAX® (Yellow Fever 17D Vaccine) (0.39) than in monkeys inoculated with a 100-fold higher dose of (CHIMERIVAX-JE™ (chimeric flavivirus vaccine comprising Japanese Encephalitis virus prM and E proteins) (0.11). These preliminary results show an acceptable neurovirulence profile and immunogenicity for (CHIMERIVAX-JE™ (chimeric flavivirus vaccine comprising Japanese Encephalitis virus prM and E proteins) vaccine. A summary of the histopathology results is provided in Table 22.

1.16 Efficacy of YF/JE Chimera in Protecting Monkeys Against Intracerebral Challenge The YF/JE chimera were given to adult rhesus monkeys without pre-existing flavivirus immunity by the subcutaneous route. Three monkeys received 4.3 log pfu and three monkeys received 5.3 log pfu of YF/JE SA14-14-2 virus. All 6 monkeys developed very low level (1–2 log/ml) viremias. All animals developed neutralizing antibodies by day 15 (earliest time tested) and titers rose by day 30. Five of six-animals survived a very severe intracerebral challenge with a highly virulent JE virus (100,000 mouse LD50 were injected IC 60 days after immunization). None of 4 sham immunized monkeys survived; all died between days 8–10 after challenge. The single death in the immunized group was a pregnant female; pregnancy could have suppressed the cellular immune response to the vaccine. The results show the immunogenicity and protective efficacy of the vaccine, while validating safety with respect to low vaccine viremia. The results of these experiments are illustrated in Tables 12–15.

1.17 Genetic Stability of the RMS

The E protein of the attenuated SA14-14-2 virus used to construct the YF/JE chimera differs from its virulent parent (SA14 or Nakayama) at 6 positions: 107, 138, 176, 177, 264, and 279. Because the presence of a single residue controlling virulence would be a disadvantage for any vaccine candidate because of the potential for reversion, studies are being undertaken to determine which residue(s) are responsible for attenuation and in particular whether a single residue is responsible for the difference.

1.18 Position 138 on the E Protein

A single mutation of an acidic residue glutamic acid (E) to a basic residue, lysine (K) at position 138 on the E protein of JE virus results in attenuation (Sumyoshi et al., J. Infect. Dis. 171:1144, 1995). Experiments were carried out to determine whether the amino acid at position 138 of the JE envelope protein (K in the vaccine chimera and E in the virulent Nakayama chimera) is a critical determinant for neurovirulence in mice. Chimeric YF/JE SA14-14-2 (K 138ΔE) virus containing the single reversion of K→E at position 138 was generated from an engineered cDNA template. The presence of the substitution and the integrity of the entire E protein of the resulting virus was verified by RT/PCR sequencing of the recovered virus. A standard fixed-dose neurovirulence test of the virus was conducted in 4-week-old outbred mice by i.c. inoculation with $10^4$ pfu of virus. The YF/JE SA14-14-2 and YF/JE Nakayama chimeric viruses were used as controls. The virulence phenotype of YF/JE SA14-14-2 (K→E) was indistinguishable from that of its attenuated parent YF/JE SA14-14-2 in this assay, with no morbidity or mortality observed in the mice during the observation period (FIG. 19).

We conclude that the single mutation at position 138 to the residue found in the JE-Nakayama virus does not exert a dominant effect on the neurovirulence of the YF/JE SA14-14-2 chimera, and that one or more additional mutations are required to establish the virulent phenotype.

1.19 Other Putative Attenuation Loci

Additional experiments to address the contributions of the other 6 residues (mentioned above) using the format described here were conducted. The mutant viruses constructed by site directed mutagenesis of the YF and JE infectious clones are listed in Table 16. The E proteins of these viruses were sequenced and confirmed to contain the desired mutations. Upon inoculation into weanling mice by the I.C. route it is possible to determine those residues involved in attenuation of the vaccine.

Additional experiments to address the contributions of other residues are underway. The mutant viruses constructed to date by site-directed mutagenesis of the YF and JE infectious clones are listed in Table 16. The methodology is as described above. Results to date confirm that at least two and possibly more than 2 mutations are responsible for the attenuation phenotype of YF/JE SA14-14-2 virus (Table 23).

1.20 Stability of the RMS in Tissue Cultures: Characterization of Genetic Changes, Neurovirulence and Immunogenicity, Serial Passages In Vitro The RMS was used to inoculate a T75 flask of FRhL2 cells at an m.o.i. of 0.1. Subsequent passages were carried out in T75 flasks and harvested 3 days post-inoculation. At each passage, the culture supernatant was assumed to hold $10^7$ pfu/ml and an aliquot corresponding to an moi of approximately 0.1 was added to a fresh flask of cells. The remainder of the culture supernatant was stored at −80° C. for later characterization.

1.21 Quasispecies and DNA Sequencing

The chimeric JE vaccine is an RNA virus. Selective pressure can cause rapid changes in the nucleic acid sequences of RNA viruses. A mutant virus that invades FRhL cells more rapidly, for example, may gain a selective advantage by competing more effectively with the original vaccine virus and take over the culture. Therefore, mutant strains of the vaccine that grow better than the original vaccine may be selected by subculturing in vitro. One concern that addressed experimentally is whether such selective pressures might lead to mutant vaccine viruses with increased virulence.

In theory, molecular evolution should occur more rapidly for RNA viruses than DNA viruses because viral RNA polymerases have higher error rates than viral DNA polymerases. According to some measurements, RNA virus mutation rates approach one mutation per replication event. This is why an RNA virus can be thought of as a family of very closely related sequences (or “quasispecies”), instead of a single unchanging sequence (a “classical species”).

Two different approaches can be taken to determine the sequence of an RNA virus:

1) purify viral genomic RNA from the culture supernatant, reverse-transcribe the RNA into cDNA and sequence this cDNA. This is the approach we have taken. It yields an averaged, or consensus sequence, such that only mutations which represent a large proportion (roughly, >20%) of the viruses in the culture can be detected.

2) Alternatively, cDNA can be cloned and individual clones sequenced. This approach would reveal the quasispecies nature of the vaccine by identifying individual mutations (deviations from the consensus sequence) in some proportion of the clones.

1.22 Biological Characterization of Serially Passaged RMS

As stated above, we demonstrated experimentally that the selective pressures exerted by serial passaging of the RMS does not lead to mutant vaccine viruses with increased virulence. Here, three biological properties of Passages 10 and 18 (P10 and P18) were examined. First, neurovirulence was tested by inoculating mice i.c. with graded doses of P1 as well as P10 and P18. Second, immunogenicity was compared by inoculating mice s.c. with graded doses of the RMS, P10 and P18. Blood was drawn from these mice 30 days post-inoculation and serum neutralizing titers were determined and compared. Finally, the growth kinetics of the RMS and of P10 and P18 were compared by inoculating FRhL cells at moi's of 0.1 and 0.01 and collecting samples of culture supernatant daily. The titers in each flask were plotted as a function of time and compared.

1.23 Stability of prM and E Genes

The M and E genes of P10 and P18 were sequenced completely from base 642 to base 2454. Both sequences were identical and carried only one mutation (A→G) resulting an amino acid substitution from H to R at position 394 on the E protein. This means that selective pressures did not lead to the loss of any of the attenuating mutations of the E gene. Codon H394 (CAC) encodes a Histidine in the RMS but we have found that the second base of this codon is mutated to a G in a significant proportion of the viruses, leading to the expression of Arginine. It is important to emphasize that a mixture of A and G are observed at this position in the sequence data. The ratio of A to G (A/G) was also determined for P1, P4, and P8. Interestingly, the ratio decreases steadily from P1 to P10, but at P18 it is back to the value seen at P8. One possible explanation for this observation is that a mutant bearing the H394R mutation gradually became as abundant as the original virus but was then out-competed by a new mutant bearing other mutations not present in the M or E genes and therefore, only detected as a rebound in the A/G ratio. We are reproducing these results by doing a second passaging experiment under identical conditions. It must also be noted that duplicate samples of viral genomic RNA were isolated, reverse-transcribed, amplified, and sequenced in parallel for each passage examined. Reported results were seen in both duplicate samples, arguing against any RT-PCR artifacts obscuring the data.

These observations show that minor genetic changes (one nucleotide substitution in the entire envelope E and M genes) have occurred in the JE sequences of the chimeric vaccine upon passaging, but that selective pressures did not lead to the loss of any of the attenuating mutations of the E gene.

1.24 Neurovirulence Phenotype of Passages 10 and 18

Groups of five female ICR mice, 3 to 4 weeks-old, received 30 $\mu$l i.c. of undiluted, P1, P10, or P18, as well as 30 $\mu$l of 10-fold dilutions. None of the mice injected with P1, P10, or P18 (doses≧7 $\log_{10}$ pfu) showed any sign of illness over a five-week period. As determined by back-titration, the doses administered (pfu) were measured as shown in Table 17.

1.25 Immunogenicity of Passages 10 and 18

Groups of five female ICR mice were injected subcutaneously (s.c.) with 100 $\mu$l of undiluted virus stock of either the RMS or P10 or P18, as well as with doses of $10^5$ and $10^4$ pfu (see Table 18, results of back-titration).

1.26 Growth Kinetics of Passages 10 and 18

Monolayers (90% confluent) of FRhL cells were infected with an moi of 0.1 or 0.01 of RMS, P10, or P18. Time points were then taken daily for seven days and the titer of each time point was determined by plaque assay. Visual observation of cytopathic effects (CPE) on FRhL cells used in this growth curve experiment show that later passages of the RMS have different growth properties than the RMS itself. CPE is clearly greater for P18 and P10 than for the RMS at 4 days postinfection showing that these viruses might replicate much faster than the RMS.

Other observations also show that the growth properties of P10 and P18 differ from those of the RMS. The titers of P1, P10, and P18 are ~$2\times10^7$, $2\times10^8$, and $3\times10^8$, respectively. The relative yields of RT-PCR products suggest higher titers of P10 and P18 compared to P1. Although the PCR data are not necessarily quantitative, they are consistent with the observed titers.

These results raise the possibility that we have discovered a variant of the vaccine that is immunogenic, attenuated for mouse neurovirulence, and that grows to titers ten-fold higher than the original vaccine (RMS) in tissue culture. Such a mutant may have value for manufacturing.

Finally, the sequences of the entire genomes of the RMS and p18 were determined and found to be identical, except for the E-H394 mutation (Table 25). There are 6 nucleotide (NT) differences (NT positions are shaded) between the published YF 17D sequences and RMS shown in bold letters. Changes in positions 5461, 5641, 8212, and 8581 are silent and do not result in amino acid substitution, whereas changes in positions 4025 (ns2a) and 7319 (ns4b) result in amino acid substitutions from V to M and from E to K, respectively. Amino acid Methionine (M) at position 4025 is unique for RMS and is not found in any other YF strains, including parent Asibi virus and other yellow fever 17D strains (e.g., 204, 213, and 17DD), whereas Lysine (K) at position 7319 is found in 17D204F, 17D213, and 17DD, but not in 17D204US or Asibi strain. Since the RMS is more attenuated than YF 17D with respect to neurovirulence, and thus has better biological attributes as a human vaccine, it is possible that the amino acid differences at positions 4025 and 7319 in the nonstructural genes of the yellow fever portion of the chimeric virus contribute to attenuation. Other workers have shown that the nonstructural genes of yellow fever virus play an important role in the attenuation of neurovirulence (Monath, "Yellow Fever," in Plotkin et al., (Eds.), Vaccines, 2$^{nd}$ edition, W. B. Saunders, Philadelphia, 1998).

1.27 Experiment to Identify Possible Interference Between YF 17D and YF/JE SA14-14-2

It is well-established that yellow fever virus encodes antigenic determinants on the NS1 protein that induce non-neutralizing, complement-fixing antibodies. Passive immunization of mice with monoclonal anti-NS1 antibodies confers protection against challenge. Active immunization with purified or recombinant NS1 protects mice and monkeys against lethal challenge. The mechanism of protection is presumed to involve antibody-mediated complement-dependent cytotoxicity.

In addition to protective determinants on NS1, CTL epitopes on other nonstructural proteins, including NS3, NS2a, and possibly NS5 may be involved in protection. Thus, infection with the YF/JE chimeric virus may stimulate humoral or cellular anti-yellow fever immunity. It is possible, therefore, that use of the chimeric vaccine may interfere with subsequent immunization against YF 17D, or that prior immunization with YF 17D may interfere with seroconversion to YF/JE SA14-14-2. Against this hypothesis is a substantial body of data showing that reimmunization with YF 17D results in a boost in yellow fever N antibodies. Those data show that it should be possible to successfully immunize against JE in an individual with prior YF immunity and vice versa.

To investigate possible interference effects, the experiment shown in Table 19 was initiated. Mice are immunized with one vaccine and subsequently boosted with the heterologous vaccine. Mice are bled every 30 days and sera tested for neutralizing antibodies against heterologous and homologous viruses.

1.28 Seroconversion Rate and Antibody Titers After Primary Immunization

Three groups (n=8) of 3–4 weeks old female outbred ICR mice were immunized with a single dose (5.3 $\log_{10}$ pfu) of CHIMERIVAX-JE™ (chimeric flavivirus vaccine comprising Japanese Encephlaitis virus prM and E proteins (YF/JE SA14-14-2), three groups (n=8) were immunized with two doses of JE-VAX® (inactivated Japanese Encephalitis virus vaccine) (0.5 ml of a 1:5 dilution of reconstituted vaccine) and three groups (n=8) were immunized with a single dose of YF-VAX® (inactivated Japanese Encephalitis virus vaccine) (0.1 ml of a 1:2 dilution of reconstituted vaccine, containing 4.4 $\log_{10}$ pfu, previously determined to induce the highest immune response to YF virus). Six groups (n=4) of mice (similar age, 3–4 weeks old) were kept as controls for booster doses at 3, 6, and 12 months post primary immunization.

All mice were bled 4 and 8 weeks after primary immunization and their neutralizing antibody titers were measured against homologous viruses in a plaque assay. 21/24 (87.5%) of the animals immunized with a single dose of CHIMERIVAX-JE™ (chimeric flavivirus vaccine comprising Japanese Encephalitis virus prM and E proteins) developed anti-JE neutralizing antibodies 1 month after immunization; at 2 months, 18/24 (75%) were seropositive. Geometric mean increased somewhat between 1 and 2 months post inoculation. In contrast, only 25%–33% of the mice immunized with YF-VAX® (Yellow Fever 17D vaccine) seroconverted and antibody responses were low. These results show that YF 17D virus and chimeric viruses derived from YF 17D are restricted in their ability to replicate in the murine host; however, when the envelope of JE virus is incorporated in the chimeric virus, the ability to replicate in and immunize mice is apparently enhanced. Mice receiving two doses of JE-VAX® (inactivated Japanese Encephalitis virus vaccine) developed high neutralizing titers against parent Nakayama virus, and titers increased between 1 and 2 months post immunization.

1.29 Secondary Immunization of CHIMERIVAX-JE™ (Chimeric Flavivirus Vaccine Comprising Japanese Encephalitis Virus prM and E Proteins) and JE-VAX® (Inactivated Japanese Enceplalitis Virus Vaccine) Immunized Mice With YF-VAX® (Yellow Fever 17D Vaccine)

Three months and six months after primary immunization with CHIMERIVAX-JET™ (chimeric flavivirus vaccine comprising Japanese Encephalitis virus prM and E proteins), mice were inoculated with YF-VAX® (Yellow Fever 17D Vaccine) (1:2 dilution of a human dose containing 4.4 $\log_{10}$ pfu). Control mice not previously immunized and of identical age received CHIMERIVAX-JE™ (chimeric flavivirus vaccine comprising Japanese Encephalitis virus prM and E proteins) only or YF-VAX® (Yellow Fever 17D Vaccine) (Groups 10–13). One month later, mice were tested for presence of YF-specific neutralizing antibodies.

At the 3 month time point, none of the control mice or mice previously immunized with CHIMERIVAX-JET™ (chimeric flavivirus vaccine comprising Japanese Encephalitis virus prM and E proteins) or JE-VAX® (inactivated Japanese Encephalitis virus vaccine) seroconverted to YF-VAX® (inactivated Japanese Encephalitis virus vaccine), again confirming the poor immunogenicity of YF-VAX® (inactivated Japanese Encephalitis virus vaccine) at the dose used. However, all mice immunized with YF-VAX® (inactivated Japanese Encephalitis virus vaccine) 6 months after primary immunization with CHIMERIVAX-JE™ (chimeric flavivirus vaccine comprising Japanese Encephalitis virus prM and E proteins) and 7/8 mice previously immunized with JE-VAX® (inactivated Japanese Encephalitis virus vaccine), seroconverted after immunization with YF-VAX® (Yellow Fever 17D Vaccine) (Table 24). There was no difference in seroconversion rate or GMT in mice with and without prior immunization with either JE vaccine.

1.30 Secondary Immunization of YF-VAX® (Yellow Fever 17D Vaccine) Immunized Mice With CHIMERIVAX-JE™ (Chimeric Flavivirus Vaccine Comprising Japanese Encephalitis Virus prM and E Proteins)

All mice previously immunized with YF-VAX® (Yellow Fever 17D Vaccine) and reimmunized with CHIMERIVAX-JE™ (chimeric flavivirus vaccine comprising Japanese Encephalitis virus prM and E proteins) 3 months later developed neutralizing antibodies to JE (group 7, Table 10). None of the controls seroconverted. Five of 6 mice (83%) previously immunized to YF-VAX® (Yellow Fever 17D Vaccine) and reimmunized with CHIMERIVAX-JE™ (chimeric flavivirus vaccine comprising Japanese Encephalitis virus prM and E proteins) 6 months later seroconverted to JE (group 8, Table 10, as did all controls (group 13)), and the GMTs were similar across these groups.

There was no evidence for cross-protection between YF and JE viruses or limitation of antibody response to sequential vaccination with these viruses. Yellow fever 17D vaccine elicits a poor antibody response in the mouse; while this limited interpretation of the data somewhat, it provided a sensitive test of any restriction in replication and immunogenicity of YF 17D virus in mice previously immunized with CHIMERIVAX-JE™ (chimeric flavivirus vaccine comprising Japanese Encephalitis virus prM and E proteins). The fact that all mice immunized with CHIMERIVAX-JE™ (chimeric flavivirus vaccine comprising Japanese Encephalitis virus prM and E proteins) responded 6 months later to immunization with YF-VAX® (Yellow Fever 17D Vaccine) and that the GMT and range of neutralizing antibody titers were similar to controls suggests that the chimeric vaccine imposed no significant barrier to yellow fever immunization.

2.0 Construction of cDNA Templates for Generation of Yellow Fever/Dengue (YF/DEN) Chimeric Viruses Derivation of chimeric Yellow Fever/Dengue (YF/DEN) viruses is described as follows, which, in principle, is carried out the same as construction of the YF/JE chimeras described above. Other flavivirus chimeras can be engineered with a similar strategy, using natural or engineered restriction sites and, for example, oligonucleotide primers as shown in Table 20.

2.1 Construction of YF/DEN Chimeric Virus

Although several molecular clones for dengue viruses have been developed, problems have commonly been encountered with stability of viral cDNA in plasmid systems, and with the efficiency of replication of the recovered virus. We chose to use a clone of DEN-2 developed by Dr. Peter Wright, Dept. of Microbiology, Monash University, Clayton, Australia, because this system is relatively efficient for regenerating virus and employs a two-plasmid system similar to our own methodology. (See Table 21 for a comparison of the sequences of Dengue-2 and YF/Den-$2_{218}$ viruses; YF/Den-$2_{218}$ contains the nucleotide and amino acid sequences of PUO-218. The NGC and PR-159 strains, which are also listed in Table 21, are other wild strains of dengue that differ from PUO-218 and can be used in the chimeras of the invention.) The complete sequence of this DEN-2 clone is available and facilitated the construction of chimeric YF/DEN templates because only a few modifications of the YF clone were required. The relevant steps are outlined as follows.

Figure 20:
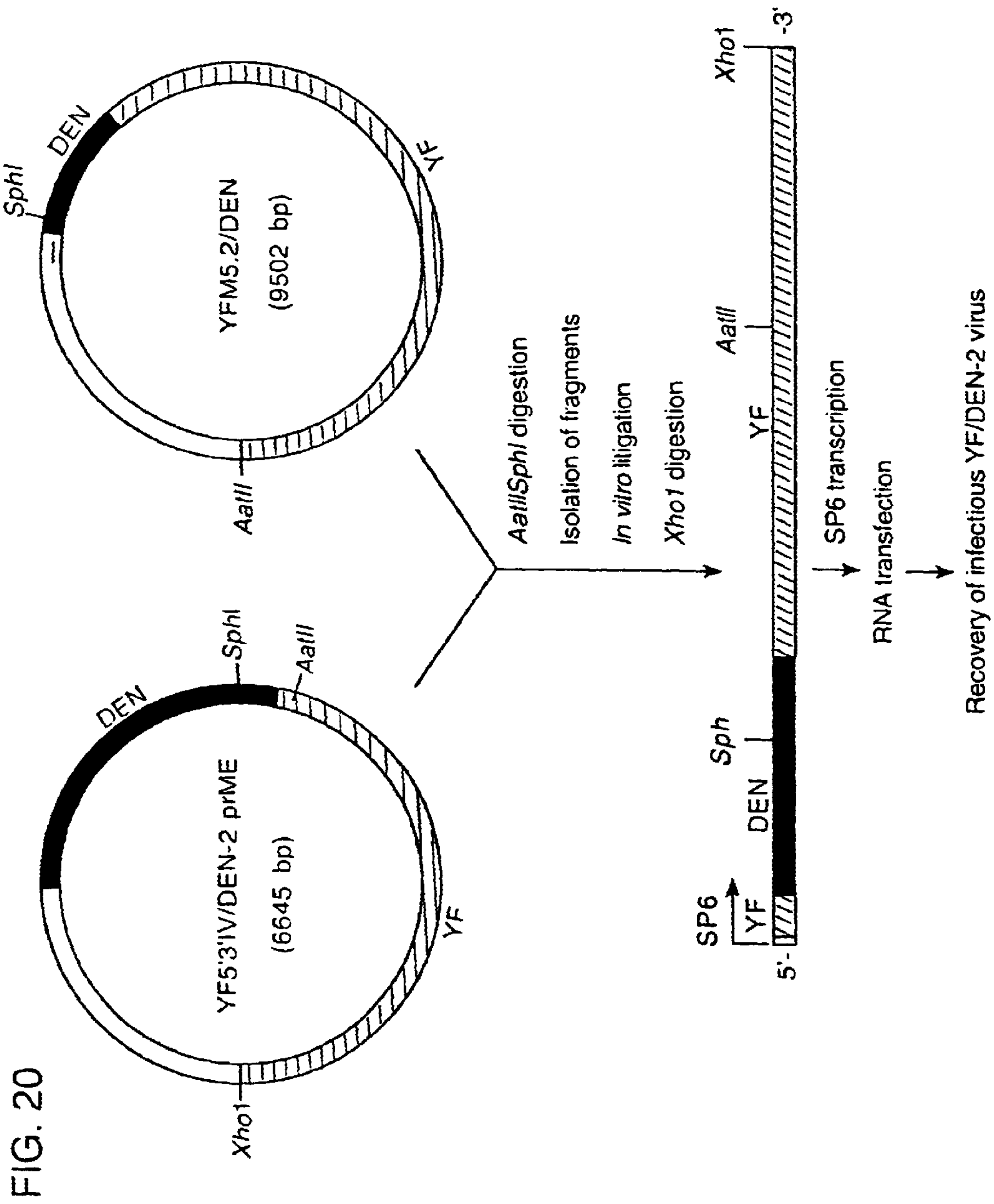
FIG. 20 is a schematic representation of a two plasmid system for generating chimeric YF/DEN-2 virus. The strategy is essentially as described for the YF/JE chimeric virus.

Similar to the two plasmid system for YF5.2iv and YF/JE viruses, the YF/DEN system uses a unique restriction site within the DEN-2 envelope protein (E) as a breakpoint for propagating the structural region (prM-E) within the two plasmids, hereinafter referred to as YF5'3'IV/DEN (prM-E') and YFM5.2/DEN (E'-E) (see FIG. 20). The two restriction sites for in vitro ligation of the chimeric template are AatII and SphI. The recipient plasmid for the 3' portion of the DEN E protein sequence is YFM5.2(NarI[+]SphI[−]). This plasmid contains the NarI site at the E/NSI junction, which was used for insertion of the carboxyl terminus of the JE E protein. It was further modified by elimination of an extra SphI site in the NS5 protein region by silent site-directed mutagenesis. This allowed insertion of DEN-2 sequence from the unique SphI site to the NarI site by simple directional cloning. The appropriate fragment of DEN-2 cDNA was derived by PCR from the DEN-2 clone MON310 furnished by Dr. Wright. PCR primers included a 5' primer flanking the SphI site and a 3' primer homologous to the DEN-2 nucleotides immediately upstream of the signalase site at the E/NS1 junction and replacing the signalase site by substitutions that create a novel site, but also introduce a NarI site. The resulting 1,170 basepair PCR fragment was then introduced into YFM5.2(NarI[+]SphI[−]).

The 5' portion of the YF/den-2 clone, including the C/prM junction was engineered by PCR. The C/prM junction was created by incorporating a TfiI restriction site at the junction using synthetic oligonucleotides. A 5' PCR fragment encompassing the flanking YF sequence 5' untranslated and capsid sequence and a 3' TfiI site, together with a 3' PCR fragment beginning with a TfiI site at the amino terminus of the dengue-2 prM protein and the flanking dengue-2 prM protein sequence, were ligated into the YF5'3'IV plasmid after intermediate construction in pBluescript. Screening with TfiI was used to confirm correct assembly of the chimeric junction in the final plasmid YF5'3'IV/DEN(prM-E).

2.2 Construction of Chimeric YF/DEN Viruses Containing Portions of Two DEN Envelope Proteins Since neutralization epitopes against DEN viruses are present on all three domains of the E protein, it is possible to construct novel chimeric virus vaccines that include sequences from two or more different DEN serotypes. In this embodiment of the invention, the C/prM junction and gene encoding the carboxyl terminal domain (Domain III) of one DEN serotype (e.g., DEN-2) and the N-terminal sequences encoding Domains I and II of another DEN serotype (e.g., DEN-1) are inserted in the YF 17D cDNA backbone. The junctions at C/prM and E/NS1 proteins are retained, as previously specified, to ensure the infectivity of the double-chimera. The resulting infectious virus progeny contains antigenic regions of two DEN serotypes and elicits neutralizing antibodies against both.

2.3 Transfection and Production of Progeny Virus

Plasmid YF5'3'IV/DEN(prME) and YFM5.2/DEN(E'-E) were cut with SphI and AatII restriction enzymes, appropriate YF and dengue fragments were isolated and ligated in vitro using T4 DNA ligase. After digestion with XhoI to allow run-off transcription, RNA was transcribed (using 50 ng of purified template) from the SP6 promoter and its integrity was verified by non-denaturing agarose gel electrophoresis. Vero cells were transfected with YF/Den-2 RNA using Lipofectin (Gibco/BRL), virus was recovered from the supernatants, amplified twice in Vero cells, and titrated in a standard plaque assay on Vero cells. The virus titer was $2\times10^6$ PFU/ml.

2.4 Nucleotide Sequencing of YF/Den-2 Chimera

Vero cells were infected with YF/DEN-2 (clone 5.75) at an MOI of 0.1. After 96 hours, cells were harvested with Trizol (Life Technologies, Inc.). Total RNA was primed with a YF-5' end NS1 minus oligo, and reverse transcribed with Superscript II RT following a long-RT protocol (Life Technologies, Inc.). Amplification of cDNA was achieved with XL-PCR kit (Perkin Elmer). Several primers specific for dengue type 2 strain PUO-218 were used in individual sequencing reactions and standard protocols for cycle sequencing were performed. Sequence homology comparisons were against the PUO-218 strain prME sequence (GenBank accession number D00345).

Sequencing showed that the YF/DEN-2 chimera prME sequence is identical to that of PUO-218 (Gruenberg et al., J. Gen. Virol 69:1391–1398, 1988). In addition, a NarI site was introduced at the 3' end of E, resulting in amino acid change Q494G (this residue is located in the transmembrane domain and not compared in Table 21). In Table 21, amino acid differences in the prME region of YF/Den2 is compared with prototype New Guinea C (NGC) virus and the attenuated dengue-2 vaccine strain PR-159 S1 (Hahn et al., Virology 162:167–180, 1988).

2.5 Growth Kinetics in Cell Culture

The growth kinetics of the YF/Den-2 chimera were compared in Vero and FeRhL cells (FIG. 16). Cells were grown to confluency in tissue culture flask (T-75). FeRhL cells were grown in MEM containing Earle's salt, L-Glu, non-essential amino acids, 10% FBS and buffered with sodium bicarbonate, and Vero cells were grown in MEM-Alpha, L-Glu, 10% FBS (both media purchased from Gibco/BRL). Cells were inoculated with YF/Den2 at 0.1 MOI. After 1 hour of incubation at 37° C., medium containing 3% FBS was added, and flasks were returned to a $CO_2$ incubator. Every 24 hours, aliquots of 0.5 ml were removed, FBS was added to a final concentration of 20%, and frozen for determination of titers in a plaque assay. Forty-eight hours post infection CPE was observed in FeRhL cells and reached 100% by day 3. In Vero cells, CPE was less dramatic and did not reached 100% by the completion of the experiment (day 5). As shown, the YF/Den2 reached its maximum titer (7.4 $\log_{10}$ pfu/ml) by day 3 and lost about one log (6.4 $\log_{10}$ pfu/ml) upon further incubation at 37° C., apparently due to death of host cells and virus degradation at this temperature. The maximum virus titer in Vero cells was achieved by day 2 grown in MEM containing Earle's salt, L-Glu, non-essential amino acids, 10% FBS and buffered with sodium bicarbonate, and Vero cells were grown in MEM-Alpha, L-Glu, 10% FBS (both media purchased from Gibco/BRL). Cells were inoculated with YF/Den2 at 0.1 MOI. After 1 hour of incubation at 37° C., medium containing 3% FBS was added, and flasks were returned to a $CO_2$ incubator. Every 24 hours, aliquots of 0.5 ml were removed, FBS was added to a final concentration of 20%, and frozen for determination of titers in a plaque assay. Forty-eight hours post infection CPE was observed in FeRhL cells and reached 100% by day 3. In Vero cells, CPE was less dramatic and did not reached 100% by the completion of the experiment (day 5). As shown, the YF/Den2 reached its maximum titer (7.4 $\log_{10}$ pfu/ml) by day 3 and lost about one log (6.4 $\log_{10}$ pfu/ml) upon further incubation at 37° C., apparently due to death of host cells and virus degradation at this temperature. The maximum virus titer in Vero cells was achieved by day 2 (7.2 $\log_{10}$ pfu/ml) and only half log virus (6.8 $\log_{10}$ pfu/ml) was lost on the following 3 days. This higher rate of viable viruses in Vero cells may be explained by incomplete CPE observed in these cells. In sum, the chimera grows well in approved cell substrate for human use.

2.6 Neurovirulence Phenotype in Suckling Mice

Although wild-type unpassaged dengue viruses replicate in brains of suckling mice and hamsters inoculated by the intracerebral route (Brandt et al., J. Virol 6:500–506, 1970), they usually induce subclinical infection and death occur only in rare cases. However, neurovirulence for mice can be achieved by extensive passage in mouse brain. Such neuro-adapted viruses can be attenuated for humans. For example, the New Guinea C (NGC), the prototype dengue 2 virus isolated in 1944 and introduced into the Americas in 1981, is not neurovirulent for suckling mice; however after sequential passage in mouse brain it became neurovirulent for mice, but was attenuated for humans (Sabin, Am. J. Trop. Med. Hyg., 1:30–50, 1952; Sabin et al., Science 101:640–642, 1945; Wisseman et al., Am. J. Trop. Med. Hyg.12:620–623, 1963). The PUO-218 strain is a wild type dengue 2 virus isolated in 1980 epidemic in Bangkok. It is closely related to the NGC strain by nucleotide sequencing (Gruenberg et al., J. Gen. Virol 69:1391–1398, 1988). When the prME genes of the PUO-218 strain were inserted into the neuroadapted NGC backbone, the chimeric virus was attenuated for 3-days old mice inoculated by the I.C. route (Peter Wright, $X^{th}$ International Congress of Virology, Jerusalem, Israel, 1996). The PUO218 neuroinvasiveness and neurovirulence. Ultimately safety studies in monkeys will be required. In initial studies, we determined if insertion of the prME of the PUO218 into YF 17D vaccine strain will affect its neurovirulence for suckling mice (Table 24). Groups of 3, 5, 7, and 9 days old suckling mice were inoculated by the I.C. route with 10,000 pfu of YF/Den-2 or YF/JE SA14-14-2 chimera and observed for paralysis or death for 21 days. For controls similar age groups were inoculated either sham with medium (I.C. or I.P.) or with 1,000 pfu of unpassaged commercial YF vaccine YF-VAX® (Yellow Fever 17D Vaccine)) by the I.P. route (it is not necessary to inoculate suckling mice with YF-VAX® (Yellow Fever 17D Vaccine) by the I.C. route because we have previously shown that this vaccine is virulent for 4-weeks old mice by this route).

Figure 22:
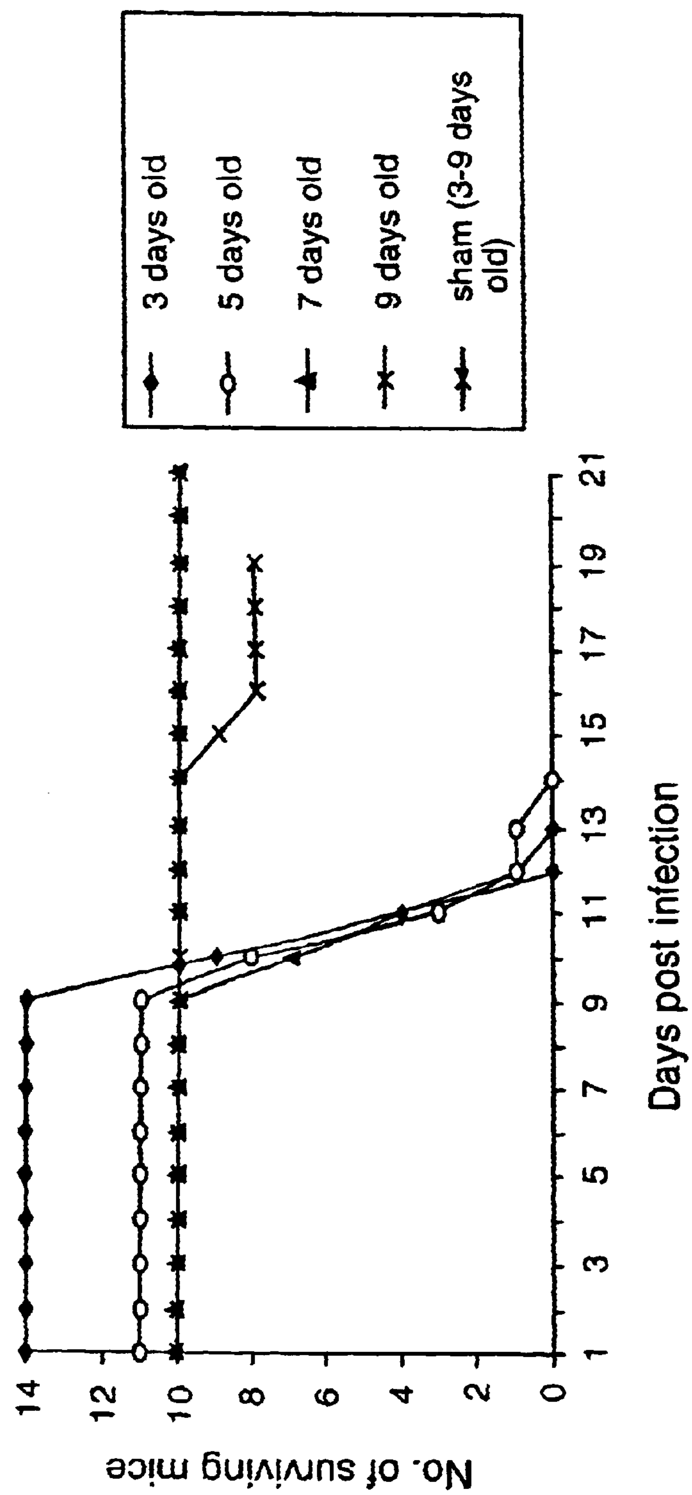
FIG. 22 is a graph showing the neurovirulence phenotype of CHIMERIVAX-DEN2™ (chimeric flavivirus vaccine comprising Dengue 2 prM and E proteins) in outbred (CD-1) suckling mice inoculated by the I.C. route with 10,000 PFU/0.02 ml.
Figure 23:
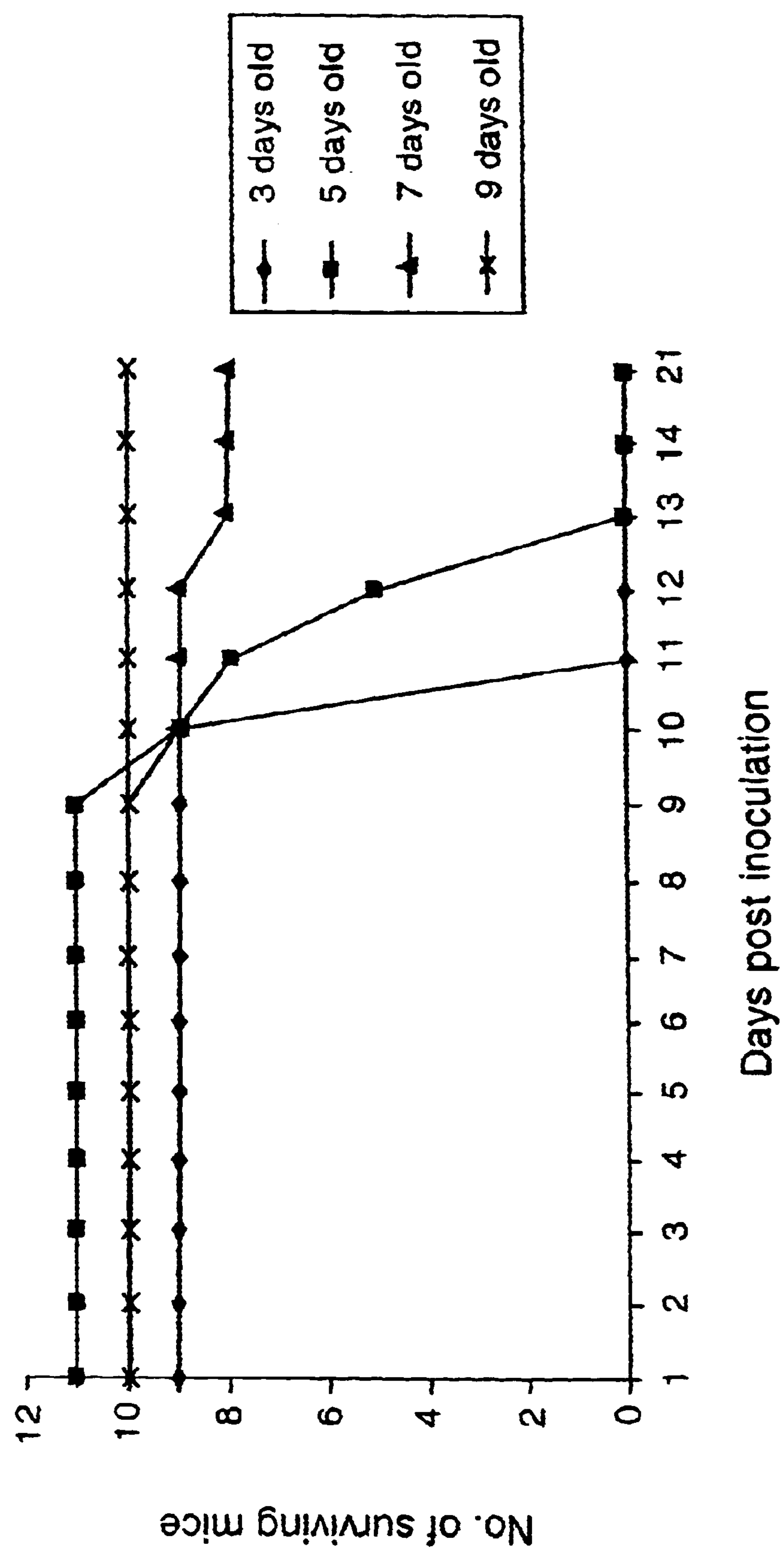
FIG. 23 is a graph showing the neurovirulence phenotype of 17D vaccine (YF-Vax® (Yellow Fever 17D Vaccine)) in outbred (CD-1) suckling mice inoculated by the I.P. route with 1000 PFU/0.02 ml.

As shown in FIG. 22, all suckling mice (3 to 7 days old) inoculated by the I.C. route with the YF/Den2 chimera died between 11 and 14 days post inoculation, whereas 8 out of 10 suckling mice (9 days old) survived. Similarly, all suckling mice (3–5 days old) inoculated with YF-VAX® (Yellow Fever 17D Vaccine) by the I.P. route, with a dose which was 10-fold lower than the YF/Den2 chimera, died between 11 to 13 days post inoculation (FIG. 23). All nine day old, as well as 8 out of 9 seven day old, mice inoculated with the YF-VAX® (Yellow Fever 17D Vaccine) survived. Similar results to the YF/Den2 chimera obtained with suckling mice inoculated with the YF/JE SA14-14-2 chimera.

As is mentioned above, when prME genes of the PUO218 strain were inserted into the NGC backbone the chimeric virus was not neurovirulent for 3 days old suckling mice inoculated by the I.C. route. In contrast, when these genes were inserted into the 17D backbone, the resulting YF/Den2 chimera demonstrated a neurovirulence phenotype (for suckling mice) similar to the YF/ JE SA14-14-2. This experiment also demonstrated that the replacement of the prME genes of the YF 17 D with prME genes of the Dengue 2 PUO218 resulted in a chimeric virus that was less neurovirulent than the 17D parent strain.

Unlike most flaviviruses, there is no correlation between neurovirulence of dengue viruses in mice and humans. Currently the most suitable animal models for dengue infection are Old World monkeys, New World monkeys, and apes that develop subclinical infection and viremia. There is, however, no animal model for the most severe illness (DHF) in humans, which occurs when individuals become infected with a heterologous serotype due to antibody dependent enhancement of infection. Today it is generally accepted that a tetravalent vaccine is required to induce protective immunity in human beings against all four serotypes to avoid sensitizing vaccinee to more severe illness DHF. For the last fifty years, many approaches have been undertaken to produce effective dengue vaccines and although dengue viruses have been satisfactory attenuated (e.g., PR-159/S-1 for Dengue 2) in many cases in vitro or in vivo correlation of attenuation were not reproducible in humans. A current strategy is to test selected live virus vaccine candidates stepwise in small numbers of human volunteers. Many laboratories around the world are exploring various strategies to produce suitable vaccine candidates. These range from subunit vaccines including prME (protein vaccine or DNA vaccine) of dengue viruses to live attenuated whole viruses (produced by tissue culture passage or recombinant DNA technology). Although some of these candidates have shown promise in preclinical and human volunteers, development of a successful dengue vaccine remained to implemented.

Evaluating the immunogenicity and protective efficacy of the YF/Den2 chimera in monkeys should shed light on selection of appropriate prME genes (form wild type or attenuated strain) for construction of all 4 serotypes of chirmeric dengue viruses.

2.7 Stability of prME Genes of CHIMERIVAX-DEN2™ (Chimeric Flavivirus Vaccine Comprising Dengue 2 prM and E Proteins) Virus in vitro The CHIMERIVAX-DEN2™ (chimeric flavivirus vaccine comprising Dengue 2 prM and E proteins) virus at passage 2 post transfection was used to inoculate a 25 $cm^2$ flask of Vero cells. Total RNA was isolated and the complete nucleotide sequence of the CHIMERIVAX-DEN2™ (chimeric flavivirus vaccine comprising Dengue 2 prM and E proteins) was determined (P3) and compared to the published sequence of the YF 17D virus (Rice et al., Science 229:726–733, 1985). There was one nucleotide difference: at position 6898 there was an A in the chimera (P3), which was a C in the 17D nucleotide sequence. No difference in the prME region was found when the sequence of CHIMERIVAX-DEN2™ (chimeric flavivirus vaccine comprising Dengue 2 prM and E proteins) was compared to its parent dengue 2 virus (PUO218 strain). Also, no mutations were found in the prME genes of the chimera upon 18 passages in VeroPM cells. Within the YF genes, however, there was one silent mutation in position 6910 (C to A), and at position 3524 the P18 virus appeared to be heterozygous (both parent nucleotides, G and mutant A, were present). This would translate into a mixture of E and K amino acids at position 354 of the NS1 protein.

Similar to the passage 3 virus, the passage 18 virus was not neurovirulent for 4 week old outbred mice inoculated by the IC route (5 $\log_{10}$ pfu was the highest dose tested). Passage 3, passage 5, passage 10, and passage 18 of CHIMERIVAX-DEN2™ (chimeric flavivirus vaccine comprising Dengue 2 prM and E proteins) were inoculated into mice by SC and IC routes, and antibody responses were compared. There were no significant differences in production of anti-dengue 2 neutralizing antibodies across 18 passages (Table 26).

2.8 Viremia, Immunogenicity, and Protective Efficacy of CHIMERIVAX-DEN2™ (Chimeric Flavivirus Vaccine Comprising Dengue 2 prM and E Proteins) in YF Immune Monkeys Because CHIMERIVAX™ (chimeric flavivirus vaccines)-viruses contain core and NS genes of the YF 17D virus, it is important to determine if preimmunity to the 17D vaccine interferes with vaccination with CHIMERIVAX-DEN2™ (chimeric flavivirus vaccine comprising Dengue 2 prM and E proteins) virus. As is discussed above, in the case of CHIMERIVAX-JE™ (chimeric flavivirus vaccine comprising Japanese Encephalitis virus prM and E proteins), there was no significant interference between YF17D immunity and CHIMERIVAX-JE™ (chimeric flavivirus vaccine comprising Japanese Encephalitis virus prM and E proteins), virus, measured by production of neutralizing antibodies in mice.

Since YF 17D vaccine and both CHIMERIVAX-JE™ (chimeric flavivirus vaccine comprising Japanese Encephalitis virus prM and E proteins) and CHIMERIVAX-DEN2™ (chimeric flavivirus vaccine comprising Dengue 2 prM and E proteins) were not highly immunogenic in mice inoculated by the SC route (see also table 26), non-human primates were used, which are more susceptible/relevant for evaluation of flavivirus vaccines for humans. Sixteen rhesus monkeys (some of which were previously immunized with YF 17D vaccine) received CHIMERIVAX-DEN2™ (chimeric flavivirus vaccine comprising Dengue 2 prM and E proteins), YF 17D vaccine, or a wild type dengue 2 virus (strain S16803). As is shown in Table 27, all YF immune monkeys seroconverted to the YF/dengue 2 or wild type dengue 2 virus, demonstrating a lack of vector immunity. These monkeys were also protected from viremia after challenge with wild type dengue 2 virus. In contrast, YF 17D immunized monkeys, as well as non-immunized animals, became viremic after challenge with wild type dengue 2 virus. Wild type dengue 2 viruses produce a high level of viremia (3–5 logs) in rhesus monkeys, which lasts between 3–6 days. Attenuation of dengue 2 viruses can therefore be estimated by comparing the level and duration of viremia with reference wild-type strains. These experiments clearly showed that core and non-structural proteins of YF 17D virus present in CHIMERIVAX-DEN2™ (chimeric flavivirus vaccine comprising Dengue 2 prM and E proteins) do not interfere with CHIMERIVAX-DEN2™ (chimeric flavivirus vaccine comprising Dengue 2 prM and E proteins) immunization.

2.9 Dose Response Effectiveness of CHIMERIVAX-DEN2™ (Chimeric Flavivirus Vaccine Comprising Dengue 2 prM and E Proteins) in Monkeys The goals of this experiment were to (i) determine the viremia profile of the vaccine candidate, using YF 17D and wild type dengue 2 virus controls, (ii) compare neutralizing antibody responses to the vaccine candidate and wildtype virus, and (iii) determine minimum dose required for protection against challenge with wild type dengue-2 virus. It was anticipated that these experiments would define the viremia profile of the CHIMERIVAX-DEN2™ (chimeric flavivirus vaccine comprising Dengue 2 prM and E proteins) virus in non-YF immune monkeys, and would determine whether immunization with a single dose results in protection of animals against challenge with a wild type dengue 2 virus. Protection in these experiments is defined as reduction of viremia in test monkeys compared to control viruses.

As is shown in table 28, all monkeys became viremic, and the duration of viremia was dose-dependent. The peak level of viremia for CHIMERIVAX-DEN2™ (chimeric flavivirus vaccine comprising Dengue 2 prM and E proteins) was between 1.3 to 1.6 $\log_{10}$ pfu, which was significantly lower than that of the wild type dengue virus (3.6 $\log_{10}$ pfu).

All monkeys developed anti-dengue 2 neutralizing antibodies by day 15. Lower dose of the vaccine resulted in lower GMTs, however, by day 30 post-immunization, all monkeys developed high titers of neutralizing antibodies, independent of the dose they received. Upon challenge, no viremia was detected in any immunized monkeys, demonstrating that even at its lowest dose (2 $\log_{10}$ pfu), CHIMERIVAX-DEN2™ (chimeric flavivirus vaccine comprising Dengue 2 prM and E proteins) had protected these animals from dengue infection (Table 29).

2.10 Growth Characteristics of CHIMERIVAX-JE™ (Chimeric Flavivirus Vaccine Comprising Japanese Encephalitis Virus prM and E Proteins) Virus in *Culex ritaeniorhynchus, Aedes albopictus*, and *Aedes aegypti* Mosquitoes As is described above, CHIMERIVAX-JE™ (chimeric flavivirus vaccine comprising Japanese Encephalitis virus prM and E proteins), which consists of a YF 17D virus backbone containing the prM and E genes from the JE vaccine strain SA14-14-2, exhibited restricted replication in non-human primates, producing only a low level viremia following peripheral inoculation. Although this reduces the likelihood that hematophagous insects could become infected by feeding on a vaccinated host, it is prudent to investigate the replication kinetics of the vaccine virus in mosquito species that are known to vector the viruses from which the chimera is derived. In this study, CHIMERIVAX-JE™ (chimeric flavivirus vaccine comprising Japanese Encephalitis virus prM and E proteins), virus was compared to its parent viruses (YF17D and JE SA14-14-2), as well as to wild type JE SA14 virus, for its ability to replicate in *Culex tritaeniorhyncus, Aedes albopictus*, and *Aedes aegypti* mosquitoes. Individual mosquitoes were exposed to the viruses by intrathoracic (IT) virus inoculation or by oral ingestion of a virus-laden blood meal.

2.11 Intrathoracic Inoculation

Mosquitoes were inoculated 7–10 days post-emergence with 0.34 ml of approximately 6.0 $\log_{10}$ pfu/ml virus suspension (~5.5 $\log_{10}$ pfu/mosquito). This route of inoculation was chosen to avoid variables, such as threshold titer, that might limit midgut infection and subsequent dissemination of the viruses. Three mosquitoes per virus were collected either at 24 hour intervals for 5–10 days or at 72 hour intervals for 18 days. Individual mosquitoes were triturated in 1 ml of M199 media (Gibco BRL, Grand Island, N.Y.) supplemented with 5% fetal calf serum, clarified by brief centrifugation, and then titrated in Vero cells to monitor virus replication.

Figure 24A:
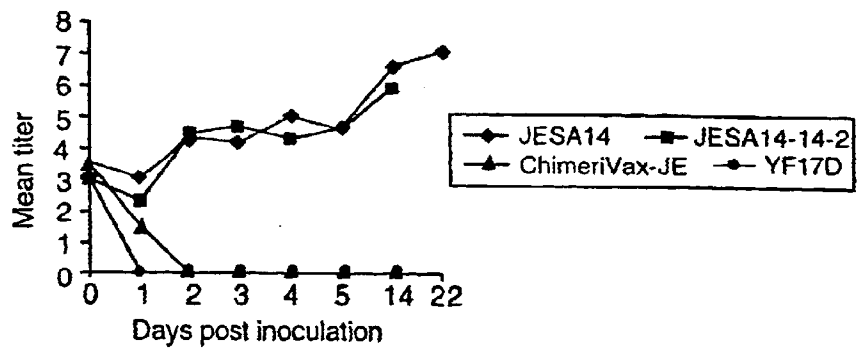
FIGS. 24A–C are graphs showing the growth of JE SA14, JE SA14-14-2, CHIMERIVAX-JE™ (chimeric flavivirus vaccine comprising Japanese Encephalitis virus prM and E proteins) and YF 17D intrathoracically inoculated mosquitoes: (A) *Cx. tritaeniorhynchus* mosquitoes, (B) *Ae. albopictus* mosquitoes, and (C) *Ae. aegypti*. Mean titer=geometric mean of the titers of three individual mosquitoes; $\log_{10}$ pfu/mosquito.

Both JE SA14 and JE SA14-14-2 viruses replicated in *Cx. tritaeniorhynchus* following IT inoculation, reaching titers at day 14 of 6.7 and 6.0 $\log_{10}$ pfu/mosquito, respectively (FIG. 24A). Additionally, IFA conducted on head squashes from JE SA14 and JE SA14-14-2-inoculated *Cx. tritaeniorhynchus* mosquitoes was positive for detection of JE virus antigen. In contrast, YF 17D and CHIMERIVAX-JE™ (chimeric flavivirus vaccine comprising Japanese Encephalitis virus prM and E proteins) did not replicate in *Cx. tritaeniorhynchus* mosquitoes. Virus titers declined rapidly following inoculation, and no virus was detectable by plaque titration assay in YF 17D or CHIMERIVAX-JE™ (chimeric flavivirus vaccine comprising Japanese Encephalitis virus prM and E proteins)-inoculated mosquitoes by days 1 and 2, respectively (FIG. 24A). IFA analysis of head squashes from *Cx. tritaeniorhynchus* mosquitoes inoculated with CHIMERIVAX-JE™ (chimeric flavivirus vaccine comprising Japanese Encephalitis virus prM and E proteins) or YF 17D was negative for JE or YF virus antigens, supporting our observation that neither the chimera nor YF 17D replicate in this mosquito species.

Figure 24B:
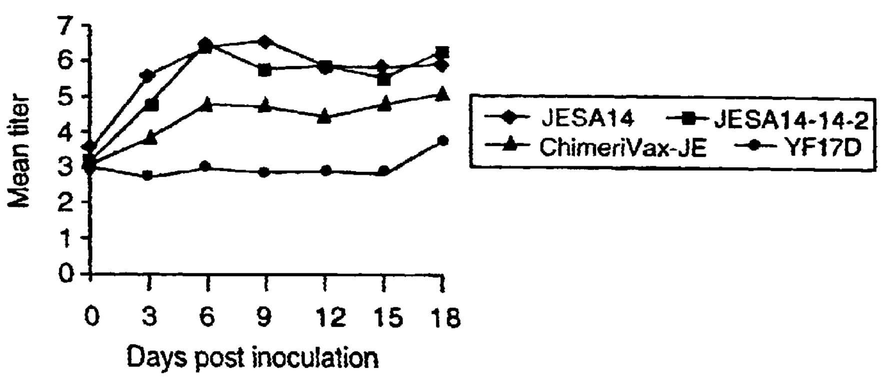
Figure 24C:
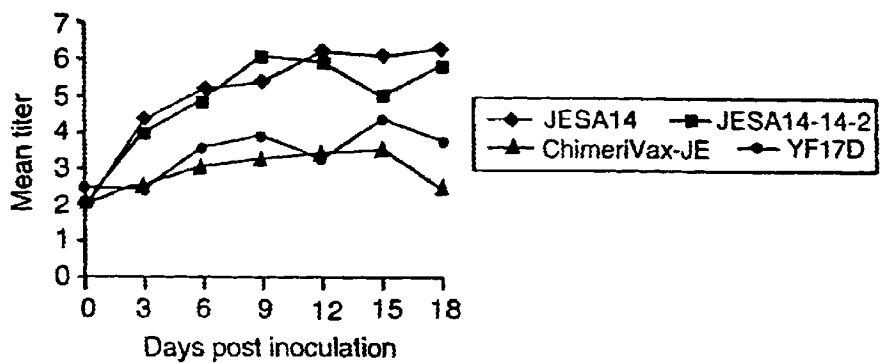

CHIMERIVAX-JE™ (chimeric flavivirus vaccine comprising Japanese Encephalitis virus prM and E proteins) did replicate in IT-inoculated *Ae. albopictus* mosquitoes, reaching a titer of 5.2 $\log_{10}$ pfu/mosquito at day 18 (FIG. 24B) and IFA results were weakly positive for both JE virus and YF virus antigens. The JE SA14 and JE SA14-14-2 viruses also replicated in respectively. YF 17D virus did not replicate to high titers in *Ae. albopictus* mosquitoes, however, a low level of detectable virus was maintained (3.8 $\log_{10}$ pfu/mosquito at day 18) (FIG. 24B) and IFA-stained head squashes were weakly positive for YF virus antigen. CHIMERIVAX-JE™ (chimeric flavivirus vaccine comprising Japanese Encephalitis virus prM and E proteins) and YF 17D inoculated IT into *Ae. aegypti* mosquitoes replicated at low levels over the 18 day incubation period (FIG. 24C). Peak titers of 3.6 and 4.4 $\log_{10}$ pfu/mosquito, respectively, were reached on day 15. IFA staining of head tissues from CHIMERIVAX-JE™ (chimeric flavivirus vaccine comprising Japanese Encephalitis virus prM and E proteins) and YF 17D IT-inoculated mosquitoes was weakly positive. Both JE SA14 and JE SA14-14-2 viruses proliferated in *Ae. aegypti* mosquitoes, reaching peak titers of 6.3 and 6.1 $\log_{10}$ pfu/mosquito on days 9 and 18, respectively.

2.12 Oral Infection

Seven to ten day old *Ae. albopictus* and *Ae. aegypti* mosquitoes were orally exposed to an artificial virus-containing blood meal that was prepared from equal parts of washed calf red blood cells (Colorado Serum Company, Denver, Colo.) and freshly harvested virus. The blood/virus mixture was heated to 37° C. immediately prior to feeding. Mosquitoes were starved for 48–72 hours prior to feeding on virus/blood soaked cotton pledgets. *Cx. tritaeniorhynchus* mosquitoes are reluctant to feed from blood-soaked pledgets, and were therefore fed using a membrane feeder. Mosquitoes were allowed to feed for 15–30 minutes, after which fully engorged mosquitoes were collected. Three mosquitoes per virus were harvested at 48–72 hour intervals over a 15–18 day period, or, in a second experiment, all mosquitoes were harvested at 22 days after feeding.

Figures 25A, 25B, 25C:
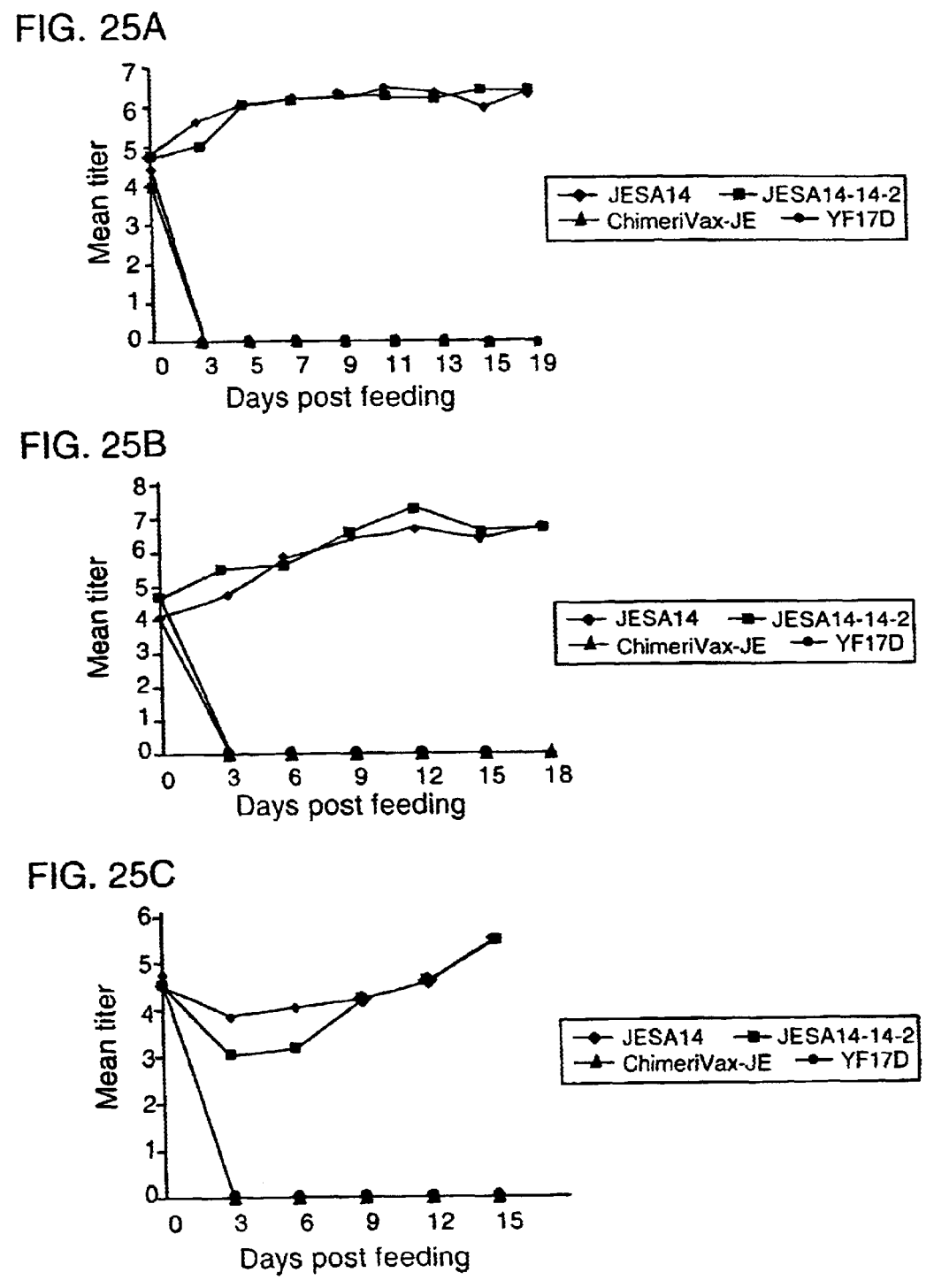

FIG. 25A illustrates growth of the viruses in orally exposed *Cx. tritaeniorhynchus* mosquitoes. Individuals that were fed a blood meal containing 6.9 $\log_{10}$ pfu/ml CHIMERIVAX-JE™ (chimeric flavivirus vaccine comprising Japanese Encephalitis virus prM and E proteins) virus did not become infected. Similar results were observed in mosquitoes that had ingested a blood meal containing YF 17D virus. In contrast, high virus titers were detected in *Cx. tritaeniorhynchus* mosquitoes that had ingested JE SA14 or JE SA14-14-2 viruses.

FIGS. 25B and 25C illustrate growth of the viruses in orally exposed *Ae. albopictus* and *Ae. aegypti* mosquitoes, respectively. Only JE SA14 and JE SA14-14-2 viruses successfully infected and replicated in these species. For example, in *Ae. aegypti* mosquitoes on day 15, the titers of JE SA14 and JE SA14-14-2 viruses were 5.4 and 5.5 $\log_{10}$ pfu, respectively. In contrast, mosquitoes that had ingested 4.7 $\log_{10}$ pfu/mosquito of YF17D virus or 4.5 $\log_{10}$ pfu/mosquito of CHIMERIVAX-JE™ (chimeric flavivirus vaccine comprising Japanese Encephalitis virus prM and E proteins) virus failed to become infected.

In a separate experiment, *Ae. aegypti* and *Ae. albopictus* mosquitoes were orally exposed to JE SA14-14-2, YF 17D, and CHIMERIVAX-JE™ (chimeric flavivirus vaccine comprising Japanese Encephalitis virus prM and E proteins) viruses and processed after 22 days extrinsic incubation to permit growth to maximum virus titers. The results of this experiment are summarized in Table 30. Only JE SA14-14-2 virus was detectable in mosquitoes. Because CHIMERIVAX-JE™ (chimeric flavivirus vaccine comprising Japanese Encephalitis virus prM and E proteins) did not grow in any of the mosquito species tested, transmission studies were not performed.

Viruses recovered from *Ae. Albopictus* after IT or oral inoculation, or from *Ae. Aegypti* after IT inoculation, were identical to their parent CHIMERIVAX-JE™ (chimeric flavivirus vaccine comprising Japanese Encephalitis virus prM and E proteins) virus (Vero2FrhL1) in the prME region.

2.13 Amplification and Sequencing of the "Late Replicating" CHIMERIVAX-JE™ (Chimeric Flavivirus Vaccine Comprising Japanese Encephalitis Virus prM and E Proteins) Viruses Isolated From Mosquitoes

*Ae. albopictus* mosquitoes inoculated with CHIMERIVAX-JE™ (chimeric flavivirus vaccine comprising Japanese Encephalitis virus prM and E proteins) by IT or oral routes and *Ae. aegypti* inoculated with CHIMERIVAX-JE™ (chimeric flavivirus vaccine comprising Japanese Encephalitis virus prM and E proteins) by IT route, were harvested on day 15 post-inoculation. After triturating in 1 ml of M199 (supplemented with 5% fetal calf serum), samples were clarified by centrifugation, filtered through a 0.2 micron filter, and used to inoculate a T-25 $cm^2$ flask of VeroPM cells, passage 144 (0.5 ml/flask). After 1 hour, virus adsorption at 37° C., 5 ml MEM-containing 5% FBS was added and flasks returned to the 37° C. $CO_2$ incubator. Viruses were harvested from supernatants 4 days later (at 2+CPE) and kept frozen at −70° C. Total RNA was extracted from infected monolayers by the use of the Trizol® reagent (Gibco/BRL), reverse-transcribed, amplified by XL PCR (Perkin-Elmer), and the prME region was sequenced. Viruses recovered from *Ae. Albopictus* after IT or oral inoculation, or from *Ae. Aegypti* after IT inoculation, were identical to their parent CHIMERIVAX-JE™ (chimeric flavivirus vaccine comprising Japanese Encephalitis virus prM and E proteins) virus (Vero2FrhL1) in the prME region.

Figure 26A:
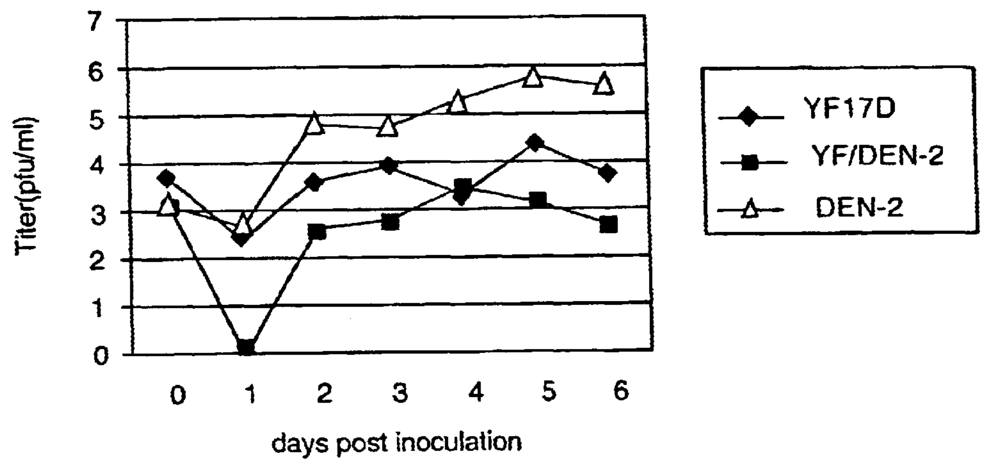
FIGS. 26A and B are graphs showing the growth of virus in IT inoculated *Ae. aegypti* (A) and *Ae. albopictus* (B) mosquitoes.
Figure 26B:
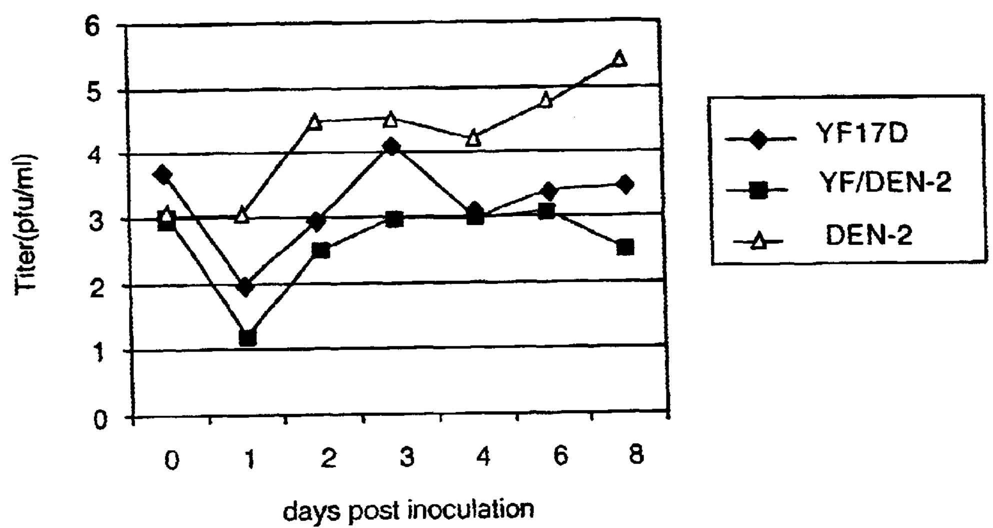

2.14 Growth Characteristics of CHIMERIVAX-DEN2™ (Chimeric Flavivirus Vaccine Comprising Dengue 2 prM and E Proteins) Virus in *Aedes albopictus* and *Aedes aegypti* Mosquitoes Similar experiments were carried out in *Ae. albopictus* and *Ae. aegypti* mosquitoes with CHIMERIVAX-DEN2™ (chimeric flavivirus vaccine comprising Dengue 2 prM and E proteins) virus. For controls, the YF17D vaccine and a dengue 2 wild type virus were used. Dengue 2 wild type virus grew to more than 5 $\log_{10}$ pfu/ml in both mosquito species inoculated by IT or oral routes. The growth of YF 17D vaccine was lower than the wild type dengue 2 virus, and did not exceed 4 $\log_{10}$ pfu/ml. Interestingly, the CHIMERIVAX-DEN2™ (chimeric flavivirus vaccine comprising Dengue 2 prM and E proteins) virus revealed the most restricted growth in both mosquito species inoculated by either route (its titer did not exceed 3 $\log_{10}$ pfu/ml) (FIG. 26).

2.15 Summary of JE and Den2 Experiments in Mosquitos

In summary, CHIMERIVAX-JE™ (chimeric flavivirus vaccine comprising Japanese Encephalitis virus prM and E proteins) virus did not replicate following ingestion by any of the three mosquito species. Additionally, replication was not detected after IT inoculation of CHIMERIVAX-JE™ (chimeric flavivirus vaccine comprising Japanese Encephalitis virus prM and E proteins) in the primary JE virus vector, *Cx. tritaeniorhynchus*. CHIMERIVAX-JE™ (chimeric flavivirus vaccine comprising Japanese Encephalitis virus prM and E proteins) exhibited moderate growth following IT inoculation into *Ae. aegypti* and *Ae. albopictus* mosquitoes, reaching titers of 3.6–5.0 $\log_{10}$ pfu/mosquito. There was no change in the virus genotype associated with replication in mosquitoes. Similar results were observed in mosquitoes of all three species that were IT inoculated or had orally ingested the YF 17D vaccine virus. In contrast, all mosquitoes either IT inoculated with, or orally fed, wild type and vaccine JE viruses became infected, reaching maximum titers of 5.4–7.3 $\log_{10}$ pfu/mosquito. The growth of CHIMERIVAX-DEN2™ (chimeric flavivirus vaccine comprising Dengue 2 prM and E proteins) in both *Ae. albopictus* and *Ae. aegypti* mosquitoes inoculated by IT or oral routes was also significantly lower than its parent wild type dengue 2 and YF17D vaccine viruses.

These results showed that CHIMERIVAX-JE™ (chimeric flavivirus vaccine comprising Japanese Encephalitis virus prM and E proteins) and CHIMERIVAX-DEN2™ (chimeric flavivirus vaccine comprising Dengue 2 prM and E proteins) viruses are restricted in their abilities to infect and replicate in these mosquito vectors. The low viremia caused by the viruses in primates and poor infectivity for mosquitoes are safeguards against secondary spread of the vaccine virus.

3.0 Construction of CHIMERIVAX-DEN1™ (Chimeric Flavivirus Comprising Dengue 1 prM and E Proteins)

A yellow fever/dengue 1 (YF/DEN-1) chimeric virus was constructed using a novel technology, which differs from the approaches used to construct Yellow fever/Japanese encephalitis (YF/JE) chimeric viruses as described by Chambers et al. (J. Virol. 73:3095–4101, 1999; see above), and the construction of YF/DEN-4 chimera (see below). We used the same two plasmid system used to create YF/DEN-4. These plasmids first encoded the yellow fever (YF) genome as created by Rice et al. (New Biol. 1:285–296, 1989). Later, the structural membrane precursor and envelope protein genes, i.e., the prME region, of the YF genome plasmids was replaced with those of the JE SA14-14-2 sequence, and the resulting plasmids were used to produce RNA in vitro, which was then transfected into cells to produce live YF/JE chimeric virus. Although the two-plasmid system was suitable for the construction of JE, DEN-2, and DEN-4 chimeras in a YF backbone, the marked instability of one of the plasmids created with DEN-1 sequences was such that we opted for a PCR alternative to replace it.

Figure 27:
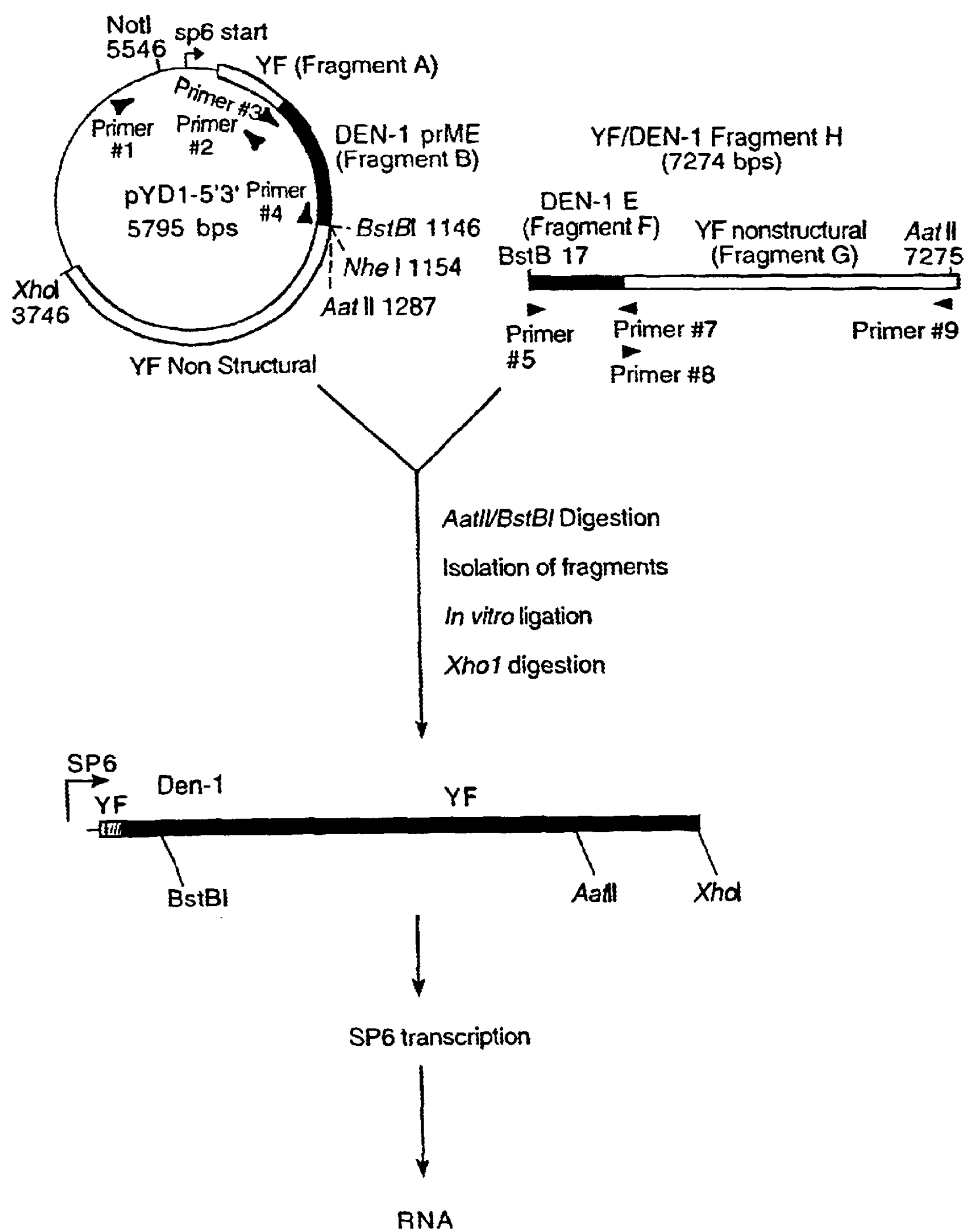
FIG. 27 is a schematic representation of an overview of construction of a YF/DEN1 chimera of the invention.
Figure 28:
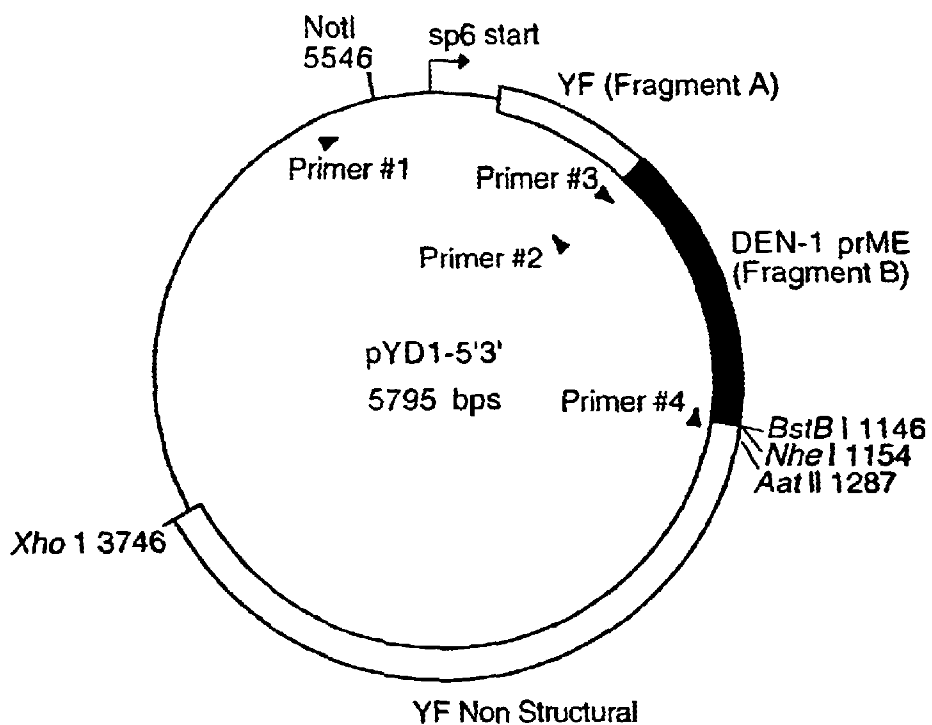
FIG. 28 is a schematic representation of a plasmid and fragment map relating to construction of a YF/DEN1 chimera of the invention.
Figure 28:
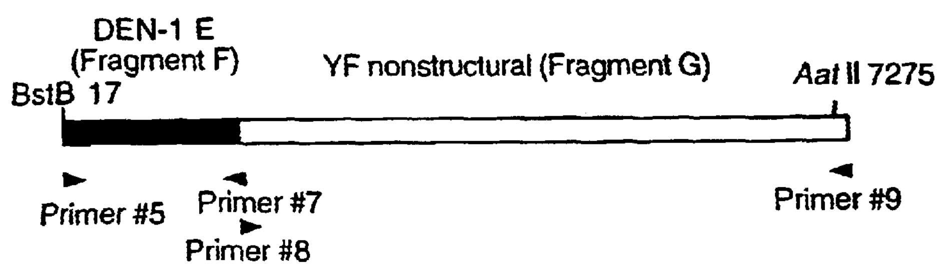

Here we describe in detail the procedures for construction of the YF/DEN-1 chimera (FIGS. 27 and 28). Dengue 1 (strain PUO359 isolated in 1980 in Thailand) was passed once in C6/36 and total RNA was isolated. The dengue 1 prME region was first amplified and sequenced using primers derived from consensus sequences (Genbank). The sequence data created was applied to primer design and was used, with the cDNA produced earlier, as a PCR starting point for assembly of chimeric YF/DEN-1 virus. A dengue 1 PCR product encoding prM and the 5' end of E was then used as a template, along with template encoding the capsid (C) of yellow fever derived from plasmid pYF5'3'IV/JE SA14-14-2, in an overlap extension PCR to result in a single fusion product, which was then cloned into a vector fragment of pYFM5'3'IV in which JE sequences were deleted. In contrast to the construction of the YF/DEN-4 (see below) and YF/JE SA14-14-2 (see above) plasmid systems, the 3' end of the DEN-1 envelope was fused to the YF nonstructural genes normally present in the pYFM5.2/JE SA14-14-2 plasmid using an overlap extension PCR similar to that used to construct the fusion of YF capsid to the DEN-1 prM and envelope gene 5' end. Next, the pYD1-5'3' plasmid was transformed into *E. coli* strain MC1061 (RecA-) for amplification, followed by midi-scale plasmid purification, while the DEN-1Env/YF5.2 (Fragment H) was gel purified. In vitro ligation of the plasmid to the PCR product resulted in full-length virus cDNA template for RNA transcription. All steps involving cDNA fragments, plasmids, and PCR products were carried out in a BL-2 lab designated for recombinant DNA work. Steps involving manipulations of infectious RNA and virus were carried out in a limited access BL-2+ virus lab.

3.1 Amplification of Dengue 1 Sequence

Dengue 1 cDNA was synthesized from RNA using the Superscript II™ method. All primers for this experiment were synthesized by Life Technologies and are listed in Table 31. Upon arrival as lyophilized material, they were dissolved to 250 $\mu$M stock solutions using RODI-water. From this, 25 $\mu$M working solutions were made. The fragment encoding the SP6 promoter and the yellow fever capsid (Fragment A) was amplified using XL-PCR Reaction Kit TM (Perkin-Elmer Part#N808–0192), with 0.5 μl (250 ng) of pYF5'3'IV plus 3.5 μl RODI-water as template and primers 1 and 2 (see Table 31). The fragment encoding dengue 1 prM and 5' end of E (Fragment B) was amplified using the XL-PCR Reaction Kit™ (Perkin-Elmer Part#N808–0192) and primers 3 and 4. The fragment encoding the 3' end of the Dengue 1 envelope gene (Fragment F) was amplified using the same protocol, but with primers 5 and 7. The fragment encompassing the YF portion of pYFM5.2 (Fragment G) was amplified using the same protocol, but with primers 8 and 9 and 1 μl of pYFM5.2/2 with 39 μl water. The PCR for fragments F and G required an annealing temperature of 50 C and an extension time of 6.5 minutes. The PCR reaction was performed using the following master mixes for each reaction.

| Upper Mix (UM) | |
|---|---|
| 3.3× buffer | 18 μl |
| RTth | 1.25 μl |
| $H_2O$ | 1 μl |
| Volume | 20.25 μl |

| Lower Mix (LM) | |
|---|---|
| 3.3× buffer | 12 μl |
| 10 mM dNTPs | 8 μl |
| 5' primer | 1 μl |
| 3' primer | 1 μl |
| $Mg(OAc)_2$ | 4 μl |
| $H_2O$ | 14 μl |
| Volume | 40 μl |

| cDNA Mix | |
|---|---|
| $H_2O$ | 36 μl |
| Dengue 1 cDNA | 4 μl |
| Volume | 40 μl |

The LM was added to a Perkin-Elmer thin-walled 0.2 ml tube. Next, Ampliwax 100 (Perkin-Elmer) was added to the tube, which was then placed in a Perkin-Elmer 2400 Thermal Cycler and heated to 80° C. for 5 minutes, and then cooled to 4° C. The cDNA and UM were then added to the top of the wax layer. The tube was then cycled in a Perkin-Elmer 2400 as follows: 94° C., 1 minute; repeat 30×(94° C., 15 seconds; 53° C., 15 seconds; 68° C., 3 minutes), 72° C., 4 minutes; 4° C., hold. The expected sizes for the fragments are as follows.

| Fragment | Approximate Size (kb) |
|---|---|
| A | 0.94 |
| B | 0.65 |
| F | 1.3 |
| G | 6.0 |

Forty μl of each fragment was then separated on a 1% Agarose/TAE gel and purified using the QIAquick Gel Extraction Kit (Qiagen cat#28704). Next, the concentrations of the purified fragments were determined by UV absorption using 1:40 dilutions in RODI-water.

| Sample | A280 | A260 | 280/260 | 260/280 | Concentration |
|---|---|---|---|---|---|
| Fragment A | 0.0116 | 0.0260 | 0.4453 | 2.2457 | 52 ng/μl |
| Fragment B | 0.0076 | 0.0202 | 0.3782 | 2.6440 | 40.4 ng/μl |
| Fragment F | 0.0160 | 0.0335 | 0.4785 | 2.0898 | 67 ng/μl |
| Fragment G | 0.0199 | 0.0380 | 0.5242 | 1.9076 | 76 ng/μl |

3.2 Recombinant PCR

To create a fusion between the yellow fever capsid and DEN-1 prM, a recombinant PCR technique known as overlap-extension PCR was used to create Fragment E. The same basic UM and LM were used, and primers 1 and 4 replaced earlier primers. The same approach was used to create a fusion between fragment F and G, resulting in fragment H. For this, primers 5 and 9 were used. The cDNA mixes were as follows:

| | Fragment E | Fragment B control | Fragment A control |
|---|---|---|---|
| $H_2O$ | 37.82 μl | 38.97 μl | 38.85 μl |
| Fragment A | 1.15 μl | 0 μl | 1.15 μl |
| Fragment B | 1.03 μl | 1.03 μl | 0 μl |
| Volume | 40 μl | 40 μl | 40 μl |
| | **Fragment H** | **Fragment F control** | **Fragment G control** |
| $H_2O$ | 38.9 μl | 39.7 μl | 39.2 μl |
| Fragment F | 0.3 μl | 0.3 μl | 0 μl |
| Fragment G | 0.8 μl | 0 μl | 0.8 μl |
| Volume | 40 μl | 40 μl | 40 μl |

The same protocol that was used for creation of fragments A, B, F, and G was used, except that only ½ the cDNA, UM, and LM were used for the control reactions. The tubes were cycled in a Perkin-Elmer 2400 as follows: 94° C., 1 minute; repeat 30×(94° C., 15 seconds; 55° C., 15 seconds; 68° C., 2 minutes; 72° C., 7 minutes; 4° C., hold, for Fragment C and its controls. For Fragment H and its controls, the annealing temperature was 50° C. and the extension time was 6.5 minutes. The expected sizes were as follows:

| Fragment | Approximate Size (kb) |
|---|---|
| E | 1.59 |
| H | 7.3 |

Forty μl of Fragment E and 50 μl of Fragment H was then separated on a 1% Agarose/TAE gel and purified using the QIAquick Gel Extraction Kit (Qiagen cat#28704). Next, the concentration of the purified fragment was determined by UV absorption using 1:40 dilutions in RODI-water.

| Sample | A280 | A260 | 280/260 | 260/280 | Concentration |
|---|---|---|---|---|---|
| Fragment E | 0.0334 | 0.0516 | 0.6473 | 1.5449 | 103.2 ng/μl |
| Fragment H | 0.0035 | 0.0068 | 0.5088 | 1.9655 | 13.6 ng/μl |

3.3 Cloning of Fragment E Into the Yellow Fever Vector

The capsid-prME fusion was cloned into the yellow fever plasmid needed, and after digestion of the purified Fragment E, as well as pYF5'3'IV, with the appropriate enzymes. The digested plasmid resulted in two bands. Lower bands seen contain a fragment of Japanese encephalitis virus equivalent to Fragment E. All restriction enzymes, buffers, and 100× BSA were from New England Biolabs. All the digestions were incubated in a Perkin-Elmer 480 cycler set to hold at 37° C. overnight.

| Fragment E Digest | |
|---|---|
| Fragment E (600 ng) | 5.8 μl |
| NEB Buffer 4 | 4 μl |
| 10× BSA | 4 μl |
| $H_2O$ | 24.2 μl |
| Not I | 1 μl |
| Nhe I | 1 μl |
| Volume | 40 μl |

| pYFMIV5'3' Digest | |
|---|---|
| pYFMIV5'3' (1.02 μg) | 2 μl |
| NEB Buffer 4 | 2 μl |
| 10× BSA | 2 μl |
| $H_2O$ | 12 μl |
| Not I | 1 μl |
| Nhe I | 1 μl |
| Volume | 20 μl |

3.4 Vector Dephosphorylation

Calf Intestinal Phosphatase (CIP) from New England Biolabs (cat#290S) was diluted 1:10 in 1×CIP Buffer. One μl of this dilution was then added to the pYFMIV5'3' digest, and incubated for 1 hour at 37° C. Then, 0.8 μl 125 mM EDTA was added to the tube, which was placed at 75° C. for 10 minutes to deactivate CIP.

3.5 Gel Excision

The digested fragment E and the digested plasmid were separated on a 1.0% Agarose/TAE gel, and were purified using the QIAquick Gel Extraction Kit (Qiagen cat#28704).

3.6 Ligations

The digested Fragment E and pYF5'3'IV were ligated using T4 DNA Ligase (New England Biolabs cat#202S) to create pYD1-5'3'. All ligation reactions were incubated in a Perkin-Elmer 480 cycler set to hold at 16° C. overnight.

| PYD1-5'3' Ligation | |
|---|---|
| Fragment E (97.5 ng) | 12.8 μl |
| pYFM5'3' (50 ng) | 3.0 μl |
| $H_2O$ | 1.2 μl |
| 10× T4 ligase buffer | 2 μl |
| T4 DNA ligase | 1 μl |
| Volume | 20 μl |

| pYFM-5'3' Control Ligation | |
|---|---|
| Fragment E (97.5 ng) | 0 μl |
| pYFM5'3' (50 ng) | 3.0 μl |
| $H_2O$ | 14 μl |
| 10× T4 ligase buffer | 2 μl |
| T4 DNA ligase | 1 μl |
| Volume | 20 μl |

3.7 Transformations

Ligation reactions were individually transformed into *E. coli* strain MC1061 (recA–). Briefly, an aliquot of MC1061 was removed from storage at –80° C. and allowed to thaw on ice for one to two minutes. 0.9 ml of cold 0.1 M $CaCl_2$ was added to the cells. One hundred μl of cells was aliquoted into three 12 ml culture tubes on ice. Ten μl of each ligation reaction was added to each culture tube, leaving the third tube as a no DNA control. Culture tubes were left on ice for 30 minutes. The tubes were heat shocked in a water bath at 42° C. for 45 seconds, and then were put back on ice for 2 minutes. 0.9 ml SOC medium was added to each culture tube and incubated at 225 pm in a shaking incubator at 37° C. for 1 hour. Each transformation mix was aliquoted into 1.5 ml microcentrifuge tubes. One hundred μl of each mix was spread onto LB/Agar-Amp (100 μg/ml) plates and labeled as "neat." Each tube was spun at 14,000 rpm in a microcentrifuge for 2–3 seconds to pellet the cells. The supernatant was poured into the waste container and the pellet resuspended in the residual broth by pipetting up and down. This material was plated (approximately 100 μl) onto LB/Agar-Amp (100 μg/ml) plates and labeled as 10×. All plates were inverted in a 37° C. incubator overnight.

3.8 Transformant Screening

Resulting bacterial colonies were patch-plated onto fresh LB/Agar-Amp (100 μg/ml) and placed inverted in a 37° C. incubator overnight. The following day, 50 μl of RODI-water was aliquoted into 0.5 ml tubes. Using a sterile plastic pick, a small amount of each patch was scraped into one of the 0.5 ml tubes containing water. These were then placed at 95° C. for 10 minutes, and spun at 14,000 rpm for 10 minutes in a microcentrifuge. To identify the proper insert in pYD1-5'3', colonies were screened by PCR using Taq Polymerase (Promega) and primers 4 and 10. The PCR reaction was performed using the following master mix.

| Component | 4 rxs | 10 rxns | 15 rxns | 20 rxns | 25 rxns | 30 rxns |
|---|---|---|---|---|---|---|
| RODI-water | 161.5 μl | 355.5 μl | 516.8 μl | 678.3 μl | 839.8 μl | 1001.3 μl |
| $H_2O$ | 25 μl | 55 μl | 80 μl | 105 μl | 130 μl | 155 μl |
| $MgCl_2$ | 10 μl | 22 μl | 32 μl | 42 μl | 52 μl | 62 μl |
| P1 (100 μM) | 1 μl | 2.2 μl | 3.2 μl | 4.2 μl | 5.2 μl | 6.2 μl |

-continued

| Component | 4 rxs | 10 rxns | 15 rxns | 20 rxns | 25 rxns | 30 rxns |
|---|---|---|---|---|---|---|
| P2 (100 μM) | 1 μl | 2.2 μl | 3.2 μl | 4.2 μl | 5.2 μl | 6.2 μl |
| dNTPs (10 mM) | 40 μl | 88 μl | 128 μl | 168 μl | 208 μl | 248 μl |
| Taq polymerase | 1.5 μl | 3.3 μl | 4.8 μl | 6.3 μl | 7.8 μl | 9.3 μl |

Forty eight μl of each master mix was added to a 0.5 ml tube along with 5 μl of the template prepared from the colony patches. Additionally, a tube using RODI-water as a template was also made as a negative control. These tubes were then placed in the Ericomp Delta Cycler and cycled as follows: 96° C., 4 minutes; 30× (94° C., 30 seconds; 50° C., 1 minute; 72° C., 1 minute 25 seconds), 72° C., 4 minutes; 4° C., Hold. The PCR products were then run on 1.5% Agarose/TAE gels to check for positive colonies.

3.9 Glycerol Stocks

One hundred twenty ml of LB-Amp (100 μg/ml) was then inoculated from a patch pYD1-5'3'/2 and shaken at 225 rpm overnight at 37° C. Two×1 ml of this culture was then spun at 14 Krpm for 2–3 seconds to pellet the cells. These were resuspended in LB-Glycerol (30%) and frozen at −80° C.

3.10 MIDI Plasmid Preparation

Qiagen Midi-Prep was performed on the remaining culture using the following modified protocol.

1. Spin 150 ml of each culture at 7 Krpm in GSA rotor for 10 minutes to pellet.
2. Decant Supernatant
3. Resuspend pellet in 4 ml P1 buffer; Transfer to 50 ml Falcon tube.
4. Rinse centrifuge bottle with 1 ml P1 buffer and transfer to the Falcon tube.
5. Add 5 ml P2 buffer; invert gently; incubate 5 minutes at room temperature or until lysed (no more than 12 minutes).
6. Add 5 ml P3 buffer; mix as above; incubate 10 minutes on ice.
7. Transfer supernatant to Qiagen Syringe Filter; Let sit for 10 minutes.
8. Equilibrate Q-100 tip with 4 ml QBT.
9. Gently push plunger to filter supernatant onto Q-100 tip.
10. Allow to drain by gravity.
11. Wash with 10 ml 2×QC.
12. Elute into 50 ml polypropylene centrifuge tube with 5 ml QF.
13. Add 14 ml 100% EtOH (or 8 ml isopropanol); Place in dry ice/ethanol bath for 10 minutes (or at −20° C. for 2 hours or at 4° C. overnight).
14. Spin at 15 K×G for 30 minutes at 4° C.
15. Wash with 5 ml 70% ethanol; Spin 15 K×G for 20 minutes.
16. Air Dry.
17. Resuspend in 150 μl EB.

| Sample | A280 | A260 | 280/260 | 260/280 | Concentration |
|---|---|---|---|---|---|
| pYD1-5'3'/2 | 0.1708 | 0.3010 | 0.5675 | 1.7621 | 602 μg/ml |

3.11 In Vitro Ligation to Create Full-length cDNA Chimeric Template and RNA Production Digestion With AatII and BstBI The plasmid and fragment H were then digested with Aat II and BstB I (NEB) in a sequential digest as follows.

| pYD1-5'3'/2 (AatII digest) | |
|---|---|
| pYD1-5'3'/2 (10 μg) | 16.6 μl |
| Buffer 4 (NEB) | 5 μl |
| Aat II (NEB) | 4 μl |
| $H_2O$ | 24.4 μl |
| Volume | 50 μl |

| Fragment H (AatII digest) | |
|---|---|
| Fragment H (0.7 μg) | 51.0 μl |
| Buffer 6 (NEB) | 5 μl |
| Aat II (NEB) | 3 μl |
| $H_2O$ | 0 μl |
| Volume | 60 μl |

Both reactions were incubated in a 37° C. block overnight. Five μl of each digestion was run out on a 1.5% Agarose/TAE gel to check for complete digestion. The digestion was then incubated at 65° C. for 20 minutes to inactivate the enzyme. 2.5 μl Bst BI (NEB) was added to each reaction and placed at 65° C. overnight. The expected results of the digest are as follows:

| pYD1-5'3'/2 | Fragment H |
|---|---|
| 5.6 kb | 7.2 kb |
| 0.14 kb | 0.1 kb |

The largest band from each reaction was gel excised and the UV concentration was determined (as previously described).

| Sample | A280 | A260 | 280/260 | 260/280 | Concentration |
|---|---|---|---|---|---|
| pYD1-5.2 fragment | 0.0089 | 0.0154 | 0.5777 | 1.7309 | 30.8 ng/μl |
| Fragment H | 0.0020 | 0.0018 | 1.1333 | 0.8824 | 3.6 ng/μl |

There was not enough fragment H for the ligation. Another 50 μl of fragment H was cleaned over a Qiagen Qiaquick column and digested with Aat II and Bst BI as described previously. The digested fragment was then gel excised as before and the UV concentration determined.

| Sample | A280 | A260 | 280/260 | 260/280 | Concentration |
|---|---|---|---|---|---|
| Fragment H | 0.0000 | 0.0021 | 0.0000 | NA | 4.2 ng/μl |

3.12 Precipitation of Fragments

The following was prepared in a 1.5 ml tube.

| | |
|---|---|
| pYD1-5'3'/2 fragment (298 ng) | 9.7 μl |
| Fragment H (3.6 ng/μl) | 38 μl |
| Fragment H (4.2 ng/μl) | 32 μl |
| Water | 20.3 μl |
| Volume | 100 μl |

The fragments were then ethanol precipitated and resuspended in 43.5 μl of water to facilitate the ligation reaction.

3.13 Ligation

The following ligation reaction was setup using high concentration T4 DNA ligase (NEB). The ligations were incubated at 16° C. overnight.

| | |
|---|---|
| Precipitated fragments | 43.5 μl |
| 100× BSA (NEB) | 0.5 μl |
| T4 DNA ligase buffer (NEB) | 5 μl |
| *T4 DNA ligase | 1 μl |
| Volume | 50 μl |

*heat reaction at 37° C. for 5 minutes, then briefly chill on ice before adding ligase 3.14 Linearization of Template The ligation was heat inactivated at 65° C. for 10 minutes. The ligated material was then linearized at the 3' end of the Yellow Fever sequence to allow proper RNA transcription. 5.5 μl of Buffer 2 (NEB) was added to the ligation, followed by 1.5 μl XhoI (NEB), and then the reaction was put at 37° C. for 2 hours.

3.15 Linear cDNA Extraction (RNAse Free Phase)

1. Add $H_2O$ to 100 μl total volume.
2. Add 1/10$^{th}$ volume 3 M Sodium Acetate
3. Add 100 μl Phenol/Chloroform/Isoamyl Alcohol and spin at 14 Krpm for 5 minutes in a microcentrifuge. Extract upper layer into RNAse-free 1.5 ml tube. Repeat once.
4. Add 100 μl RNAse-free Chloroform. Spin at 14 Krpm for 5 minutes in a microcentrifuge. Extract upper layer into RNAse-free 1.5 ml tube. Repeat once.
5. Add 200 μl 100% RNAse-free ethanol.
6. Place on dry-ice/ethanol bath for 10 minutes.
7. Spin at 14 Krpm for 20 minutes in a microcentrifuge.
8. Wash with 200 μl 70% ethanol (RNAse-free).
9. Repeat 70% ethanol wash two more times.
10. Dry in Speed-Vac for 8 minutes (or until no more ethanol-is present).
11. Resuspend in 22 μl nuclease free water from the SP6 kit listed below.

3.16 SP6 Transcription

The following reaction was setup using the SP6 transcriptase kit (Epicentre) and Rnasin (Promega) in an RNAse-free 1.5 ml tube using RNAse-free tips in a BL-2 hood. The reaction was then placed in a 40° C. water bath for 1 hour.

| | |
|---|---|
| Capping NTP solution | 6 μl |
| 10× buffer | 2 μl |
| 20 mM Cap Analog | 3 μl |
| 100 mM DTT | 2 μl |
| Linearized DNA | 5 μl |
| Rnasin | 0.5 μl |
| SP6 transcriptase | 2 μl |
| Volume | 20.5 μl |

3.17 Transfection With RNA

Three six well tissue culture plates were seeded with Vero-PM cells (p#162 from Cell Culture Facility) (2 plates at 1×10$^6$ cells/well and 1 plate at 2×10$^6$ cells/well) in growth media (Minimum Essential Media, Sodium Pyruvate, Non-Essential Amino Acids, Penicillin/Streptomycin, and 5% Fetal Bovine Serum) and placed in a 37° C. $CO_2$ incubator until confluent.

The following transfection reactions were made using Lipofectin (Life Technologies) and RNAse-free PBS (Sigma).

| YF/DEN-1 | |
|---|---|
| PBS | 250 μl |
| Lipofectin | 20 μl |
| YF/DEN-1 RNA | 10 μl |
| Volume | 280 μl |

| Total RNA control | |
|---|---|
| PBS | 250 μl |
| Lipofectin | 20 μl |
| YF/JE total RNA | 10 μl |
| Volume | 280 μl |

| Lipofectin control | |
|---|---|
| PBS | 260 μl |
| Lipofectin | 20 μl |
| Volume | 280 μl |

1. Allow reactions to sit at room temperature for 10 minutes, and then remove Media from the six well plates.
2. Wash 3 times with PBS.
3. Remove last of PBS.
4. Overlay with each lipofectin reaction (add the YF/DEN-1 RNA to the 2×10$^6$ cells/well plate). Add 280 μl media to the remaining wells.
5. Rock for 10 minutes at room temperature.
6. Wash 2 times with media.
7. Add 2 ml of media to each well and place in the 37° C. $CO_2$ incubator for 4 days or more.

3.18 Harvest of the First Vero-PM Passage (P1)

The supernatant from YF/DEN-1 was harvested on day 6 by splitting the 2 ml of supernatant between two cryovials (each containing 1 ml FBS) that were labeled YF/DEN-1 (PCR) (P1). The cell monolayer was harvested with 1 ml Trizol into a 1.5 ml tube. All vials and tubes were then placed at −80° C.

3.19 Amplification of YF/DEN-1

Vero-PM Passage #2

1. Three T-25 flasks containing Vero-PM cells (p#166) were obtained from the Cell Culture Facility. A frozen aliquot of YF/DEN-1 (PCR) (P1) was removed from the −80° C. freezer, thawed, and then placed on ice. The same was done for an aliquot of YF/JE (frozen stock from the P1 control transfection) to be used as a control.
2. Media was removed from each T-25 flask.
3. One ml of YF/DEN-1 (PCR) (P1) was added to the first flask, 1 ml of media only (the same as was used in the transfection) was added to the second flask, and 1 ml of YF/JE(P1) was added to the third flask.
4. Each flask was then put in the 37° C., 5% $CO_2$ incubator for 1 hour with rocking every 10 minutes.
5. Four ml of media was then added to each flask.
6. The flasks were then placed in the 37° C., 5% $CO_2$ incubator for 4 days.

Harvest P2 and Passage #3

1. The supernatant from YF/DEN-1 flask was harvested on day 7.
2. Five hundred ml of YF/DEN-1 (P2) was harvested and subsequently overlayed onto a T-25 flask containing Vero-PM cells (p#168 from the Cell Culture Facility).
3. Five hundred ml of media (same as used for transfection) was added to the monolayer.
4. One ml of media only was added to a control flask.
5. The flasks were placed in a 37° C. $CO_2$ incubator and rocked every 15 minutes for 1 hour.
6. Meanwhile, the remaining YF/DEN-1(P2) was harvested into 4 cryovials containing 1 ml FBS and 1 cryovial containing 0.5 ml FBS and labeled as YF/DEN-1(P2). The cell monolayer was harvested with 3 ml Trizol into 1.5 ml tubes. All vials were placed at −80° C. in a box labeled YF/DEN-1.
7. After infection (Step 5), 4 ml of media was added to each flask and were transferred to the incubator for 4 or more days.

Harvest of P3

The supernatant from YF/DEN-(P3) was harvested on day 5 by splitting the 5 ml of supernatant between five cryovials (each containing 1 ml FBS), which were labeled YF/DEN-1 (P3). The cell monolayer was harvested with 3 ml Trizol into 1.5 ml tubes. All vials and tubes were then placed at −80° C.

3.20 Virus Identification

The RNA from P3 was extracted using Trizol methods according to the manufacturer's protocol, RT-PCR was performed followed by sequencing of the YF/DEN-1 prME region 5', 3'junctions, inclusive. The expected sequence of the prME region was confirmed.

4.0 Construction of CHIMERIVAX-DEN3™ (Chimeric Flavivirus Comprising Dengue 3 Virus and preM and E Proteins)

A viable yellow fever/dengue type 3 chimera (YF/DEN3) was constructed that contains the pre-membrane (prM) and envelope (E) genes of dengue type 3 virus (DEN3) replacing the corresponding prM-E region of the genome of the attenuated 17D yellow fever virus (YF). Virion RNA of wild-type DEN3 (strain PaH881/88) was used as a template to synthesize by RT-PCR two cDNA fragments that cover the DEN3 prM-E region. These fragments were cloned and sequenced. A modified protocol was used to prepare infectious YF/DEN3 in vitro RNA transcripts in which three appropriate DNA fragments were ligated in vitro followed by linearization with XhoI and in vitro transcription with SP6 RNA polymerase (standard ChimeriVax protocol employs two-fragment ligation). Following transfection of Vero PM cells with the RNA transcripts, virus-specific CPE was detectable as early as on day 5 post-transfection (and on day 3 post-infection in subsequent passages). The presence of the chimeric virus in the post-transfection (postinfection) media and the DEN3-specificity of its prM-E region were confirmed by RT-PCR and sequencing.

These results demonstrate that a chimeric YF virus containing DEN3-specific envelope is readily recoverable. The obtained YF/DEN3 chimera is a candidate part of our proposed tetravalent vaccine directed against all four dengue virus serotypes (dengue types 1–4).

The purpose of these experiments was to determine whether it is possible to create a viable YF/DEN3 chimera containing DEN3-specific envelope. At the same time, the proposed chimera was designed to contain the prM-E region from a pathogenic wild type strain of DEN3 (a prerequisite for high immunogenicity) in a backbone of the 17D vaccine strain of YF that includes the 5' and 3' UTRs, the C gene, and the nonstructural protein genes, NS1-5, (a prerequisite for safety).

Figure 29:
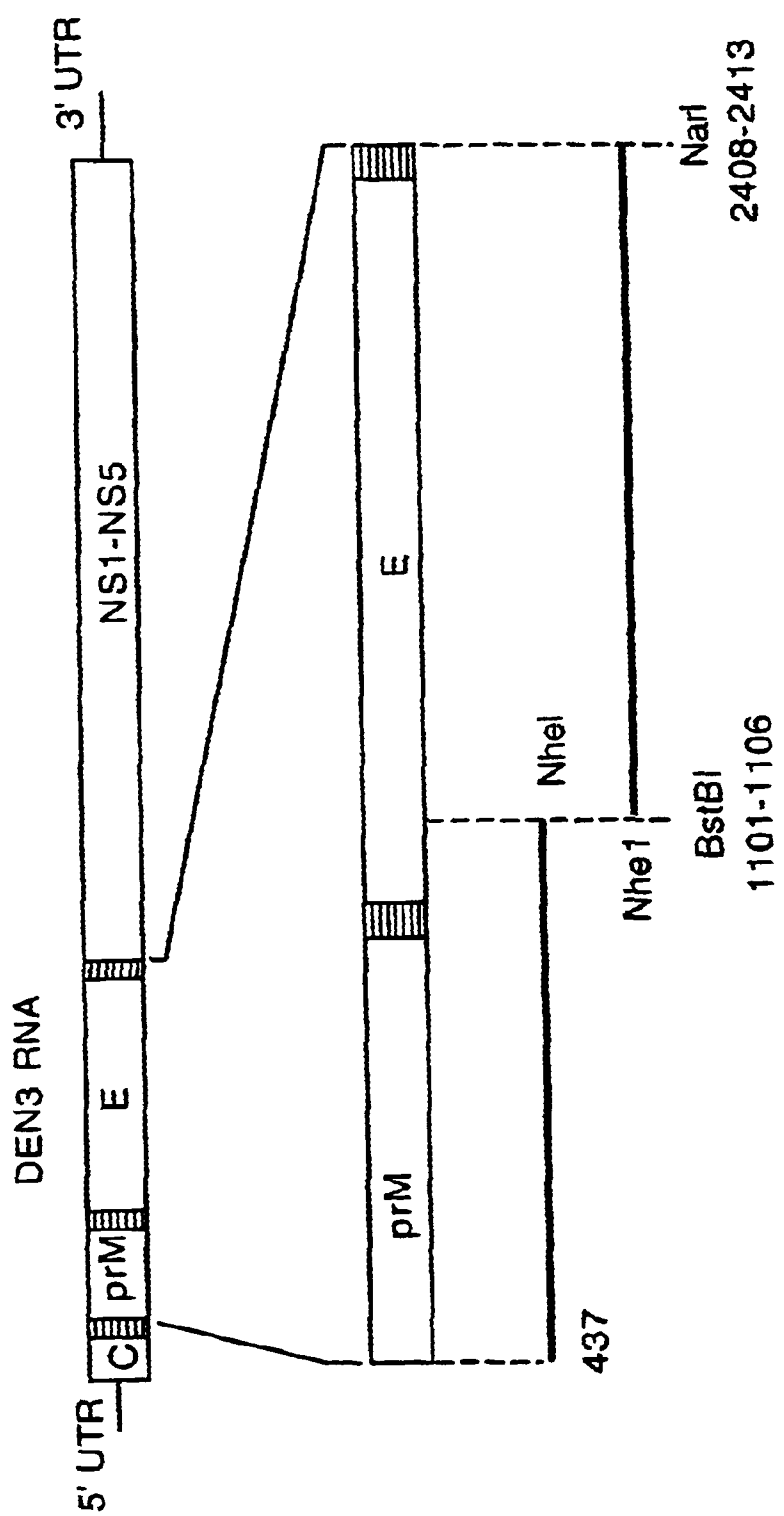
FIG. 29 is a schematic representation of RT-PCR amplification of the prM-E region of the PaH881/88 DEN3 virus genome. The virus genome is shown on the top diagram. Regions encoding hydrophobic signals for corresponding downstream proteins are shadowed. The prM-E region was amplified in two fragments (black solid lines). Restriction sites introduced for subsequent in-frame in vitro ligation into YF backbone (BstBI and NarI) and cloning (NheI) are indicated.

To engineer a YF/DEN3 chimera containing the prM-E cassette from DEN3 in place of the prM-E cassette of YF we first wanted to use the two-plasmid approach that was successful in previous studies where 17D YF virus (Rice et al., New Biol. 1:285–296, 1989) and the YF/JE chimera (Chambers et al., J. Virol. 73:3095–3101, 1999) were recovered following in vitro transcription and transfection. The DEN3 (strain PaH881/88) prM-E region was RT-PCR amplified in two adjacent fragments (FIG. 29). To determine consensus sequence of this region of the parental virus, the RT-PCT fragments were directly sequenced in both directions. Since oligonucleotide primers used to synthesize these fragments were designed based on the published sequence of the H87 reference strain of DEN3 (Osatomi et al., Virology 176:643–647, 1990), actual viral sequences in the primer areas (at the beginning of prM, nucleotides 437–459; at the junction between the two fragments, nucleotides 1079–1131; and at the end of E, nucleotides 2385–2413) could not be determined. A total of 83 nucleotides changes were found compared to H87 strain. The rate of nucleotides differences, 4.44%, was similar to that (4.5%) reported previously by Delenda et al. (J. Gen. Virol. 75:1569–1578, 1994) who sequenced roughly 80% of PaH881/88 E gene. Although the majority of nucleotides differences in the 80% E area coincided with those found by Delenda et al. (V. Deubel, personal communication) (53 changes coincided), there were 4 additional changes that were not found by Delenda et al. In addition, we did not observe 3 of the changes reported by these authors. The PaH881/88 virus (a starting material in our experiments) was isolated from a patient by single amplification in mosquito AP61 cells. We propagated this virus in C6/36, another mosquito cell line. Sequences of both our P1 and P3 viruses were found to be identical indicating that there was no selective pressure on the virus in C6/36 cells. Therefore, it is more likely that the few discrepancies were due to sequencing mistakes in (Delenda et al., J. Gen. Virol. 75:1569–1578, 1994). They resulted in three discrepancies in the amino acid sequence of the corresponding region of E protein (C-terminally truncated E; compare Table 32 below with Table 1 in Delenda et al., J. Gen. Virol. 75:1569–1578, 1994). A complete list of amino acid differences we found in the prM-E region between the H87 and PaH881/88 strains is given in Table 33 (a total of 12 changes).

Figure 30:
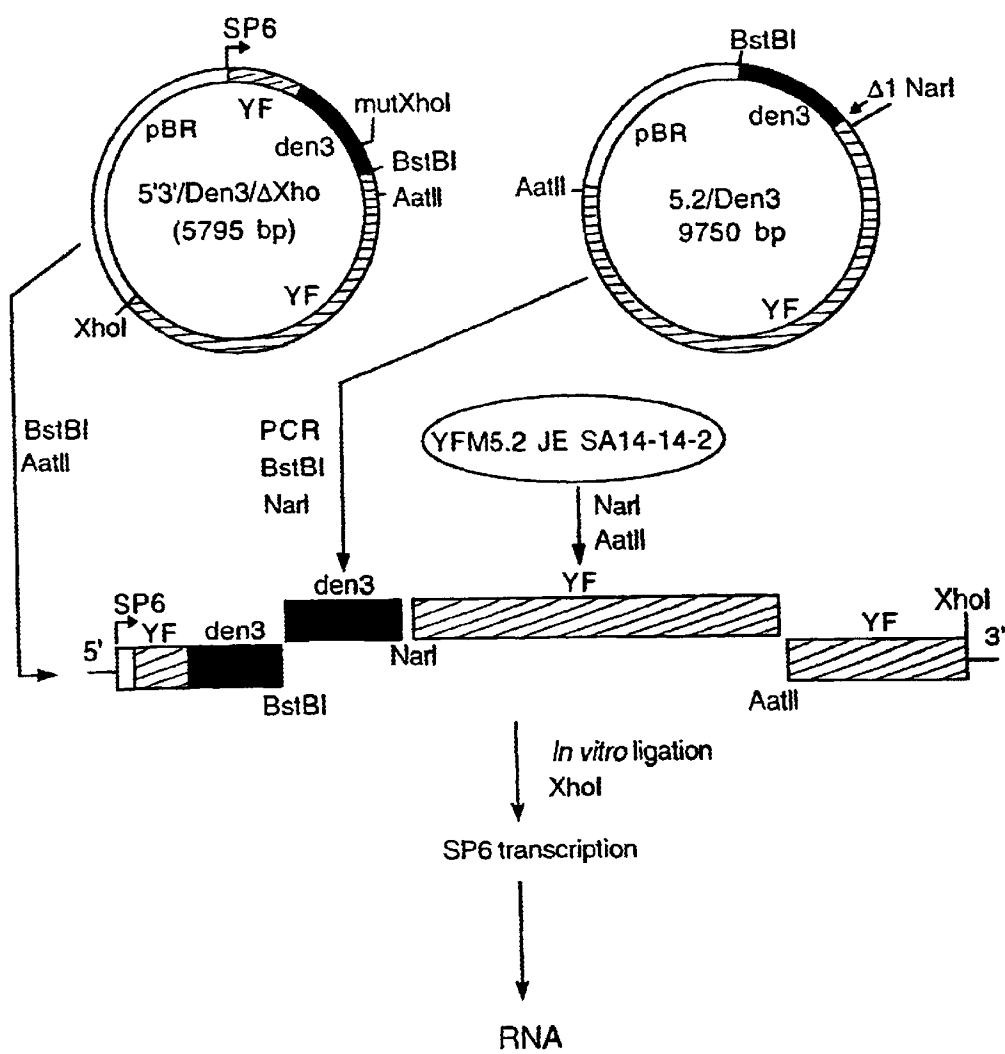
FIG. 30 is a schematic representation of construction of a YF/DEN3 chimera of the invention. YF- and DEN3-specific sequences are shown as shadowed and black boxes, respectively. The chimeric YF/DEN3 genome was reconstituted by in vitro ligation of three fragments: the large BstBI-AatII portion of 5'3'/Den3/DXho plasmid, a PCR fragment containing the DEN3-specific part of 5.2/Den3 without the one nucleotide deletion (D1) digested with BstBI and EheI (an isoschizomer of NarI), and the large EheI-AatII fragment of YFM5.2 JE SA14-14-2. Ligation products were linearized with XhoI and then transcribed in vitro with SP6 RNA polymerase. Vero PM cells were transfected with in vitro RNA transcripts to recover the chimeric virus.

The RT-PCR fragments were used to replace corresponding JE-specific sequences in YFM5'3'IV JE SA14-14-2 and YFM5.2 JE SA14-14-2 plasmids, which resulted in 5'3'/DEN3 and 5.2/Den3 plasmids (FIG. 30). Inserts of both plasmids were sequenced. Since an extra XhoI site was found in the DEN3-specific region of 5'3'/Den3, the site was ablated by silent mutagenesis that resulted in 5'3'/Den3/DXho plasmid. The insert of this plasmid was also sequenced to ensure the absence of mutations introduced by PCR.

Difficulties were encountered in obtaining high quality 5.2/Den3 plasmid without mutations within its DEN3-specific region. Different growth conditions of plasmid-containing cultures and modifications in the extraction protocol (e.g., reduction of alkali concentration in the lysis buffer), as well as growth of the plasmid in different *E. coli* strains were examined to overcome these difficulties. Finally, a clone of the plasmid (#26) was selected (propagated in ABLE C cells) that was of high quality and contained no nucleotide changes except for a single one nucleotide deletion at the 3' end of the DEN3 insert which could be easily eliminated by PCR (other sequenced clones contained more mutations). Therefore, the standard ChimeriVax procedure for preparation of infectious in vitro RNA transcripts that employs two fragment ligation prior to in vitro transcription was modified. According to the standard protocol, the large BstBI-AatII fragment from 5.2/Den3 would be ligated with the large BstBI-AatII fragment of 5'3'/Den3/DXho (see in FIG. 30). Instead, to correct the deletion, three-fragment ligation was done (FIG. 30). The DEN-3 part of 5.2/Den3 was PCR-amplified on the #26 clone template with high-fidelity LA Taq polymerase and digested with BstBI and EheI (isoschizomer of NarI). The opposite PCR primer was expected to correct the deletion. Second fragment, corresponding to the NarI-AatII part of 5.2/Den3, was derived by digestion of YFM5.2 JE SA14-14-2 with EheI and AatII. The two fragments were ligated with the large BstBI-AatII fragment of 5'3'/Den3/Xho. Ligation products were digested with XhoI and transcribed in vitro with SP6 RNA polymerase.

Vero PM cells (at passage 149) grown in 6 well plates were transfected with the in vitro RNA transcripts. A first indication that the expected YF/DEN3 chimera was present was the appearance of CPE characteristic of other chimeras created to date based on the YF backbone. It was first noticeable :on day 5 post-transfection and became apparent (~10% of detached and rounded cells) on day 7 when virus-containing medium was harvested (P1). Subsequent P2 and P3 viruses were obtained by infecting fresh monolayers of Vero PM cells (at passages 150 and 151, respectively) with the P1 and P2 viruses (1 and 0.5 ml of the viruses were used for each infection, respectively) and harvesting the virus when apparent CPE (~10%) was observable (on days 3 and 4 for P2, and day 3 for P3).

The presence and DEN3-specificity of the YF/DEN3 chimera was confirmed by RT-PCR with YF- and/or DEN3-specific primers using P1 and P2 virion and intracellular RNAs as templates. All these reactions yielded specific RT-PCR products of expected sizes. As was expected, when DEN3-specific primers were used for RT-PCR on a control YF/JE RNA template, no product was recovered. The entire prM-E region of the P2 virus was sequenced. This also confirmed that the chimera contained the DEN3 envelope glycoprotein genes. In addition to the silent mutation introduced to ablate the XhoI site in the E gene, only one more silent nucleotide change was detected in the virus (A G at nucleotide 2341 in the chimeric genome that corresponds to nucleotide 2296 in the parental DEN3). Since one of the DNA fragments used in the three-fragment ligation was synthesized by PCR (albeit on a plasmid template with known sequence), it is possible that the P1-3 viruses described here contain minor subpopulations with mutations introduced by PCR. To ensure homogeneity, these viruses can be plaque-purified and then sequenced. In addition, we are currently developing alternative cloning techniques that, if necessary, will allow recreation of the YF/DEN3 genome without using the intermediate PCR step. For instance, the DEN3-specific BstBI-NarI fragment of 5.2/Den3 plasmid was recently cloned without any mutations in low-copy number vectors (pCL and pACYC series). This fragment can be excised from the new plasmids and used instead of the PCR fragment in the three-fragment ligation to regenerate the chimera.

In conclusion, the prM-E region of the PaH881/88 DEN3 was sequenced and cloned. We demonstrate that a recombinant flavivirus genome (e.g., YF/DEN3 in this study) can be reconstituted in vitro by using three-fragment ligation (instead of two-fragment ligation used previously to create other YF chimeras). This approach can be helpful in overcoming technical difficulties that are often encountered during cloning of genetic material from many flaviviruses in *E. coli* (especially dengue viruses). A viable 17D YF/DEN3 chimeric virus was recovered which is yet another successful example of the usefulness of the approach developed by Chambers et al. (J. Virol. 73:3095–3101, 1999; see above), in which the prM-E cassette of a heterologous flavivirus is inserted into the YF backbone such that the hydrophobic signal for prM remains YF-specific.

The materials and methods used to make and characterize the YF/DEN3 chimera are described as follows.

4.1 Virus and Cells

DEN3 strain PaH881/88 was isolated from a patient by single amplification in AP61 (mosquito) cells. C6/36 cells were maintained in MEM (Gibco, Cat. #11095–072) supplemented with 10% FBS (HyClone, Cat. #SH30070103) and 1×non-essential amino acids (Sigma, Cat. #M7145) (OraVax ML-8 medium, Lot #108H2308) at 28° C. under 5% $CO_2$. DEN3 was passaged two times by infecting monolayers of C6/36 at an unknown MOI and harvesting virus-containing growth media on day 7 post-infection (P1 and P2) and one time by infecting C6/36 cells with the P2 virus at an MOI of ~0.01 pfu/cell and harvesting the medium on day 6 (P3; pronounced virus-specific CPE was observed in P3). Virus-containing media were mixed with an equal volume of FBS, aliquoted and stored at 70° C. Following transfection/infection, Vero PM cells were maintained in MEM (Gibco, Cat. #11095–080, Lot #1017611) supplemented with 5% heat-deactivated FBS (OraVax Lot #AGE6578) and penicillin/streptomycin (100 U/0.1 mg per ml; Sigma, Cat. #P-0781, Lot #78H2386) at 37° C. under 5% $CO_2$.

4.2 RNA Extraction

DEN3 virion RNA was extracted from 0.5 ml of clarified P3 virus-containing medium using TRI Reagent-LS (Molecular Research Center, Inc., Cat. #TS-120) according to the manufacturer's procedure and redissolved in 10 $\mu$l $H_2O$. Alternatively, (e.g., to confirm the presence of YF/DEN3 chimera), intracellular RNA from infected cells was extracted using TRI Reagent (Molecular Research Center, Cat. #TR-118).

4.4 Reverse Transcription, PCR, and Sequencing

First strand cDNA syntheses were done in a total volume of 20 μl using 2.5 μl of DEN3 virion RNA as a template, indicated oligonucleotide primers (see below) and SuperScript II reverse transcriptase (Gibco, Cat. #18064-014) according to the manufacturer's procedure. Prior to PCR, RT products were treated with RNAse H (Promega). High-fidelity PCR on RT products or indicated plasmid DNAs as templates was done using the GeneAmp XL PCR kit (Perkin Elmer, Cat. #N808-0192), or the TaKaRa LA Taq polymerase kit (Pan Vera, Cat. #TAK RR002M) according to the protocols provided by the kit manufacturers with a GeneAmp 2400 thermnocycler (Perkin Elmer). Sequencing of indicated PCR products or plasmid DNAs was done using the ABI Prism dRhodamine Terminator Cycle Sequencing kit (Perkin Elmer, Cat. #403042). Sequencing reaction products were resolved with ABI Prism 310 automated sequencer (Perkin Elmer). Data were analyzed using Sequencher 3.0 software and stored on the Internet (ORAVAX/VOLTEMP/GROUPS/LABTECH/KOSTIA/folder "KP sequencing data"/Exp.##). With each area of interest, both DNA strands were sequenced and analyzed. Oligonucleotide primers are listed in Table 32.

Primers were ordered from Custom Primers (Life Technologies/GibcoBRL). In the names of primers, numbers indicate approximate localization of oligos on the DEN3 genome and "+/−" indicates orientation of each primer, with the following exceptions: oligo 5 is colinear with a region of YFM5'3' series of plasmids upstream from the NotI cloning site; oligos 6 (opposite) and 7 (direct) are YF-specific; the former corresponds to the end of YF C gene; oligos 15 (direct) and 16 (opposite) were designed for amplification and sequencing of inserts in the YFM5.2 series of plasmids and correspond to regions of the plasmids located within ~60 nucleotides upstream and downstream from the corresponding inserts, respectively; oligo 8 (direct) was used to mutate the XhoI site at nucleotide 1052 of the recombinant YF/DEN3 genome (within 5'3'/Den3 plasmid); and oligo 17 is colinear with the SP6 promoter and a few of the 5' terminal nucleotides from YF.

4.3 DNA Manipulations

Standard molecular biology techniques were in accordance with Maniatis et al., Molecular Cloning: a Laboratory Manual, 2$^{nd}$ Edn. Cold Spring Harbor Laboratory Press, Cold Spring Harbor, N.Y., 1992. All restriction enzymes, except for EheI (Fermentas) and T4 DNA ligase, were from New England Biolabs.

4.4 Construction of 5'3'/Den3/DXho Plasmid

The 5' terminal part of the DEN3 prM-E region was synthesized on purified virion RNA of the P3 virus by RT-high-fidelity PCR (XL PCR) using oligonucleotide primers 1 and 2. It starts precisely at the beginning of the coding region for prM protein (at nucleotide 437; DEN3 nucleotide numbering is according to the sequence of H87 reference strain (Osatomi et al., Virology 176:643–647, 1990)) that is generated by signalase and ends at nucleotide 1106 and thus contains the entire prM and approximately one-seventh of the E gene. In addition to DEN3 sequences, the resulting RT-PCR product contains the last 23 nucleotides of the YF C gene for subsequent overlapping PCR (at its 5' end). The last six nucleotides of DEN3 sequence (nucleotides 1101–1106) are changed to a BstBI site by introduction of three silent nucleotide changes for subsequent in vitro ligation, which is followed by a NheI site for cloning.

To combine the RT-PCR product with the upstream YF-specific sequences, a fragment of YFM5'3'IV JE SA14-14-2 plasmid (an analog of 5'3'/Den3 plasmid used to generate a similar YF/JE chimera (Chambers et al., J. Virol. 73:3095–3101, 1999; see above)) containing SP6 RNA polymerase promoter followed by the 17D YF 5' UTR and C gene (first 481 nucleotides of YF genome) was amplified by XL PCR with oligos 5 and 6. For overlapping PCR, the resulting DNA fragment was mixed with the RT-PCR product and XL PCR amplified with oligos 2 and 5. Consensus sequence of the dengue type 3 region was determined by sequencing the RT-PCR and the overlapping PCR products in both directions using oligos 1, 2, 5, 7, 9, and 10.

The overlapping PCR product was used to replace the short NotI-NheI fragment in YFM5'3'IV JE SA14-14-2. The replaced region of the resulting 5'3'/Den3, which is a pBR322-based plasmid maintained in *E. coli* MC1061RecA- cells, was sequenced using oligos 1, 2, 9, 10, and 17, and a correct clone (#3) was selected, which does not have any mutations compared to the consensus sequence.

Sequencing revealed that the DEN3-specific portion of 5'3'/Den3 contains an additional XhoI site located in the beginning of E gene (nucleotides 1007–1012 in DEN3 genome). Another XhoI site used for linearization prior to in vitro transcription (see below) is located at the end of YF sequence in 5'3'/Den3. The additional site was destroyed by silent oligonucleotide-directed mutagenesis (LA PCR; DEN3-specific C at nucleotide 1009 was changed to G) using oligo 8, resulting in a plasmid 5'3'/Den3/DXho. The entire region of the plasmid replaced during mutagenesis was sequenced with oligos 1, 2, 9, 10, and 17 and a clone (#10) was selected that does not have any mutations, except for the desired C to G nucleotide change.

4.5 Construction of 5.2/Den3 Plasmid

The 3' terminal part of DEN3 prM-E region was RT-PCR amplified (XL PCR) on the P3 virion RNA template using primers 3 and 4. It starts with BstBI site introduced at nucleotides 1101–1106 for in-frame ligation with 5'3'/Den3/DXho plasmid and ends with a NarI site introduced precisely at the 3' end of E gene (nucleotides 2408–2413) for in-frame ligation with YF NS1. The NarI site that leads to Q to G change of the penultimate amino acid residue in the DEN3 E was used previously to generate YF/JE chimera (Chambers et al., J. Virol. 73:3095–3101, 1999; see above). An NheI cloning site was placed upstream from the BstBI site. The consensus sequence of this DEN3 region was determined by sequencing of the RT-PCR product in both orientations using oligos 3, 4, 11, 12, 13, and 14.

The PCR product was cloned in place of the short NheI-NarI fragment in YFM5.2 JE SA14-14-2 plasmid (Chambers et al., J. Virol. 73:3095–3101, 1999; see above), resulting in the 5.2/Den3 plasmid. Originally it was propagated in *E. coli* MC1061 RecA- cells, and the DNA extracted from these cells was of poor quality (partially denatured), which hindered restriction digestions. Subsequently, several of the extracted plasmid clones were propagated in *E. coli* ABLE C cells (Stratagene), and good quality DNAs were recovered. Six of these clones were thoroughly analyzed by restriction analysis and then sequenced. For sequencing, the DEN3-specific insert with adjacent regions of the vector was PCR amplified using oligos 15 and 16, and the product was sequenced in both orientations with oligos 11, 12, 13, 14, 15, and 16. Clone #26 was chosen for subsequent manipulations. It contains no mutations, compared to the consensus sequence, except for a single nucleotide deletion (nucleotide 2407, in the region of the opposite PCR primer 4).

4.6 In vitro Transcription and Transfection

These techniques were essentially as described by Rice et al. (New Biol. 1:285–296, 1989). Approximately 1 μg total of equimolar amounts of appropriate gel-purified DNA fragments were ligated overnight in 20 μl volume at 40° C. T4 DNA ligase was heat-inactivated (10 minutes, 65° C.). Ligation products were digested with XhoI to provide run-off transcription, phenol-chloroform extracted, and precipitated with ethanol. The resulting DNA was transcribed in vitro with SP6 RNA polymerase in the presence of m7G(5')ppp(5')G cap analog and Rnasin in a 20 μl reaction (AmpliScribe SP6 Kit With Cap Analog; Epicentre Technologies; Cat. #AS2606C2). RNA transcripts were analyzed by electrophoresis of 2 μl aliquots in 1% agarose gel. Monolayers of Vero PM cells grown in 6 well tissue culture plates were transfected with RNA transcripts using Lipofectin reagent (Gibco, Cat. #18292-011). Following transfections, cells were incubated as is described above, and virus-containing media were harvested on indicated days post-transfection, mixed with equal volume of FBS, aliquoted and stored at −70° C.

5.0 Construction of CHIMERIVAX-DEN4™ (Chimeric Flavivirus Comprising Dengue 4 Virus prM and E Proteins)

Figure 31:
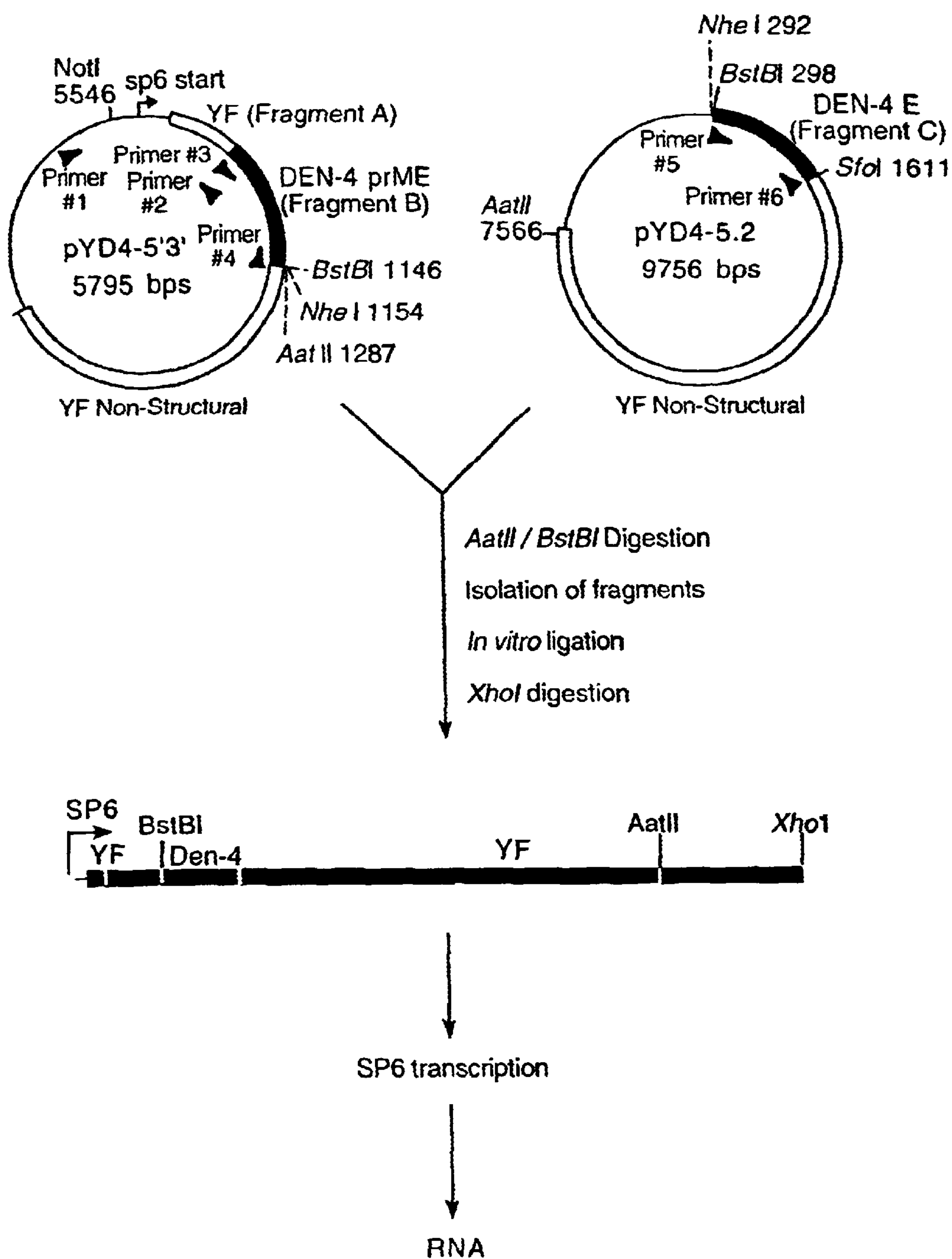
FIG. 31 is a schematic representation of an overview of construction of a YF/DEN4 chimera of the invention.
Figure 32:
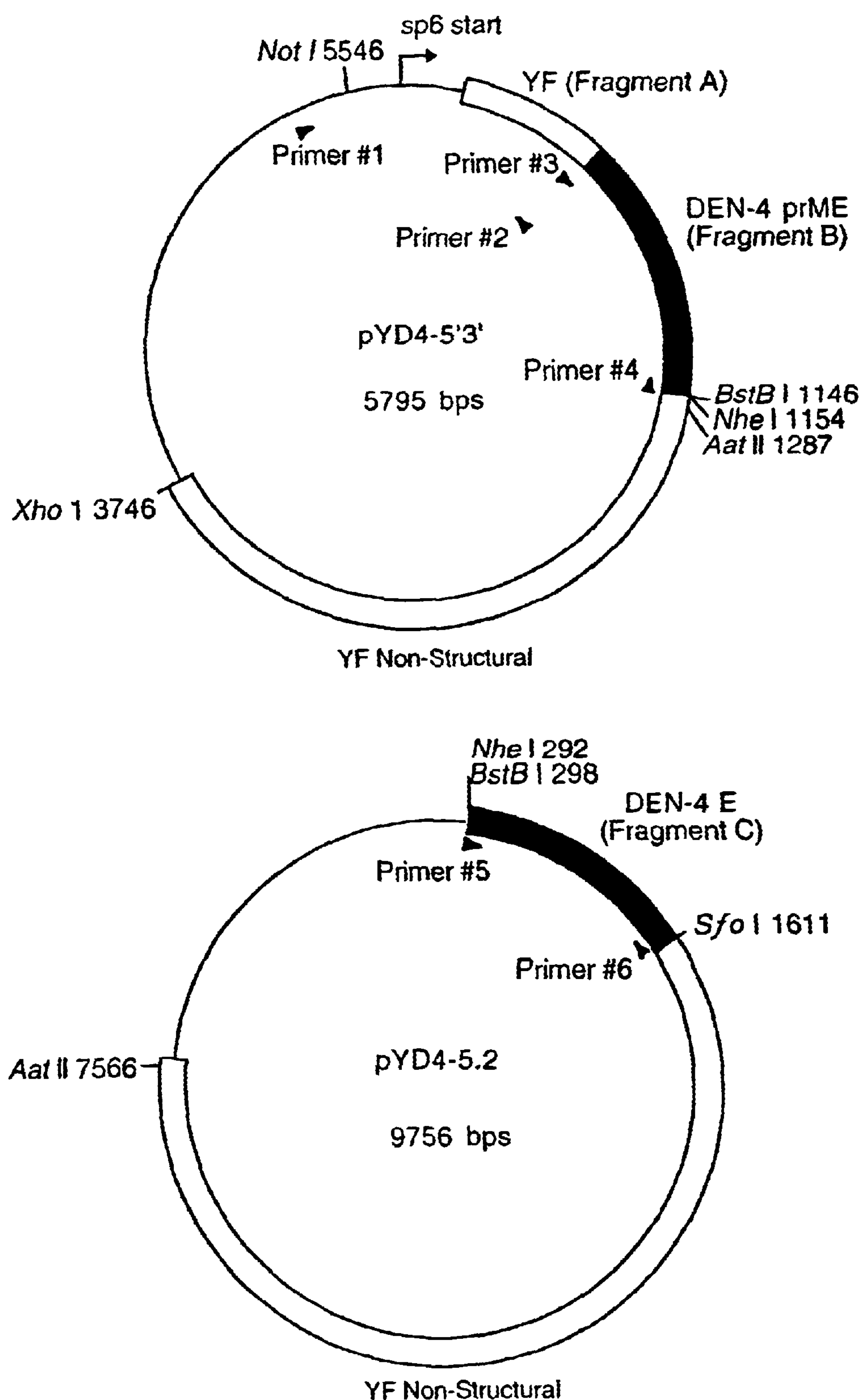
FIG. 32 is a schematic representation of a plasmid and fragment map relating to construction of a YF/DEN4 chimera of the invention.

The purpose was to generate yellow fever/dengue 4 (YF/DEN-4) chimeric virus as a dengue vaccine candidate (see FIGS. 31 and 32). To attain this, we used a technology derived from the construction of Yellow fever/Japanese encephalitis (YF/JE SA14-14-2) chimeric virus (Chambers et al., J. Virol. 73:3095–3101, 1999). It consists of a two plasmid system which originally encoded the yellow fever (YF) genome. These YF plasmids were created by Charlie Rice (Rice et al., New Biol. 1:285–296, 1989). The structural membrane precursor and envelope protein genes, i.e., the prME portion, of the YF genome plasmids with that of JE SA14-14-2 sequence and used the resulting plasmids to produce RNA in vitro, which was then transfected into cells to produce live YF/JE chimeric virus. The system seemed suitable to construct other flavivirus chimeras using YF as backbone and here we describe the use of dengue 4 as a start point. The dengue 4 strain, #1228 isolated in 1978 in Indonesia and passaged twice in mosquitoes, was passed once in C6/36 and total RNA was isolated to synthesize cDNA for PCR of the prME region as needed for cloning. Here we describe in detail the procedures for construction of the YF/DEN-4 chimera. The dengue 4 prME region was first amplified and sequenced using primers derived from consensus sequences (Genbank). The sequence data created was applied to primer design which were used, with the cDNA produced earlier, as PCR starting point for assembly of the two-plasmid system for dengue 4 (i.e., by replacing the corresponding prME JE sequences in each plasmid). A PCR product encoding dengue prM and 5' end of E was used as template, along with template encoding the capsid (C) gene of yellow fever derived from the plasmid pYF5'3'IV/JE SA14-14-2, in an overlap extension PCR to result in a single fusion product which was then cloned into a fragment of pYFM5'3'IV where JE sequences were deleted. The 3' end of dengue 4 envelope protein gene was also amplified and then cloned into a vector fragment of pYFM5.2/JE SA14-14-2, resulting in replacement of JE sequence with that of dengue 4. Both plasmids were then transformed into *E. coli* strain MC1061 (RecA-) and midi-scale plasmid cultures were grown. In vitro ligation of the two plasmids resulted in full-length virus DNA template of YF/DEN-4 for RNA transcription. All steps involving cDNA fragments and plasmids were carried out in a BL-2 lab designated for recombinant DNA work. Steps involving manipulations of infectious RNA and virus were carried out in a limited access BL-2+virus lab.

5.1 Amplification of Dengue 4 Sequence

Dengue 4 cDNA was synthesized from RNA using the Superscript II™ method. All primers for this experiment were synthesized by Life Technologies and are listed in Table 34. Upon arrival as lyophilized material, primers were dissolved to 250 mM stock solutions in RODI-water. From this, 25 mM working solutions were made. The fragment encoding the SP6 promoter and yellow fever capsid (Fragment A) was amplified using the XL-PCR Reaction Kit TM (Perkin-Elmer Part #N808–0192), 0.5 ml (250 ng) of template pYF5'3'IV plus 3.5 ml RODI-water, and primers 1 and 2. The fragment encoding dengue 4 prM and the 5' end of E (Fragment B) was amplified using the XL-PCR Reaction Kit TM (Perkin-Elmer Part #N808–0192) and primers 3 and 4. The fragment encoding the 3' end of dengue 4 envelope (Fragment C) was amplified using the same protocol but using primers 5 and 6. Each PCR reaction was performed as indicated in master mixes (see section 3.1, above).

For each reaction, the lower mix (LM) was added to a Perkin-Elmer thin-walled 0.2 ml tube. Next, Ampliwax 100 (Perkin-Elmer) was added to the tube, which was then placed in a Perkin-Elmer 2400 Thermal Cycler and heated to 80° C. for 5 minutes, and then cooled to 4° C. The cDNA and UM were then added to the top of the wax layer. The tube was then cycled in a Perkin-Elmer 2400 as follows: 94° C., 1 minute; repeat 30 ×(94° C., 15 seconds; 53° C., 15 seconds; 68° C., 3 minutes), 72° C., 4 minutes; 4° C., hold. The expected sizes of the PCR fragments for cloning were as follows:

| Fragment | Approximate Size (kb) |
|---|---|
| A | 0.940 |
| B | 0.650 |
| C | 1.300 |

Forty μl of each fragment was then separated on a 1% Agarose/TAE gel and purified using the QIAquick Gel Extraction Kit (Qiagen cat. #28704). Next, the concentration of the purified fragments was determined by UV absorption using 1:40 dilutions in RODI-water.

| Sample | A280 | A260 | 280/260 | 260/280 | Concentration |
|---|---|---|---|---|---|
| Fragment A | 0.0247 | 0.0340 | 0.7271 | 1.3754 | 68 ng/μl |
| Fragment B | 0.0086 | 0.0152 | 0.5643 | 1.7721 | 30 ng/μl |
| Fragment C | 0.0099 | 0.0179 | 0.5536 | 1.8065 | 36 ng/μl |

5.2 Recombinant PCR

To create a fusion between the yellow fever capsid gene and the 5' end of the dengue 4 prM, a recombinant PCR technique, Overlap-extension PCR was used to create Fragment E. The same basic UM and LM were used and primers 1 and 4 replaced earlier primers; the cDNA templates used were mixes shown below:

| | Fragment E | Fragment A control | Fragment B control |
|---|---|---|---|
| $H_2O$ | 37.8 μl | 39.1 μl | 38.7 μl |
| Fragment A | 0.9 μl | 0.9 μl | 0 μl |
| Fragment B | 1.3 μl | 0 μl | 1.3 μl |
| Volume | 40 μl | 40 μl | 40 μl |

The same protocol that was used for creation of Fragments A, B, and C was used except that only ½ of the cDNA, UM, and LM were used for the control reactions. The tube was then cycled in a Perkin-Elmer 2400 cycler as follows: 94° C., 1 minute; repeat 30×(94° C., 15 seconds; 55° C., 15 seconds; 68° C., 2 minutes; 72° C., 7 minutes; 4° C., hold. The expect follows.

| Fragment | Approximate Size (kb) |
|---|---|
| E | 1.59 |
| A control | no product |
| B control | no product |

Forty μl of Fragment E was then separated on a 1% Agarose/TAE gel and purified using the QIAquick Gel Extraction Kit (Qiagen cat. #28704). Next, the concentration of the purified fragment was determined by UV absorption using 1:40 dilutions in RODI-water.

| Sample | A280 | A260 | 280/260 | 260/280 | Concentration |
|---|---|---|---|---|---|
| Fragment E | 0.0049 | 0.0110 | 0.4489 | 2.2276 | 22 ng/μl |

5.3 Cloning of Fragments C and E Into Yellow Fever Vectors

The fragments were then cloned into the yellow fever two-plasmid system by digestion of the purified Fragments C and E as well as the plasmids pYF5'3'IV and pYFM5.2/2 with appropriate restriction enzymes as shown below. The digested plasmids resulted in two bands. The smaller bands contain a fragment of Japanese encephalitis corresponding to either Fragment C or Fragment E for the new dengue 4 constructs. All restriction enzymes, buffers, and 100×BSA were from New England Biolabs. All the digestions were carried in a Perkin-Elmer 480 cycler set to hold at 37° C. overnight.

| Fragment E digest | |
|---|---|
| Fragment E (528 ng) | 27 μl |
| NEB buffer 4 | 4 μl |
| 10× BSA | 4 μl |
| $H_2O$ | 3 μl |
| Not I | 1 μl |
| Nhe I | 1 μl |
| Volume | 40 μl |

| pYF5.2 digest | |
|---|---|
| pYF5.2 (1 μg) | 9.5 μl |
| NEB buffer 2 | 2 μl |
| 10× BSA | 2 μl |
| $H_2O$ | 4 μl |
| Sfo I | 1.5 μl |
| Nhe I | 1 μl |
| Volume | 20 μl |

| pYFMIV5'3' digest | |
|---|---|
| pYFMIV5'3' (1.02 μg) | 2 μl |
| NEB buffer 4 | 2 μl |
| 10× BSA | 2 μl |
| $H_2O$ | 12 μl |
| Not I | 1 μl |
| Nhe I | 1 μl |
| Volume | 20 μl |

| Fragment C digest | |
|---|---|
| Fragment C (710 ng) | 20 μl |
| NEB buffer 2 | 4 μl |
| 10× BSA | 4 μl |
| $H_2O$ | 9.5 μl |
| Sfo I | 1.5 μl |
| Nhe I | 1 μl |
| Volume | 40 μl |

5.4 Vector Dephosphorylation

Calf Intestinal Phosphatase (CIP) from New England Biolabs (cat. #290S) was diluted 1:10 in 1×CIP Buffer. One μl of this dilution was then added to the pYFMIV5'3' digest. 0.62 μl of stock CIP was added directly to the pYF5.2 digest. Both were incubated for 1 hour at 37° C. Then, 0.8 μl 125 mM EDTA was added to the two tubes and placed at 75° C. for 10 minutes to inactivate CIP

5.5 Gel Excision

The digested PCR fragments were separated on a 1.0% Agarose/TAE gel, while the digested plasmids were separated on a 0.8% Agarose/TAE gel. All were purified using the QIAquick Gel Extraction Kit (Qiagen cat. #28704).

5.6 Ligations

The digested Fragment E and pYF5'3'IV were ligated using T4 DNA Ligase (New England Biolabs cat. #202S) to create pYD4-5'3'. The digested Fragment C and pYFM5.2 were ligated to create pYD4-5.2. All ligation reactions were incubated in a Perkin-Elmer 480 cycler set to hold at 16° C. overnight.

| PYD4-5'3' Ligation | |
|---|---|
| Fragment E (97.5 ng) | 9.5 μl |
| pYFM5'3' (50 ng) | 3.6 μl |
| $H_2O$ | 3.9 μl |

-continued

| PYD4-5'3' Ligation | |
|---|---|
| 10× T4 ligase buffer | 2 μl |
| T4 DNA ligase | 1 μl |
| Volume | 20 μl |

| PYD4-5.2 Ligation | |
|---|---|
| Fragment C (56 ng) | 4.5 μl |
| pYFM5.2 (70 ng) | 8.8 μl |
| $H_2O$ | 3.7 μl |
| 10× T4 ligase buffer | 2 μl |
| T4 DNA ligase | 1 μl |
| Volume | 20 μl |

| pYFM-5'3' Control Ligation | |
|---|---|
| Fragment E | 0 μl |
| pYFM5'3' (50 ng) | 3.6 μl |
| $H_2O$ | 13.4 μl |
| 10× T4 ligase buffer | 2 μl |
| T4 DNA ligase | 1 μl |
| Volume | 20 μl |

| pYF5.2 Control Ligation | |
|---|---|
| Fragment C | 0 μl |
| pYFM5.2 (70 ng) | 8.8 μl |
| $H_2O$ | 8.2 μl |
| 10× T4 ligase buffer | 2 μl |
| T4 DNA ligase | 1 μl |
| Volume | 20 μl |

5.7 Transformations

All four ligation reactions were transformed into *E. coli* strain MC1061 (recA-). An aliquot of MC1061 (OraVax Notebook 661–4) was removed from storage at −80° C. and allowed to thaw on ice for one to two minutes. 0.9 ml of cold 0.1 M $CaCl_2$ was added to the cells. One hundred μl of cells was aliquoted into five 12 ml culture tubes on ice. Ten μl of each ligation reaction was added to each culture tube, leaving the fifth tube as a negative (no DNA) control. Culture tubes were left on ice for 30 minutes. The tubes were heat shocked in a water bath at 42° C. for 45 seconds. The tubes were put back on ice for 2 minutes. 0.9 ml SOC medium was added to each culture tube and incubated at 225 pm in a shaking incubator at 37° C. for 1 hour. Each transformation mix was aliquoted into 1.5 ml microcentrifuge tubes. One hundred μl of each was spread onto LB/Agar-Amp (100 μg/ml) plates and labeled as "neat." Each tube was spun at 14 Krpm in a microcentrifuge for 2–3 seconds to pellet the cells. The supernatant was poured into the waste container and the pellet resuspended in the residual broth by pipetting up and down. This material was plated (approximately 100 μl) onto LB/Agar-Amp (100 μg/ml) plates and labeled as 10×. All plates were inverted in a 37° C. incubator overnight.

5.8 Transformant Screening

The resulting bacterial colonies were patch-plated onto fresh LB/Agar-Amp (100 μg/ml) and placed inverted in a 37° C. incubator overnight. The following day, 50 μl of RODI-water was aliquoted into 0.5 ml tubes. Using a sterile plastic pick, a small amount of each patch was scraped into one of the 0.5 ml tubes containing water. These were then placed at 95° C. for 10 minutes and spun at 14,000 rpm for 10 minutes in a microcentrifuge. To identify the proper insert in pYD4-5'3', colonies were screened by PCR using Taq Polymerase (Promega) and primers 4 and 7. The pYD4-5.2 was screened using primers 5 and 6. The PCR reaction was performed using the following master mix.

| Component | 4 rxns | 10 rxns | 15 rxns | 20 rxns | 25 rxns | 30 rxns |
|---|---|---|---|---|---|---|
| RODI-water | 161.5 μl | 355.5 μl | 516.8 μl | 678.3 μl | 839.8 μl | 1001.3 μl |
| $H_2O$ | 25 μl | 55 μl | 80 μl | 105 μl | 130 μl | 155 μl |
| $MgCl_2$ | 10 μl | 22 μl | 32 μl | 42 μl | 52 μl | 62 μl |
| P1 (100 μM) | 1 μl | 2.2 μl | 3.2 μl | 4.2 μl | 5.2 μl | 6.2 μl |
| P2 (100 μM) | 1 μl | 2.2 μl | 3.2 μl | 4.2 μl | 5.2 μl | 6.2 μl |
| dNTPs (10 mM) | 40 μl | 88 μl | 128 μl | 168 μl | 208 μl | 248 μl |
| Taq Polymerase | 1.5 μl | 3.3 μl | 4.8 μl | 6.3 μl | 7.8 μl | 9.3 μl |

Forty eight μl of each master mix was added to a 0.5 ml tube along with 5 ml of the template prepared from the colony patches. Additionally, a tube using RODI-water as a template was also made as a negative control. These tubes were then placed in the Ericomp Delta Cycler and cycled as follows: 96° C., 4 minutes; 30×(94° C., 30 seconds; 50° C., 1 minute; 72° C., 1 minutes 25 seconds), 72° C., 4 minutes; 4° C. hold. The PCR products were then run on 1.5% Agarose/TAE gels to check for positive colonies.

5.9 Glycerol Stocks

Five ml of LB-Amp (100 μg/ml) was then inoculated from a patch pYD4-5'3'/2 or pYD4-5.2/1 and shaken at 225 rpm overnight at 37° C. One ml of this culture was then spun at 14 Krpm for 2–3 seconds to pellet the cells. This was then resuspended in LB-Glycerol (30%) and frozen at −80° C.

5.10 MIDI Plasmid Preparation

Fifty μl of each glycerol stock was added to 150 ml LB-Amp (100 μg/ml) in separate 4 L flasks and shaken at 225 rpm overnight at 37° C. Qiagen Midi-Prep (Qiagen) was performed using the following modified protocol.

1. Spin 150 ml of each culture at 7 Krpm in GSA rotor for 10 minutes to pellet.
2. Decant Supernatant.
3. Resuspend pellet in 4 ml P1 Buffer; transfer to 50 ml Falcon tube.
4. Rinse centrifuge bottle with 2 ml P1 buffer and transfer to the Falcon tube.
5. Add 6 ml P2 buffer; invert gently; 5 minutes at room temperature or until lysed (no more than 12 minutes).
6. Add 6 ml P3; mix as above; 10 minutes on ice.
7. Transfer supernatant to Qiagen Syringe Filter; let sit for 10 minutes.
8. Equilibrate Q-100 tip with 4 ml QBT.
9. Gently push plunger to filter supernatant onto Q-100 tip.
10. Allow to drain by gravity.
11. Wash with 2×10 ml QC.
12. Elute into 50 ml polypropylene centrifuge tube with 5 ml QF.
13. Add 14 ml 100% ETOH (or 8 ml isopropanol); Place in dry ice/ethanol bath for 10 minutes (or at −20° C. for 2 hours or at 4° C. overnight).

14. Spin at 15 K×G for 30 minutes at 4° C.
15. Wash with 5 ml 70% ethanol; Spin 15 K×G for 20 minutes.
16. Air Dry.
17. Resuspend in 150 μl EB.

DNA Concentrations Were Measured as Before.

| Sample | A280 | A260 | 280/260 | 260/280 | Concentration |
|---|---|---|---|---|---|
| pYD4-5'3'/2 | 0.0516 | 0.0939 | 0.5498 | 1.1817 | 1.87.8 ng/μl |
| pYD4-5.2/1 | 0.0900 | 0.1407 | 0.6399 | 1.5629 | 281.4 ng/μl |

5.11 In Vitro Ligation to Create Full-length cDNA Chimeric Template and RNA Production Digestion With AatII and BstBI Plasmids pYD4-5'3'/2 and pYD4-5.2/1 were digested with AatII and BstBI (NEB) in a sequential digest as follows.

| YD4-5'3'/2 (AatII digest) | |
|---|---|
| pYD4-5'3'/2 (8 μg) | 42.5 μl |
| Buffer 4 (NEB) | 5 μl |
| AatII (NEB) | 2 μl |
| $H_2O$ | 0.5 μl |
| Volume | 50 μl |

| YD4-5.2/1 (AatII digest) | |
|---|---|
| pYD4-5.2 (10 μg) | 35.5 μl |
| Buffer 4 (NEB) | 5 μl |
| AatII (NEB) | 2 μl |
| $H_2O$ | 7.5 μl |
| Volume | 50 μl |

Both reactions were incubated in a 37° C. block for 2 hours. Five μl of each digest was run out on a 1.5% Agarose/TAE gel to check for complete digestion. The pYD4-5'3'/2 digest did not cut completely so the reaction was cleaned over a Qiaprep spin column (Qiagen). The digest was repeated using this material and 3 μl of Aat II. In addition, 3 μl of Aat II was added to the existing pYD4-5.2/1 reaction. Both were incubated in a 37° C. block, overnight. After confirmation of digest on another gel (as previously described), 2.5 μl Bst BI (NEB) was added to each reaction and placed at 65° C. for 3 hours. The results of the digest were as follows.

| PYD4-5'3'/2 | PYD4-5.2/1 |
|---|---|
| 5.6 kb | 7.2 kb |
| | 2.0 kb |
| 0.14 kb | 0.4 kb |

The largest band from each reaction was gel excised as and the UV concentration was determined (as previously described).

5.12 Ligation

The following ligation reaction was setup using high concentration T4 DNA ligase (NEB). The ligations were incubated at 16° C. overnight.

| | |
|---|---|
| $H_2O$ | 13.5 μl |
| pYD4-5.2 fragment (600 ng) | 23 μl |
| pYD4-5'3' fragment (300 ng) | 7 μl |
| 100x BSA (NEB) | 0.5 μl |
| T2 DNA ligase buffer (NEB) | 5 μl |
| *T4 DNA ligase | 1 μl |
| Volume | 50 μl |

*Heat reaction at 37° C. for 5 minutes, then briefly chill on ice before adding ligase

5.13 Linearization of Template

The ligation was heat inactivated at 65° C. for 10 minutes. The ligated material was then linearized at 3' end of the yellow fever sequence to allow proper RNA transcription, as follows: 5.5 ml Buffer 2 (NEB) was added to the ligation, followed by 1.5 μl XhoI (NEB), and this reaction mixture was placed at 37° C. for 2 hours.

5.14 Linear cDNA Extraction (RNAse Free Phase)

1. Add $H_2O$ to 100 μl total volume.
2. Add 1/10$^{th}$ volume 3 M Sodium Acetate.
3. Add 100 μl Phenol/Chloroform/Isoamyl Alcohol and spin at 14 Krpm for 5 minutes in a microcentrifuge. Extract upper layer into RNAse-free 1.5 ml tube. Repeat once.
4. Add 100 μl RNAse-free Chloroform. Spin at 14 Krpm for 5 minutes in a microcentrifuge. Extract upper layer into RNAse-free 1.5 ml tube. Repeat once.
5. Add 200 μl 100% RNASE-free ethanol.
6. Place on dry-ice/ethanol bath for 10 minutes.
7. Spin at 14 Krpm for 20 minutes in a microcentrifuge.
8. Wash with 200 μl 70% ethanol (RNAse-free).
9. Repeat 70% ethanol wash two more times.
10. Dry in Speed-Vac for 8 minutes (or until no more ethanol is present).
11. Resuspend in 22 μl nuclease free water from the SP6 kit listed below.

5.15 SP6 Transcription

The following reaction was setup using the SP6 transcriptase kit (Epicentre) and Rnasin (Promega) in an RNAse-free 1.5 ml tube using RNAse-free tips in a BL-2 hood. The reaction was then placed in a 40° C. water bath for 1 hour.

| | |
|---|---|
| Capping NTP solution | 6 μl |
| 10x buffer | 2 μl |
| 20 mM Cap Analog | 3 μl |
| 100 mM DTT | 2 μl |
| Linearized DNA | 5 μl |
| Rnasin | 0.5 μl |
| SP6 transcriptase | 2 μl |
| Volume | 20.5 μl |

5.16 RNA Transfection

Two six well tissue culture plates were seeded with Vero-PM (p#153 OraVax notebook#743–7) cells at $7.4\times10^5$ cells/well in growth media (Gibco MEM; Sodium Pyruvate; NEAA; Penicillin/Streptomycin; 5% fetal bovine serum), and placed in a 37° C. $CO_2$ incubator until confluent.

The following transfection reactions were made using Lipofectin (Life Technologies) and RNAse-free PBS (Sigma), and allowed to sit at room temperature for 10 minutes.

| YF/DEN-4 | |
|---|---|
| PBS | 250 μl |
| Lipofectin | 20 μl |
| YF/DEN-4 RNA | 10 μl |
| Volume | 280 μl |

| Total RNA control | |
|---|---|
| PBS | 250 μl |
| Lipofectin | 20 μl |
| YF/JE total RNA | 10 μl |
| Volume | 280 μl |

| Lipofectin control | |
|---|---|
| PBS | 260 μl |
| Lipofectin | 20 μl |
| Volume | 280 μl |

1. Remove Media from the 6 well plates.
2. Wash 3 times with PBS.
3. Remove last of PBS.
4. Overlay with each lipofectin reaction. Add 280 μl PBS for the remaining wells.
5. Rock for 10 minutes at room temperature.
6. Wash 2 times with media (MEM, Sodium Pyruvate, NEAA, P/S, 5% FBS).
7. Add 2 ml of media to each well and place in the 37° C. $CO_2$ incubator for 4 days or more.

5.17 Chimeric Virus Harvest

The supernatant from YF/DEN-4 was harvested on day 6 by splitting the 2 ml of supernatant between two cryovials (each containing 1 ml FBS), which were labeled YF/DEN-4 (P1). The cell monolayer was harvested with 1 ml Trizol into a 1.5 ml tube. All vials and tubes were then placed at −80° C.

5.18 Amplification of YF/DEN-4

Passage #2

1. Three T-25 flasks containing Vero-PM cells (p#149) were obtained from the Cell Culture Facility. A frozen aliquot of YF/DEN-4 (P1) was removed from the −80° C. freezer, thawed, then placed on ice. The same was done for an aliquot of YF/JE (frozen stock from the P1 control transfection).
2. Media was removed from each T-25 flask.
3. Five hundred μl of YF/DEN-4(P1) was added to the first flask, 500 μl of media (MEalphaM, NEAA, Sodium Pyruvate, 5% FBS, P/S) was added to the second flask, and 500 μl of YF/JE(P1) was added to the third flask.
4. Two hundred μl of the media was added to each flask to ensure complete coverage.
5. Each flask was then put in the 37° C. $CO_2$ incubator for 1 hour with rocking every 15 minutes.
6. 4.5 ml of media was then added to each flask.
7. The flasks were then placed in the 37° C. $CO_2$ incubator for 4 days.

Harvest P2

The supernatant from YF/DEN-4 was harvested on day 4 by splitting the 5 ml of supernatant between five cryovials (each containing 1 ml FBS), which were labeled YF/DEN-4 (P2). The cell monolayer was harvested in 3 ml Trizol and aliquoted into 3 tubes. All vials and tubes were then placed at −80° C.

Passage#3 (Titration of P2)

1. A 12 well tissue culture plate containing Vero-PM cells (p#163) was obtained from the Cell Culture Facility. A frozen aliquot of YF/DEN-4 (P2) was removed from the −80° C. freezer, thawed, and then placed on ice.
2. Serial dilutions were made in a 24 well tissue culture plate ending at $10^{-4}$ in a total volume of 300 μl. The plate was then placed on ice.
3. The media was removed from each well of the 12 well plate and 100 μl of virus stock, as well as each dilution, was added to the wells in duplicate. One hundred μl of media only was added to the last set of wells as a negative control.
4. The plate was then put in the 37° C. $CO_2$ incubator for 1 hour with rocking every 20 minutes.
5. The 1$^{st}$ overlay was made by preheating 25 ml M199(2×), 1.5 ml FBS, and 0.5 ml PSA at 42° C. in a 50 ml Falcon tube (tube #1). Additionally, 23 ml Agarose (0.6% in water) was heated at 42° C. in a 50 ml Falcon tube (tube #2). At the end of the 1 hour incubation, tube #1 was added to tube #2 and mixed thoroughly.
6. One ml of this overlay was then added to the edge of each well.
7. The plate was then put in the 37° C. $CO_2$ incubator for 4 days.
8. The 2$^{nd}$ overlay was made by preheating 25 ml M199(2×), 1.5 ml FBS, 1.5 ml Neutral Red, and 0.5 ml PSA at 42° C. in a 50 ml Falcon tube (tube #1). Additionally, 21.5 ml Agarose (0.6% in water) was heated at 42° C. in a 50 ml Falcon tube (tube #2). Tube #1 was added to tube #2 an mixed thoroughly.
9. One ml of this overlay was added to the center of each well.
10. It was then placed in the 37° C. $CO_2$ incubator Titration of P2 results Instead of titer determination, plaques were picked for purification to segregate a mixed population of large and small plaques observed. The RNA from P2 was extracted using Trizol methods according to the manufacturer's protocol, RT-PCR was performed followed by sequencing of the YF/DEN-4 prME region 5', 3' junctions, inclusive. The expected sequence of the prME was confirmed.

6.0 Construction of Chimeric Templates for Other Flaviviruses

Procedures for generating full-length cDNA templates encoding chimeric YF/MVE, YF/SLE, YF/WN, YF/TBE viruses are similar to those described above for the YF/DEN-2 system. Table 20 illustrates the features of the strategy for generating YF 17D-based chimeric viruses. The unique restriction sites used for in vitro ligation, and the chimeric primers for engineering the C/prM and E/NS1 junctions are also shown. Sources of cDNA for these heterologous flaviviruses are readily available (MVE: Dalgarno et al., J. Mol. Biol. 187:309–323, 1986; SLE: Trent et al., Virology 156:293–304, 1987; TBE: Mandl et al., Virology 166:197–205, 1988; Dengue 1: Mason et al., Virology 161:262–267, 1987; Dengue 2: Deubel et al., Virology 155:365–377, 1986; Dengue 3: Hahn et al., Virology 162:167–180, 1988; Dengue 4: Zhao et al., Virology 155:77–88, 1986).

An alternative approach to engineering additional chimeric viruses is to create the C/prM junction by blunt end ligation of PCR-derived restriction fragments having ends that meet at this junction and 5' and 3' termini that flank appropriate restriction sites for introduction into YF5'3'IV or an intermediate plasmid such as pBS-KS(+). The option to use a chimeric oligonucleotide or blunt-end ligation will vary, depending on the availability of unique restriction sites within the envelope protein coding region of the virus in question.

6.1 Construction of YF Viruses Encoding HCV Antigens

Because the structural proteins E1 and E2 of HCV are not homologous to the structural proteins of the flaviviruses described above, the strategy for expression of these proteins involves insertion within a nonessential region of the genome, such that all of these proteins are then co-expressed with yellow fever proteins during viral replication in infected cells. The region to be targeted for insertion of the proteins is the N terminal portion of the NS1 protein, since the entire NS1 protein is not required for viral replication. Because of the potential problems with stability of the YF genome in the presence of heterologous sequence exceeding the normal size of the genome (approximately 10,000 nucleotides), the detection strategy described below can be used. In addition, deletion of NS1 may be advantageous in the chimeric YF/Flavivirus systems described above, because partial deletion of this protein may abrogate the immunity to YF associated with antibodies against NS I, and thus avoid problems with vector immunity if more than one chimeric vaccine was to be needed in a given recipient, or if a YF vaccine had been previously given or needed at a future point.

The strategy involves creating a series of in-frame deletions within the NS1 coding region of the YFM5.2 plasmid, in conjunction with engineering a translational termination codon at the end of E, and a series of two IRESs (internal ribosome entry sites). One IRES is immediately downstream of the termination codon and allows for expression of an open reading frame within the region between E and NS1. The second IRES initiates translation from truncated NS1 proteins, providing expression of the remainder of the YF nonstructural polyprotein. These derivatives are tested for recovery of infectious virus and the construct with the largest deletion is used for insertion of foreign sequences (e.g., HCV proteins) in the first IRES. This particular construct can also serve as a basis for determining whether deletion of NS1 will affect vector-specific immunity in the context of YF/Flavivirus chimeric viruses expressing prM-E, as described above.

Figure 21:
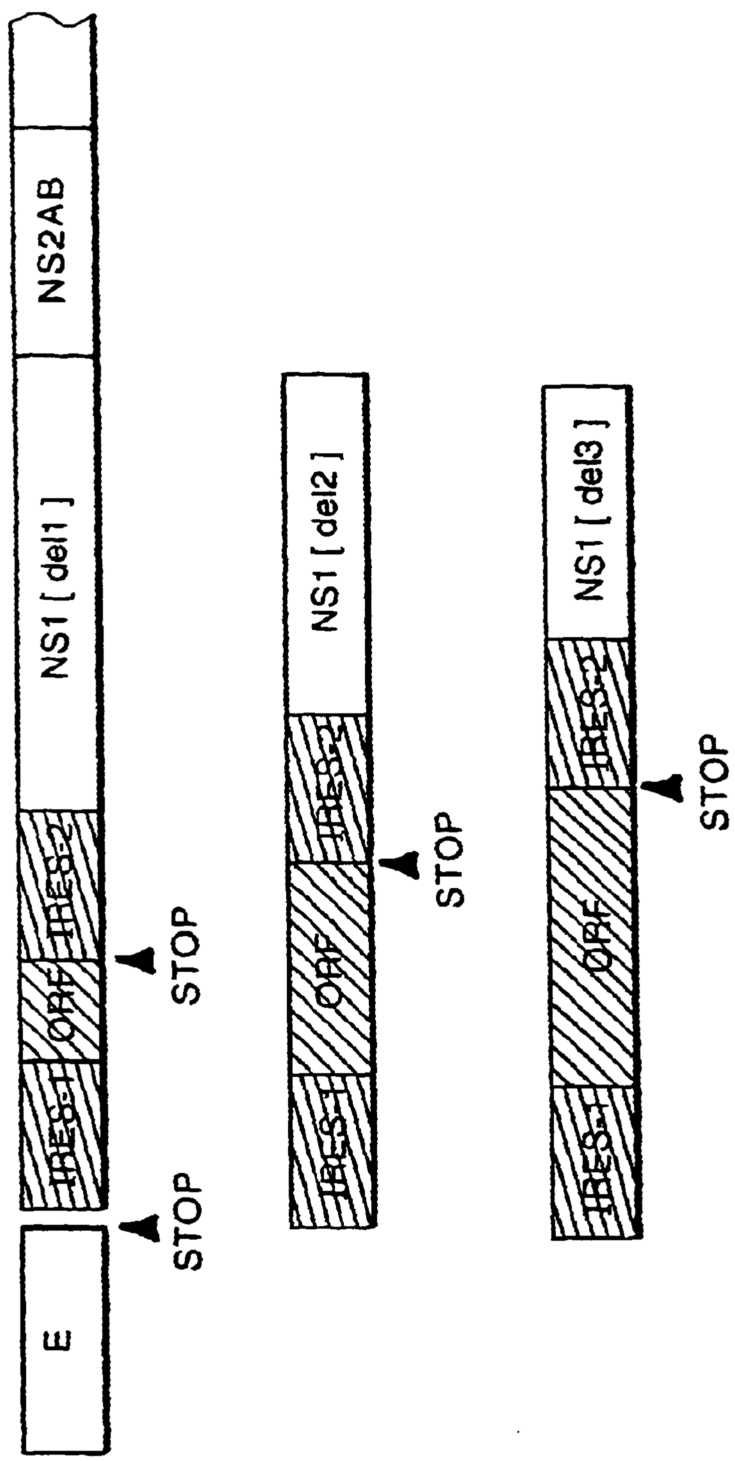
FIG. 21 is a schematic representation of the structure of modified YF clones designed to delete portions of the NS1 protein and/or express foreign proteins under control of an internal ribosome entry site (IRES). The figure shows only the E/NS1 region of the viral genome. A translational stop codon is introduced at the carboxyl terminus of the envelope (E) protein. Downstream translation is initiated within an intergenic open reading frame (ORF) by IRES-1, driving expression of foreign proteins (e.g., HCV proteins E1 and/or E2). The second IRES (IRES-2) controls translational initiation of the YF nonstructural region, in which nested, truncated NS1 proteins (e.g., NS1del-1, NS1del-2, or NS1del-3) are expressed. The size of the NS1 deletion is inversely proportional to that of the ORF linked to IRES-1.

The insertion of nucleotides encoding E1, E2, and/or E1 plus E2 HCV proteins is limited by the size of the deletion tolerated in the NS1 protein. Because of this, truncated HCV proteins can be used to enhance stability within the modified YF clone. The HCV proteins are engineered with an N-terminal signal sequence immediately following the IRES and a termination codon at the C terminus. This construction will direct the HCV proteins into the endoplasmic reticulum for secretion from the cell. The strategy for this construction is shown schematically in FIG. 21. Plasmids encoding HCV proteins of genotype I can be used for these constructions, for example, HCV plasmids obtained from Dr. Charles Rice at Washington University (Grakoui et al., J. Virology 67:1385–1395, 1993), who has expressed this region of the virus in processing systems and within a replication-complement full-length HCV clone.

6.2 PrM Cleavage Deletion Mutants as Attenuating Vaccine candidates for Flaviviruses Additional chimeric viruses included in the invention contain mutations that prevent prM cleavage, such as mutations in the prM cleavage site. For example, the prM cleavage site in flavivirus infectious clones of interest, such as dengue, TBE, SLE, and others can be mutated by site-directed mutagenesis. Any or all of the amino acids in the cleavage site, as set forth above, can be deleted or substituted. A nucleic acid fragment containing the mutated prM-E genes can then be inserted into a yellow fever virus vector using the methods described above. The prM deletion can be used with or without other attenuating mutations, for example, mutations in the E protein, to be inserted into the yellow fever virus. These mutants have advantages over single substitution mutants as vaccine candidates, because it is almost impossible to revert the deleted sequence and restore virulence.

The following chimeric flaviviruses of the invention were deposited with the American Type Culture Collection (ATCC) in Rockville, Md., U.S.A. under the terms of the Budapest Treaty and granted a deposit date of Jan. 6, 1998: Chimeric Yellow Fever 17D/Dengue Type 2 Virus (YF/DEN-2; ATCC accession number ATCC VR-2593) and Chimeric Yellow Fever 17D/Japanese Encephalitis SA14-14-2 Virus (YF/JE A1.3; ATCC accession number ATCC VR-2594).

TABLE 1

Sequence comparison of JE strains and YF/JE chimeras

| Virus | E 107 | E 138 | E 176 | E 177 | E 227 | E 243 | E 244 | E 264 | E 279 | E 315 |
|---|---|---|---|---|---|---|---|---|---|---|
| JE SA14-14-2 | F | K | V | T | S | K | G | H | M | V |
| YF/JE SA14-14-2 | F | K | V | A | S | E | G | H | M | V |
| YF-JE Nakayama | L | E | I | T | P | E | E | Q | K | A |
| JE Nakayama | L | E | I | T | P | E | E | Q | K | A |
| JE SA14 | L | E | I | T | S | E | G | Q | K | V |

TABLE 2

Characterization of YF/JE chimeras

| Clone | Yield (μg) | Infectivity plaques/100 ng LLC-MK2 | PBS log titer VERO | RNAse log titer VERO | DNAse log titer VERO |
|---|---|---|---|---|---|
| YF5.2Iv | 5.5 | 15 | 7.2 | 0 | 7 |
| YF/JE-S | 7.6 | 50 | 6.2 | 0 | 6.2 |
| YF/JE-N | 7 | 60 | 5 | 0 | 5.4 |

TABLE 3

Plaque reduction neutralization titers on YF/JE chimeras

| Virus | non-immune ascitic fluid | YF ascitic fluid | JE ascitic fluid | non-immune IgG | YF IgG |
|---|---|---|---|---|---|
| YF5.2iv | <1.3 | 3.7 | <1.3 | <2.2 | >4.3 |
| JE SA14-14-2 | <1.3 | <1.3 | 3.4 | <2.2 | <2.2 |
| YF/ JE $SA_{14}$-14-2 | <1.3 | <1.3 | 3.1 | <2.2 | <1.9 |
| YF/JE Nakayama | <1.3 | <1.3 | 3.4 | <2.2 | <2.2 |
| JE Nakayama virus | <1.3 | <1.3 | 3.4 | not determined | not determined |

TABLE 4

Neurovirulence of YF/JE SA14-14-2 Chimera 3 week old male ICR mice

| | log dose I.C. | % Mortality | |
|---|---|---|---|
| YF5.2iv | 4 | 100 | (7/7) |
| YF/JE SA14-14-2 | 4 | 0 | (0/7) |
| YF/JE SA14-14-2 | 5 | 0 | (0/7) |
| YF/JE SA14-14-2 | 6 | 0 | (0/8) |

TABLE 5

Neuroinvasiveness of YF/JE Chimeras 3 week old male ICR mice

| | log dose (intraperitoneal) | % mortality | |
|---|---|---|---|
| YF/JE Nakayama | 4 | 0 | (0/5) |
| YF/JE Nakayama | 5 | 0 | (0/4) |
| YF/JE Nakayama | 6 | 0 | (0/4) |
| YF/JE SA14-14-2 | 4 | 0 | (0/5) |
| YF/JE SA14-14-2 | 5 | 0 | (0/4) |
| YF/JE SA14-14-2 | 6 | 0 | (0/4) |

TABLE 6

Doses and routes of virus inoculation into groups of 4-week-old ICR mice

| Group | YF/JE s.c. $log_{10}$ pfu | YF/JE i.c. $log_{10}$ pfu | YF-VAX ® (Yellow Fever 17D Vaccine) s.c. $log_{10}$ pfu | YF-VAX ® (Yellow Fever 17D Vaccine) i.c. $log_{10}$ pfu | mice |
|---|---|---|---|---|---|
| 1 | 5 | 4.5 | 4.7 | 4.2 | 20 |
| 2 | 4 | 4 | 4.4 | 3.9 | 20 |
| 3 | 3 | 3 | 3.4 | 3.4 | 20 |
| 4 | 2 | 2 | 2.4 | 2.4 | 20 |
| 5 | 1 | 1 | 1.4 | 1.4 | 20 |

TABLE 6-continued

Doses and routes of virus inoculation into groups of 4-week-old ICR mice

| Group | YF/JE s.c. $log_{10}$ pfu | YF/JE i.c. $log_{10}$ pfu | YF-VAX ® (Yellow Fever 17D Vaccine) s.c. $log_{10}$ pfu | YF-VAX ® (Yellow Fever 17D Vaccine) i.c. $log_{10}$ pfu | mice |
|---|---|---|---|---|---|
| 6 | JE-VAX ® (inactivated Japanese Encephalitis virus vaccine) (BIKEN) 1:30, day 0, 7, s.c. | | | | 5 |
| 7 | JE-VAX ® (inactivated Japanese Encephalitis virus vaccine) (BIKEN) 1:300, day 0, 7, s.c. | | | | 5 |
| 8 | control s.c. (medium + 10% FBS) | | | | 5 |
| 9 | control i.c. (medium + 10% FBS) | | | | 5 |

TABLE 7

Geometric mean neutralizing antibody titers 3 and 8 weeks after immunization, outbred mice inoculated with graded doses of vaccines by the s.c. route

| | Dose | Antibody titer (GMT + SD) vs. | | | |
|---|---|---|---|---|---|
| | | JE | | YF 17D | |
| Vaccine | $log_{10}$PFU | 3w | 8w | 3w | 8w |
| YF/JE | 5.0 | 151 ± 93 | 5,614 ± 3514 | | |
| | 4.0 | 38 ± 60 | 127 ± 247 | | |
| | 3.0 | 19 ± 65 | 43 ± 560 | | |
| | 2.0 | 7 ± 12 | 3 ± 71 | | |
| | 1.0 | 2 ± 8 | 0 | | |
| YF 17D | 4.7 | | | 2 ± 4 | 18 ± 13 |
| | 4.4 | | | 35 ± 24 | 250 ± 109 |
| | 3.4 | | | 9 ± 20 | 54 ± 179 |
| | 2.4 | | | 1 ± 0 | 53 ± 22 |
| | 1.4 | | | 0 | 46 ± 18 |

TABLE 8

Immunogenicity and protection vs. challenge Mice were immunized on Day 0 with live vaccines and on days 0, 7, and 20 with JE-VAX ® (inactivated Japanese Encephalitis virus vaccine), bled on day 21 and challenged on day 28.

| Virus | No./ group | Dose (pfu) | Route | Total no. mice |
|---|---|---|---|---|
| 1. YF/JE (SA14-14-2 RMS)* | 8 | $10^2$–$10^5$ | sc | 32 |
| 2. YF 17D (iv5.2) (Vero) | 8 | $10^2$–$10^5$ | sc | 32 |
| 3. YF 17D (PMC) | 8 | $10^2$–$10^5$ | sc | 32 |
| 4. JE Nakayama | 8 | $10^2$–$10^5$ | sc | 32 |
| 5. JE SA14-14-2 (BHKP1)** | 8 | $10^2$–$10^5$ | sc | 32 |
| 6. YF/JE (Nakayama)# | 8 | $10^2$–$10^5$ | sc | 32 |
| 7. JE-VAX ® (inactivated Japanese Encephalitis virus vaccine) Connaught lot EJN*151B | 8 | 100 ul 1:300 dilution on Day 0, 7 and 100 ul 1:5 dilution on D 20 | sc | 8 |
| 8. None (challenged) | 8 | — | ip | 8 |
| 9. None (unchallenged) | 8 | — | — | 8 |

*YF/JE SA14-14-2 vaccine candidate
**Chinese live vaccine, passed once in BHK cells
Chimeric YF/JE virus, with prM-E insert of wild-type JE Nakayama

TABLE 9

Protection of C57/BL6 mice by a single SC inoculum of graded doses of live virus vaccines against IP challenge with 158 LD50 of wild-type JE virus (IC-37). Mice were challenged 28 days after immunization.

| | Number of survivors/number challenged (% survivors) by vaccine dose ($log_{10}$ pfu) | | | | | | |
|---|---|---|---|---|---|---|---|
| Vaccine | None | 1 | 2 | 3 | 4 | 5 | Other |
| Yellow fever 17D (YF-VAX ® (Yellow Fever 17D vaccine) unpassaged) | | NT* | 3/8 (37.5%) | 1/8 (12.5%) | 1/8 (12.5%) | 2/8 (25%) | |
| Yellow fever 17D (YF5.2 iv infectious clone) | | NT | 0/8 (0%) | 1/8 (12.5%) | 1/8 (12.5%) | 1/8 (12.5%) | |
| Yellow fever/JE SA14-14-2 chimera | | 1/8 (12.5%) | 2/8 (25%) | 7/7 (100%) | 7/8 (87.5%) | 7/7 (100%) | |
| Chinese JE vaccine SA14-14-2 (BHK1) | | NT | 1/8 (12.5%) | 1/8 (12.5%) | 0.8 (0%) | 3/8 (37.5%) | |
| Wild-Type JE (Nakayama)# | | NT | 2/7 (29%) | 1/6 (17%) | 1/3 (33%) | 1/4 (25%) | |
| YF/JE (Nakayama) | | | 3/3 (100%) | 5/5 (100%) | 3/3 (100%) | ^ | |
| Mouse brain vaccine (JE-VAX ® (inactivated Japanese Encephalitis virus vaccine))** | | | | | | | 7/8 (87.5%) |
| Control (challenge) | 1/8 (12.5%) | | | | | | |
| Control (no challenge) | 8/8 (100%) | | | | | | |

*Not tested;
Some mice died as a result of inoculation of the wild-type virus at high doses, thus fewer mice remained for challenge;
**Three doses at 1 week intervals;
^ No mice survived initial inoculation at this dose

TABLE 10

Geometric mean neutralizing antibody titers, C57/BL6 mice 21 days after immunization with a single SC inoculum of graded doses of live virus vaccines and 1 day after the third dose of inactivated JE-VAX ™ (inactivated Japanese Encephalitis virus vaccine).

| Vaccine | Dose ($log_{10}$PFU) | Antibody titer (GMT ± SD) vs. JEV | Antibody titer (GMT ± SD) vs. YF 17D |
|---|---|---|---|
| YF/JE SA14-14-2 | 5 | 44.8 ± 25.2 | |
| | 4 | 26.5 ± 23.1 | |
| | 3 | 6.2 ± 4.9 | |
| | 2 | 1.1 ± 0.35 | |
| | 1 | 1 ± 0 | |
| SA14-14-2(BHK1) | 5 | 2.5 ± 4.3 | |
| | 4 | 3.5 ± 20.5 | |
| | 3 | 4.7 ± 15.5 | |
| | 2 | 1 ± 0 | |
| JE Nakayama | 5 | 1.32 ± 1 | |
| | 4 | 4 ± 4.0 | |
| | 3 | 1.6 ± 1.8 | |
| | 2 | 1 ± 0 | |
| JF/JE-Nakayama | 5 | 10 ± 70* | |
| | 4 | 102.5 ± 45.7 | |
| | 3 | 76.8 ± 63.9 | |
| | 2 | 19.8 ± 8.1 | |
| JE-VAX ® (inactivated Japanese Encephalitis vaccine) (mouse brain) | 3 doses** | 2.8 ± 6.5 | |

TABLE 10-continued

Geometric mean neutralizing antibody titers, C57/BL6 mice 21 days after immunization with a single SC inoculum of graded doses of live virus vaccines and 1 day after the third dose of inactivated JE-VAX ™ (inactivated Japanese Encephalitis virus vaccine).

| Vaccine | Dose ($log_{10}$PFU) | Antibody titer (GMT ± SD) vs. JEV | Antibody titer (GMT ± SD) vs. YF 17D |
|---|---|---|---|
| YF-VAX ® (Yellow Fever 17D vaccine) | 5 | | 11 ± 9.6 |
| | 4 | | 13.8 ± 19.1 |
| | 3 | | 4.3 ± 11.7 |
| | 2 | | 1 ± 0 |
| YF5.2iv (17D infect. clone) | 5 | | 29.3 ± 47.1 |
| | 4 | | 11 ± 15.2 |
| | 3 | | 8 ± 19.4 |
| | 2 | | 2.1 ± 3.2 |
| Controls | 0 | 1 ± 0 | |

*only 2/8 mice survived immunization with this virus; the low antibody titers in these animals probably reflect low level virus replication consistent with survival.
**3 doses on days 0, 7, 20; animals were bled on day 21, 1 day after their third immunization. The day 20 boost was performed with a higher dose of vaccine, thus antibody titers pre-challenge are expected to be higher than those shown here.

TABLE 11

Geometric mean neutralizing antibody titers (GMT) in 3 monkeys 2 and 4 weeks post inoculation with a single dose of YF-VAX ® (Yellow Fever 17D vaccine) or CHIMERIVAX ™ (chimeric flavivirus vaccine) by the I.C. route

| | | GMT | | | |
|---|---|---|---|---|---|
| | | JE | | YF | |
| Vaccine | Dose (log 10 pfu) | 2W | 4W | 2W | 4W |
| CHIMERIVAX ™ (chimeric flavivirus vaccine) | 7.0 | 75 | 3200 | | |
| YF-VAX ® (Yellow Fever 17D vaccine) | 5.0 | | | 66 | 4971 |

TABLE 12

Immunization and protection: rhesus monkeys
Screening III test for flavivirus antibodies: negative

| Group | N | Virus | Dose, route ($log_{10}$PFU/0.5 ml) | JE Challenge Day 60 |
|---|---|---|---|---|
| 1 | 3 | YF/JE SA14-14-2 | 4.3 SC | 5.0 IC |
| 2 | 3 | YF/JE SA14-14-2 | 5.3 SC | 5.0 IC |
| 3 | 4 | Saline/sham | — SC | 5.0 IC |

• Viremia days 1–7 after immunization and challenge
• Neutralization test days 0, 15, 30, 45, and 60 after immunization and days 15 and 30 after challenge
• Necropsy day 30 post challenge

TABLE 13

Viremia, rhesus monkeys immunized with ChimeriVax ™ by the SC route

| | Dose | Day post-inoculation | | | | | | |
|---|---|---|---|---|---|---|---|---|
| Monkey | $log_{10}$PFU | 0 | 1 | 2 | 3 | 4 | 5 | 6 |
| R423 | 4.3 | <1.0* | <1.0 | <1.0 | 1.1 | 1.7 | 1.0 | <1.0 |
| R073 | | <1.0 | <1.0 | <1.0 | 1.0 | 1.0 | <1.0 | <1.0 |
| R364 | | <1.0 | 1.0 | <1.0 | 1.0 | 1.0 | <1.0 | <1.0 |
| R756 | 5.3 | <1.0 | 1.0 | 1.0 | 1.6 | 1.0 | <1.0 | <1.0 |
| R174 | | <1.0 | 1.3 | 1.8 | 1.6 | 1.1 | <1.0 | <1.0 |
| R147 | | <1.0 | 2.0 | 1.6 | 1.0 | 1.0 | <1.0 | <1.0 |

*$log_{10}$PFU/ml

TABLE 14

JE neutralizing antibody responses, rhesus monkeys immunized with ChimeriVax ™ by the SC Route
50% PRNT titers, heat-inactivated serum, no added complement

| | Dose | Day post-innoculation | | |
|---|---|---|---|---|
| Monkey | $log_{10}$PFU | Baseline | 15 | 30 |
| R423 | 4.3 | <10 | 160 | 2560 |
| R073 | | <10 | 80 | 640 |
| R364 | | <10 | 160 | 320 |
| R756 | 5.3 | <10 | 20 | 320 |
| R174 | | <10 | 640 | 2560 |
| R147 | | <10 | 160 | 2560 |

TABLE 15

Protection against IC challenge, rhesus monkeys immunized with ChimeriVax ™ by the SC route
Monkeys challenged IC on Day 60 with 100,000 pfu/mouse LD50

| Vaccine Dose $log_{10}$PFU | No. survived/No. tested |
|---|---|
| 4.3 | 2/3 (67%)* |
| 5.3 | 3/3 (100%) |
| Sham | 0/4 (0%) |

*1 monkey that died was a pregnant female

TABLE 16

List of chimeric YF/JE mutants (1 to 9) constructed to identify residues involved in attenuation of the CHIMERIVAX ™ (chimeric flavivirus vaccine). Mutated amino acids on the E-proteins are shown in bold letters.

| | | CHIMERIVAX ™ (chimeric flavivirus | Mutant Viruses | | | | | | | | | | |
|---|---|---|---|---|---|---|---|---|---|---|---|---|---|
| Positions | Nakayama | vaccine) | 1 | 2 | 3 | 4 | 5 | 6 | 7 | 8 | 9 | 10 | 11 |
| 107 | L | F | L | F | F | L | L | F | L | F | L | F | L |
| 138 | E | K | K | E | K | K | E | E | E | **E** | E | E | E |
| 176 | I | V | V | V | I | **I** | **V** | **I** | **I** | V | V | **I** | **I** |
| 177 | T | A | A | A | **T** | **T** | **A** | T | **T** | A | A | T | T |
| 227 | P | S | S | S | S | S | S | S | S | **P** | **P** | **P** | **P** |
| 264 | Q | H | H | H | H | H | H | H | H | **Q** | **Q** | **Q** | **Q** |
| 279 | K | M | M | M | M | M | M | M | M | **K** | **K** | **K** | **K** |

TABLE 17

| Group | Dose administered i.c. (pfu) | | |
|---|---|---|---|
| | P1 | P10 | P18 |
| Neat | $\geqq 6 \times 10^4$ | $1 \times 10^6$ | $2 \times 10^7$ |
| $10^{-1}$ | $\geqq 6 \times 10^3$ | $1 \times 10^5$ | $2 \times 10^6$ |

TABLE 18

| Group | Dose administered s.c. (pfu) | | |
|---|---|---|---|
| | RMS | P10 | P18 |
| Neat | $2 \times 10^5$ | $2 \times 10^7$ | $3 \times 10^7$ |
| $10^5$ | $1 \times 10^5$ | $5 \times 10^5$ | $5 \times 10^4$ |
| $10^4$ | $1 \times 10^4$ | $5 \times 10^4$ | $5 \times 10^3$ |

TABLE 19

Design of an experiment to determine cross-protection/interference between YF 17D and YF/JE SA14-14-2

| # of female ICR mice | 1st Vaccine¶ | 2nd vaccine 3 months | 6 months | 12 months |
|---|---|---|---|---|
| 8 | YF/JE SA14-14-2 | YF-VAX ® (Yellow Fever 17D Vaccine) | | |
| 8 | YF/JE SA14-14-2 | | YF-VAX ® (Yellow Fever 17D Vaccine) | |
| 8 | YF/JE SA14-14-2 | | | YF-VAX ® (Yellow Fever 17D Vaccine) |
| 8 | JE-VAX ® (inactivated Japanese Encephalitis virus vaccine) | YF-VAX ® (Yellow Fever 17D Vaccine) | | |
| 8 | JE-VAX ® (inactivated Japanese Encephalitis virus vaccine) | | YF-VAX ® (Yellow Fever 17D Vaccine) | |

TABLE 19-continued

Design of an experiment to determine cross-protection/interference between YF 17D and YF/JE SA14-14-2

| # of female ICR mice | 1st Vaccine¶ | 2nd vaccine 3 months | 6 months | 12 months |
|---|---|---|---|---|
| 8 | JE-VAX ® (inactivated Japanese Encephalitis virus vaccine) | | | YF-VAX ® (Yellow Fever 17D Vaccine) |
| 8 | YF-VAX ® (Yellow Fever 17D Vaccine) | YF/JE SA14-14-2 | | |
| 8 | YF-VAX ® (Yellow Fever 17D Vaccine) | | YF/JE SA14-14-2 | |
| 8 | YF-VAX ® (Yellow Fever 17D Vaccine) | | | YF/JE SA14-14-2 |
| 4 | | YF-VAX ® (Yellow Fever 17D Vaccine) | | |
| 4 | | YF/JE SA14-14-2 | | |
| 4 | | | YF-VAX ® (Yellow Fever 17D Vaccine) | |
| 4 | | | YF/JE SA14-14-2 | |
| 4 | | | | YF-VAX ® (Yellow Fever 17D Vaccine) |
| 4 | | | | YF/JE SA14-14-2 |

¶One dose of YF/JE SA14-14-2, 5.3 $\log_{10}$pfu/mouse, sc.
One dose of YF-VAX ® (Yellow Fever 17D Vaccine), 4.4 $\log_{10}$pfu/mouse, sc.
Two doses of JE-VAX ® (inactivated Japanese Encephalitis virus vaccine) (PMC), 0.5 ml of 1:5 dilution administered ip at 1 week intervals.

TABLE 20

Engineering of YF/Flavivirus chimeras

| Virus | Chimeric C/prM junction[1] | Chimeric E/NS1 junction[2] | 5' ligation[3] | 3' ligation[4] | Sites[5] eliminated or (created) |
|---|---|---|---|---|---|
| YF/WN | X-cactgggagagcttgaaggtc (SEQ ID NO: 1) | aaagccagttgcagccgcggtttaa (SEQ ID NO: 2) | AatII | NsiI | |
| YF/DEN-1 | X-aaggtagactggtgggctccc (SEQ ID NO: 3) | gatcctcaggtaccaaccgcggtttaa (SEQ ID NO: 4) | AatII | SphI | SphI in DEN |
| YF/DEN-2 | X-aaggtagattggtgtgcattg (SEQ ID NO: 5) | aaccctcagtaccacccgcggttta (SEQ ID NO: 6) | AatII | SphI | |
| YF/DEN-3 | X-aaggtgaattgaagtgctcta (SEQ ID NO: 7) | acccccagcaccacccgcggttta (SEQ ID NO: 8) | AatII | SphI | XhoI in DEN (SphI in DEN) |
| YF/DEN-4 | X-aaaaggaacagttgttctcta (SEQ ID NO: 9) | acccgaagtgtcaaccgaggtttaa (SEQ ID NO: 10) | AatII | NsiI | |

TABLE 20-continued

Engineering of YF/Flavivirus chimeras

| Virus | Chimeric C/prM junction[1] | Chimeric E/NS1 junction[2] | 5' ligation[3] | 3' ligation[4] | Sites[5] eliminated or (created) |
|---|---|---|---|---|---|
| YF/SLE | X-aacgtgaatagttggatagtc (SEQ ID NO: 11) | accgttggtcgcacccgcggttta (SEQ ID NO: 12) | AatII | SphI | AatII in SLE |
| YF/MVE | X-aatttcgaaaggtggaaggtc (SEQ ID NO: 13) | gaccggtgtttacagccgcggtttaa (SEQ ID NO: 14) | AatII | AgeI | (AgeI in YF) |
| YF/TBE | X-tactgcgaacgacgttgccac (SEQ ID NO: 15) | actgggaacctcacccgcggtttaa (SEQ ID NO: 16) | AatII | AgeI | (AgeI in YF) |

[1, 2]: The column illustrates the oligonucleotide used to generate chimeric YF/Flavivirus primers corresponding to the C/prM or E/NS1 juction. (See text). X = carboxyl terminal coding sequence of the YF capsid. The underlined region corresponds to the targeted heterologous sequence immediately upstream of the NarI site (antisence-ccgcgg). The site allows insertion of PCR products into the Yfm5.2 (NarI) plasmid required for generating full-length dCNA templates. Other nucleotides are specific to the heterologous virus. Oligonucleotide primers are listed 5' to 3'.
[3, 4]: The unique restriction sites used for creating restriction fragments that can be isolated and ligated in vitro to produce full-length chimeric cDNA templates are listed. Because some sequences do not contain convenient sites, engineering of appropriate sites is required in some cases (footnote 5).
[5]: In parentheses are the restriction enzyme sites that must be created either in the YF backbone or the heterologous virus to allow efficient in vitro ligation. Sites not in parentheses must be eliminated. All such modifications are done by silent mutagenesis of the cDNA for the respective clone. Blank spaces indicate that no modification of the cDNA clones is required.

TABLE 21

Sequence comparison of Dengue-2 and YF/Den-$2_{218}$ viruses

| Virus | prM 28 | 31 | 55 | 57 | 125 | 152 | 161 |
|---|---|---|---|---|---|---|---|
| YF/$D2_{218}$ | E | V | L | R | I | A | V |
| PUO-218 | E | V | L | R | I | A | V |
| NGC | E | V | F | R | T | A | V |
| PR-159 (S1) | K | T | F | K | T | V | I |

| Virus | ENVELOPE 71 | 81 | 126 | 129 | 139 | 141 | 162 | 164 | 202 | 203 | 335 | 352 | 390 | 402 | 484 |
|---|---|---|---|---|---|---|---|---|---|---|---|---|---|---|---|
| YF/$D2_{218}$ | E | S | E | V | I | V | I | V | E | N | I | I | N | F | I |
| PUO-218 | E | S | E | V | I | V | I | V | E | N | I | I | N | F | I |
| NGC | D | S | K | V | I | I | I | I | E | N | I | I | N | I | V |
| PR-159 (S1) | E | T | E | I | V | I | V | I | K | D | T | T | D | F | I |

TABLE 22

Summary of histopathology results, monkeys inoculated with YF-VAX ® (Yellow Fever 17D vaccine) or YF/JE SA14-14-2 by the IC route

| YF-VAX ® (Yellow Fever 17D vaccine) | | | CHIMERIVAX-JE ™ (chimeric flavivirus vaccine comprising Japanese Encephalitis virus prM and E proteins) | | |
|---|---|---|---|---|---|
| Monkey No. | Discriminator area score | Discriminator plus target area score | Monkey No. | Discriminator area score | Discriminator plus target area score |
| N030 | 0.21 | 0.64 | N191 | 0 | 0.17 |
| N492 | 0.04 | 0.36 | N290 | 0.09 | 0.06 |
| N479 | 0 | 0.17 | N431 | 0.13 | 0.09 |
| Group Means | 0.08 | 0.39 | | 0.07 | 0.11 |

TABLE 23

List of initial chimeric YF/JE mutants constructed to identify residues involved in attenuation of the CHIMERIVAX ™ (chimeric flavivirus vaccine). Reverted amino acids on the E-proteins are shown in BOLD

| Positions on E-Protein | Nakayama | CHIMERIVAX ™ (chimeric flavivirus vaccine) | MUTANT VIRUSES | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| 107 | L | F | **L** | F | F | **L** | L | F | L | F | L | F | L |
| 138 | E | K | K | **E** | K | K | E | E | E | E | E | E | E |
| 176 | I | V | V | V | I | I | V | I | I | V | V | I | I |
| 177 | T | A | A | A | T | T | A | T | T | A | A | T | T |
| 227 | P | S | S | S | S | S | S | S | S | P | P | P | P |
| 264 | Q | H | H | H | H | H | H | H | H | Q | Q | Q | Q |
| 279 | K | M | M | M | M | M | M | M | M | K | K | K | K |

TABLE 24

Experiment to determine neurovirulence and neuroinvasiveness phenotypes of vaccine candidates in suckling mice

| Virus | Route | AGE OF MICE (DAYS) | | | |
|---|---|---|---|---|---|
| | | 3 | 5 | 7 | 9 |
| YF/Den-2 | I.C. | $10^4$* | $10^4$ | $10^4$ | $10^4$ |
| YF/JESA14-14-2 | I.C. | $10^4$ | $10^4$ | $10^4$ | $10^4$ |
| YF 17D | I.P. | $10^3$ | $10^3$ | $10^3$ | $10^3$ |
| MED + 5% FBS | I.C., I.P. | — | — | — | — |

*PFU/0.02 ml of inoculum

TABLE 25

Summary of differences between virulent (Asibi) and attenuated (17D, 17DD, RMS, P18) yellow fever viruses

| Gene | NT | Asibi | 17D204US | RMS | P18 | 17D204F | 17D213 | 17DD | AA |
|---|---|---|---|---|---|---|---|---|---|
| C | 304 | G | A | A | A | A | A | A | |
| non-M | 374 | T | C | C | C | C | C | C | |
| M | 643 | A | A | — | — | A | A | G | |
| E | 654 | C | T | — | — | T | T | T | L F |
| | 683 | A | G | — | — | G | G | A | |
| | 1127 | G | A | — | — | A | A | A | G R |
| | 1140 | C | T | — | — | T | T | C | A V |
| | 1431 | A | A | — | — | A | C | A | N T |
| | 1436 | G | G | — | — | G | G | A | D S |
| | 1437 | A | A | | | A | A | G | |
| | 1482 | C | T | — | — | T | T | T | A V |
| | 1491 | C | T | — | — | T | T | T | T I |
| | 1558 | C | C | — | — | C | C | A | |
| | 1572 | A | C | — | — | C | C | C | K T |
| | 1750 | C | T | — | — | T | T | T | |
| | 1819 | C | T | — | — | T | T | T | |
| | 1870 | G | A | — | — | A | A | A | M I |
| | 1887 | C | T | — | — | T | T | T | S F |
| | 1946 | C | T | — | — | T | T | C | P S |
| | 1965 | A | G | — | — | G | G | G | K R |
| | 2110 | G | G | — | — | G | G | A | |
| | 2112 | C | G | — | — | G | G | G | T R |
| | 2142 | C | A | — | — | A | A | A | P H |
| | 2219 | G | A | — | — | A | A | G | A T |
| | 2320 | C | C | — | — | C | C | T | T I |
| | 2356 | C | T | — | — | T | T | T | |

TABLE 25-continued

Summary of differences between virulent (Asibi) and attenuated (17D, 17DD, RMS, P18) yellow fever viruses

| Gene | NT | Asibi | 17D204US | RMS | P18 | 17D204F | 17D213 | 17DD | AA |
|---|---|---|---|---|---|---|---|---|---|
| NS1 | 2687 | C | T | T | T | T | T | T | F L |
| | 2704 | A | G | G | G | G | G | G | |
| | 3274 | G | A | A | A | A | A | A | |
| | 3371 | A | G | G | G | G | G | G | V I |
| | 3699 | T | T | T | T | T | T | C | |
| | 3613 | G | A | A | A | A | A | A | |
| | 3637 | C | C | C | C | C | C | T | |
| ns2a | 3817 | G.A | G | G | G | G | G | G | |
| | 3860 | A | G | G | G | G | G | G | V M |
| | 3915 | T.A | T | T | T | T | T | T | |
| | 4007 | A | G | G | G | G | G | G | A T |
| | 4013 | C | T | T | T | T | C | T | F L |
| | 4022 | A | G | G | G | G | G | G | A T |
| | 4025 | G | G | A | A | G | G | G | V M |
| | 4054 | C | T | T | T | T | T | C | |
| | 4056 | C | T | T | T | T | T | T | F S |
| ns2b | 4204 | C | C | C | C | C | C | T | |
| | 4289 | A | C | C | C | C | C | C | L I |
| | 4387 | A | G | G | G | G | G | G | |
| | 4505 | A | C | C | C | C | C | C | L I |
| | 4507 | T | C | C | C | C | C | C | |
| NS3 | 4612 | T | C | C | C | C | C | T | |
| | 4864 | G.A | G | G | G | G | G | G | |
| | 4873 | T | G | G | G | G | G | T | |
| | 4942 | A | A | A | A | A | A | G | |
| | 4957 | C | C | C | C | C | C | T | |
| | 4972 | G | G | G | G | G | G | A | |
| | 5115 | A | A | A | A | A | A | G | O R |
| | 5131 | G.T | G | G | G | G | G | G | M M.I |
| | 5153 | A | G | G | G | G | G | A | V I |
| | 5194 | T | C | C | C | C | C | C | |
| | 5225 | A | C | C | C | C | C | C | |
| | 5362 | C | C | C | C | C | T | A | |
| | 5431 | C | T | T | T | T | T | T | |
| NS3 | 5461 | T | T | C | C | T | T | T | |
| | 5473 | C | T | T | T | T | T | T | |
| | 5641 | G | A | G | G | A | G | G | |
| | 6013 | C | T | T | T | T | T | T | |
| | 6023 | G | A | A | A | A | A | A | N D |
| ns4a | 6070 | C | C | C | C | C | C | T | |
| | 6448 | G | T | T | T | T | T | T | |
| | 6514 | T | T | T | T | T | T | C | |
| | 6529 | T | C | C | C | T | T | T | |
| | 6625 | A | A | A | A | A | C | C | |
| | 6758 | A | G | G | G | a | A | A | V I |
| | 6829 | T | C | C | C | C | C | C | |
| | 6876 | T | C | C | C | C | C | C | A V |
| ns4b | 7171 | A | G | G | G | G | G | G | M I |
| | 7319 | G | G | A | A | A | A | A | E K |
| | 7497 | T | T | T | T | T | C | T | L S |
| | 7571 | C | A | A | A | A | A | C | |
| NS5 | 7580 | T | C | C | C | C | C | C | H Y |
| | 7642 | T | C | C | C | C | C | C | |
| | 7701 | A | G | G | G | G | G | A | R O |
| | 7945 | C | T | T | T | T | T | T | |
| | 7975 | C | C | C | C | C | C | T | |
| | 8008 | T | C | C | C | C | C | C | |
| | 8029 | T | T | T | T | T | T | C | |
| | 8212 | C | C | T | T | c | C | C | |
| | 8581 | A | A | C | C | a | A | A | |
| | 8629 | C | T | T | T | T | T | T | |
| | 8808 | A | A | A | A | A | A | G | N S |
| | 9397 | A | A | A | A | A | A | G | |
| | 9605 | A | G | G | G | A | A | A | D N |
| | 10075 | G.T | G | G | G | G | G | G | M M.I |
| | 10142 | G | A | A | A | A | A | A | K E |
| | 10243 | G | A | A | A | A | A | A | |
| | 10285 | T | C | C | C | C | C | C | |
| | 10312 | A | G | G | G | G | G | G | |
| | 10316 | T.C | T | T | T | T | T | T | S S.P |

TABLE 25-continued

Summary of differences between virulent (Asibi) and attenuated (17D, 17DD, RMS, P18) yellow fever viruses

| Gene | NT | Asibi | 17D204US | RMS | P18 | 17D204F | 17D213 | 17DD | AA |
|---|---|---|---|---|---|---|---|---|---|
| 3' NC | 10339 | C | G | G | G | G | G | G | |
| | 10367 | T | C | C | C | C | C | C | |
| | 10418 | T | C | C | C | C | C | C | |
| | 10454 | A | G | A | A | A | A | A | |
| | 10550 | T | C | C | C | C | C | T | |
| | 10722 | G | G | G | G | A | G | G | |
| | 10800 | G | A | A | A | A | A | A | |
| | 10847 | A | C | C | C | C | C | C | |

NT: nucleotide numbers are from 5' terminus of the genome. Where clonal differences were present, both nucleotides as well as amino acids (if appropriate) are shown. If nucleotide change results in an amino acid substitution, the amino acid (AA) is shown from left to right (e.g. from Asibi to 17D).
—: The genes for prME in RMS (YF17D/JESA14-14-2) and P18 (passage 18th of the RMS) are from JEV strain SA14-14-2, therefore not comparable with YFV sequences. Sequences for Asibi is taken from Hahn et al. 1987.
17D204US from Rice et al. 1985,
17D204F from Dupuy et al. 1989.
RMS and P18 are unpublished sequences (OraVax, Inc.,),
17D213 and 17DD from Duarte dos Santos et al. 1994.
Note that there is no sequence difference between PMS and passage 18th. There are 6 nucleotide differences (nucleotide positions are shaded) between published YF17D sequence and RMS shown in bold letters; changes in 5461, 5641, 8212 and 8581 are silent and do not result in amino acid substitution. Changes in position 4025 and 7319 result in amino acid substitution.

TABLE 26

Immunogenicity of CHIMERIVAX ™ (chimeric flavivirus vaccine comprising Dengue-2 virus prM and E proteins) passed in Vero cells for mice.

| Passage level[a] | Dose ($Log_{10}$pfu) | GMT[b] SC | GMT[b] IC |
|---|---|---|---|
| P3 | 5 | 1 ± 0[c] | 61 ± 47 |
| | 4 | 1 ± 0 | 7 ± 15 |
| P5 | 5 | 1 ± 0 | 46 ± 16 |
| | 4 | 1 ± 0 | 9 ± 20 |
| P10 | 5 | 1.8 ± 7.7 | 46 ± 53 |
| | 4 | 1 ± 0 | 7 ± 15 |
| P18 | 5 | 1 ± 0 | 53 ± 17 |
| | 4 | 1 ± 0 | 2 ± 16 |

[a]CHIMERIVAX ™ (chimeric flavivirus vaccine comprising Dengue-2 virus prM and E proteins) virus was passaged in $Vero_{PM}$ cells (P141–147) at MOI of 0.1–0.5 and harvested 2–3 days PI.
[b]Geometric Mean Titers measured as the last dilution of sera which resulted in 50% reduction in number of virus plaques.
[c]Titers less than 1:10

TABLE 27

Immunization and challenge of yellow fever immune monkeys

| | | Seroconversion | | Viremic after wt Den2 |
|---|---|---|---|---|
| 1st Vaccine | 2nd Vaccine | Den2 | YF | challenge |
| YF17D | CHIMERIVAX ™ (chimeric flavivirus vaccine comprising Dengue-2 virus prM and E proteins) | 3/3 | 3/3 | 0/3 |
| YF17D | Dengue-2 wt | 4/4 | 4/4 | 0/4 |
| YF17D | YF 17D | 0/3 | 3/3 | 3/3 |
| YF17D | None | 0/2 | 2/2 | 2/2 |
| None | None | 0/2 | 0/2 | 2/2 |

TABLE 28

Viremia in rhesus monkeys inoculated SC with graded doses of ChimeriVax ™-Den-2 virus.

| Virus | Dose ($Log_{10}$PFU) | No. viremic (%) | Duration (days) mean | Titer mean peak |
|---|---|---|---|---|
| ChimeriVax ™-Den-2 | 2.0 | 4/4 (100) | 3.2 | 1.6 |
| | 3.0 | 5/5 (100) | 3.8 | 1.6 |
| | 4.0 | 5/5 (100) | 4.0 | 1.3 |
| | 5.0 | 4/4 (100) | 4.3 | 1.4 |
| Dengue-2 (18603) | 4.0 | 4/4 (100) | 5 | 3.6 |

TABLE 29

Neutralizing antibody responses in monkeys inoculated with graded doses of ChimeriVax ™-Den-2 and protection against wild-type dengue-2 challenge

| Dose | No. | GMT by day | | | No. Viremic after Challenge |
|---|---|---|---|---|---|
| $Log_{10}$PFU | seroconverted | 0 | 15 | 30 | (D60) |
| 2.0 | 4/4 | <10 | 47 | 316 | 0/4 |
| 3.0 | 5/5 | <10 | 112 | 275 | 0/5 |
| 4.0 | 5/5 | <10 | 269 | 316 | 0/5 |
| 5.0 | 4/4 | <10 | 631 | 376 | 0/4 |
| Sham | 0/4 | <10 | <10 | <10 | 4/4 |

TABLE 30

Mean virus titer in orally exposed mosquitos 22 days post feeding

| Mosquito Species | Virus | # Infected/ # Fed | Mean Titer* |
|---|---|---|---|
| *Ae. aegypti* | JE SA14-14-2 | 20/20 | 6.0 |
| | YF 17D | 0/30 | <1.0 |
| | ChimeriVax ™-JE | 0/40 | <1.0 |

TABLE 30-continued

| Mosquito Species | Virus | # Infected/ # Fed | Mean Titer* |
|---|---|---|---|
| | Mean virus titer in orally exposed mosquitos 22 days post feeding | | |
| *Ae. albopictus* | JE SA14-14-2 | 38/38 | 5.8 |
| | YF 17D | 0/44 | <1.0 |
| | ChimeriVax ™-JE | 0/56 | <1.0 |

*$\log_{10}$pfu/ml

TABLE 31

| Primers (restriction sites are underlined) |
|---|
| #1) YFM5'3(4.56)+ (GTGAGCATTGAGAAAGCGCCACGCTTC) (SEQ ID NO: 17) |
| #2) YF0.481– (TCCACCCGTCATCAACAGCATTCCCAAAATTAG) (SEQ ID NO: 18) |
| #3) 1DE 0.42+ (GAATGCTGTTGATGACGGGTGGATTTCATCTGACCACACGAGGG) (SEQ ID NO: 19) |
| #4) 1DE 1.095– (NheI/BstBI)(GCCGCTAGCTTTTCGAAGGACGGCAGGGTTTGTGACTTC) (SEQ ID NO: 20) |
| #5) 1DE 1.102+ (BstBI)(GCCATGCATTTCGAAAACTGTGCATCGAAGCTAAAATATC) (SEQ ID NO: 21) |
| #7) 1DE 2.409FUSE– (GGCGCATCCTTGATCGGCGCCAACCATGACTCCTAGGTACAG) (SEQ ID NO: 22) |
| #8) YF NarI+ (GGCGCCGATCAAGGATGCGCCATC) (SEQ ID NO: 23) |
| #9) YF 8.545– (CCAAGAGGTCATGTACTCAG) (SEQ ID NO: 24) |
| #10) SP6YFa+ (ATTTAGGTGACACTATAGAGTAAATCCTGTGTGCTAATT) (SEQ ID NO: 25) |

TABLE 32

| No. Sequence | Name |
|---|---|
| | Oligonucleotide primers. |
| 1 | 3D 0.432+ 5'-GAATGCTGTTGATGACGGGTGGATTCCACTTAACTTCACGAGATGG (SEQ ID NO: 26) |
| 2 | 3DE 1.095– 5'-GCCGCTAGCCTTTCGAAGGGTCGCCAGCTGAGTGGCCTC (SEQ ID NO: 27) |
| 3 | 3DE 1.102+ 5'-GCCGCTAGCTTCGAAAGCTATGCATTGAGGGAAAAATTAC (SEQ ID NO: 28) |
| 4 | 3DE 2.409– 5'-GCCGCCGGCGCCCACCACGACCCCCAGATAGAGTG (SEQ ID NO: 29) |
| 5 | YFM5'3'(4.65)+ 5'-GTGAGCATTGAGAAAGCGCCACGCTTC (SEQ ID NO: 30) |
| 6 | YF 0.481– 5'-TCCACCCGTCATCAACAGCATTCCCAAAATTAG (SEQ ID NO: 31) |
| 7 | YF 0.2+ 5'-ATGGTACGACGAGGAGTTCGC (SEQ ID NO: 32) |
| 8 | Kpd3/–Xho/+ 5'-GGTTGATGTGGTGCTGGAGCACGGTGGGTGTG (SEQ ID NO: 33) |
| 9 | PsD3/.7+ 5'-TACATCGACATGGGTGAC (SEQ ID NO: 34) |
| 10 | KPsD3/.75– 5'-GACATGGGGAGCTAACGC (SEQ ID NO: 35) |

TABLE 32-continued

Oligonucleotide primers.

| No. Sequence | Name |
|---|---|
| 11 | KPsD3/1.5–<br>5'-CCCGAGGGTTCCATATTCAGG<br>(SEQ ID NO: 36) |
| 12 | KPsD3/1.6+<br>5'-GGAACAGGAAAGAGCTTC<br>(SEQ ID NO: 37) |
| 13 | KPsD3/1.9–<br>5'-GAGTATTGTCCCATGCTG<br>(SEQ ID NO: 38) |
| 14 | KPsD3/2.1+<br>5'-GGAATTGGAGACAAAGCC<br>(SEQ ID NO: 39) |
| 15 | KPs5.2 0.23+<br>5'-TGGATAGTGGACAGACAGTGG<br>(SEQ ID NO: 40) |
| 16 | KPs5.2 1.66–<br>5'-CTCTAAATATGAAGATACCATC<br>(SEQ ID NO: 41) |
| 17 | SP6-yfa<br>5'-ATTTAGGTGACACTATAGAGTAAATCCTGTGTGTCTAATT<br>(SEQ ID NO: 42) |

TABLE 33

Amino acid differences in the prM-E region of DEN3 H87 and PaH881/88 strains

| Position H87(PaH881/88 | | Position H87(PaH881/88 | |
|---|---|---|---|
| (nt/gene)[1] | (codon change) | (a.a)[2] | (a.a change) |
| 599/prM | CAC CTC | 168 | H L |
| 605/prM | ACC GCC | 171 | T A |
| 932/prM | CAC GCA | 280 | T A |
| 1373/E | GAC AAC | 427 | D N |
| 1394/E | GAA GAC | 434 | E D |
| 1424/E | TCC CCC | 444 | S P |
| 1439/E | GCT GTT | 449 | A V |
| 1607/E | AAA GAG | 505 | K E |
| 1742/E | ACC AAC | 550 | T N |
| 1805/E | AAA GAA | 571 | K E |
| 2105/E | AGG AAG | 671 | R K |
| 2366/E | ATT GTT | 758 | I V |

[1]Positions of nucleotides in the DEN 3 genome; numbering is according to (Osatomi et al., Virology 176:643–647, 1990).
[2]Positions of amino acid residues in the DEN3 polyprotein; numbering is according to (Osatomi et al., Virology 176:643–647, 1990).

TABLE 34

1) YFM5'3'(4.56+ (GTGAGCATTGAGAAAGCGCCACGCTTC)
(SEQ ID NO: 43)
2) YF0.481– (TCCACCCGTCATCAACAGCATTCCCAAAATTAG)
(SEQ ID NO: 44)
3) 4DE 0.432+ (GAATGCTGTTGATGACGGGTGAATTTCACCTGTCAACAAGAGACGG)
(SEQ ID NO: 45)
4) 4DEE 1.095– (GCCGCTAGCGGTTCGAAATAGAGCCACTTCCTTGGCTGT)
(SEQ ID NO: 46)
5) 4DE 1.102+ (GCCGCTAGCTTCGAACCTATTGCATTGAAGCCTCGATATC)
(SEQ ID NO: 47)
6) 4DE 2.409– (GCCGCCGGCGCCAACTGTGAAACCTAGAAACACAG)
(SEQ ID NO: 48)
7) sp6YFa+ (ATTTAGGTGACACTATAGAGTAAATCCTGTGTGCTAATT)
(SEQ ID NO: 49)

OTHER EMBODIMENTS

Other embodiments are within the following claims. For example, the prM-E protein genes of other flaviviruses of medical importance can be inserted into the yellow fever vaccine virus backbone to produce vaccines against other medically important flaviviruses (see, e.g., Monath et al., “Flaviviruses,” In Virology, Fields (ed.), Raven-Lippincott, New York, 1995, Volume I, 961–1034). Examples of additional flaviviruses from which genes to be inserted into the chimeric vectors of the invention can be obtained include, e.g., Kunjin, Central European Encephalitis, Russian Spring-Summer Encephalitis, Powassan, Kyasanur Forest Disease, and Omsk Hemorrhagic Fever viruses. In addition, genes from even more distantly related viruses can be inserted into the yellow fever vaccine virus to construct novel vaccines.

Vaccine Production and Use

The vaccines of the invention are administered in amounts, and by using methods, that can readily be determined by persons of ordinary skill in this art. The vaccines can be administered and formulated, for example, in the same manner as the yellow fever 17D vaccine, e.g., as a clarified suspension of infected chicken embryo tissue, or a fluid harvested from cell cultures infected with the chimeric yellow fever virus. Thus, the live, attenuated chimeric virus is formulated as a sterile aqueous solution containing between 100 and 1,000,000 infectious units (e.g., plaque-forming units or tissue culture infectious doses) in a dose volume of 0.1 to 1.0 ml, to be administered by, for example, intramuscular, subcutaneous, or intradermal routes. In addition, because flaviviruses may be capable of infecting the human host via the mucosal routes, such as the oral route (Gresikova et al., "Tick-borne Encephalitis," In *The Arboviruses, Ecology and Epidemiology*, Monath (ed.), CRC Press, Boca Raton, Fla., 1988, Volume IV, 177–203), the vaccine virus can be administered by a mucosal route to achieve a protective immune response. The vaccine can be administered as a primary prophylactic agent in adults or children at risk of flavivirus infection. The vaccines can also be used as secondary agents for treating flavivirus-infected patients by stimulating an immune response against the flavivirus.

It may be desirable to use the yellow fever vaccine vector system for immunizing a host against one virus (for example, Japanese Encephalitis virus) and to later reimmunize the same individual against a second or third virus using a different chimeric construct. A significant advantage of the chimeric yellow fever system is that the vector will not elicit strong immunity to itself. Nor will prior immunity to yellow fever virus preclude the use of the chimeric vaccine as a vector for heterologous gene expression. These advantages are due to the removal of the portion of the yellow fever vaccine E gene that encodes neutralizing (protective) antigens to yellow fever, and replacement with another, heterologous gene that does not provide cross-protection against yellow fever. Although YF 17D virus nonstructural proteins may play a role in protection, for example, by eliciting antibodies against NS1, which is involved in complement-dependent antibody mediated lysis of infected cells (Schlesinger et al., J. Immunology 135:2805–2809, 1985), or by inducing cytotoxic T cell responses to NS3 or other proteins of the virus, it is unlikely that these responses will abrogate the ability of a live virus vaccine to stimulate neutralizing antibodies. This is supported by the facts that (1) individuals who have been previously infected with JE virus respond to vaccination with YF 17D similarly to persons without previous JE infection, and (2) individuals who have previously received the YF 17D vaccine respond to revaccination with a rise in neutralizing antibody titers (Sweet et al., Am. J. Trop. Med. Hyg. 11:562–569, 1962). Thus, the chimeric vector can be used in populations that are immune to yellow fever because of prior natural infection or vaccination, and can be used repeatedly, or to immunize simultaneously or sequentially with several different constructs, including yellow fever chimeras with inserts from, for example, Japanese Encephalitis, St. Louis Encephalitis, or West Nile viruses.

For vaccine applications, adjuvants that are known to those skilled in the art can be used. Adjuvants that can be used to enhance the immunogenicity of the chimeric vaccines include, for example, liposomal formulations, synthetic adjuvants, such as saponins (e.g., QS21), muramyl dipeptide, monophosphoryl lipid A, or polyphosphazine. Although these adjuvants are typically used to enhance immune responses to inactivated vaccines, they can also be used with live vaccines. In the case of a chimeric vaccine delivered via a mucosal route, for example, orally, mucosal adjuvants such as the heat-labile toxin of *E. coli* (LT) or mutant derivations of LT are useful adjuvants. In addition, genes encoding cytokines that have adjuvant activities can be inserted into the yellow fever vectors. Thus, genes encoding cytokines, such as a-interferon, GM-CSF, IL-2, IL-12, IL-13, or IL-5, can be inserted together with heterologous flavivirus genes to produce a vaccine that results in enhanced immune responses, or to modulate immunity directed more specifically towards cellular, humoral, or mucosal responses.

In addition to vaccine applications, as one skilled in the art can readily understand, the vectors of the invention can be used in gene therapy methods to introduce therapeutic gene products into a patient's cells and in cancer therapy. In these methods, genes encoding therapeutic gene products are inserted into the vectors, for example, in place of the gene encoding the prM-E protein.

Yellow fever 17D virus targets cells of the lymphoid and reticuloendothelial systems, including precursors in bone marrow, monocytes, macrophages, T cells, and B cells (Monath, "Pathobiology of the Flaviviruses," pp. 375–425, in Schlesinger & Schlesinger (Eds.), "The Togaviridae and Flaviviridae," Plenum Press, New York 1986). The yellow fever 17D virus thus naturally targets cells involved in antigen presentation and immune stimulation. Replication of the virus in these cells, with high-level expression of heterologous genes, makes yellow fever 17D vaccine virus an ideal vector for gene therapy or immunotherapy against cancers of the lymphoreticular system and leukemias, for example. Additional advantages are that (1) the flavivirus genome does not integrate into host cell DNA, (2) yellow fever virus appears to persist in the host for prolonged periods, and (3) that heterologous genes can be inserted at the 3' end of the yellow fever vector, as described above in the strategy for producing a Hepatitis C vaccine. Yellow fever 17D virus can be used as a vector carrying tumor antigens for induction of immune responses for cancer immunotherapy. As a second application, yellow fever 17D can be used to target lymphoreticular tumors and express heterologous genes that have anti-tumor effects, including cytokines, such as TNF-alpha. As a third application, yellow fever 17D can be used to target heterologous genes to bone marrow to direct expression of bioactive molecules required to treat hematologic diseases, such as, for example, neutropenia; an example of a bioactive molecule that can be used in such an application is GM-CSF, but other appropriate bioactive molecules can be selected by those skilled in the art.

An additional advantage of the yellow fever vector system is that flaviviruses replicate in the cytoplasm of cells, so that the virus replication strategy does not involve integration of the viral genome into the host cell (Chambers et al., "Flavivirus Genome Organization, Expression, and Replication," In *Annual Review of Microbiology* 44:649–688, 1990), providing an important safety measure.

All references cited herein are incorporated by reference in their entirety.

What is claimed is:

1. A chimeric live, infectious, attenuated virus, comprising a yellow fever virus in which the nucleotide sequences encoding the pre-membrane and envelope proteins are replaced with the nucleotide sequences encoding pre-membrane and envelope proteins of a Dengue virus.

2. The chimeric virus of claim 1, wherein said Dengue virus is selected from the group consisting of Dengue types 1, 2, 3, and 4.

3. The chimeric virus of claim 2, wherein said nucleotide sequences derived from said Dengue virus are derived from two or more different Dengue strains.

4. The chimeric virus of claim 1, wherein said nucleotide sequences encoding said pre-membrane and envelope proteins of said Dengue virus comprise a substitution or deletion in the R-X-R/K-R sequence at the cleavage site of the pre-membrane protein that prevents cleavage of the pre-membrane protein to produce the membrane protein.

5. The chimeric virus of claim 1, wherein said chimeric virus comprises a signal sequence at the amino acid terminus of said pre-membrane protein, and said signal sequence is that of yellow fever virus.

6. The chimeric virus of claim 1, wherein said Dengue virus is a Dengue-1 virus.

7. The chimeric virus of claim 1, wherein said Dengue virus is a Dengue-2 virus.

8. The chimeric virus of claim 1, wherein said Dengue virus is a Dengue-3 virus.

9. The chimeric virus of claim 1, wherein said Dengue virus is a Dengue-4 virus.

* * * * *

UNITED STATES PATENT AND TRADEMARK OFFICE

CERTIFICATE OF CORRECTION

PATENT NO. : 6,696,281 B1
DATED : February 24, 2004
INVENTOR(S) : Thomas J. Chambers et al.

It is certified that error appears in the above-identified patent and that said Letters Patent is hereby corrected as shown below:

Title page,
Item [75], Inventors, add the following:

-- ; Juan Arroyo, Gaithersburg, MD (US) --

Signed and Sealed this

Twentieth Day of April, 2004

JON W. DUDAS
*Acting Director of the United States Patent and Trademark Office*

UNITED STATES PATENT AND TRADEMARK OFFICE

CERTIFICATE OF CORRECTION

PATENT NO. : 6,696,281 B1
APPLICATION NO. : 09/452638
DATED : February 24, 2004
INVENTOR(S) : Thomas J. Chambers et al.

It is certified that error appears in the above-identified patent and that said Letters Patent is hereby corrected as shown below:

Column 8,
Line 5, replace “favors” with --favor--.

Column 9, Line 51, replace “trariscriptase” with --transcriptase--

Column 11, Line 8, replace “Mclda” with --McIda--.

Column 12, Line 28, replace “reversed” with --reverse--.

Column 14, Line 29, replace “10381))” with --10381)--.

Column 16,
Line 11, replace “of the of the” with --of the--.
Line 45, replace “elicits” with --elicit--.

Column 18,
Line 62, replace “E proteins.” with --E proteins).--; and
Line 66, replace “(CHIMERIVAX-JE™” with --CHIMERIVAX-JE™--.

Column 19,
Line 1, replace “+target” with --+ target--;
Line 4, replace “(CHIMERIVAX-JE™” with --CHIMERIVAX-JE™--;
Line 8, replace “(CHIMERIVAX-JE™” with --CHIMERIVAX-JE™--;
Line 22, replace “six-animals” with --six animals--; and
Line 55, replace “138ΔE” with --138→E--.

Column 23,
Line 26, replace “E proteins” with --E proteins)--;
Line 26, replace “Encephlaitis” with --Encephalitis--.
Line 31, replace “YF-VAX® (inactivated Japanese Encephalitis virus vaccine)” with --YF-VAX® (Yellow Fever 17D Vaccine)--; and
Line 63, replace “Enceplalitis” with --Encephalitis--.
Line 67, replace “CHIMERIVAX-JET™” with --CHIMERIVAX-JE™--.

UNITED STATES PATENT AND TRADEMARK OFFICE

CERTIFICATE OF CORRECTION

PATENT NO. : 6,696,281 B1
APPLICATION NO. : 09/452638
DATED : February 24, 2004
INVENTOR(S) : Thomas J. Chambers et al.

It is certified that error appears in the above-identified patent and that said Letters Patent is hereby corrected as shown below:

Column 24,
Line 10, replace "CHIMERIVAX-JET™" with --CHIMERIVAX-JE™--;
Line 14, replace "YF-VAX® (inactivated Japanese Encephalitis virus vaccine)" with --YF-VAX® (Yellow Fever 17D Vaccine)--;
Line 16, replace "YF-VAX® (inactivated Japanese Encephalitis virus vaccine)" with --YF-VAX® (Yellow Fever 17D Vaccine)--; and
Line 18, replace "YF-VAX® (inactivated Japanese Encephalitis virus vaccine)" with --YF-VAX® (Yellow Fever 17D Vaccine)--.

Column 27,
Line 36, replace "occur" with --occurs--; and
Line 66, replace "Vaccine))" with --Vaccine)--.

Column 28,
Line 60, replace "chirmeric" with --chimeric--.

Column 29, Line 45, replace "E proteins)," with --E proteins)--.

Column 30, Line 51, replace "ritaeniorhynchus" with --triateniorhynchus--.

Column 43,
Line 41, at "Harvest of P3", decrease indent to begin new section.
Line 53, replace "5', 3'junctions" with --5',3' junctions--.

Column 45, Line 48, replace ":on" with --on--.

Column 47, Line 14, replace "thermnocycler" with --thermocycler--.

Column 50,
Line 5, replace "BL-2+virus" with --BL-2+ virus--.
Line 64, replace "Overlap" with --overlap--.

Column 51, Line 17, replace "The expect follows" with --The expected sizes were as follows.--.

UNITED STATES PATENT AND TRADEMARK OFFICE

CERTIFICATE OF CORRECTION

PATENT NO. : 6,696,281 B1
APPLICATION NO. : 09/452638
DATED : February 24, 2004
INVENTOR(S) : Thomas J. Chambers et al.

It is certified that error appears in the above-identified patent and that said Letters Patent is hereby corrected as shown below:

Column 52, Line 44, replace "CIP" with --CIP.--.

Column 54, Line 30, replace "1 minutes" with --1 minute--.

Column 55, Line 11, replace "1.87.8 ng/µl" with --187.8 ng/µl--.

Column 61, In Table 2, Under Clone, replace "YF5.2Iv" with --YF5.21v--.

Column 66, Table 16, replace the column labeled "Mutant Viruses" with --

| Mutant Viruses | | | | | | | | | | |
|---|---|---|---|---|---|---|---|---|---|---|
| 1 | 2 | 3 | 4 | 5 | 6 | 7 | 8 | 9 | 10 | 11 |
| L | F | F | L | L | F | L | F | L | F | L |
| K | E | K | K | E | E | E | E | E | E | E |
| V | V | I | I | V | I | I | V | V | I | I |
| A | A | T | T | A | T | T | A | A | T | T |
| S | S | S | S | S | S | S | P | P | P | P |
| H | H | H | H | H | H | H | Q | Q | Q | Q |
| M | M | M | M | M | M | M | K | K | K | K |

--.

Column 68,

In Table 20, In Virus YF/DEN-1, Under Chimeric E/NS1 junction[2], replace "gatcctcaggtaccaaccgcggtttaa" with --gatcctcagtaccaaccgcggtttaa--.

In Table 20, In Virus YF/DEN-4, Under Chimeric E/NS1 junction[2], replace "acccgaagtgtcaaccgaggtttaa" with --acccgaagtgtcaaccgcggtttaa--.

In Table 20, In Virus YF/SLE, Under Chimeric E/NS1 junction[2], replace "accgttggtcgcacccgcggttta" with --accgttggtcgcacccgcggtttaa--.

UNITED STATES PATENT AND TRADEMARK OFFICE

CERTIFICATE OF CORRECTION

PATENT NO. : 6,696,281 B1 
APPLICATION NO. : 09/452638
DATED : February 24, 2004
INVENTOR(S) : Thomas J. Chambers et al.

It is certified that error appears in the above-identified patent and that said Letters Patent is hereby corrected as shown below:

Column 69,

In Table 20-cont, in footnotes 1,2: replace "antisence" with --antisense--;
In Table 20-cont, in footnotes 1,2: replace "dCNA" with --cDNA--.
In Table 21, Under ENVELOPE, In Virus PR-159(S1) under 71, replace "E" with --D--.

Column 71,

In Table 23, Under MUTANT VIRUSES, In E-Protein 107, Under 11, replace "L" with --L--.
In Table 25, replace rows NT# 304-1127,

"

| Gene | NT | Asibi | 17D204US | RMS | P18 | 17D204F | 17D213 | 17DD | A |
|---|---|---|---|---|---|---|---|---|---|
| C | 304 | G | A | A | A | A | A | A | |
| non-M | 374 | T | C | C | C | C | C | C | |
| M | 643 | A | A | — | — | A | A | G | |
| E | 654 | C | T | — | — | T | T | T | LF |
| | 683 | A | G | — | — | G | G | A | |
| | 1127 | G | A | — | — | A | A | A | GR |

" with --

| Gene | NT | Asibi | 17D204US | RMS | P18 | 17D204F | 17D213 | 17DD | AA |
|---|---|---|---|---|---|---|---|---|---|
| C | 304 | G | A | A | A | A | A | A | |
| | 370 | T | C | C | C | C | C | C | |
| non-M | 643 | A | A | -- | -- | A | A | G | |
| M | 854 | C | T | -- | -- | T | T | T | LF |
| | 883 | A | G | -- | -- | G | G | A | |
| E | 1127 | G | A | -- | -- | A | A | A | GR |
| | 1140 | C | T | -- | -- | T | T | C | AV |
| | 1431 | A | A | -- | -- | A | C | A | NT |

--.

In Table 25, Under NT, replace "2320" with --2220--.

UNITED STATES PATENT AND TRADEMARK OFFICE

CERTIFICATE OF CORRECTION

PATENT NO. : 6,696,281 B1
APPLICATION NO. : 09/452638
DATED : February 24, 2004
INVENTOR(S) : Thomas J. Chambers et al.

It is certified that error appears in the above-identified patent and that said Letters Patent is hereby corrected as shown below:

Column 73,

In Table 25-continued, in NT #4013, in the column labeled "17D213", replace "C" with --T--, and in the column labeled "17DD", replace "T" with --C--;

Column 79,

In Table 32-continued, in the row labeled "17", in the DNA sequence listing, replace "ATTTAGGTGACACTATAGAGTAAATCCTGTGTGTCTAATT" with --ATTTAGGTGACACTATAGAGTAAATCCTGTGTGCTAATT-- ; and In Table 33, Under Position H87 (PaH881/88), in 932/prM, Under (codon change) replace "CAC GCA" with --ACA GCA--.

In Table 34, row 1, replace "(4.56+" with --(4.56)+--.

Signed and Sealed this

Twenty-fifth Day of March, 2008

JON W. DUDAS
*Director of the United States Patent and Trademark Office*

UNITED STATES PATENT AND TRADEMARK OFFICE

CERTIFICATE OF CORRECTION

PATENT NO. : 6,696,281 B1
APPLICATION NO. : 09/452638
DATED : February 24, 2004
INVENTOR(S) : Thomas J. Chambers et al.

It is certified that error appears in the above-identified patent and that said Letters Patent is hereby corrected as shown below:

In the Claims

Column 154, Claim 5, Line 24, replace “amino acid terminus” with --amino terminus--.

Signed and Sealed this
Twenty-fourth Day of September, 2013

Teresa Stanek Rea
*Deputy Director of the United States Patent and Trademark Office*

SEQUENCE LISTING

```
<160> NUMBER OF SEQ ID NOS:  85

<210> SEQ ID NO 1
<211> LENGTH: 21
<212> TYPE: DNA
<213> ORGANISM: Artificial Sequence
<220> FEATURE:
<223> OTHER INFORMATION: derived from Yellow Fever virus and West Nile
      virus

<400> SEQUENCE: 1

cactgggaga gcttgaaggt c                                                21


<210> SEQ ID NO 2
<211> LENGTH: 25
<212> TYPE: DNA
<213> ORGANISM: Artificial Sequence
<220> FEATURE:
<223> OTHER INFORMATION: derived from Yellow Fever virus and West Nile
      virus

<400> SEQUENCE: 2

aaagccagtt gcagccgcgg tttaa                                            25


<210> SEQ ID NO 3
<211> LENGTH: 21
<212> TYPE: DNA
<213> ORGANISM: Artificial Sequence
<220> FEATURE:
<223> OTHER INFORMATION: derived from Yellow Fever virus and Dengue-1
      virus

<400> SEQUENCE: 3

aaggtagact ggtgggctcc c                                                21


<210> SEQ ID NO 4
<211> LENGTH: 26
<212> TYPE: DNA
<213> ORGANISM: Artificial Sequence
<220> FEATURE:
<223> OTHER INFORMATION: derived from Yellow Fever virus and Dengue-1
      virus

<400> SEQUENCE: 4

gatcctcagt accaaccgcg gtttaa                                           26


<210> SEQ ID NO 5
<211> LENGTH: 21
<212> TYPE: DNA
<213> ORGANISM: Artificial Sequence
<220> FEATURE:
<223> OTHER INFORMATION: derived from Yellow Fever virus and Dengue-2
      virus

<400> SEQUENCE: 5

aaggtagatt ggtgtgcatt g                                                21


<210> SEQ ID NO 6
<211> LENGTH: 26
<212> TYPE: DNA
<213> ORGANISM: Artificial Sequence
<220> FEATURE:
<223> OTHER INFORMATION: derived from Yellow Fever virus and Dengue-2
      virus

<400> SEQUENCE: 6
```

aaccctcagt accacccgcg gtttaa 26

<210> SEQ ID NO 7
<211> LENGTH: 21
<212> TYPE: DNA
<213> ORGANISM: Artificial Sequence
<220> FEATURE:
<223> OTHER INFORMATION: derived from Yellow Fever virus and Dengue-3 virus

<400> SEQUENCE: 7
aaggtgaatt gaagtgctct a 21

<210> SEQ ID NO 8
<211> LENGTH: 25
<212> TYPE: DNA
<213> ORGANISM: Artificial Sequence
<220> FEATURE:
<223> OTHER INFORMATION: derived from Yellow Fever virus and Dengue-3 virus

<400> SEQUENCE: 8
acccccagca ccacccgcgg tttaa 25

<210> SEQ ID NO 9
<211> LENGTH: 21
<212> TYPE: DNA
<213> ORGANISM: Artificial Sequence
<220> FEATURE:
<223> OTHER INFORMATION: derived from Yellow Fever virus and Dengue-4 virus

<400> SEQUENCE: 9
aaaaggaaca gttgttctct a 21

<210> SEQ ID NO 10
<211> LENGTH: 25
<212> TYPE: DNA
<213> ORGANISM: Artificial Sequence
<220> FEATURE:
<223> OTHER INFORMATION: derived from Yellow Fever virus and Dengue-4 virus

<400> SEQUENCE: 10
acccgaagtg tcaaccgcgg tttaa 25

<210> SEQ ID NO 11
<211> LENGTH: 21
<212> TYPE: DNA
<213> ORGANISM: Artificial Sequence
<220> FEATURE:
<223> OTHER INFORMATION: derived from Yellow Fever virus and St. Louis Encephalitis virus

<400> SEQUENCE: 11
aacgtgaata gttggatagt c 21

<210> SEQ ID NO 12
<211> LENGTH: 25
<212> TYPE: DNA
<213> ORGANISM: Artificial Sequence
<220> FEATURE:
<223> OTHER INFORMATION: derived from Yellow Fever virus and St. Louis Encephalitis virus

<400> SEQUENCE: 12

-continued

```
accgttggtc gcacccgcgg tttaa                                            25


<210> SEQ ID NO 13
<211> LENGTH: 21
<212> TYPE: DNA
<213> ORGANISM: Artificial Sequence
<220> FEATURE:
<223> OTHER INFORMATION: derived from Yellow Fever virus and Murray
      Valley Encephalitis virus

<400> SEQUENCE: 13

aatttcgaaa ggtggaaggt c                                                21


<210> SEQ ID NO 14
<211> LENGTH: 26
<212> TYPE: DNA
<213> ORGANISM: Artificial Sequence
<220> FEATURE:
<223> OTHER INFORMATION: derived from Yellow Fever virus and Murray
      Valley Encephalitis virus

<400> SEQUENCE: 14

gaccggtgtt tacagccgcg gtttaa                                           26


<210> SEQ ID NO 15
<211> LENGTH: 21
<212> TYPE: DNA
<213> ORGANISM: Artificial Sequence
<220> FEATURE:
<223> OTHER INFORMATION: derived from Yellow Fever virus and Tick-Borne
      Encephalitis virus

<400> SEQUENCE: 15

tactgcgaac gacgttgcca c                                                21


<210> SEQ ID NO 16
<211> LENGTH: 25
<212> TYPE: DNA
<213> ORGANISM: Artificial Sequence
<220> FEATURE:
<223> OTHER INFORMATION: derived from Yellow Fever virus and Tick-Borne
      Encephalitis virus

<400> SEQUENCE: 16

actgggaacc tcacccgcgg tttaa                                            25


<210> SEQ ID NO 17
<211> LENGTH: 27
<212> TYPE: DNA
<213> ORGANISM: Yellow Fever virus

<400> SEQUENCE: 17

gtgagcattg agaaagcgcc acgcttc                                          27


<210> SEQ ID NO 18
<211> LENGTH: 33
<212> TYPE: DNA
<213> ORGANISM: Yellow Fever virus

<400> SEQUENCE: 18

tccacccgtc atcaacagca ttcccaaaat tag                                   33


<210> SEQ ID NO 19
<211> LENGTH: 43
<212> TYPE: DNA
<213> ORGANISM: Dengue virus
```

<400> SEQUENCE: 19
gaatgctgtt gatgacgggt ggatttcatc tgaccacacg agg 43

<210> SEQ ID NO 20
<211> LENGTH: 39
<212> TYPE: DNA
<213> ORGANISM: Dengue virus

<400> SEQUENCE: 20
gccgctagct tttcgaagga cggcagggtt tgtgacttc 39

<210> SEQ ID NO 21
<211> LENGTH: 40
<212> TYPE: DNA
<213> ORGANISM: Dengue virus

<400> SEQUENCE: 21
gccatgcatt tcgaaaactg tgcatcgaag ctaaaatatc 40

<210> SEQ ID NO 22
<211> LENGTH: 42
<212> TYPE: DNA
<213> ORGANISM: Dengue virus

<400> SEQUENCE: 22
ggcgcatcct tgatcggcgc caaccatgac tcctaggtac ag 42

<210> SEQ ID NO 23
<211> LENGTH: 24
<212> TYPE: DNA
<213> ORGANISM: Yellow Fever virus

<400> SEQUENCE: 23
ggcgccgatc aaggatgcgc catc 24

<210> SEQ ID NO 24
<211> LENGTH: 20
<212> TYPE: DNA
<213> ORGANISM: Yellow Fever virus

<400> SEQUENCE: 24
ccaagaggtc atgtactcag 20

<210> SEQ ID NO 25
<211> LENGTH: 39
<212> TYPE: DNA
<213> ORGANISM: Yellow Fever virus

<400> SEQUENCE: 25
atttaggtga cactatagag taaatcctgt gtgctaatt 39

<210> SEQ ID NO 26
<211> LENGTH: 46
<212> TYPE: DNA
<213> ORGANISM: Dengue-3 virus

<400> SEQUENCE: 26
gaatgctgtt gatgacgggt ggattccact taacttcacg agatgg 46

<210> SEQ ID NO 27
<211> LENGTH: 39
<212> TYPE: DNA

<213> ORGANISM: Dengue-3 virus

<400> SEQUENCE: 27
gccgctagcc tttcgaaggg tcgccagctg agtggcctc 39

<210> SEQ ID NO 28
<211> LENGTH: 40
<212> TYPE: DNA
<213> ORGANISM: Dengue-3 virus

<400> SEQUENCE: 28
gccgctagct tcgaaagcta tgcattgagg gaaaaattac 40

<210> SEQ ID NO 29
<211> LENGTH: 35
<212> TYPE: DNA
<213> ORGANISM: Dengue-3 virus

<400> SEQUENCE: 29
gccgccggcg cccaccacga cccccagata gagtg 35

<210> SEQ ID NO 30
<211> LENGTH: 27
<212> TYPE: DNA
<213> ORGANISM: Dengue-3 virus

<400> SEQUENCE: 30
gtgagcattg agaaagcgcc acgcttc 27

<210> SEQ ID NO 31
<211> LENGTH: 33
<212> TYPE: DNA
<213> ORGANISM: Dengue-3 virus

<400> SEQUENCE: 31
tccacccgtc atcaacagca ttcccaaaat tag 33

<210> SEQ ID NO 32
<211> LENGTH: 21
<212> TYPE: DNA
<213> ORGANISM: Dengue-3 virus

<400> SEQUENCE: 32
atggtacgac gaggagttcg c 21

<210> SEQ ID NO 33
<211> LENGTH: 32
<212> TYPE: DNA
<213> ORGANISM: Dengue-3 virus

<400> SEQUENCE: 33
ggttgatgtg gtgctggagc acggtgggtg tg 32

<210> SEQ ID NO 34
<211> LENGTH: 18
<212> TYPE: DNA
<213> ORGANISM: Dengue-3 virus

<400> SEQUENCE: 34
tacatcgaca tgggtgac 18

<210> SEQ ID NO 35
<211> LENGTH: 18

<212> TYPE: DNA
<213> ORGANISM: Dengue-3 virus

<400> SEQUENCE: 35
gacatgggga gctaacgc 18

<210> SEQ ID NO 36
<211> LENGTH: 21
<212> TYPE: DNA
<213> ORGANISM: Dengue-3 virus

<400> SEQUENCE: 36
cccgagggtt ccatattcag g 21

<210> SEQ ID NO 37
<211> LENGTH: 18
<212> TYPE: DNA
<213> ORGANISM: Dengue-3 virus

<400> SEQUENCE: 37
ggaacaggaa agagcttc 18

<210> SEQ ID NO 38
<211> LENGTH: 18
<212> TYPE: DNA
<213> ORGANISM: Dengue-3 virus

<400> SEQUENCE: 38
gagtattgtc ccatgctg 18

<210> SEQ ID NO 39
<211> LENGTH: 18
<212> TYPE: DNA
<213> ORGANISM: Dengue-3 virus

<400> SEQUENCE: 39
ggaattggag acaaagcc 18

<210> SEQ ID NO 40
<211> LENGTH: 21
<212> TYPE: DNA
<213> ORGANISM: Dengue-3 virus

<400> SEQUENCE: 40
tggatagtgg acagacagtg g 21

<210> SEQ ID NO 41
<211> LENGTH: 22
<212> TYPE: DNA
<213> ORGANISM: Dengue-3 virus

<400> SEQUENCE: 41
ctctaaatat gaagatacca tc 22

<210> SEQ ID NO 42
<211> LENGTH: 39
<212> TYPE: DNA
<213> ORGANISM: Dengue-3 virus

<400> SEQUENCE: 42
atttaggtga cactatagag taaatcctgt gtgctaatt 39

<210> SEQ ID NO 43

-continued

<211> LENGTH: 27
<212> TYPE: DNA
<213> ORGANISM: Dengue-3 virus

<400> SEQUENCE: 43
gtgagcattg agaaagcgcc acgcttc 27

<210> SEQ ID NO 44
<211> LENGTH: 33
<212> TYPE: DNA
<213> ORGANISM: Dengue-3 virus

<400> SEQUENCE: 44
tccacccgtc atcaacagca ttcccaaaat tag 33

<210> SEQ ID NO 45
<211> LENGTH: 46
<212> TYPE: DNA
<213> ORGANISM: Dengue-3 virus

<400> SEQUENCE: 45
gaatgctgtt gatgacgggt gaatttcacc tgtcaacaag agacgg 46

<210> SEQ ID NO 46
<211> LENGTH: 39
<212> TYPE: DNA
<213> ORGANISM: Dengue-3 virus

<400> SEQUENCE: 46
gccgctagcg gttcgaaata gagccacttc cttggctgt 39

<210> SEQ ID NO 47
<211> LENGTH: 40
<212> TYPE: DNA
<213> ORGANISM: Dengue-3 virus

<400> SEQUENCE: 47
gccgctagct tcgaacctat tgcattgaag cctcgatatc 40

<210> SEQ ID NO 48
<211> LENGTH: 35
<212> TYPE: DNA
<213> ORGANISM: Dengue-3 virus

<400> SEQUENCE: 48
gccgccggcg ccaactgtga aacctagaaa cacag 35

<210> SEQ ID NO 49
<211> LENGTH: 39
<212> TYPE: DNA
<213> ORGANISM: Dengue-3 virus

<400> SEQUENCE: 49
atttaggtga cactatagag taaatcctgt gtgctaatt 39

<210> SEQ ID NO 50
<211> LENGTH: 1983
<212> TYPE: DNA
<213> ORGANISM: Dengue-2 virus
<220> FEATURE:
<221> NAME/KEY: CDS
<222> LOCATION: (1)...(1983)

<400> SEQUENCE: 50

-continued

```
ttc cat cta acc aca cgt aac gga gaa cca cac atg atc gtc agt aga        48
Phe His Leu Thr Thr Arg Asn Gly Glu Pro His Met Ile Val Ser Arg
 1               5                  10                  15

caa gag aaa ggg aaa agt ctt ttg ttt aaa aca gag gat ggc gtg aac        96
Gln Glu Lys Gly Lys Ser Leu Leu Phe Lys Thr Glu Asp Gly Val Asn
            20                  25                  30

atg tgc acc ctc atg gcc atg gac ctt ggt gaa ttg tgt gaa gac aca       144
Met Cys Thr Leu Met Ala Met Asp Leu Gly Glu Leu Cys Glu Asp Thr
        35                  40                  45

atc acg tac aag tgt ccc ctt ctc agg cag aat gag cca gaa gac ata       192
Ile Thr Tyr Lys Cys Pro Leu Leu Arg Gln Asn Glu Pro Glu Asp Ile
    50                  55                  60

gac tgc tgg tgc aac tcc acg tcc acg tgg gta acc tat ggg act tgt       240
Asp Cys Trp Cys Asn Ser Thr Ser Thr Trp Val Thr Tyr Gly Thr Cys
 65                 70                  75                  80

acc acc acg gga gaa cat aga aga gaa aaa aga tca gtg gca ctc gtt       288
Thr Thr Thr Gly Glu His Arg Arg Glu Lys Arg Ser Val Ala Leu Val
                85                  90                  95

cca cat gtg gga atg gga ctg gag acg cga act gaa aca tgg atg tca       336
Pro His Val Gly Met Gly Leu Glu Thr Arg Thr Glu Thr Trp Met Ser
            100                 105                 110

tca gaa ggg gct tgg aaa cat gcc cag aga att gaa att tgg atc ctg       384
Ser Glu Gly Ala Trp Lys His Ala Gln Arg Ile Glu Ile Trp Ile Leu
        115                 120                 125

aga cat cca ggc ttc acc ata atg gca gca atc ctg gca tac acc ata       432
Arg His Pro Gly Phe Thr Ile Met Ala Ala Ile Leu Ala Tyr Thr Ile
    130                 135                 140

ggg acg aca cat ttc cag aga gca ctg att ttc atc tta ctg aca gct       480
Gly Thr Thr His Phe Gln Arg Ala Leu Ile Phe Ile Leu Leu Thr Ala
145                 150                 155                 160

gtc gct cct tca atg aca atg cgt tgc ata gga ata tca aat aga gac       528
Val Ala Pro Ser Met Thr Met Arg Cys Ile Gly Ile Ser Asn Arg Asp
                165                 170                 175

ttt gta gaa ggg gtt tca gga gga agc tgg gtt gac ata gtc tta gaa       576
Phe Val Glu Gly Val Ser Gly Gly Ser Trp Val Asp Ile Val Leu Glu
            180                 185                 190

cat gga agc tgt gtg acg acg atg gca aaa aac aaa cca aca ttg gat       624
His Gly Ser Cys Val Thr Thr Met Ala Lys Asn Lys Pro Thr Leu Asp
        195                 200                 205

ttt gaa ctg ata aaa aca gaa gcc aaa cag cct gcc acc cta agg aag       672
Phe Glu Leu Ile Lys Thr Glu Ala Lys Gln Pro Ala Thr Leu Arg Lys
    210                 215                 220

tac tgt ata gag gca aag cta acc aac aca aca aca gaa tct cgt tgc       720
Tyr Cys Ile Glu Ala Lys Leu Thr Asn Thr Thr Thr Glu Ser Arg Cys
225                 230                 235                 240

cca aca caa ggg gaa ccc agc cta aat gaa gag cag gat aaa agg ttc       768
Pro Thr Gln Gly Glu Pro Ser Leu Asn Glu Glu Gln Asp Lys Arg Phe
                245                 250                 255

gtc tgc aaa cac tcc atg gta gac aga gga tgg gga aat gga tgt gga       816
Val Cys Lys His Ser Met Val Asp Arg Gly Trp Gly Asn Gly Cys Gly
            260                 265                 270

tta ttt gga aag gga ggc att gtg acc tgt gct atg ttc aca tgc aaa       864
Leu Phe Gly Lys Gly Gly Ile Val Thr Cys Ala Met Phe Thr Cys Lys
        275                 280                 285

aag aac atg gag gga aaa gtt gtg cag cca gaa aac ttg gaa tac acc       912
Lys Asn Met Glu Gly Lys Val Val Gln Pro Glu Asn Leu Glu Tyr Thr
    290                 295                 300

att gtg gta aca ccc cac tca ggg gaa gag cat gcg gtc gga aat gac       960
Ile Val Val Thr Pro His Ser Gly Glu Glu His Ala Val Gly Asn Asp
305                 310                 315                 320
```

```
aca gga aaa cat ggc aag gaa atc aaa gta aca cca cag agt tcc atc      1008
Thr Gly Lys His Gly Lys Glu Ile Lys Val Thr Pro Gln Ser Ser Ile
                325                 330                 335

aca gaa gca gaa ttg aca ggt tat ggc act gtc acg atg gag tgc tct      1056
Thr Glu Ala Glu Leu Thr Gly Tyr Gly Thr Val Thr Met Glu Cys Ser
            340                 345                 350

ccg aga aca ggc ctc gac ttc aat gag atg gtg ttg ctg cag atg gaa      1104
Pro Arg Thr Gly Leu Asp Phe Asn Glu Met Val Leu Leu Gln Met Glu
        355                 360                 365

aat aaa gct tgg ctg gtg cat agg caa tgg ttc cta gac ctg ccg tta      1152
Asn Lys Ala Trp Leu Val His Arg Gln Trp Phe Leu Asp Leu Pro Leu
    370                 375                 380

cca tgg ctg ccc gga gcg gac aca caa ggg tca aat tgg ata caa aaa      1200
Pro Trp Leu Pro Gly Ala Asp Thr Gln Gly Ser Asn Trp Ile Gln Lys
385                 390                 395                 400

gaa aca ttg gtc act ttc aaa aat cct cat gcg aag aaa cag gat gtt      1248
Glu Thr Leu Val Thr Phe Lys Asn Pro His Ala Lys Lys Gln Asp Val
                405                 410                 415

gtt gtt tta gga tcc caa gaa ggg gcc atg cac aca gca ctc aca ggg      1296
Val Val Leu Gly Ser Gln Glu Gly Ala Met His Thr Ala Leu Thr Gly
            420                 425                 430

gcc aca gaa atc caa atg tca tca gga aac tta ctc ttc aca gga cat      1344
Ala Thr Glu Ile Gln Met Ser Ser Gly Asn Leu Leu Phe Thr Gly His
        435                 440                 445

ctc aag tgc agg ctg aga atg gac aag cta cag ctc aaa gga atg tca      1392
Leu Lys Cys Arg Leu Arg Met Asp Lys Leu Gln Leu Lys Gly Met Ser
    450                 455                 460

tac tct atg tgc aca gga aag ttt aaa gtt gtg aag gaa ata gca gaa      1440
Tyr Ser Met Cys Thr Gly Lys Phe Lys Val Val Lys Glu Ile Ala Glu
465                 470                 475                 480

aca caa cat gga aca ata gtt atc agg gtg cag tat gaa ggg gac ggc      1488
Thr Gln His Gly Thr Ile Val Ile Arg Val Gln Tyr Glu Gly Asp Gly
                485                 490                 495

tct cca tgt aaa atc cct ttt gag ata atg gat ttg gaa aaa aga cat      1536
Ser Pro Cys Lys Ile Pro Phe Glu Ile Met Asp Leu Glu Lys Arg His
            500                 505                 510

gtc tta ggt cgc ctg atc aca gtc aac cca att gtg aca gaa aaa gat      1584
Val Leu Gly Arg Leu Ile Thr Val Asn Pro Ile Val Thr Glu Lys Asp
        515                 520                 525

agc cca gtc aac ata gaa gca gaa cct cca ttc gga gac agc tac atc      1632
Ser Pro Val Asn Ile Glu Ala Glu Pro Pro Phe Gly Asp Ser Tyr Ile
    530                 535                 540

atc ata gga gta gag ccg gga caa ctg aag ctc aac tgg ttt aag aaa      1680
Ile Ile Gly Val Glu Pro Gly Gln Leu Lys Leu Asn Trp Phe Lys Lys
545                 550                 555                 560

gga agt tct atc ggc caa atg ttt gag aca aca atg agg ggg gcg aag      1728
Gly Ser Ser Ile Gly Gln Met Phe Glu Thr Thr Met Arg Gly Ala Lys
                565                 570                 575

aga atg gcc att ttg ggt gac aca gcc tgg gat ttt gga tcc ctg gga      1776
Arg Met Ala Ile Leu Gly Asp Thr Ala Trp Asp Phe Gly Ser Leu Gly
            580                 585                 590

gga gtg ttt aca tct ata gga aaa gcc ctc cac caa gtc ttt gga gca      1824
Gly Val Phe Thr Ser Ile Gly Lys Ala Leu His Gln Val Phe Gly Ala
        595                 600                 605

atc tat gga gct gcc ttc agt ggg gtc tca tgg act atg aaa atc ctc      1872
Ile Tyr Gly Ala Ala Phe Ser Gly Val Ser Trp Thr Met Lys Ile Leu
    610                 615                 620

ata gga gtc att atc aca tgg ata gga atg aat tca cgc agc acc tca      1920
Ile Gly Val Ile Ile Thr Trp Ile Gly Met Asn Ser Arg Ser Thr Ser
```

-continued

```
625                 630                 635                 640

ctg tct gtg tca cta gta ttg gtg gga gtc gtg acg ctg tat ttg gga      1968
Leu Ser Val Ser Leu Val Leu Val Gly Val Val Thr Leu Tyr Leu Gly
                645                 650                 655

gtt atg gtg ggc gcc                                                  1983
Val Met Val Gly Ala
            660


<210> SEQ ID NO 51
<211> LENGTH: 661
<212> TYPE: PRT
<213> ORGANISM: Dengue-2 virus

<400> SEQUENCE: 51

Phe His Leu Thr Thr Arg Asn Gly Glu Pro His Met Ile Val Ser Arg
 1               5                  10                  15

Gln Glu Lys Gly Lys Ser Leu Leu Phe Lys Thr Glu Asp Gly Val Asn
            20                  25                  30

Met Cys Thr Leu Met Ala Met Asp Leu Gly Glu Leu Cys Glu Asp Thr
        35                  40                  45

Ile Thr Tyr Lys Cys Pro Leu Leu Arg Gln Asn Glu Pro Glu Asp Ile
    50                  55                  60

Asp Cys Trp Cys Asn Ser Thr Ser Thr Trp Val Thr Tyr Gly Thr Cys
65                  70                  75                  80

Thr Thr Thr Gly Glu His Arg Arg Glu Lys Arg Ser Val Ala Leu Val
                85                  90                  95

Pro His Val Gly Met Gly Leu Glu Thr Arg Thr Glu Thr Trp Met Ser
            100                 105                 110

Ser Glu Gly Ala Trp Lys His Ala Gln Arg Ile Glu Ile Trp Ile Leu
        115                 120                 125

Arg His Pro Gly Phe Thr Ile Met Ala Ala Ile Leu Ala Tyr Thr Ile
    130                 135                 140

Gly Thr Thr His Phe Gln Arg Ala Leu Ile Phe Ile Leu Leu Thr Ala
145                 150                 155                 160

Val Ala Pro Ser Met Thr Met Arg Cys Ile Gly Ile Ser Asn Arg Asp
                165                 170                 175

Phe Val Glu Gly Val Ser Gly Gly Ser Trp Val Asp Ile Val Leu Glu
            180                 185                 190

His Gly Ser Cys Val Thr Thr Met Ala Lys Asn Lys Pro Thr Leu Asp
        195                 200                 205

Phe Glu Leu Ile Lys Thr Glu Ala Lys Gln Pro Ala Thr Leu Arg Lys
    210                 215                 220

Tyr Cys Ile Glu Ala Lys Leu Thr Asn Thr Thr Thr Glu Ser Arg Cys
225                 230                 235                 240

Pro Thr Gln Gly Glu Pro Ser Leu Asn Glu Glu Gln Asp Lys Arg Phe
                245                 250                 255

Val Cys Lys His Ser Met Val Asp Arg Gly Trp Gly Asn Gly Cys Gly
            260                 265                 270

Leu Phe Gly Lys Gly Gly Ile Val Thr Cys Ala Met Phe Thr Cys Lys
        275                 280                 285

Lys Asn Met Glu Gly Lys Val Val Gln Pro Glu Asn Leu Glu Tyr Thr
    290                 295                 300

Ile Val Val Thr Pro His Ser Gly Glu Glu His Ala Val Gly Asn Asp
305                 310                 315                 320

Thr Gly Lys His Gly Lys Glu Ile Lys Val Thr Pro Gln Ser Ser Ile
```

-continued

```
                325                 330                 335

Thr Glu Ala Glu Leu Thr Gly Tyr Gly Thr Val Thr Met Glu Cys Ser
            340                 345                 350

Pro Arg Thr Gly Leu Asp Phe Asn Glu Met Val Leu Leu Gln Met Glu
        355                 360                 365

Asn Lys Ala Trp Leu Val His Arg Gln Trp Phe Leu Asp Leu Pro Leu
    370                 375                 380

Pro Trp Leu Pro Gly Ala Asp Thr Gln Gly Ser Asn Trp Ile Gln Lys
385                 390                 395                 400

Glu Thr Leu Val Thr Phe Lys Asn Pro His Ala Lys Lys Gln Asp Val
                405                 410                 415

Val Val Leu Gly Ser Gln Glu Gly Ala Met His Thr Ala Leu Thr Gly
            420                 425                 430

Ala Thr Glu Ile Gln Met Ser Ser Gly Asn Leu Leu Phe Thr Gly His
        435                 440                 445

Leu Lys Cys Arg Leu Arg Met Asp Lys Leu Gln Leu Lys Gly Met Ser
    450                 455                 460

Tyr Ser Met Cys Thr Gly Lys Phe Lys Val Val Lys Glu Ile Ala Glu
465                 470                 475                 480

Thr Gln His Gly Thr Ile Val Ile Arg Val Gln Tyr Glu Gly Asp Gly
                485                 490                 495

Ser Pro Cys Lys Ile Pro Phe Glu Ile Met Asp Leu Glu Lys Arg His
            500                 505                 510

Val Leu Gly Arg Leu Ile Thr Val Asn Pro Ile Val Thr Glu Lys Asp
        515                 520                 525

Ser Pro Val Asn Ile Glu Ala Glu Pro Pro Phe Gly Asp Ser Tyr Ile
    530                 535                 540

Ile Ile Gly Val Glu Pro Gly Gln Leu Lys Leu Asn Trp Phe Lys Lys
545                 550                 555                 560

Gly Ser Ser Ile Gly Gln Met Phe Glu Thr Thr Met Arg Gly Ala Lys
                565                 570                 575

Arg Met Ala Ile Leu Gly Asp Thr Ala Trp Asp Phe Gly Ser Leu Gly
            580                 585                 590

Gly Val Phe Thr Ser Ile Gly Lys Ala Leu His Gln Val Phe Gly Ala
        595                 600                 605

Ile Tyr Gly Ala Ala Phe Ser Gly Val Ser Trp Thr Met Lys Ile Leu
    610                 615                 620

Ile Gly Val Ile Ile Thr Trp Ile Gly Met Asn Ser Arg Ser Thr Ser
625                 630                 635                 640

Leu Ser Val Ser Leu Val Leu Val Gly Val Val Thr Leu Tyr Leu Gly
                645                 650                 655

Val Met Val Gly Ala
            660
```

<210> SEQ ID NO 52
<211> LENGTH: 10892
<212> TYPE: DNA
<213> ORGANISM: Artificial Sequence
<220> FEATURE:
<223> OTHER INFORMATION: derived from Yellow Fever virus and Japanese Encephalitis virus
<221> NAME/KEY: CDS
<222> LOCATION: (119)...(10381)

<400> SEQUENCE: 52

```
agtaaatcct gtgtgctaat tgaggtgcat tggtctgcaa atcgagttgc taggcaataa     60
```

-continued

```
acacatttgg attaatttta atcgttcgtt gagcgattag cagagaactg accagaac      118

atg tct ggt cgt aaa gct cag gga aaa acc ctg ggc gtc aat atg gta      166
Met Ser Gly Arg Lys Ala Gln Gly Lys Thr Leu Gly Val Asn Met Val
 1               5                  10                  15

cga cga gga gtt cgc tcc ttg tca aac aaa ata aaa caa aaa aca aaa      214
Arg Arg Gly Val Arg Ser Leu Ser Asn Lys Ile Lys Gln Lys Thr Lys
            20                  25                  30

caa att gga aac aga cct gga cct tca aga ggt gtt caa gga ttt atc      262
Gln Ile Gly Asn Arg Pro Gly Pro Ser Arg Gly Val Gln Gly Phe Ile
        35                  40                  45

ttt ttc ttt ttg ttc aac att ttg act gga aaa aag atc aca gcc cac      310
Phe Phe Phe Leu Phe Asn Ile Leu Thr Gly Lys Lys Ile Thr Ala His
    50                  55                  60

cta aag agg ttg tgg aaa atg ctg gac cca aga caa ggc ttg gct gtt      358
Leu Lys Arg Leu Trp Lys Met Leu Asp Pro Arg Gln Gly Leu Ala Val
 65                  70                  75                  80

cta agg aaa gtc aag aga gtg gtg gcc agt ttg atg aga gga ttg tcc      406
Leu Arg Lys Val Lys Arg Val Val Ala Ser Leu Met Arg Gly Leu Ser
                85                  90                  95

tca agg aaa cgc cgt tcc cat gat gtt ctg act gtg caa ttc cta att      454
Ser Arg Lys Arg Arg Ser His Asp Val Leu Thr Val Gln Phe Leu Ile
            100                 105                 110

ttg gga atg ctg ttg atg acg ggt gga atg aag ttg tcg aat ttc cag      502
Leu Gly Met Leu Leu Met Thr Gly Gly Met Lys Leu Ser Asn Phe Gln
        115                 120                 125

ggg aag ctt ttg atg acc atc aac aac acg gac att gca gac gtt atc      550
Gly Lys Leu Leu Met Thr Ile Asn Asn Thr Asp Ile Ala Asp Val Ile
    130                 135                 140

gtg att ccc acc tca aaa gga gag aac aga tgt tgg gtt cgg gca atc      598
Val Ile Pro Thr Ser Lys Gly Glu Asn Arg Cys Trp Val Arg Ala Ile
145                 150                 155                 160

gac gtc ggc tac atg tgt gag gac act atc acg tac gaa tgt cct aag      646
Asp Val Gly Tyr Met Cys Glu Asp Thr Ile Thr Tyr Glu Cys Pro Lys
                165                 170                 175

ctt acc atg ggc aat gat cca gag gat gtg gat tgc tgg tgt gac aac      694
Leu Thr Met Gly Asn Asp Pro Glu Asp Val Asp Cys Trp Cys Asp Asn
            180                 185                 190

caa gaa gtc tac gtc caa tat gga cgg tgc acg cgg acc agg cat tcc      742
Gln Glu Val Tyr Val Gln Tyr Gly Arg Cys Thr Arg Thr Arg His Ser
        195                 200                 205

aag cga agc agg aga tcc gtg tcg gtc caa aca cat ggg gag agt tca      790
Lys Arg Ser Arg Arg Ser Val Ser Val Gln Thr His Gly Glu Ser Ser
    210                 215                 220

cta gtg aat aaa aaa gag gct tgg ctg gat tca acg aaa gcc aca cga      838
Leu Val Asn Lys Lys Glu Ala Trp Leu Asp Ser Thr Lys Ala Thr Arg
225                 230                 235                 240

tat ctc atg aaa act gag aac tgg atc ata agg aat cct ggc tat gct      886
Tyr Leu Met Lys Thr Glu Asn Trp Ile Ile Arg Asn Pro Gly Tyr Ala
                245                 250                 255

ttc ctg gcg gcg gta ctt ggc tgg atg ctt ggc agt aac aac ggt caa      934
Phe Leu Ala Ala Val Leu Gly Trp Met Leu Gly Ser Asn Asn Gly Gln
            260                 265                 270

cgc gtg gta ttt acc atc ctc ctg ctg ttg gtc gct ccg gct tac agt      982
Arg Val Val Phe Thr Ile Leu Leu Leu Leu Val Ala Pro Ala Tyr Ser
        275                 280                 285

ttt aat tgt ctg gga atg ggc aat cgt gac ttc ata gaa gga gcc agt     1030
Phe Asn Cys Leu Gly Met Gly Asn Arg Asp Phe Ile Glu Gly Ala Ser
    290                 295                 300
```

-continued

```
ggg gcc act tgg gtg gac ttg gtg cta gaa gga gac agc tgc ttg aca      1078
Gly Ala Thr Trp Val Asp Leu Val Leu Glu Gly Asp Ser Cys Leu Thr
305                 310                 315                 320

atc atg gca aac gac aaa cca aca ttg gac gtc cgc atg att aac atc      1126
Ile Met Ala Asn Asp Lys Pro Thr Leu Asp Val Arg Met Ile Asn Ile
                325                 330                 335

gaa gct agc caa ctt gct gag gtc aga agt tac tgc tat cat gct tca      1174
Glu Ala Ser Gln Leu Ala Glu Val Arg Ser Tyr Cys Tyr His Ala Ser
            340                 345                 350

gtc act gac atc tcg acg gtg gct cgg tgc ccc acg act gga gaa gcc      1222
Val Thr Asp Ile Ser Thr Val Ala Arg Cys Pro Thr Thr Gly Glu Ala
        355                 360                 365

cac aac gag aag cga gct gat agt agc tat gtg tgc aaa caa ggc ttc      1270
His Asn Glu Lys Arg Ala Asp Ser Ser Tyr Val Cys Lys Gln Gly Phe
    370                 375                 380

act gac cgt ggg tgg ggc aac gga tgt gga ttt ttc ggg aag gga agc      1318
Thr Asp Arg Gly Trp Gly Asn Gly Cys Gly Phe Phe Gly Lys Gly Ser
385                 390                 395                 400

att gac aca tgt gca aaa ttc tcc tgc acc agt aaa gcg att ggg aga      1366
Ile Asp Thr Cys Ala Lys Phe Ser Cys Thr Ser Lys Ala Ile Gly Arg
                405                 410                 415

aca atc cag cca gaa aac atc aaa tac aaa gtt ggc att ttt gtg cat      1414
Thr Ile Gln Pro Glu Asn Ile Lys Tyr Lys Val Gly Ile Phe Val His
            420                 425                 430

gga acc acc act tcg gaa aac cat ggg aat tat tca gcg caa gtt ggg      1462
Gly Thr Thr Thr Ser Glu Asn His Gly Asn Tyr Ser Ala Gln Val Gly
        435                 440                 445

gcg tcc cag gcg gca aag ttt aca gta aca ccc aat gct cct tcg gta      1510
Ala Ser Gln Ala Ala Lys Phe Thr Val Thr Pro Asn Ala Pro Ser Val
    450                 455                 460

gcc ctc aaa ctt ggt gac tac gga gaa gtc aca ctg gac tgt gag cca      1558
Ala Leu Lys Leu Gly Asp Tyr Gly Glu Val Thr Leu Asp Cys Glu Pro
465                 470                 475                 480

agg agt gga ctg aac act gaa gcg ttt tac gtc atg acc gtg ggg tca      1606
Arg Ser Gly Leu Asn Thr Glu Ala Phe Tyr Val Met Thr Val Gly Ser
                485                 490                 495

aag tca ttt ctg gtc cat agg gag tgg ttt cat gac ctc gct ctc ccc      1654
Lys Ser Phe Leu Val His Arg Glu Trp Phe His Asp Leu Ala Leu Pro
            500                 505                 510

tgg acg tcc cct tcg agc aca gcg tgg aga aac aga gaa ctc ctc atg      1702
Trp Thr Ser Pro Ser Ser Thr Ala Trp Arg Asn Arg Glu Leu Leu Met
        515                 520                 525

gaa ttt gaa ggg gcg cac gcc aca aaa cag tcc gtt gtt gct ctt ggg      1750
Glu Phe Glu Gly Ala His Ala Thr Lys Gln Ser Val Val Ala Leu Gly
    530                 535                 540

tca cag gaa gga ggc ctc cat cat gcg ttg gca gga gcc atc gtg gtg      1798
Ser Gln Glu Gly Gly Leu His His Ala Leu Ala Gly Ala Ile Val Val
545                 550                 555                 560

gag tac tca agc tca gtg atg tta aca tca ggc cac ctg aaa tgt agg      1846
Glu Tyr Ser Ser Ser Val Met Leu Thr Ser Gly His Leu Lys Cys Arg
                565                 570                 575

ctg aaa atg gac aaa ctg gct ctg aaa ggc aca acc tat ggc atg tgt      1894
Leu Lys Met Asp Lys Leu Ala Leu Lys Gly Thr Thr Tyr Gly Met Cys
            580                 585                 590

aca gaa aaa ttc tcg ttc gcg aaa aat ccg gtg gac act ggt cac gga      1942
Thr Glu Lys Phe Ser Phe Ala Lys Asn Pro Val Asp Thr Gly His Gly
        595                 600                 605

aca gtt gtc att gaa ctc tcc tac tct ggg agt gat ggc ccc tgc aaa      1990
Thr Val Val Ile Glu Leu Ser Tyr Ser Gly Ser Asp Gly Pro Cys Lys
    610                 615                 620
```

```
att ccg att gtt tcc gtt gcg agc ctc aat gac atg acc ccc gtt ggg     2038
Ile Pro Ile Val Ser Val Ala Ser Leu Asn Asp Met Thr Pro Val Gly
625                 630                 635                 640

cgg ctg gtg aca gtg aac ccc ttc gtc gcg act tcc agt gcc aac tca     2086
Arg Leu Val Thr Val Asn Pro Phe Val Ala Thr Ser Ser Ala Asn Ser
                645                 650                 655

aag gtg ctg gtc gag atg gaa ccc ccc ttc gga gac tcc tac atc gta     2134
Lys Val Leu Val Glu Met Glu Pro Pro Phe Gly Asp Ser Tyr Ile Val
            660                 665                 670

gtt gga agg gga gac aag cag atc aac cac cat tgg cac aaa gct gga     2182
Val Gly Arg Gly Asp Lys Gln Ile Asn His His Trp His Lys Ala Gly
        675                 680                 685

agc acg ctg ggc aag gcc ttt tca aca act ttg aag gga gct caa aga     2230
Ser Thr Leu Gly Lys Ala Phe Ser Thr Thr Leu Lys Gly Ala Gln Arg
    690                 695                 700

ctg gca gcg ttg ggc gac aca gcc tgg gac ttt ggc tct att gga ggg     2278
Leu Ala Ala Leu Gly Asp Thr Ala Trp Asp Phe Gly Ser Ile Gly Gly
705                 710                 715                 720

gtc ttc aac tcc ata gga aga gcc gtt cac caa gtg ttt ggt ggt gcc     2326
Val Phe Asn Ser Ile Gly Arg Ala Val His Gln Val Phe Gly Gly Ala
                725                 730                 735

ttc aga aca ctc ttt ggg gga atg tct tgg atc aca caa ggg cta atg     2374
Phe Arg Thr Leu Phe Gly Gly Met Ser Trp Ile Thr Gln Gly Leu Met
            740                 745                 750

ggt gcc cta ctg ctc tgg atg ggc gtc aac gca cga gac cga tca att     2422
Gly Ala Leu Leu Leu Trp Met Gly Val Asn Ala Arg Asp Arg Ser Ile
        755                 760                 765

gct ttg gcc ttc tta gcc aca gga ggt gtg ctc gtg ttc tta gcg acc     2470
Ala Leu Ala Phe Leu Ala Thr Gly Gly Val Leu Val Phe Leu Ala Thr
    770                 775                 780

aat gtg ggc gcc gat caa gga tgc gcc atc aac ttt ggc aag aga gag     2518
Asn Val Gly Ala Asp Gln Gly Cys Ala Ile Asn Phe Gly Lys Arg Glu
785                 790                 795                 800

ctc aag tgc gga gat ggt atc ttc ata ttt aga gac tct gat gac tgg     2566
Leu Lys Cys Gly Asp Gly Ile Phe Ile Phe Arg Asp Ser Asp Asp Trp
                805                 810                 815

ctg aac aag tac tca tac tat cca gaa gat cct gtg aag ctt gca tca     2614
Leu Asn Lys Tyr Ser Tyr Tyr Pro Glu Asp Pro Val Lys Leu Ala Ser
            820                 825                 830

ata gtg aaa gcc tct ttt gaa gaa ggg aag tgt ggc cta aat tca gtt     2662
Ile Val Lys Ala Ser Phe Glu Glu Gly Lys Cys Gly Leu Asn Ser Val
        835                 840                 845

gac tcc ctt gag cat gag atg tgg aga agc agg gca gat gag atc aat     2710
Asp Ser Leu Glu His Glu Met Trp Arg Ser Arg Ala Asp Glu Ile Asn
    850                 855                 860

gcc att ttt gag gaa aac gag gtg gac att tct gtt gtc gtg cag gat     2758
Ala Ile Phe Glu Glu Asn Glu Val Asp Ile Ser Val Val Val Gln Asp
865                 870                 875                 880

cca aag aat gtt tac cag aga gga act cat cca ttt tcc aga att cgg     2806
Pro Lys Asn Val Tyr Gln Arg Gly Thr His Pro Phe Ser Arg Ile Arg
                885                 890                 895

gat ggt ctg cag tat ggt tgg aag act tgg ggt aag aac ctt gtg ttc     2854
Asp Gly Leu Gln Tyr Gly Trp Lys Thr Trp Gly Lys Asn Leu Val Phe
            900                 905                 910

tcc cca ggg agg aag aat gga agc ttc atc ata gat gga aag tcc agg     2902
Ser Pro Gly Arg Lys Asn Gly Ser Phe Ile Ile Asp Gly Lys Ser Arg
        915                 920                 925

aaa gaa tgc ccg ttt tca aac cgg gtc tgg aat tct ttc cag ata gag     2950
Lys Glu Cys Pro Phe Ser Asn Arg Val Trp Asn Ser Phe Gln Ile Glu
```

-continued

```
    930                 935                 940

gag ttt ggg acg gga gtg ttc acc aca cgc gtg tac atg gac gca gtc     2998
Glu Phe Gly Thr Gly Val Phe Thr Thr Arg Val Tyr Met Asp Ala Val
945                 950                 955                 960

ttt gaa tac acc ata gac tgc gat gga tct atc ttg ggt gca gcg gtg     3046
Phe Glu Tyr Thr Ile Asp Cys Asp Gly Ser Ile Leu Gly Ala Ala Val
                965                 970                 975

aac gga aaa aag agt gcc cat ggc tct cca aca ttt tgg atg gga agt     3094
Asn Gly Lys Lys Ser Ala His Gly Ser Pro Thr Phe Trp Met Gly Ser
            980                 985                 990

cat gaa gta aat ggg aca tgg atg atc cac acc ttg gag gca tta gat     3142
His Glu Val Asn Gly Thr Trp Met Ile His Thr Leu Glu Ala Leu Asp
        995                 1000                1005

tac aag gag tgt gag tgg cca ctg aca cat acg att gga aca tca gtt     3190
Tyr Lys Glu Cys Glu Trp Pro Leu Thr His Thr Ile Gly Thr Ser Val
    1010                1015                1020

gaa gag agt gaa atg ttc atg ccg aga tca atc gga ggc cca gtt agc     3238
Glu Glu Ser Glu Met Phe Met Pro Arg Ser Ile Gly Gly Pro Val Ser
1025                1030                1035                1040

tct cac aat cat atc cct gga tac aag gtt cag acg aac gga cct tgg     3286
Ser His Asn His Ile Pro Gly Tyr Lys Val Gln Thr Asn Gly Pro Trp
                1045                1050                1055

atg cag gta cca cta gaa gtg aag aga gaa gct tgc cca ggg act agc     3334
Met Gln Val Pro Leu Glu Val Lys Arg Glu Ala Cys Pro Gly Thr Ser
            1060                1065                1070

gtg atc att gat ggc aac tgt gat gga cgg gga aaa tca acc aga tcc     3382
Val Ile Ile Asp Gly Asn Cys Asp Gly Arg Gly Lys Ser Thr Arg Ser
        1075                1080                1085

acc acg gat agc ggg aaa gtt att cct gaa tgg tgt tgc cgc tcc tgc     3430
Thr Thr Asp Ser Gly Lys Val Ile Pro Glu Trp Cys Cys Arg Ser Cys
    1090                1095                1100

aca atg ccg cct gtg agc ttc cat ggt agt gat ggg tgt tgg tat ccc     3478
Thr Met Pro Pro Val Ser Phe His Gly Ser Asp Gly Cys Trp Tyr Pro
1105                1110                1115                1120

atg gaa att agg cca agg aaa acg cat gaa agc cat ctg gtg cgc tcc     3526
Met Glu Ile Arg Pro Arg Lys Thr His Glu Ser His Leu Val Arg Ser
                1125                1130                1135

tgg gtt aca gct gga gaa ata cat gct gtc cct ttt ggt ttg gtg agc     3574
Trp Val Thr Ala Gly Glu Ile His Ala Val Pro Phe Gly Leu Val Ser
            1140                1145                1150

atg atg ata gca atg gaa gtg gtc cta agg aaa aga cag gga cca aag     3622
Met Met Ile Ala Met Glu Val Val Leu Arg Lys Arg Gln Gly Pro Lys
        1155                1160                1165

caa atg ttg gtt gga gga gta gtg ctc ttg gga gca atg ctg gtc ggg     3670
Gln Met Leu Val Gly Gly Val Val Leu Leu Gly Ala Met Leu Val Gly
    1170                1175                1180

caa gta act ctc ctt gat ttg ctg aaa ctc aca gtg gct gtg gga ttg     3718
Gln Val Thr Leu Leu Asp Leu Leu Lys Leu Thr Val Ala Val Gly Leu
1185                1190                1195                1200

cat ttc cat gag atg aac aat gga gga gac gcc atg tat atg gcg ttg     3766
His Phe His Glu Met Asn Asn Gly Gly Asp Ala Met Tyr Met Ala Leu
                1205                1210                1215

att gct gcc ttt tca atc aga cca ggg ctg ctc atc ggc ttt ggg ctc     3814
Ile Ala Ala Phe Ser Ile Arg Pro Gly Leu Leu Ile Gly Phe Gly Leu
            1220                1225                1230

agg acc cta tgg agc cct cgg gaa cgc ctt gtg ctg acc cta gga gca     3862
Arg Thr Leu Trp Ser Pro Arg Glu Arg Leu Val Leu Thr Leu Gly Ala
        1235                1240                1245

gcc atg gtg gag att gcc ttg ggt ggc gtg atg ggc ggc ctg tgg aag     3910
```

-continued

```
Ala Met Val Glu Ile Ala Leu Gly Gly Val Met Gly Gly Leu Trp Lys
    1250                1255                1260

tat cta aat gca gtt tct ctc tgc atc ctg aca ata aat gct gtt gct     3958
Tyr Leu Asn Ala Val Ser Leu Cys Ile Leu Thr Ile Asn Ala Val Ala
1265                1270                1275                1280

tct agg aaa gca tca aat acc atc ttg ccc ctc atg gct ctg ttg aca     4006
Ser Arg Lys Ala Ser Asn Thr Ile Leu Pro Leu Met Ala Leu Leu Thr
                1285                1290                1295

cct gtc act atg gct gag gtg aga ctt gcc gca atg ttc ttt tgt gcc     4054
Pro Val Thr Met Ala Glu Val Arg Leu Ala Ala Met Phe Phe Cys Ala
            1300                1305                1310

atg gtt atc ata ggg gtc ctt cac cag aat ttc aag gac acc tcc atg     4102
Met Val Ile Ile Gly Val Leu His Gln Asn Phe Lys Asp Thr Ser Met
        1315                1320                1325

cag aag act ata cct ctg gtg gcc ctc aca ctc aca tct tac ctg ggc     4150
Gln Lys Thr Ile Pro Leu Val Ala Leu Thr Leu Thr Ser Tyr Leu Gly
    1330                1335                1340

ttg aca caa cct ttt ttg ggc ctg tgt gca ttt ctg gca acc cgc ata     4198
Leu Thr Gln Pro Phe Leu Gly Leu Cys Ala Phe Leu Ala Thr Arg Ile
1345                1350                1355                1360

ttt ggg cga agg agt atc cca gtg aat gag gca ctc gca gca gct ggt     4246
Phe Gly Arg Arg Ser Ile Pro Val Asn Glu Ala Leu Ala Ala Ala Gly
                1365                1370                1375

cta gtg gga gtg ctg gca gga ctg gct ttt cag gag atg gag aac ttc     4294
Leu Val Gly Val Leu Ala Gly Leu Ala Phe Gln Glu Met Glu Asn Phe
            1380                1385                1390

ctt ggt ccg att gca gtt gga gga ctc ctg atg atg ctg gtt agc gtg     4342
Leu Gly Pro Ile Ala Val Gly Gly Leu Leu Met Met Leu Val Ser Val
        1395                1400                1405

gct ggg agg gtg gat ggg cta gag ctc aag aag ctt ggt gaa gtt tca     4390
Ala Gly Arg Val Asp Gly Leu Glu Leu Lys Lys Leu Gly Glu Val Ser
    1410                1415                1420

tgg gaa gag gag gcg gag atc agc ggg agt tcc gcc cgc tat gat gtg     4438
Trp Glu Glu Glu Ala Glu Ile Ser Gly Ser Ser Ala Arg Tyr Asp Val
1425                1430                1435                1440

gca ctc agt gaa caa ggg gag ttc aag ctg ctt tct gaa gag aaa gtg     4486
Ala Leu Ser Glu Gln Gly Glu Phe Lys Leu Leu Ser Glu Glu Lys Val
                1445                1450                1455

cca tgg gac cag gtt gtg atg acc tcg ctg gcc ttg gtt ggg gct gcc     4534
Pro Trp Asp Gln Val Val Met Thr Ser Leu Ala Leu Val Gly Ala Ala
            1460                1465                1470

ctc cat cca ttt gct ctt ctg ctg gtc ctt gct ggg tgg ctg ttt cat     4582
Leu His Pro Phe Ala Leu Leu Leu Val Leu Ala Gly Trp Leu Phe His
        1475                1480                1485

gtc agg gga gct agg aga agt ggg gat gtc ttg tgg gat att ccc act     4630
Val Arg Gly Ala Arg Arg Ser Gly Asp Val Leu Trp Asp Ile Pro Thr
    1490                1495                1500

cct aag atc atc gag gaa tgt gaa cat ctg gag gat ggg att tat ggc     4678
Pro Lys Ile Ile Glu Glu Cys Glu His Leu Glu Asp Gly Ile Tyr Gly
1505                1510                1515                1520

ata ttc cag tca acc ttc ttg ggg gcc tcc cag cga gga gtg gga gtg     4726
Ile Phe Gln Ser Thr Phe Leu Gly Ala Ser Gln Arg Gly Val Gly Val
                1525                1530                1535

gca cag gga ggg gtg ttc cac aca atg tgg cat gtc aca aga gga gct     4774
Ala Gln Gly Gly Val Phe His Thr Met Trp His Val Thr Arg Gly Ala
            1540                1545                1550

ttc ctt gtc agg aat ggc aag aag ttg att cca tct tgg gct tca gta     4822
Phe Leu Val Arg Asn Gly Lys Lys Leu Ile Pro Ser Trp Ala Ser Val
        1555                1560                1565
```

-continued

```
aag gaa gac ctt gtc gcc tat ggt ggc tca tgg aag ttg gaa ggc aga      4870
Lys Glu Asp Leu Val Ala Tyr Gly Gly Ser Trp Lys Leu Glu Gly Arg
    1570                1575                1580

tgg gat gga gag gaa gag gtc cag ttg atc gcg gct gtt cca gga aag      4918
Trp Asp Gly Glu Glu Glu Val Gln Leu Ile Ala Ala Val Pro Gly Lys
1585                1590                1595                1600

aac gtg gtc aac gtc cag aca aaa ccg agc ttg ttc aaa gtg agg aat      4966
Asn Val Val Asn Val Gln Thr Lys Pro Ser Leu Phe Lys Val Arg Asn
                1605                1610                1615

ggg gga gaa atc ggg gct gtc gct ctt gac tat ccg agt ggc act tca      5014
Gly Gly Glu Ile Gly Ala Val Ala Leu Asp Tyr Pro Ser Gly Thr Ser
            1620                1625                1630

gga tct cct att gtt aac agg aac gga gag gtg att ggg ctg tac ggc      5062
Gly Ser Pro Ile Val Asn Arg Asn Gly Glu Val Ile Gly Leu Tyr Gly
        1635                1640                1645

aat ggc atc ctt gtc ggt gac aac tcc ttc gtg tcc gcc ata tcc cag      5110
Asn Gly Ile Leu Val Gly Asp Asn Ser Phe Val Ser Ala Ile Ser Gln
    1650                1655                1660

act gag gtg aag gaa gaa gga aag gag gag ctc caa gag atc ccg aca      5158
Thr Glu Val Lys Glu Glu Gly Lys Glu Glu Leu Gln Glu Ile Pro Thr
1665                1670                1675                1680

atg cta aag aaa gga atg aca act gtc ctt gat ttt cat cct gga gct      5206
Met Leu Lys Lys Gly Met Thr Thr Val Leu Asp Phe His Pro Gly Ala
                1685                1690                1695

ggg aag aca aga cgt ttc ctc cca cag atc ttg gcc gag tgc gca cgg      5254
Gly Lys Thr Arg Arg Phe Leu Pro Gln Ile Leu Ala Glu Cys Ala Arg
            1700                1705                1710

aga cgc ttg cgc act ctt gtg ttg gcc ccc acc agg gtt gtt ctt tct      5302
Arg Arg Leu Arg Thr Leu Val Leu Ala Pro Thr Arg Val Val Leu Ser
        1715                1720                1725

gaa atg aag gag gct ttt cac ggc ctg gac gtg aaa ttc cac aca cag      5350
Glu Met Lys Glu Ala Phe His Gly Leu Asp Val Lys Phe His Thr Gln
    1730                1735                1740

gct ttt tcc gct cac ggc agc ggg aga gaa gtc att gat gcc atg tgc      5398
Ala Phe Ser Ala His Gly Ser Gly Arg Glu Val Ile Asp Ala Met Cys
1745                1750                1755                1760

cat gcc acc cta act tac agg atg ttg gaa cca act agg gtt gtt aac      5446
His Ala Thr Leu Thr Tyr Arg Met Leu Glu Pro Thr Arg Val Val Asn
                1765                1770                1775

tgg gaa gtg atc att atg gat gaa gcc cat ttt ttg gat cca gct agc      5494
Trp Glu Val Ile Ile Met Asp Glu Ala His Phe Leu Asp Pro Ala Ser
            1780                1785                1790

ata gcc gct aga ggt tgg gca gcg cac aga gct agg gca aat gaa agt      5542
Ile Ala Ala Arg Gly Trp Ala Ala His Arg Ala Arg Ala Asn Glu Ser
        1795                1800                1805

gca aca atc ttg atg aca gcc aca ccg cct ggg act agt gat gaa ttt      5590
Ala Thr Ile Leu Met Thr Ala Thr Pro Pro Gly Thr Ser Asp Glu Phe
    1810                1815                1820

cca cat tca aat ggt gaa ata gaa gat gtt caa acg gac ata ccc agt      5638
Pro His Ser Asn Gly Glu Ile Glu Asp Val Gln Thr Asp Ile Pro Ser
1825                1830                1835                1840

gag ccc tgg aac aca ggg cat gac tgg atc ctg gct gac aaa agg ccc      5686
Glu Pro Trp Asn Thr Gly His Asp Trp Ile Leu Ala Asp Lys Arg Pro
                1845                1850                1855

acg gca tgg ttc ctt cca tcc atc aga gct gca aat gtc atg gct gcc      5734
Thr Ala Trp Phe Leu Pro Ser Ile Arg Ala Ala Asn Val Met Ala Ala
            1860                1865                1870

tct ttg cgt aag gct gga aag agt gtg gtg gtc ctg aac agg aaa acc      5782
Ser Leu Arg Lys Ala Gly Lys Ser Val Val Val Leu Asn Arg Lys Thr
        1875                1880                1885
```

-continued

```
ttt gag aga gaa tac ccc acg ata aag cag aag aaa cct gac ttt ata     5830
Phe Glu Arg Glu Tyr Pro Thr Ile Lys Gln Lys Lys Pro Asp Phe Ile
    1890                1895                1900

ttg gcc act gac ata gct gaa atg gga gcc aac ctt tgc gtg gag cga     5878
Leu Ala Thr Asp Ile Ala Glu Met Gly Ala Asn Leu Cys Val Glu Arg
1905                1910                1915                1920

gtg ctg gat tgc agg acg gct ttt aag cct gtg ctt gtg gat gaa ggg     5926
Val Leu Asp Cys Arg Thr Ala Phe Lys Pro Val Leu Val Asp Glu Gly
                1925                1930                1935

agg aag gtg gca ata aaa ggg cca ctt cgt atc tcc gca tcc tct gct     5974
Arg Lys Val Ala Ile Lys Gly Pro Leu Arg Ile Ser Ala Ser Ser Ala
            1940                1945                1950

gct caa agg agg ggg cgc att ggg aga aat ccc aac aga gat gga gac     6022
Ala Gln Arg Arg Gly Arg Ile Gly Arg Asn Pro Asn Arg Asp Gly Asp
        1955                1960                1965

tca tac tac tat tct gag cct aca agt gaa aat aat gcc cac cac gtc     6070
Ser Tyr Tyr Tyr Ser Glu Pro Thr Ser Glu Asn Asn Ala His His Val
    1970                1975                1980

tgc tgg ttg gag gcc tca atg ctc ttg gac aac atg gag gtg agg ggt     6118
Cys Trp Leu Glu Ala Ser Met Leu Leu Asp Asn Met Glu Val Arg Gly
1985                1990                1995                2000

gga atg gtc gcc cca ctc tat ggc gtt gaa gga act aaa aca cca gtt     6166
Gly Met Val Ala Pro Leu Tyr Gly Val Glu Gly Thr Lys Thr Pro Val
                2005                2010                2015

tcc cct ggt gaa atg aga ctg agg gat gac cag agg aaa gtc ttc aga     6214
Ser Pro Gly Glu Met Arg Leu Arg Asp Asp Gln Arg Lys Val Phe Arg
            2020                2025                2030

gaa cta gtg agg aat tgt gac ctg ccc gtt tgg ctt tcg tgg caa gtg     6262
Glu Leu Val Arg Asn Cys Asp Leu Pro Val Trp Leu Ser Trp Gln Val
        2035                2040                2045

gcc aag gct ggt ttg aag acg aat gat cgt aag tgg tgt ttt gaa ggc     6310
Ala Lys Ala Gly Leu Lys Thr Asn Asp Arg Lys Trp Cys Phe Glu Gly
    2050                2055                2060

cct gag gaa cat gag atc ttg aat gac agc ggt gaa aca gtg aag tgc     6358
Pro Glu Glu His Glu Ile Leu Asn Asp Ser Gly Glu Thr Val Lys Cys
2065                2070                2075                2080

agg gct cct gga gga gca aag aag cct ctg cgc cca agg tgg tgt gat     6406
Arg Ala Pro Gly Gly Ala Lys Lys Pro Leu Arg Pro Arg Trp Cys Asp
                2085                2090                2095

gaa agg gtg tca tct gac cag agt gcg ctg tct gaa ttt att aag ttt     6454
Glu Arg Val Ser Ser Asp Gln Ser Ala Leu Ser Glu Phe Ile Lys Phe
            2100                2105                2110

gct gaa ggt agg agg gga gct gct gaa gtg cta gtt gtg ctg agt gaa     6502
Ala Glu Gly Arg Arg Gly Ala Ala Glu Val Leu Val Val Leu Ser Glu
        2115                2120                2125

ctc cct gat ttc ctg gct aaa aaa ggt gga gag gca atg gat acc atc     6550
Leu Pro Asp Phe Leu Ala Lys Lys Gly Gly Glu Ala Met Asp Thr Ile
    2130                2135                2140

agt gtg ttc ctc cac tct gag gaa ggc tct agg gct tac cgc aat gca     6598
Ser Val Phe Leu His Ser Glu Glu Gly Ser Arg Ala Tyr Arg Asn Ala
2145                2150                2155                2160

cta tca atg atg cct gag gca atg aca ata gtc atg ctg ttt ata ctg     6646
Leu Ser Met Met Pro Glu Ala Met Thr Ile Val Met Leu Phe Ile Leu
                2165                2170                2175

gct gga cta ctg aca tcg gga atg gtc atc ttt ttc atg tct ccc aaa     6694
Ala Gly Leu Leu Thr Ser Gly Met Val Ile Phe Phe Met Ser Pro Lys
            2180                2185                2190

ggc atc agt aga atg tct atg gcg atg ggc aca atg gcc ggc tgt gga     6742
Gly Ile Ser Arg Met Ser Met Ala Met Gly Thr Met Ala Gly Cys Gly
```

-continued

```
        2195                2200                2205

tat ctc atg ttc ctt gga ggc gtc aaa ccc act cac atc tcc tat gtc     6790
Tyr Leu Met Phe Leu Gly Gly Val Lys Pro Thr His Ile Ser Tyr Val
    2210                2215                2220

atg ctc ata ttc ttt gtc ctg atg gtg gtt gtg atc ccc gag cca ggg     6838
Met Leu Ile Phe Phe Val Leu Met Val Val Val Ile Pro Glu Pro Gly
2225                2230                2235                2240

caa caa agg tcc atc caa gac aac caa gtg gca tac ctc att att ggc     6886
Gln Gln Arg Ser Ile Gln Asp Asn Gln Val Ala Tyr Leu Ile Ile Gly
                2245                2250                2255

atc ctg acg ctg gtt tca gcg gtg gca gcc aac gag cta ggc atg ctg     6934
Ile Leu Thr Leu Val Ser Ala Val Ala Ala Asn Glu Leu Gly Met Leu
            2260                2265                2270

gag aaa acc aaa gag gac ctc ttt ggg aag aag aac tta att cca tct     6982
Glu Lys Thr Lys Glu Asp Leu Phe Gly Lys Lys Asn Leu Ile Pro Ser
        2275                2280                2285

agt gct tca ccc tgg agt tgg ccg gat ctt gac ctg aag cca gga gct     7030
Ser Ala Ser Pro Trp Ser Trp Pro Asp Leu Asp Leu Lys Pro Gly Ala
    2290                2295                2300

gcc tgg aca gtg tac gtt ggc att gtt aca atg ctc tct cca atg ttg     7078
Ala Trp Thr Val Tyr Val Gly Ile Val Thr Met Leu Ser Pro Met Leu
2305                2310                2315                2320

cac cac tgg atc aaa gtc gaa tat ggc aac ctg tct ctg tct gga ata     7126
His His Trp Ile Lys Val Glu Tyr Gly Asn Leu Ser Leu Ser Gly Ile
                2325                2330                2335

gcc cag tca gcc tca gtc ctt tct ttc atg gac aag ggg ata cca ttc     7174
Ala Gln Ser Ala Ser Val Leu Ser Phe Met Asp Lys Gly Ile Pro Phe
            2340                2345                2350

atg aag atg aat atc tcg gtc ata atg ctg ctg gtc agt ggc tgg aat     7222
Met Lys Met Asn Ile Ser Val Ile Met Leu Leu Val Ser Gly Trp Asn
        2355                2360                2365

tca ata aca gtg atg cct ctg ctc tgt ggc ata ggg tgc gcc atg ctc     7270
Ser Ile Thr Val Met Pro Leu Leu Cys Gly Ile Gly Cys Ala Met Leu
    2370                2375                2380

cac tgg tct ctc att tta cct gga atc aaa gcg cag cag tca aag ctt     7318
His Trp Ser Leu Ile Leu Pro Gly Ile Lys Ala Gln Gln Ser Lys Leu
2385                2390                2395                2400

gca cag aga agg gtg ttc cat ggc gtt gcc aag aac cct gtg gtt gat     7366
Ala Gln Arg Arg Val Phe His Gly Val Ala Lys Asn Pro Val Val Asp
                2405                2410                2415

ggg aat cca aca gtt gac att gag gaa gct cct gaa atg cct gcc ctt     7414
Gly Asn Pro Thr Val Asp Ile Glu Glu Ala Pro Glu Met Pro Ala Leu
            2420                2425                2430

tat gag aag aaa ctg gct cta tat ctc ctt ctt gct ctc agc cta gct     7462
Tyr Glu Lys Lys Leu Ala Leu Tyr Leu Leu Leu Ala Leu Ser Leu Ala
        2435                2440                2445

tct gtt gcc atg tgc aga acg ccc ttt tca ttg gct gaa ggc att gtc     7510
Ser Val Ala Met Cys Arg Thr Pro Phe Ser Leu Ala Glu Gly Ile Val
    2450                2455                2460

cta gca tca gct gcc tta ggg ccg ctc ata gag gga aac acc agc ctt     7558
Leu Ala Ser Ala Ala Leu Gly Pro Leu Ile Glu Gly Asn Thr Ser Leu
2465                2470                2475                2480

ctt tgg aat gga ccc atg gct gtc tcc atg aca gga gtc atg agg ggg     7606
Leu Trp Asn Gly Pro Met Ala Val Ser Met Thr Gly Val Met Arg Gly
                2485                2490                2495

aat cac tat gct ttt gtg gga gtc atg tac aat cta tgg aag atg aaa     7654
Asn His Tyr Ala Phe Val Gly Val Met Tyr Asn Leu Trp Lys Met Lys
            2500                2505                2510

act gga cgc cgg ggg agc gcg aat gga aaa act ttg ggt gaa gtc tgg     7702
```

-continued

```
Thr Gly Arg Arg Gly Ser Ala Asn Gly Lys Thr Leu Gly Glu Val Trp
        2515                2520                2525

aag agg gaa ctg aat ctg ttg gac aag cga cag ttt gag ttg tat aaa      7750
Lys Arg Glu Leu Asn Leu Leu Asp Lys Arg Gln Phe Glu Leu Tyr Lys
    2530                2535                2540

agg acc gac att gtg gag gtg gat cgt gat acg gca cgc agg cat ttg      7798
Arg Thr Asp Ile Val Glu Val Asp Arg Asp Thr Ala Arg Arg His Leu
2545                2550                2555                2560

gcc gaa ggg aag gtg gac acc ggg gtg gcg gtc tcc agg ggg acc gca      7846
Ala Glu Gly Lys Val Asp Thr Gly Val Ala Val Ser Arg Gly Thr Ala
                2565                2570                2575

aag tta agg tgg ttc cat gag cgt ggc tat gtc aag ctg gaa ggt agg      7894
Lys Leu Arg Trp Phe His Glu Arg Gly Tyr Val Lys Leu Glu Gly Arg
            2580                2585                2590

gtg att gac ctg ggg tgt ggc cgc gga ggc tgg tgt tac tac gct gct      7942
Val Ile Asp Leu Gly Cys Gly Arg Gly Gly Trp Cys Tyr Tyr Ala Ala
        2595                2600                2605

gcg caa aag gaa gtg agt ggg gtc aaa gga ttt act ctt gga aga gac      7990
Ala Gln Lys Glu Val Ser Gly Val Lys Gly Phe Thr Leu Gly Arg Asp
    2610                2615                2620

ggc cat gag aaa ccc atg aat gtg caa agt ctg gga tgg aac atc atc      8038
Gly His Glu Lys Pro Met Asn Val Gln Ser Leu Gly Trp Asn Ile Ile
2625                2630                2635                2640

acc ttc aag gac aaa act gat atc cac cgc cta gaa cca gtg aaa tgt      8086
Thr Phe Lys Asp Lys Thr Asp Ile His Arg Leu Glu Pro Val Lys Cys
                2645                2650                2655

gac acc ctt ttg tgt gac att gga gag tca tca tcg tca tcg gtc aca      8134
Asp Thr Leu Leu Cys Asp Ile Gly Glu Ser Ser Ser Ser Ser Val Thr
            2660                2665                2670

gag ggg gaa agg acc gtg aga gtt ctt gat act gta gaa aaa tgg ctg      8182
Glu Gly Glu Arg Thr Val Arg Val Leu Asp Thr Val Glu Lys Trp Leu
        2675                2680                2685

gct tgt ggg gtt gac aac ttc tgt gtg aag gtg tta gct cca tac atg      8230
Ala Cys Gly Val Asp Asn Phe Cys Val Lys Val Leu Ala Pro Tyr Met
    2690                2695                2700

cca gat gtt ctt gag aaa ctg gaa ttg ctc caa agg agg ttt ggc gga      8278
Pro Asp Val Leu Glu Lys Leu Glu Leu Leu Gln Arg Arg Phe Gly Gly
2705                2710                2715                2720

aca gtg atc agg aac cct ctc tcc agg aat tcc act cat gaa atg tac      8326
Thr Val Ile Arg Asn Pro Leu Ser Arg Asn Ser Thr His Glu Met Tyr
                2725                2730                2735

tac gtg tct gga gcc cgc agc aat gtc aca ttt act gtg aac caa aca      8374
Tyr Val Ser Gly Ala Arg Ser Asn Val Thr Phe Thr Val Asn Gln Thr
            2740                2745                2750

tcc cgc ctc ctg atg agg aga atg agg cgt cca act gga aaa gtg acc      8422
Ser Arg Leu Leu Met Arg Arg Met Arg Arg Pro Thr Gly Lys Val Thr
        2755                2760                2765

ctg gag gct gac gtc atc ctc cca att ggg aca cgc agt gtt gag aca      8470
Leu Glu Ala Asp Val Ile Leu Pro Ile Gly Thr Arg Ser Val Glu Thr
    2770                2775                2780

gac aag gga ccc ctg gac aaa gag gcc ata gaa gaa agg gtt gag agg      8518
Asp Lys Gly Pro Leu Asp Lys Glu Ala Ile Glu Glu Arg Val Glu Arg
2785                2790                2795                2800

ata aaa tct gag tac atg acc tct tgg ttt tat gac aat gac aac ccc      8566
Ile Lys Ser Glu Tyr Met Thr Ser Trp Phe Tyr Asp Asn Asp Asn Pro
                2805                2810                2815

tac agg acc tgg cac tac tgt ggc tcc tat gtc aca aaa acc tcc gga      8614
Tyr Arg Thr Trp His Tyr Cys Gly Ser Tyr Val Thr Lys Thr Ser Gly
            2820                2825                2830
```

-continued

```
agt gcg gcg agc atg gta aat ggt gtt att aaa att ctg aca tat cca     8662
Ser Ala Ala Ser Met Val Asn Gly Val Ile Lys Ile Leu Thr Tyr Pro
        2835                2840                2845

tgg gac agg ata gag gag gtc aca aga atg gca atg act gac aca acc     8710
Trp Asp Arg Ile Glu Glu Val Thr Arg Met Ala Met Thr Asp Thr Thr
    2850                2855                2860

cct ttt gga cag caa aga gtg ttt aaa gaa aaa gtt gac acc aga gca     8758
Pro Phe Gly Gln Gln Arg Val Phe Lys Glu Lys Val Asp Thr Arg Ala
2865                2870                2875                2880

aag gat cca cca gcg gga act agg aag atc atg aaa gtt gtc aac agg     8806
Lys Asp Pro Pro Ala Gly Thr Arg Lys Ile Met Lys Val Val Asn Arg
                2885                2890                2895

tgg ctg ttc cgc cac ctg gcc aga gaa aag aac ccc aga ctg tgc aca     8854
Trp Leu Phe Arg His Leu Ala Arg Glu Lys Asn Pro Arg Leu Cys Thr
            2900                2905                2910

aag gaa gaa ttt att gca aaa gtc cga agt cat gca gcc att gga gct     8902
Lys Glu Glu Phe Ile Ala Lys Val Arg Ser His Ala Ala Ile Gly Ala
        2915                2920                2925

tac ctg gaa gaa caa gaa cag tgg aag act gcc aat gag gct gtc caa     8950
Tyr Leu Glu Glu Gln Glu Gln Trp Lys Thr Ala Asn Glu Ala Val Gln
    2930                2935                2940

gac cca aag ttc tgg gaa ctg gtg gat gaa gaa agg aag ctg cac caa     8998
Asp Pro Lys Phe Trp Glu Leu Val Asp Glu Glu Arg Lys Leu His Gln
2945                2950                2955                2960

caa ggc agg tgt cgg act tgt gtg tac aac atg atg ggg aaa aga gag     9046
Gln Gly Arg Cys Arg Thr Cys Val Tyr Asn Met Met Gly Lys Arg Glu
                2965                2970                2975

aag aag ctg tca gag ttt ggg aaa gca aag gga agc cgt gcc ata tgg     9094
Lys Lys Leu Ser Glu Phe Gly Lys Ala Lys Gly Ser Arg Ala Ile Trp
            2980                2985                2990

tat atg tgg ctg gga gcg cgg tat ctt gag ttt gag gcc ctg gga ttc     9142
Tyr Met Trp Leu Gly Ala Arg Tyr Leu Glu Phe Glu Ala Leu Gly Phe
        2995                3000                3005

ctg aat gag gac cat tgg gct tcc agg gaa aac tca gga gga gga gtg     9190
Leu Asn Glu Asp His Trp Ala Ser Arg Glu Asn Ser Gly Gly Gly Val
    3010                3015                3020

gaa ggc att ggc tta caa tac cta gga tat gtg atc aga gac ctg gct     9238
Glu Gly Ile Gly Leu Gln Tyr Leu Gly Tyr Val Ile Arg Asp Leu Ala
3025                3030                3035                3040

gca atg gat ggt ggt gga ttc tac gcg gat gac acc gct gga tgg gac     9286
Ala Met Asp Gly Gly Gly Phe Tyr Ala Asp Asp Thr Ala Gly Trp Asp
                3045                3050                3055

acg cgc atc aca gag gca gac ctt gat gat gaa cag gag atc ttg aac     9334
Thr Arg Ile Thr Glu Ala Asp Leu Asp Asp Glu Gln Glu Ile Leu Asn
            3060                3065                3070

tac atg agc cca cat cac aaa aaa ctg gca caa gca gtg atg gaa atg     9382
Tyr Met Ser Pro His His Lys Lys Leu Ala Gln Ala Val Met Glu Met
        3075                3080                3085

aca tac aag aac aaa gtg gtg aaa gtg ttg aga cca gcc cca gga ggg     9430
Thr Tyr Lys Asn Lys Val Val Lys Val Leu Arg Pro Ala Pro Gly Gly
    3090                3095                3100

aaa gcc tac atg gat gtc ata agt cga cga gac cag aga gga tcc ggg     9478
Lys Ala Tyr Met Asp Val Ile Ser Arg Arg Asp Gln Arg Gly Ser Gly
3105                3110                3115                3120

cag gta gtg act tat gct ctg aac acc atc acc aac ttg aaa gtc caa     9526
Gln Val Val Thr Tyr Ala Leu Asn Thr Ile Thr Asn Leu Lys Val Gln
                3125                3130                3135

ttg atc aga atg gca gaa gca gag atg gtg ata cat cac caa cat gtt     9574
Leu Ile Arg Met Ala Glu Ala Glu Met Val Ile His His Gln His Val
            3140                3145                3150
```

```
caa gat tgt gat gaa tca gtt ctg acc agg ctg gag gca tgg ctc act     9622
Gln Asp Cys Asp Glu Ser Val Leu Thr Arg Leu Glu Ala Trp Leu Thr
        3155                3160                3165

gag cac gga tgt gac aga ctg aag agg atg gcg gtg agt gga gac gac     9670
Glu His Gly Cys Asp Arg Leu Lys Arg Met Ala Val Ser Gly Asp Asp
    3170                3175                3180

tgt gtg gtc cgg ccc atc gat gac agg ttc ggc ctg gcc ctg tcc cat     9718
Cys Val Val Arg Pro Ile Asp Asp Arg Phe Gly Leu Ala Leu Ser His
3185                3190                3195                3200

ctc aac gcc atg tcc aag gtt aga aag gac ata tct gaa tgg cag cca     9766
Leu Asn Ala Met Ser Lys Val Arg Lys Asp Ile Ser Glu Trp Gln Pro
                3205                3210                3215

tca aaa ggg tgg aat gat tgg gag aat gtg ccc ttc tgt tcc cac cac     9814
Ser Lys Gly Trp Asn Asp Trp Glu Asn Val Pro Phe Cys Ser His His
            3220                3225                3230

ttc cat gaa cta cag ctg aag gat ggc agg agg att gtg gtg cct tgc     9862
Phe His Glu Leu Gln Leu Lys Asp Gly Arg Arg Ile Val Val Pro Cys
        3235                3240                3245

cga gaa cag gac gag ctc att ggg aga gga agg gtg tct cca gga aac     9910
Arg Glu Gln Asp Glu Leu Ile Gly Arg Gly Arg Val Ser Pro Gly Asn
    3250                3255                3260

ggc tgg atg atc aag gaa aca gct tgc ctc agc aaa gcc tat gcc aac     9958
Gly Trp Met Ile Lys Glu Thr Ala Cys Leu Ser Lys Ala Tyr Ala Asn
3265                3270                3275                3280

atg tgg tca ctg atg tat ttt cac aaa agg gac atg agg cta ctg tca    10006
Met Trp Ser Leu Met Tyr Phe His Lys Arg Asp Met Arg Leu Leu Ser
                3285                3290                3295

ttg gct gtt tcc tca gct gtt ccc acc tca tgg gtt cca caa gga cgc    10054
Leu Ala Val Ser Ser Ala Val Pro Thr Ser Trp Val Pro Gln Gly Arg
            3300                3305                3310

aca aca tgg tcg att cat ggg aaa ggg gag tgg atg acc acg gaa gac    10102
Thr Thr Trp Ser Ile His Gly Lys Gly Glu Trp Met Thr Thr Glu Asp
        3315                3320                3325

atg ctt gag gtg tgg aac aga gta tgg ata acc aac aac cca cac atg    10150
Met Leu Glu Val Trp Asn Arg Val Trp Ile Thr Asn Asn Pro His Met
    3330                3335                3340

cag gac aag aca atg gtg aaa aaa tgg aga gat gtc cct tat cta acc    10198
Gln Asp Lys Thr Met Val Lys Lys Trp Arg Asp Val Pro Tyr Leu Thr
3345                3350                3355                3360

aag aga caa gac aag ctg tgc gga tca ctg att gga atg acc aat agg    10246
Lys Arg Gln Asp Lys Leu Cys Gly Ser Leu Ile Gly Met Thr Asn Arg
                3365                3370                3375

gcc acc tgg gcc tcc cac atc cat tta gtc atc cat cgt atc cga acg    10294
Ala Thr Trp Ala Ser His Ile His Leu Val Ile His Arg Ile Arg Thr
            3380                3385                3390

ctg att gga cag gag aaa tac act gac tac cta aca gtc atg gac agg    10342
Leu Ile Gly Gln Glu Lys Tyr Thr Asp Tyr Leu Thr Val Met Asp Arg
        3395                3400                3405

tat tct gtg gat gct gac ctg caa ctg ggt gag ctt atc tgaaacacca     10391
Tyr Ser Val Asp Ala Asp Leu Gln Leu Gly Glu Leu Ile
    3410                3415                3420

tctaacagga ataaccggga tacaaaccac gggtggagaa ccggactccc cacaacctga  10451

aaccgggata taaaccacgg ctggagaacc gggctccgca cttaaaatga aacagaaacc  10511

gggataaaaa ctacggatgg agaaccggac tccacacatt gagacagaag aagttgtcag  10571

cccagaaccc cacacgagtt ttgccactgc taagctgtga ggcagtgcag gctgggacag  10631

ccgacctcca ggttgcgaaa aacctggttt ctgggacctc ccaccccaga gtaaaaagaa  10691
```

-continued

```
cggagcctcc gctaccaccc tcccacgtgg tggtagaaag acggggtcta gaggttagag  10751

gagaccctcc agggaacaaa tagtgggacc atattgacgc cagggaaaga ccggagtggt  10811

tctctgcttt tcctccagag gtctgtgagc acagtttgct caagaataag cagacctttg  10871

gatgacaaac acaaaaccac t                                            10892
```

```
<210> SEQ ID NO 53
<211> LENGTH: 3421
<212> TYPE: PRT
<213> ORGANISM: Artificial Sequence
<220> FEATURE:
<223> OTHER INFORMATION: derived from Yellow Fever virus and Japanese
      Encephalitis virus

<400> SEQUENCE: 53

Met Ser Gly Arg Lys Ala Gln Gly Lys Thr Leu Gly Val Asn Met Val
 1               5                  10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Met Lys Leu Ser Asn Phe Gln
        115                 120                 125

Gly Lys Leu Leu Met Thr Ile Asn Asn Thr Asp Ile Ala Asp Val Ile
    130                 135                 140

Val Ile Pro Thr Ser Lys Gly Glu Asn Arg Cys Trp Val Arg Ala Ile
145                 150                 155                 160

Asp Val Gly Tyr Met Cys Glu Asp Thr Ile Thr Tyr Glu Cys Pro Lys
                165                 170                 175

Leu Thr Met Gly Asn Asp Pro Glu Asp Val Asp Cys Trp Cys Asp Asn
            180                 185                 190

Gln Glu Val Tyr Val Gln Tyr Gly Arg Cys Thr Arg Thr Arg His Ser
        195                 200                 205

Lys Arg Ser Arg Arg Ser Val Ser Val Gln Thr His Gly Glu Ser Ser
    210                 215                 220

Leu Val Asn Lys Lys Glu Ala Trp Leu Asp Ser Thr Lys Ala Thr Arg
225                 230                 235                 240

Tyr Leu Met Lys Thr Glu Asn Trp Ile Ile Arg Asn Pro Gly Tyr Ala
                245                 250                 255

Phe Leu Ala Ala Val Leu Gly Trp Met Leu Gly Ser Asn Asn Gly Gln
            260                 265                 270

Arg Val Val Phe Thr Ile Leu Leu Leu Leu Val Ala Pro Ala Tyr Ser
        275                 280                 285

Phe Asn Cys Leu Gly Met Gly Asn Arg Asp Phe Ile Glu Gly Ala Ser
    290                 295                 300

Gly Ala Thr Trp Val Asp Leu Val Leu Glu Gly Asp Ser Cys Leu Thr
305                 310                 315                 320
```

-continued

```
Ile Met Ala Asn Asp Lys Pro Thr Leu Asp Val Arg Met Ile Asn Ile
            325                 330                 335

Glu Ala Ser Gln Leu Ala Glu Val Arg Ser Tyr Cys Tyr His Ala Ser
        340                 345                 350

Val Thr Asp Ile Ser Thr Val Ala Arg Cys Pro Thr Thr Gly Glu Ala
    355                 360                 365

His Asn Glu Lys Arg Ala Asp Ser Ser Tyr Val Cys Lys Gln Gly Phe
    370                 375                 380

Thr Asp Arg Gly Trp Gly Asn Gly Cys Gly Phe Phe Gly Lys Gly Ser
385                 390                 395                 400

Ile Asp Thr Cys Ala Lys Phe Ser Cys Thr Ser Lys Ala Ile Gly Arg
            405                 410                 415

Thr Ile Gln Pro Glu Asn Ile Lys Tyr Lys Val Gly Ile Phe Val His
        420                 425                 430

Gly Thr Thr Thr Ser Glu Asn His Gly Asn Tyr Ser Ala Gln Val Gly
    435                 440                 445

Ala Ser Gln Ala Ala Lys Phe Thr Val Thr Pro Asn Ala Pro Ser Val
    450                 455                 460

Ala Leu Lys Leu Gly Asp Tyr Gly Glu Val Thr Leu Asp Cys Glu Pro
465                 470                 475                 480

Arg Ser Gly Leu Asn Thr Glu Ala Phe Tyr Val Met Thr Val Gly Ser
            485                 490                 495

Lys Ser Phe Leu Val His Arg Glu Trp Phe His Asp Leu Ala Leu Pro
        500                 505                 510

Trp Thr Ser Pro Ser Ser Thr Ala Trp Arg Asn Arg Glu Leu Leu Met
    515                 520                 525

Glu Phe Glu Gly Ala His Ala Thr Lys Gln Ser Val Val Ala Leu Gly
    530                 535                 540

Ser Gln Glu Gly Gly Leu His His Ala Leu Ala Gly Ala Ile Val Val
545                 550                 555                 560

Glu Tyr Ser Ser Ser Val Met Leu Thr Ser Gly His Leu Lys Cys Arg
            565                 570                 575

Leu Lys Met Asp Lys Leu Ala Leu Lys Gly Thr Thr Tyr Gly Met Cys
        580                 585                 590

Thr Glu Lys Phe Ser Phe Ala Lys Asn Pro Val Asp Thr Gly His Gly
    595                 600                 605

Thr Val Val Ile Glu Leu Ser Tyr Ser Gly Ser Asp Gly Pro Cys Lys
    610                 615                 620

Ile Pro Ile Val Ser Val Ala Ser Leu Asn Asp Met Thr Pro Val Gly
625                 630                 635                 640

Arg Leu Val Thr Val Asn Pro Phe Val Ala Thr Ser Ser Ala Asn Ser
            645                 650                 655

Lys Val Leu Val Glu Met Glu Pro Pro Phe Gly Asp Ser Tyr Ile Val
        660                 665                 670

Val Gly Arg Gly Asp Lys Gln Ile Asn His His Trp His Lys Ala Gly
    675                 680                 685

Ser Thr Leu Gly Lys Ala Phe Ser Thr Thr Leu Lys Gly Ala Gln Arg
    690                 695                 700

Leu Ala Ala Leu Gly Asp Thr Ala Trp Asp Phe Gly Ser Ile Gly Gly
705                 710                 715                 720

Val Phe Asn Ser Ile Gly Arg Ala Val His Gln Val Phe Gly Gly Ala
            725                 730                 735

Phe Arg Thr Leu Phe Gly Gly Met Ser Trp Ile Thr Gln Gly Leu Met
```

-continued

```
            740                 745                 750

Gly Ala Leu Leu Leu Trp Met Gly Val Asn Ala Arg Asp Arg Ser Ile
        755                 760                 765

Ala Leu Ala Phe Leu Ala Thr Gly Gly Val Leu Val Phe Leu Ala Thr
    770                 775                 780

Asn Val Gly Ala Asp Gln Gly Cys Ala Ile Asn Phe Gly Lys Arg Glu
785                 790                 795                 800

Leu Lys Cys Gly Asp Gly Ile Phe Ile Phe Arg Asp Ser Asp Asp Trp
                805                 810                 815

Leu Asn Lys Tyr Ser Tyr Tyr Pro Glu Asp Pro Val Lys Leu Ala Ser
            820                 825                 830

Ile Val Lys Ala Ser Phe Glu Glu Gly Lys Cys Gly Leu Asn Ser Val
        835                 840                 845

Asp Ser Leu Glu His Glu Met Trp Arg Ser Arg Ala Asp Glu Ile Asn
    850                 855                 860

Ala Ile Phe Glu Glu Asn Glu Val Asp Ile Ser Val Val Val Gln Asp
865                 870                 875                 880

Pro Lys Asn Val Tyr Gln Arg Gly Thr His Pro Phe Ser Arg Ile Arg
                885                 890                 895

Asp Gly Leu Gln Tyr Gly Trp Lys Thr Trp Gly Lys Asn Leu Val Phe
            900                 905                 910

Ser Pro Gly Arg Lys Asn Gly Ser Phe Ile Ile Asp Gly Lys Ser Arg
        915                 920                 925

Lys Glu Cys Pro Phe Ser Asn Arg Val Trp Asn Ser Phe Gln Ile Glu
    930                 935                 940

Glu Phe Gly Thr Gly Val Phe Thr Thr Arg Val Tyr Met Asp Ala Val
945                 950                 955                 960

Phe Glu Tyr Thr Ile Asp Cys Asp Gly Ser Ile Leu Gly Ala Ala Val
                965                 970                 975

Asn Gly Lys Lys Ser Ala His Gly Ser Pro Thr Phe Trp Met Gly Ser
            980                 985                 990

His Glu Val Asn Gly Thr Trp Met Ile His Thr Leu Glu Ala Leu Asp
        995                 1000                1005

Tyr Lys Glu Cys Glu Trp Pro Leu Thr His Thr Ile Gly Thr Ser Val
    1010                1015                1020

Glu Glu Ser Glu Met Phe Met Pro Arg Ser Ile Gly Gly Pro Val Ser
1025                1030                1035                1040

Ser His Asn His Ile Pro Gly Tyr Lys Val Gln Thr Asn Gly Pro Trp
                1045                1050                1055

Met Gln Val Pro Leu Glu Val Lys Arg Glu Ala Cys Pro Gly Thr Ser
            1060                1065                1070

Val Ile Ile Asp Gly Asn Cys Asp Gly Arg Gly Lys Ser Thr Arg Ser
        1075                1080                1085

Thr Thr Asp Ser Gly Lys Val Ile Pro Glu Trp Cys Cys Arg Ser Cys
    1090                1095                1100

Thr Met Pro Pro Val Ser Phe His Gly Ser Asp Gly Cys Trp Tyr Pro
1105                1110                1115                1120

Met Glu Ile Arg Pro Arg Lys Thr His Glu Ser His Leu Val Arg Ser
                1125                1130                1135

Trp Val Thr Ala Gly Glu Ile His Ala Val Pro Phe Gly Leu Val Ser
            1140                1145                1150

Met Met Ile Ala Met Glu Val Val Leu Arg Lys Arg Gln Gly Pro Lys
        1155                1160                1165
```

-continued

```
Gln Met Leu Val Gly Gly Val Val Leu Leu Gly Ala Met Leu Val Gly
    1170                1175                1180

Gln Val Thr Leu Leu Asp Leu Leu Lys Leu Thr Val Ala Val Gly Leu
1185                1190                1195                1200

His Phe His Glu Met Asn Asn Gly Gly Asp Ala Met Tyr Met Ala Leu
                1205                1210                1215

Ile Ala Ala Phe Ser Ile Arg Pro Gly Leu Leu Ile Gly Phe Gly Leu
            1220                1225                1230

Arg Thr Leu Trp Ser Pro Arg Glu Arg Leu Val Leu Thr Leu Gly Ala
        1235                1240                1245

Ala Met Val Glu Ile Ala Leu Gly Gly Val Met Gly Gly Leu Trp Lys
    1250                1255                1260

Tyr Leu Asn Ala Val Ser Leu Cys Ile Leu Thr Ile Asn Ala Val Ala
1265                1270                1275                1280

Ser Arg Lys Ala Ser Asn Thr Ile Leu Pro Leu Met Ala Leu Leu Thr
                1285                1290                1295

Pro Val Thr Met Ala Glu Val Arg Leu Ala Ala Met Phe Phe Cys Ala
            1300                1305                1310

Met Val Ile Ile Gly Val Leu His Gln Asn Phe Lys Asp Thr Ser Met
        1315                1320                1325

Gln Lys Thr Ile Pro Leu Val Ala Leu Thr Leu Thr Ser Tyr Leu Gly
    1330                1335                1340

Leu Thr Gln Pro Phe Leu Gly Leu Cys Ala Phe Leu Ala Thr Arg Ile
1345                1350                1355                1360

Phe Gly Arg Arg Ser Ile Pro Val Asn Glu Ala Leu Ala Ala Ala Gly
                1365                1370                1375

Leu Val Gly Val Leu Ala Gly Leu Ala Phe Gln Glu Met Glu Asn Phe
            1380                1385                1390

Leu Gly Pro Ile Ala Val Gly Gly Leu Leu Met Met Leu Val Ser Val
        1395                1400                1405

Ala Gly Arg Val Asp Gly Leu Glu Leu Lys Lys Leu Gly Glu Val Ser
    1410                1415                1420

Trp Glu Glu Glu Ala Glu Ile Ser Gly Ser Ser Ala Arg Tyr Asp Val
1425                1430                1435                1440

Ala Leu Ser Glu Gln Gly Glu Phe Lys Leu Leu Ser Glu Glu Lys Val
                1445                1450                1455

Pro Trp Asp Gln Val Val Met Thr Ser Leu Ala Leu Val Gly Ala Ala
            1460                1465                1470

Leu His Pro Phe Ala Leu Leu Leu Val Leu Ala Gly Trp Leu Phe His
        1475                1480                1485

Val Arg Gly Ala Arg Arg Ser Gly Asp Val Leu Trp Asp Ile Pro Thr
    1490                1495                1500

Pro Lys Ile Ile Glu Glu Cys Glu His Leu Glu Asp Gly Ile Tyr Gly
1505                1510                1515                1520

Ile Phe Gln Ser Thr Phe Leu Gly Ala Ser Gln Arg Gly Val Gly Val
                1525                1530                1535

Ala Gln Gly Gly Val Phe His Thr Met Trp His Val Thr Arg Gly Ala
            1540                1545                1550

Phe Leu Val Arg Asn Gly Lys Lys Leu Ile Pro Ser Trp Ala Ser Val
        1555                1560                1565

Lys Glu Asp Leu Val Ala Tyr Gly Gly Ser Trp Lys Leu Glu Gly Arg
    1570                1575                1580
```

-continued

```
Trp Asp Gly Glu Glu Glu Val Gln Leu Ile Ala Ala Val Pro Gly Lys
1585                1590                1595                1600

Asn Val Val Asn Val Gln Thr Lys Pro Ser Leu Phe Lys Val Arg Asn
                1605                1610                1615

Gly Gly Glu Ile Gly Ala Val Ala Leu Asp Tyr Pro Ser Gly Thr Ser
            1620                1625                1630

Gly Ser Pro Ile Val Asn Arg Asn Gly Glu Val Ile Gly Leu Tyr Gly
        1635                1640                1645

Asn Gly Ile Leu Val Gly Asp Asn Ser Phe Val Ser Ala Ile Ser Gln
    1650                1655                1660

Thr Glu Val Lys Glu Glu Gly Lys Glu Glu Leu Gln Glu Ile Pro Thr
1665                1670                1675                1680

Met Leu Lys Lys Gly Met Thr Thr Val Leu Asp Phe His Pro Gly Ala
                1685                1690                1695

Gly Lys Thr Arg Arg Phe Leu Pro Gln Ile Leu Ala Glu Cys Ala Arg
            1700                1705                1710

Arg Arg Leu Arg Thr Leu Val Leu Ala Pro Thr Arg Val Val Leu Ser
        1715                1720                1725

Glu Met Lys Glu Ala Phe His Gly Leu Asp Val Lys Phe His Thr Gln
    1730                1735                1740

Ala Phe Ser Ala His Gly Ser Gly Arg Glu Val Ile Asp Ala Met Cys
1745                1750                1755                1760

His Ala Thr Leu Thr Tyr Arg Met Leu Glu Pro Thr Arg Val Val Asn
                1765                1770                1775

Trp Glu Val Ile Ile Met Asp Glu Ala His Phe Leu Asp Pro Ala Ser
            1780                1785                1790

Ile Ala Ala Arg Gly Trp Ala Ala His Arg Ala Arg Ala Asn Glu Ser
        1795                1800                1805

Ala Thr Ile Leu Met Thr Ala Thr Pro Pro Gly Thr Ser Asp Glu Phe
    1810                1815                1820

Pro His Ser Asn Gly Glu Ile Glu Asp Val Gln Thr Asp Ile Pro Ser
1825                1830                1835                1840

Glu Pro Trp Asn Thr Gly His Asp Trp Ile Leu Ala Asp Lys Arg Pro
                1845                1850                1855

Thr Ala Trp Phe Leu Pro Ser Ile Arg Ala Ala Asn Val Met Ala Ala
            1860                1865                1870

Ser Leu Arg Lys Ala Gly Lys Ser Val Val Val Leu Asn Arg Lys Thr
        1875                1880                1885

Phe Glu Arg Glu Tyr Pro Thr Ile Lys Gln Lys Lys Pro Asp Phe Ile
    1890                1895                1900

Leu Ala Thr Asp Ile Ala Glu Met Gly Ala Asn Leu Cys Val Glu Arg
1905                1910                1915                1920

Val Leu Asp Cys Arg Thr Ala Phe Lys Pro Val Leu Val Asp Glu Gly
                1925                1930                1935

Arg Lys Val Ala Ile Lys Gly Pro Leu Arg Ile Ser Ala Ser Ser Ala
            1940                1945                1950

Ala Gln Arg Arg Gly Arg Ile Gly Arg Asn Pro Asn Arg Asp Gly Asp
        1955                1960                1965

Ser Tyr Tyr Tyr Ser Glu Pro Thr Ser Glu Asn Asn Ala His His Val
    1970                1975                1980

Cys Trp Leu Glu Ala Ser Met Leu Leu Asp Asn Met Glu Val Arg Gly
1985                1990                1995                2000

Gly Met Val Ala Pro Leu Tyr Gly Val Glu Gly Thr Lys Thr Pro Val
```

-continued

```
                2005                2010                2015

Ser Pro Gly Glu Met Arg Leu Arg Asp Asp Gln Arg Lys Val Phe Arg
            2020                2025                2030

Glu Leu Val Arg Asn Cys Asp Leu Pro Val Trp Leu Ser Trp Gln Val
        2035                2040                2045

Ala Lys Ala Gly Leu Lys Thr Asn Asp Arg Lys Trp Cys Phe Glu Gly
    2050                2055                2060

Pro Glu Glu His Glu Ile Leu Asn Asp Ser Gly Glu Thr Val Lys Cys
2065                2070                2075                2080

Arg Ala Pro Gly Gly Ala Lys Lys Pro Leu Arg Pro Arg Trp Cys Asp
                2085                2090                2095

Glu Arg Val Ser Ser Asp Gln Ser Ala Leu Ser Glu Phe Ile Lys Phe
            2100                2105                2110

Ala Glu Gly Arg Arg Gly Ala Ala Glu Val Leu Val Val Leu Ser Glu
        2115                2120                2125

Leu Pro Asp Phe Leu Ala Lys Lys Gly Gly Glu Ala Met Asp Thr Ile
    2130                2135                2140

Ser Val Phe Leu His Ser Glu Glu Gly Ser Arg Ala Tyr Arg Asn Ala
2145                2150                2155                2160

Leu Ser Met Met Pro Glu Ala Met Thr Ile Val Met Leu Phe Ile Leu
                2165                2170                2175

Ala Gly Leu Leu Thr Ser Gly Met Val Ile Phe Phe Met Ser Pro Lys
            2180                2185                2190

Gly Ile Ser Arg Met Ser Met Ala Met Gly Thr Met Ala Gly Cys Gly
        2195                2200                2205

Tyr Leu Met Phe Leu Gly Gly Val Lys Pro Thr His Ile Ser Tyr Val
    2210                2215                2220

Met Leu Ile Phe Phe Val Leu Met Val Val Val Ile Pro Glu Pro Gly
2225                2230                2235                2240

Gln Gln Arg Ser Ile Gln Asp Asn Gln Val Ala Tyr Leu Ile Ile Gly
                2245                2250                2255

Ile Leu Thr Leu Val Ser Ala Val Ala Ala Asn Glu Leu Gly Met Leu
            2260                2265                2270

Glu Lys Thr Lys Glu Asp Leu Phe Gly Lys Lys Asn Leu Ile Pro Ser
        2275                2280                2285

Ser Ala Ser Pro Trp Ser Trp Pro Asp Leu Asp Leu Lys Pro Gly Ala
    2290                2295                2300

Ala Trp Thr Val Tyr Val Gly Ile Val Thr Met Leu Ser Pro Met Leu
2305                2310                2315                2320

His His Trp Ile Lys Val Glu Tyr Gly Asn Leu Ser Leu Ser Gly Ile
                2325                2330                2335

Ala Gln Ser Ala Ser Val Leu Ser Phe Met Asp Lys Gly Ile Pro Phe
            2340                2345                2350

Met Lys Met Asn Ile Ser Val Ile Met Leu Leu Val Ser Gly Trp Asn
        2355                2360                2365

Ser Ile Thr Val Met Pro Leu Leu Cys Gly Ile Gly Cys Ala Met Leu
    2370                2375                2380

His Trp Ser Leu Ile Leu Pro Gly Ile Lys Ala Gln Gln Ser Lys Leu
2385                2390                2395                2400

Ala Gln Arg Arg Val Phe His Gly Val Ala Lys Asn Pro Val Val Asp
                2405                2410                2415

Gly Asn Pro Thr Val Asp Ile Glu Glu Ala Pro Glu Met Pro Ala Leu
            2420                2425                2430
```

```
Tyr Glu Lys Lys Leu Ala Leu Tyr Leu Leu Leu Ala Leu Ser Leu Ala
        2435                2440                2445

Ser Val Ala Met Cys Arg Thr Pro Phe Ser Leu Ala Glu Gly Ile Val
    2450                2455                2460

Leu Ala Ser Ala Ala Leu Gly Pro Leu Ile Glu Gly Asn Thr Ser Leu
2465                2470                2475                2480

Leu Trp Asn Gly Pro Met Ala Val Ser Met Thr Gly Val Met Arg Gly
                2485                2490                2495

Asn His Tyr Ala Phe Val Gly Val Met Tyr Asn Leu Trp Lys Met Lys
            2500                2505                2510

Thr Gly Arg Arg Gly Ser Ala Asn Gly Lys Thr Leu Gly Glu Val Trp
        2515                2520                2525

Lys Arg Glu Leu Asn Leu Leu Asp Lys Arg Gln Phe Glu Leu Tyr Lys
    2530                2535                2540

Arg Thr Asp Ile Val Glu Val Asp Arg Asp Thr Ala Arg Arg His Leu
2545                2550                2555                2560

Ala Glu Gly Lys Val Asp Thr Gly Val Ala Val Ser Arg Gly Thr Ala
                2565                2570                2575

Lys Leu Arg Trp Phe His Glu Arg Gly Tyr Val Lys Leu Glu Gly Arg
            2580                2585                2590

Val Ile Asp Leu Gly Cys Gly Arg Gly Gly Trp Cys Tyr Tyr Ala Ala
        2595                2600                2605

Ala Gln Lys Glu Val Ser Gly Val Lys Gly Phe Thr Leu Gly Arg Asp
    2610                2615                2620

Gly His Glu Lys Pro Met Asn Val Gln Ser Leu Gly Trp Asn Ile Ile
2625                2630                2635                2640

Thr Phe Lys Asp Lys Thr Asp Ile His Arg Leu Glu Pro Val Lys Cys
                2645                2650                2655

Asp Thr Leu Leu Cys Asp Ile Gly Glu Ser Ser Ser Ser Ser Val Thr
            2660                2665                2670

Glu Gly Glu Arg Thr Val Arg Val Leu Asp Thr Val Glu Lys Trp Leu
        2675                2680                2685

Ala Cys Gly Val Asp Asn Phe Cys Val Lys Val Leu Ala Pro Tyr Met
    2690                2695                2700

Pro Asp Val Leu Glu Lys Leu Glu Leu Leu Gln Arg Arg Phe Gly Gly
2705                2710                2715                2720

Thr Val Ile Arg Asn Pro Leu Ser Arg Asn Ser Thr His Glu Met Tyr
                2725                2730                2735

Tyr Val Ser Gly Ala Arg Ser Asn Val Thr Phe Thr Val Asn Gln Thr
            2740                2745                2750

Ser Arg Leu Leu Met Arg Arg Met Arg Arg Pro Thr Gly Lys Val Thr
        2755                2760                2765

Leu Glu Ala Asp Val Ile Leu Pro Ile Gly Thr Arg Ser Val Glu Thr
    2770                2775                2780

Asp Lys Gly Pro Leu Asp Lys Glu Ala Ile Glu Glu Arg Val Glu Arg
2785                2790                2795                2800

Ile Lys Ser Glu Tyr Met Thr Ser Trp Phe Tyr Asp Asn Asp Asn Pro
                2805                2810                2815

Tyr Arg Thr Trp His Tyr Cys Gly Ser Tyr Val Thr Lys Thr Ser Gly
            2820                2825                2830

Ser Ala Ala Ser Met Val Asn Gly Val Ile Lys Ile Leu Thr Tyr Pro
        2835                2840                2845
```

-continued

```
Trp Asp Arg Ile Glu Glu Val Thr Arg Met Ala Met Thr Asp Thr Thr
    2850                2855                2860

Pro Phe Gly Gln Gln Arg Val Phe Lys Glu Lys Val Asp Thr Arg Ala
2865                2870                2875                2880

Lys Asp Pro Pro Ala Gly Thr Arg Lys Ile Met Lys Val Val Asn Arg
                2885                2890                2895

Trp Leu Phe Arg His Leu Ala Arg Glu Lys Asn Pro Arg Leu Cys Thr
            2900                2905                2910

Lys Glu Glu Phe Ile Ala Lys Val Arg Ser His Ala Ala Ile Gly Ala
        2915                2920                2925

Tyr Leu Glu Glu Gln Glu Gln Trp Lys Thr Ala Asn Glu Ala Val Gln
    2930                2935                2940

Asp Pro Lys Phe Trp Glu Leu Val Asp Glu Glu Arg Lys Leu His Gln
2945                2950                2955                2960

Gln Gly Arg Cys Arg Thr Cys Val Tyr Asn Met Met Gly Lys Arg Glu
                2965                2970                2975

Lys Lys Leu Ser Glu Phe Gly Lys Ala Lys Gly Ser Arg Ala Ile Trp
            2980                2985                2990

Tyr Met Trp Leu Gly Ala Arg Tyr Leu Glu Phe Glu Ala Leu Gly Phe
        2995                3000                3005

Leu Asn Glu Asp His Trp Ala Ser Arg Glu Asn Ser Gly Gly Gly Val
    3010                3015                3020

Glu Gly Ile Gly Leu Gln Tyr Leu Gly Tyr Val Ile Arg Asp Leu Ala
3025                3030                3035                3040

Ala Met Asp Gly Gly Gly Phe Tyr Ala Asp Asp Thr Ala Gly Trp Asp
                3045                3050                3055

Thr Arg Ile Thr Glu Ala Asp Leu Asp Asp Glu Gln Glu Ile Leu Asn
            3060                3065                3070

Tyr Met Ser Pro His His Lys Lys Leu Ala Gln Ala Val Met Glu Met
        3075                3080                3085

Thr Tyr Lys Asn Lys Val Val Lys Val Leu Arg Pro Ala Pro Gly Gly
    3090                3095                3100

Lys Ala Tyr Met Asp Val Ile Ser Arg Arg Asp Gln Arg Gly Ser Gly
3105                3110                3115                3120

Gln Val Val Thr Tyr Ala Leu Asn Thr Ile Thr Asn Leu Lys Val Gln
                3125                3130                3135

Leu Ile Arg Met Ala Glu Ala Glu Met Val Ile His His Gln His Val
            3140                3145                3150

Gln Asp Cys Asp Glu Ser Val Leu Thr Arg Leu Glu Ala Trp Leu Thr
        3155                3160                3165

Glu His Gly Cys Asp Arg Leu Lys Arg Met Ala Val Ser Gly Asp Asp
    3170                3175                3180

Cys Val Val Arg Pro Ile Asp Asp Arg Phe Gly Leu Ala Leu Ser His
3185                3190                3195                3200

Leu Asn Ala Met Ser Lys Val Arg Lys Asp Ile Ser Glu Trp Gln Pro
                3205                3210                3215

Ser Lys Gly Trp Asn Asp Trp Glu Asn Val Pro Phe Cys Ser His His
            3220                3225                3230

Phe His Glu Leu Gln Leu Lys Asp Gly Arg Arg Ile Val Val Pro Cys
        3235                3240                3245

Arg Glu Gln Asp Glu Leu Ile Gly Arg Gly Arg Val Ser Pro Gly Asn
    3250                3255                3260

Gly Trp Met Ile Lys Glu Thr Ala Cys Leu Ser Lys Ala Tyr Ala Asn
```

-continued

```
3265                3270                3275                3280

Met Trp Ser Leu Met Tyr Phe His Lys Arg Asp Met Arg Leu Leu Ser
                3285                3290                3295

Leu Ala Val Ser Ser Ala Val Pro Thr Ser Trp Val Pro Gln Gly Arg
            3300                3305                3310

Thr Thr Trp Ser Ile His Gly Lys Gly Glu Trp Met Thr Thr Glu Asp
        3315                3320                3325

Met Leu Glu Val Trp Asn Arg Val Trp Ile Thr Asn Asn Pro His Met
    3330                3335                3340

Gln Asp Lys Thr Met Val Lys Lys Trp Arg Asp Val Pro Tyr Leu Thr
3345                3350                3355                3360

Lys Arg Gln Asp Lys Leu Cys Gly Ser Leu Ile Gly Met Thr Asn Arg
                3365                3370                3375

Ala Thr Trp Ala Ser His Ile His Leu Val Ile His Arg Ile Arg Thr
            3380                3385                3390

Leu Ile Gly Gln Glu Lys Tyr Thr Asp Tyr Leu Thr Val Met Asp Arg
        3395                3400                3405

Tyr Ser Val Asp Ala Asp Leu Gln Leu Gly Glu Leu Ile
    3410                3415                3420


<210> SEQ ID NO 54
<211> LENGTH: 10
<212> TYPE: PRT
<213> ORGANISM: Yellow Fever virus

<400> SEQUENCE: 54

Leu Ser Ser Arg Lys Arg Arg Ser His Asp
 1               5                  10


<210> SEQ ID NO 55
<211> LENGTH: 20
<212> TYPE: PRT
<213> ORGANISM: Yellow Fever virus

<400> SEQUENCE: 55

Val Leu Thr Val Gln Phe Leu Ile Leu Gly Met Leu Leu Met Thr Gly
 1               5                  10                  15

Gly Val Thr Leu
            20


<210> SEQ ID NO 56
<211> LENGTH: 32
<212> TYPE: PRT
<213> ORGANISM: Japanese Encephalitis virus

<400> SEQUENCE: 56

Gly Arg Lys Gln Asn Lys Arg Gly Gly Asn Glu Gly Ser Ile Met Trp
 1               5                  10                  15

Leu Ala Ser Leu Ala Val Val Ile Ala Tyr Ala Gly Ala Met Lys Leu
            20                  25                  30


<210> SEQ ID NO 57
<211> LENGTH: 11
<212> TYPE: PRT
<213> ORGANISM: Tick-Borne Encephalitis virus

<400> SEQUENCE: 57

Gln Lys Arg Gly Lys Arg Arg Ser Ala Thr Asp
 1               5                  10
```

<210> SEQ ID NO 58
<211> LENGTH: 19
<212> TYPE: PRT
<213> ORGANISM: Tick-Borne Encephalitis virus

<400> SEQUENCE: 58

Trp Met Ser Trp Leu Leu Val Ile Thr Leu Leu Gly Met Thr Leu Ala
1 5 10 15

Ala Thr Val

<210> SEQ ID NO 59
<211> LENGTH: 11
<212> TYPE: PRT
<213> ORGANISM: Murray Valley Encephalitis virus

<400> SEQUENCE: 59

Gly Lys Lys Gln Lys Lys Arg Gly Gly Ser Glu
1 5 10

<210> SEQ ID NO 60
<211> LENGTH: 19
<212> TYPE: PRT
<213> ORGANISM: Murray Valley Encephalitis virus

<400> SEQUENCE: 60

Thr Ser Val Leu Met Val Ile Phe Met Leu Ile Gly Phe Ala Ala Ala
1 5 10 15

Leu Lys Leu

<210> SEQ ID NO 61
<211> LENGTH: 11
<212> TYPE: PRT
<213> ORGANISM: Saint Louis Encephalitis virus

<400> SEQUENCE: 61

Arg Arg Pro Ser Lys Lys Arg Gly Gly Thr Arg
1 5 10

<210> SEQ ID NO 62
<211> LENGTH: 15
<212> TYPE: PRT
<213> ORGANISM: Saint Louis Encephalitis virus

<400> SEQUENCE: 62

Ser Leu Leu Gly Leu Ala Ala Leu Ile Gly Leu Ala Ser Ser Leu
1 5 10 15

<210> SEQ ID NO 63
<211> LENGTH: 10
<212> TYPE: PRT
<213> ORGANISM: Dengue-1 virus

<400> SEQUENCE: 63

Ile Asn Met Arg Arg Lys Arg Ser Val Thr
1 5 10

<210> SEQ ID NO 64
<211> LENGTH: 14
<212> TYPE: PRT
<213> ORGANISM: Dengue-1 virus

<400> SEQUENCE: 64

Met Leu Leu Met Leu Leu Pro Thr Ala Leu Ala Phe His Leu 1 5 10

<210> SEQ ID NO 65
<211> LENGTH: 10
<212> TYPE: PRT
<213> ORGANISM: Dengue-2 virus

<400> SEQUENCE: 65

Ile Leu Asn Arg Arg Arg Arg Thr Ala Gly
1 5 10

<210> SEQ ID NO 66
<211> LENGTH: 14
<212> TYPE: PRT
<213> ORGANISM: Dengue-2 virus

<400> SEQUENCE: 66

Met Ile Ile Met Leu Ile Pro Thr Val Met Ala Phe His Leu
1 5 10

<210> SEQ ID NO 67
<211> LENGTH: 10
<212> TYPE: PRT
<213> ORGANISM: Dengue-3 virus

<400> SEQUENCE: 67

Ile Ile Asn Lys Arg Lys Lys Thr Ser Leu
1 5 10

<210> SEQ ID NO 68
<211> LENGTH: 14
<212> TYPE: PRT
<213> ORGANISM: Dengue-3 virus

<400> SEQUENCE: 68

Cys Leu Met Met Met Leu Pro Ala Thr Leu Ala Phe His Leu
1 5 10

<210> SEQ ID NO 69
<211> LENGTH: 10
<212> TYPE: PRT
<213> ORGANISM: Dengue-4 virus

<400> SEQUENCE: 69

Ile Leu Asn Gly Arg Lys Arg Ser Thr Ile
1 5 10

<210> SEQ ID NO 70
<211> LENGTH: 14
<212> TYPE: PRT
<213> ORGANISM: Dengue-4 virus

<400> SEQUENCE: 70

Thr Leu Leu Cys Leu Ile Pro Thr Val Met Ala Phe Ser Leu
1 5 10

<210> SEQ ID NO 71
<211> LENGTH: 24
<212> TYPE: PRT
<213> ORGANISM: Dengue-4 virus

<400> SEQUENCE: 71

Ile Leu Asn Gly Arg Lys Arg Ser Thr Ile Thr Leu Leu Cys Leu Ile
1 5 10 15

```
Pro Thr Val Met Ala Phe Ser Leu
            20


<210> SEQ ID NO 72
<211> LENGTH: 30
<212> TYPE: PRT
<213> ORGANISM: Tick-Borne Encephalitis virus

<400> SEQUENCE: 72

Gln Lys Arg Gly Lys Arg Arg Ser Ala Val Asp Trp Thr Gly Trp Leu
 1               5                  10                  15

Leu Val Val Val Leu Leu Gly Val Thr Leu Ala Ala Thr Val
            20                  25                  30


<210> SEQ ID NO 73
<211> LENGTH: 30
<212> TYPE: PRT
<213> ORGANISM: Yellow Fever virus

<400> SEQUENCE: 73

Leu Ser Ser Arg Lys Arg Arg Ser His Asp Val Leu Thr Val Gln Phe
 1               5                  10                  15

Leu Ile Leu Gly Met Leu Leu Met Thr Gly Gly Val Thr Leu
            20                  25                  30


<210> SEQ ID NO 74
<211> LENGTH: 24
<212> TYPE: PRT
<213> ORGANISM: Dengue-2 virus

<400> SEQUENCE: 74

Ile Leu Asn Arg Arg Arg Arg Thr Ala Gly Met Ile Ile Met Leu Ile
 1               5                  10                  15

Pro Thr Val Met Ala Phe His Leu
            20


<210> SEQ ID NO 75
<211> LENGTH: 30
<212> TYPE: PRT
<213> ORGANISM: Yellow Fever virus

<400> SEQUENCE: 75

Leu Ser Ser Arg Lys Arg Arg Ser His Asp Val Leu Thr Val Gln Phe
 1               5                  10                  15

Leu Ile Leu Gly Met Leu Leu Met Thr Gly Gly Val Thr Leu
            20                  25                  30


<210> SEQ ID NO 76
<211> LENGTH: 7
<212> TYPE: PRT
<213> ORGANISM: Dengue-2 virus

<400> SEQUENCE: 76

Ile Leu Asn Arg Arg Arg Arg
 1               5


<210> SEQ ID NO 77
<211> LENGTH: 17
<212> TYPE: PRT
<213> ORGANISM: Dengue-2 virus

<400> SEQUENCE: 77

Thr Ala Gly Met Ile Ile Met Leu Ile Pro Thr Val Met Ala Phe His
```

-continued

```
 1               5                   10                  15

Leu


<210> SEQ ID NO 78
<211> LENGTH: 7
<212> TYPE: PRT
<213> ORGANISM: Japanese Encephalitis virus

<400> SEQUENCE: 78

Tyr Ala Gly Ala Met Lys Leu
 1               5


<210> SEQ ID NO 79
<211> LENGTH: 7
<212> TYPE: PRT
<213> ORGANISM: Yellow Fever virus

<400> SEQUENCE: 79

Met Thr Gly Gly Val Thr Leu
 1               5


<210> SEQ ID NO 80
<211> LENGTH: 7
<212> TYPE: PRT
<213> ORGANISM: Artificial Sequence
<220> FEATURE:
<223> OTHER INFORMATION: derived from Japanese Encephalitis virus and
      Yellow Fever virus

<400> SEQUENCE: 80

Met Thr Gly Gly Met Lys Leu
 1               5


<210> SEQ ID NO 81
<211> LENGTH: 7
<212> TYPE: PRT
<213> ORGANISM: Japanese Encephalitis virus

<400> SEQUENCE: 81

Asn Lys Arg Gly Gly Asn Glu
 1               5


<210> SEQ ID NO 82
<211> LENGTH: 7
<212> TYPE: PRT
<213> ORGANISM: Yellow Fever virus

<400> SEQUENCE: 82

Lys Arg Arg Ser His Asp Val
 1               5


<210> SEQ ID NO 83
<211> LENGTH: 10
<212> TYPE: PRT
<213> ORGANISM: Japanese Encephalitis virus

<400> SEQUENCE: 83

Thr Asn Val His Ala Asp Thr Gly Cys Ala
 1               5                   10


<210> SEQ ID NO 84
<211> LENGTH: 10
<212> TYPE: PRT
<213> ORGANISM: Yellow Fever virus
```

-continued

```
<400> SEQUENCE: 84

Leu Gly Val Gly Ala Asp Gln Gly Cys Ala
 1              5                   10


<210> SEQ ID NO 85
<211> LENGTH: 10
<212> TYPE: PRT
<213> ORGANISM: Artificial Sequence
<220> FEATURE:
<223> OTHER INFORMATION: derived from Japanese Encephalitis virus and
      Yellow Fever virus

<400> SEQUENCE: 85

Thr Asn Val Gly Ala Asp Gln Gly Cys Ala
 1              5                   10
```